US009910044B2

(12) United States Patent
Ray et al.

(10) Patent No.: US 9,910,044 B2
(45) Date of Patent: Mar. 6, 2018

(54) METHODS FOR IDENTIFYING ARTHROPOD REPELLENTS BASED ON MODULATION OF SPECIFIC IONOTROPIC RECEPTORS, AND COMPOUNDS AND COMPOSITIONS IDENTIFIED BY SUCH METHODS

(71) Applicant: The Regents of the University of California, Oakland, CA (US)

(72) Inventors: Anandasankar Ray, Riverside, CA (US); Pinky Kain, Riverside, CA (US); Christine Pham, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/853,710

(22) Filed: Sep. 14, 2015

(65) Prior Publication Data
US 2015/0377897 A1 Dec. 31, 2015

Related U.S. Application Data

(63) Continuation of application No. PCT/US2014/029524, filed on Mar. 14, 2014.

(60) Provisional application No. 61/785,572, filed on Mar. 14, 2013.

(51) Int. Cl.
*G01N 33/68* (2006.01)

(52) U.S. Cl.
CPC ... *G01N 33/68* (2013.01); *G01N 2333/43573* (2013.01); *G01N 2333/705* (2013.01); *G01N 2500/04* (2013.01)

(58) Field of Classification Search
CPC ... G01N 2333/43573; G01N 2333/705; G01N 2500/04; G01N 33/68; A01N 31/16
See application file for complete search history.

(56) References Cited

U.S. PATENT DOCUMENTS

| | | | |
|---|---|---|---|
| 4,469,613 A | 9/1984 | Munteanu et al. | |
| 4,496,467 A | 1/1985 | Munteanu et al. | |
| 4,548,764 A | 10/1985 | Munteanu et al. | |
| 5,089,469 A | 2/1992 | Zampino et al. | |
| 5,175,175 A | 12/1992 | Wilson et al. | |
| 5,354,783 A | 10/1994 | Marin et al. | |
| 6,267,953 B1 | 7/2001 | Bernier et al. | |
| 6,372,804 B1 | 4/2002 | Ikemoto et al. | |
| 6,719,959 B1 | 4/2004 | Gonzalez et al. | |
| 6,800,279 B2 | 10/2004 | Bernier et al. | |
| 6,958,146 B2 | 10/2005 | Askham et al. | |
| 7,867,479 B2 | 1/2011 | Dunham et al. | |
| 8,048,683 B2 | 11/2011 | Grau et al. | |
| 8,092,790 B2 | 1/2012 | Dunham et al. | |
| 8,945,595 B2 | 2/2015 | Ray et al. | |
| 9,307,763 B2 | 4/2016 | Ray et al. | |
| 9,491,942 B2 | 11/2016 | Ray et al. | |
| 2002/0028191 A1 | 3/2002 | Bernier et al. | |
| 2004/0223998 A1 | 11/2004 | Iyer et al. | |
| 2004/0242699 A1 | 12/2004 | Askham et al. | |
| 2005/0008714 A1 | 1/2005 | Enan | |
| 2006/0189690 A1 | 8/2006 | Dunham et al. | |
| 2006/0193881 A1 | 8/2006 | Bedoukian | |
| 2007/0142795 A1 | 6/2007 | Cohen et al. | |
| 2007/0157323 A1 | 7/2007 | Carlson et al. | |
| 2009/0047379 A1 | 2/2009 | Dewis et al. | |
| 2009/0148398 A1 | 6/2009 | Vander et al. | |
| 2009/0176229 A1* | 7/2009 | Tracey, Jr. | C07K 14/43581 435/6.11 |
| 2009/0196838 A1 | 8/2009 | Gupta et al. | |
| 2010/0074972 A1 | 3/2010 | Rouseff et al. | |
| 2010/0144888 A1 | 6/2010 | Bessette | |
| 2010/0247684 A1 | 9/2010 | Reid et al. | |
| 2011/0244056 A1 | 10/2011 | Santra | |
| 2011/0263585 A1* | 10/2011 | Bernasconi | A01N 43/38 514/229.2 |
| 2012/0015841 A1* | 1/2012 | Shekdar | G01N 33/502 506/9 |

(Continued)

FOREIGN PATENT DOCUMENTS

| | | |
|---|---|---|
| CN | 1809368 A | 7/2006 |
| JP | 2000-290104 A | 10/2000 |

(Continued)

OTHER PUBLICATIONS

Abramson et al., "Proboscis Conditioning Experiments with Honeybees, *Apis mellifera caucasica*, with Butyric Acid and DEET Mixture as Conditioned and Unconditioned Stimuli", Journal of Insect Science, vol. 10, No. 122, 2010, pp. 1-17.

Abuin et al., "Functional Architecture of Olfactory Ionotropic Glutamate Receptors", Neuron, vol. 69, No. 1, Jan. 13, 2011, pp. 44-60.

Al et al., "Acid Sensing by the *Drosophila* Olfactory System", Nature, vol. 468, No. 7324, Dec. 2, 2010, pp. 691-695.

Andreev et al, "New Insect Repellents for Protection of Humans and Animals from Bloodsucking Flies, Mosquitoes, Midges, and Gnats", Chemical Abstracts Service, Columbus, Ohio, US; 1958, XP-002744302, Database Accession No. 1960:64502. (English Abstract Submitted).

(Continued)

*Primary Examiner* — Audrea Buckley
(74) *Attorney, Agent, or Firm* — Morrison & Foerster LLP

(57) ABSTRACT

Provided herein are screening methods for identifying arthropod repellent compounds based on modulation of ionotropic receptors, including an Ir40a receptor, an Ir93a receptor and an Ir25a receptor. Further provided are screening systems related to these methods. Such systems may include a sample that has one or more of the ionotropic receptors; and one or more compounds that each is a repellent for at least one arthropod species, wherein the one or more compound each modulates the activity of such ionotropic receptor(s). Further provided are one or more compounds identified using the screening methods described herein, and compositions containing such compounds.

28 Claims, 11 Drawing Sheets

(56) References Cited

U.S. PATENT DOCUMENTS

| | | |
|---|---|---|
| 2013/0236417 A1 | 9/2013 | Ray et al. |
| 2015/0126437 A1 | 5/2015 | Ray et al. |
| 2015/0223458 A1 | 8/2015 | Ray et al. |
| 2016/0003805 A1 | 1/2016 | Ray et al. |
| 2017/0079274 A1 | 3/2017 | Ray et al. |

FOREIGN PATENT DOCUMENTS

| | | |
|---|---|---|
| WO | 98/23150 A1 | 6/1998 |
| WO | 00/65910 A1 | 11/2000 |
| WO | 02/00021 A2 | 1/2002 |
| WO | 2007/056043 A2 | 5/2007 |
| WO | 2010/102049 A2 | 9/2010 |
| WO | 2010/143752 A2 | 12/2010 |
| WO | 2011/040252 A1 | 4/2011 |
| WO | 2012/018153 A1 | 2/2012 |
| WO | 2013/059364 A2 | 4/2013 |

OTHER PUBLICATIONS

Baccino et al., "Sharing an Olfactory Experience: The Impact of Oral Communication", Food Quality and Preference, vol. 21, 2010, pp. 443-452.

Bar-Zeev et al., "The Response of the Adults of the Khapra Beetle Trogoderma Granarium Everts (*Coleoptera, Dermestidae*) to Various Synthetic Compounds", Rivista Di Parassitologia, vol. XL, No. 1/2, 1979, pp. 49-55.

Bell et al., "Behavior Reveals Selective Summation and Max Pooling among Olfactory Processing Channels", Neuron, vol. 91, Jul. 20, 2016, pp. 425-438.

Bellmann et al., "Optogenetically Induced Olfactory Stimulation in *Drosophila* Larvae Reveals the Neuronal Basis of Odor-Aversion behavior", Frontiers in Behavioral Neuroscience, vol. 4, Article 27, Jun. 2010, pp. 1-10.

Benton et al., "Variant Ionotropic Glutamate Receptors as Chemosensory Receptors in *Drosophila*", Cell, vol. 136, Jan. 9, 2009, pp. 149-162.

Bernier et al., "Analysis of Human Skin Emanations by Gas Chromatography/Mass Spectrometry. 1. Thermal Desorption of Attractants for the Yellow Fever Mosquito (*Aedes aegypti*) from Handled Glass Beads", Analytical Chemistry, vol. 71, No. 1, Jan. 1, 1999, pp. 1-7.

Bernier et al., "Analysis of Human Skin Emanations by Gas Chromatography/Mass Spectrometry. 2. Identification of Volatile Compounds that are Candidate Attractants for the Yellow Fever Mosquito (*Aedes aegypti*)", Analytical Chemistry, vol. 72, No. 4, Feb. 15, 2000, pp. 747-756.

Boeckh et al., "Acylated 1,3-Aminopropanols as Repellents against Bloodsucking Arthropods", Pesticide Science, vol. 48, 1996, pp. 359-373.

Bohbot et al., "Selectivity of Odorant Receptors in Insects", Frontiers in Cellular Neuroscience, vol. 6, Article 29, Jul. 2012, pp. 1-4.

Braks et al., "Infochemicals in Mosquito Host Selection: Human Skin Microflora and Plasmodium Parasites", Parasitology Today, vol. 15, No. 10, 1999, pp. 409-413.

Bruyne et al., "Odor Coding in a Model Olfactory Organ: The *Drosophila* Maxillary Palp", The Journal of Neuroscience, vol. 19, No. 11, Jun. 1, 1999, pp. 4520-4532.

Burton, D. J., "Intrinsic Mosquito Repellency Values of Some Chemical Compounds", American Perfumer and Cosmetics, vol. 84, Apr. 1969, pp. 41-44.

Butler, Declan, "Mosquitoes Score in Chemical War", Nature, vol. 475, Jul. 7, 2011, 1 page.

Cardé et al., "Host Finding by Female Mosquitoes: Mechanisms of Orientation to Host Odours and Other Cues", Olfaction in Vector-Host Interactions, 2010, pp. 115-141.

Cardé et al., "Navigational Strategies Used by Insects to Find Distant, Wind-Borne Sources of Odor", J. Chem. Ecol., vol. 34, 2008, pp. 854-866.

Carey et al., "Odorant Reception in the Malaria Mosquito *Anopheles gambiae*", Nature, 2010, pp. 1-7.

Chang et al., "LIBSVM: A Library for Support Vector Machines", This LIBSVM implementation document was created in 2001 and has been maintained at http://www.csie.ntu.edu.tw/~cjlin/papers/libsvm.pdf, 2001, pp. 1-39.

"Chemical Products Catalog (Shanghai)", Scientific and Technical Information Research Institute of Bureau of Chemical Industry, Shanghai, Feb. 1992, pp. 177, 180, 450. (See Communication under 37 CFR § 1.98(a) (3)).

Chiang et al., "Three-Dimensional Reconstruction of Brain-wide Wiring Networks in *Drosophila* at Single-Cell Resolution", Current Biology, vol. 21, No. 1, Jan. 11, 2011, pp. 1-11.

Cook et al., "The Use of Push-Pull Strategies in Integrated Pest Management", Annu. Rev. Entomol, vol. 52, 2007, pp. 375-400.

Cooperband et al., "Orientation of Culex Mosquitoes to Carbon Dioxidebaited Traps: Flight Manoeuvres and Trapping Efficiency", Medical and Veterinary Entomology, vol. 20, 2006, pp. 11-26.

Corbel et al., "Evidence for Inhibition of Cholinesterases in Insect and Mammalian Nervous Systems by the Insect Repellent Deet", BMC Biology, vol. 7, No. 47, 2009, pp. 1-11.

Cork et al., "Identification of Electrophysiologically-Active Compounds for the Malaria Mosquito, *Anopheles gambiae*, in Human Sweat Extracts", Medical and Veterinary Entomology, vol. 10, 1996, pp. 269-276.

Cortes et al., "Support-Vector Networks", Machine Learning, vol. 20, 1995, pp. 273-297.

Croset et al., "Ancient Protostome Origin of Chemosensory Ionotropic Glutamate Receptors and the Evolution of Insect Taste and Olfaction", PLoS Genetics, vol. 6, No. 8, e1001064, Aug. 2010, pp. 1-20.

Curran et al., "Comparison of the Volatile Organic Compounds Present in Human Odor Using SPME-GC/MS", Journal of Chemical Ecology, vol. 31, No. 7, Jul. 2005, pp. 1607-1619.

Dekker et al., "Carbon Dioxide Instantly Sensitizes Female Yellow Fever Mosquitoes to Human Skin Odours", The Journal of Experimental Biology, vol. 208, 2005, pp. 2963-2972.

Dekker et al., "Identification of Mosquito Repellent Odours from Ocimum Forskolei", Parasites & Vectors, vol. 4, No. 183, 2011, pp. 1-7.

Dekker et al., "Moment-to-Moment Flight Manoeuvres of the Female Yellow Fever Mosquito (*Aedes aegypti* L.) in response to Plumes of Carbon Dioxide and Human Skin Odour", The Journal of Experimental Biology, vol. 214, 2011, pp. 3480-3494.

Dekker et al., "Structure of Host-Odour Plumes Influences Catch of *Anopheles gambiae* S.S. and Aedes Aegypti in a Dualchoice Olfactometer", Physiological Entomology, vol. 26, 2001, pp. 124-134.

Ditzen et al., "Insect Odorant Receptors are Molecular Targets of the Insect Repellent DEET", Science, vol. 319, 2008, pp. 1838-1842.

Douglas et al., "Chemical Odorant of Colonial Seabird Repels Mosquitoes", Journal of Medical Entomology, vol. 42, No. 4, Jul. 2005, pp. 647-651.

Enjin et al., "Humidity Sensing in *Drosophila*", Current Biology, vol. 26, May 23, 2016, pp. 1-7.

Erdelyan et al., "Functional Validation of the Carbon Dioxide Receptor Genes in *Aedes aegypti* Mosquitoes using RNA Interference", Insect Molecular Biology, vol. 21, No. 1, 2012, pp. 119-127.

Final Office Action received for U.S. Appl. No. 12/398,164, dated Apr. 16, 2014, 17 pages.

Final Office Action received for U.S. Appl. No. 12/398,164, dated Apr. 20, 2012, 10 pages.

Fischler et al., "The Detection of Carbonation by the *Drosophila* Gustatory System", Nature, vol. 448, Aug. 30, 2007, pp. 1054-1057.

Gallagher et al., "Analyses of Volatile Organic Compounds from Human Skin", Br J Dermatol., vol. 159, No. 4, Sep. 2008, pp. 780-791.

Gaudin et al., "Carboxamides Combining Favorable Olfactory Properties with Insect Repellency", Chemistry & Biodiversity, vol. 5, 2008, pp. 617-635.

Ghaninia et al., "Natural Odor Ligands for Olfactory Receptor Neurons of the Female Mosquito *Aedes aegypti*: Use of Gas

(56) References Cited

OTHER PUBLICATIONS

Chromatography-linked Single Sensillum Recordings", The Journal of Experimental Biology, vol. 211, 2008, pp. 3020-3027.

Gillies, M. T., "The Role of Carbon Dioxide in Host-Finding by Mosquitoes (*Diptera: Culicidae*): A Review", Bull. Ent. Res., vol. 70, 1980, pp. 525-532.

Godavarthy et al., "Improved Structure-Property Relationship Models for Prediction of Critical Properties", Fluid Phase Equilibria, vol. 264, 2008, pp. 122-136.

Grant et al., Olfaction in Mosquito-Host Interactions, Ciba Foundation Symposium 200, 1996, 10 pages.

Gupta et al., "Discovery and Design of New Arthropod/Insect Repellents by Computer-Aided Molecular Modeling", Insect Repellents Principles, Methods, and Uses, 2006, pp. 195-228.

Gutierrez-Osuna, Ricardo, "Pattern Analysis for Machine Olfaction: A Review", IEEE Sensors Journal, vol. 2, No. 3, Jun. 2002, pp. 189-202.

Haasen et al., "Pharmacological Profiling of Chemokine Receptor-Directed Compounds Using High-Content Screening", Journal of Biomolecular Screening, vol. 13, No. 1, 2008, pp. 40-53.

Haddad et al., "A Metric for Odorant Comparison", Nature Methods, 2008, pp. 1-5.

Halbert et al., "Plant-Derived Compounds and Extracts with Potential as Aphid Repellents", Annals of Applied Biology, vol. 154, 2009, pp. 303-307.

Hallem et al., "Coding of Odors by a Receptor Repertoire", Cell, vol. 125, Apr. 7, 2006, pp. 143-160.

Hawkins et al., "Conformer Generation with OMEGA: Algorithm and Validation Using High Quality Structures from the Protein Databank and Cambridge Structural Database", J. Chem. Inf. Model, vol. 50, No. 4, 2010, pp. 572-584.

Hayes et al, "Identification of a Host Compound and its Practical Applications: 4-Allylanisole as a Bark Beetle Repellent", Chemical Abstracts Service, 1994, Feb. 1-2, 1994, pp. 69-79.

Healy et al., "Activation of Anopheles Gambiae Mosquitoes by Carbon Dioxide and Human Breath", Medical Veterinary Entomology, vol. 9, 1995, pp. 331-336.

Healy et al., "Human Sweat and 2-Oxopentanoic Acid Elicit a Landing Response from Anopheles Gambiae", Medical Veterinary Entomology, vol. 14, 2000, pp. 195-200.

Hou et al., "The Effect of Repellents on Penetration into Packaging by Stored-Product Insects", Journal of Stored Products Research, vol. 40, 2004, pp. 47-54.

Hwang et al., "Isolation and Identification of Mosquito Repellents in Artemisia Vulgaris", Journal of Chemical Ecology, vol. 11, No. 9, pp. 1297-1306. (English Abstract Submitted).

Ibrahim et al., "Toxicity and Inhibition of Feeding and Tunneling Response of Naphthalene and 10 Derivatives on the Formosan Subterranean Termite (*Isoptera rhinotermitidae*)", Journal of Economic Entomology, vol. 103, No. 6, Dec. 2010, pp. 2132-2139. (English Abstract Submitted).

Ihndris et al., "Effect of Promising Insect Repellents on Plastics and Paints", Database Accession No. 1955:86558, 1955, vol. 33, No. 7, 2 pages. (English Abstract Submitted).

Innocent et al., "Constituents of the Essential Oil of *Suregada zanzibariensis* Leaves are S.S", Journal of Insect Science, vol. 10, No. 57, 2010, pp. 1-8.

International Preliminary Report on Patentability received for PCT Patent Application No. PCT/US2010/026108, dated Sep. 15, 2011, 8 pages.

International Preliminary Report on Patentability received for PCT Patent Application No. PCT/US2011/032804, dated Oct. 26, 2012, 9 pages.

International Preliminary Report on Patentability received for PCT Patent Application No. PCT/US2012/060130, dated Apr. 24, 2014, 9 pages.

International Preliminary Report on Patentability received for PCT Patent Application No. PCT/US2012/060673, dated May 1, 2014, 7 pages.

International Preliminary Report on Patentability received for PCT Patent Application No. PCT/US2014/029201, dated Sep. 24, 2015, 8 pages.

International Preliminary Report on Patentability received for PCT Patent Application No. PCT/US2014/029524, dated Sep. 24, 2015, 9 pages.

International Search Report and Written Opinion received for PCT Patent Application No. PCT/US2010/026108, dated Oct. 19, 2010, 12 pages.

International Search Report and Written Opinion received for PCT Patent Application No. PCT/US2012/060130, dated Mar. 18, 2013, 13 pages.

International Search Report and Written Opinion received for PCT Patent Application No. PCT/US2012/060673, dated Apr. 1, 2013, 11 pages.

International Search Report and Written Opinion received for PCT Patent Application No. PCT/US2014/029201, dated Oct. 7, 2014, 5 pages.

International Search Report and Written Opinion received for PCT Patent Application No. PCT/US2014/029524, dated Aug. 11, 2014, 5 pages.

International Search Report received for PCT Patent Application No. PCT/US2011/032804, dated Dec. 26, 2011, 5 pages.

International Written Opinoin received for PCT Patent Application No. PCT/US2011/032804, dated Dec. 26, 2011, 7 pages.

Invitation to Pay Additional Fees received for PCT Patent Application No. PCT/US2014/029201, dated Jul. 24, 2014, 2 pages.

Jacquin-Joly et al., "Insect Olfactory Receptors: Contributions of Molecular Biology to Chemical Ecology", Journal of Chemical Ecology, vol. 30. No. 12, Dec. 2004, pp. 2359-2397.

Jawara et al., "Field Testing of Different Chemical Combinations as Odour Baits for Trapping Wild Mosquitoes in the Gambia", PLoS One, vol. 6, No. 5, e19676, 2011, pp. 1-7.

Jones et al., "Allosteric Antagonism of Insect Odorant Receptor Ion Channels", PLoS One, vol. 7, No. 1, e30304, Jan. 2012, pp. 1-7.

Jones, Walton, "Olfactory Carbon Dioxide Detection by Insects and Other Animals", Molecules and Cells, vol. 35, Feb. 28, 2013, pp. 87-92.

Jones et al., "Two Chemosensory Receptors Together Mediate Carbon Dioxide Detection in *Drosophila*", Nature, vol. 445, Jan. 4, 2007, pp. 86-90.

Kain et al., "Odour Receptors and Neurons for DEET and New Insect Repellents", Nature, vol. 502, Oct. 24, 2013, pp. 507-512.

Kain et al., "Retraction: Odour Receptors and Neurons for DEET and New Insect Repellents", Nature, vol. 536, 2016, p. No. 488.

Kao et al., "The Biochemical Basis for the Anti-inflammatory and Cytoprotective Actions of Ethyl Pyruvate and Related Compounds", Biochemical Pharmacology, vol. 80, 2010, pp. 151-159.

Karatzoglou et al., "Support Vector Machines in R", Journal of Statistical Software, vol. 15, No. 9, Apr. 2006, pp. 1-28.

Katritzky et al., "Synthesis and Bioassay of Improved Mosquito Repellents Predicted from Chemical Structure", PNAS, vol. 105, No. 21, May 27, 2008, pp. 7359-7364.

Kellogg, F.E., "Water Vapour and Carbon Dioxide Receptors in Aedes Aegypti", J. Insect Physiol., vol. 16, 1970, pp. 99-108.

Kline et al., "Olfactometric Evaluation of Spatial Repellents for Aedes Aegypti", Journal of Medical Entomology, vol. 40, No. 4, Jul. 2003, pp. 463-467.

Klocke et al., "1, 8-Cineole (Eucalyptol), A Mosquito Feeding and Ovipositional Repellent from Volatile Oil of Hemizonia Fitchii (*Asteraceae*)", Journal of Chemical Ecology, vol. 13, No. 12, 1987, pp. 2131-2141.

Klun et al., "Comparative Resistance of Anopheles Albimanus and Aedes aegypti to N,N-Diethyl-3-Methylbenzamide (Deet) and 2-Methylpiperidinyl-3-Cyclohexen-1-Carboxamide (Al3-37220) in Laboratory Human-Volunteer Repellent Assays", Journal of Medical Entomology, vol. 41, No. 3, May 2004, pp. 418-422.

Knecht et al., "Distinct Combinations of Variant Ionotropic Glutamate Receptors Mediate Thermosensation and Hygrosensation in *Drosophila*", Elife, vol. 5, e17879, 2016, pp. 1-15.

Knudsen et al., "Diversity and Distribution of Floral Scent", The Botanical Review, vol. 72, No. 1, Mar. 31, 2006, pp. 1-120.

(56) References Cited

OTHER PUBLICATIONS

Kovalenko et al., "Repellent properties of Mannich Bases Derived from Hydroxy- and Aminobenzoic Acid Esters", Database Accession No. 1983:535492, 1983, 2 pages. (English Abstract Submitted).
Krajick, K., "Medical Entomology. Keeping the Bugs at Bay", Science, vol. 313, No. 5783, Jul. 7, 2006, pp. 36-38.
Kreher et al., "Translation of Sensory Input into Behavioral Output via an Olfactory System", Neuron, vol. 59, No. 1, Jul. 10, 2008, pp. 110-124.
Krzywinski et al., "Analysis of the Complete Mitochondrial DNA from Anopheles Funestus: An Improved Dipteran Mitochondrial Genome Annotation and a Temporal Dimension of Mosquito Evolution", Molecular Phylogenetics and Evolution, vol. 39, No. 2, 2006, pp. 417-423.
Lacey et al., "Activation, Orientation and Landing of female Culex Quinquefasciatus in Response to Carbon Dioxide and Odour from Human Feet: 3-D Flight Analysis in a Wind Tunnel", Medical Veterinary Entomology, vol. 25, 2011, pp. 94-103.
Leal W S et al., "Medicinal Alkaloid as a Sex Pheromone", Nature, vol. 385, Jan. 16, 1997, p. 213.
Lee et al., "Avoiding DEET through Insect Gustatory Receptors", Neuron, vol. 67, No. 4, Aug. 26, 2010, pp. 555-561.
Lee et al., "Multiple Gustatory Receptors Required for the Caffeine Response in *Drosophila*", Proceedings of The National Academy of Sciences, vol. 106, No. 11, Mar. 17, 2009, pp. 4495-4500.
Linduska et al., "Flea Repellents for Use on Clothing", Journal of Economic Entomology, vol. 39, No. 6, Dec. 1946, pp. 767-769.
Liu et al., "Distinct Olfactory Signaling Mechanisms in the Malaria Vector Mosquito Anopheles Gambiae", Plos Biology, vol. 8, No. 8, e1000467, Aug. 2010, pp. 1-7.
Lu et al., "Odor Coding in the Maxillary Palp of the Malaria Vector Mosquito Anopheles Gambiae", Current Biology, vol. 17, No. 18, Sep. 18, 2007, pp. 1533-1544.
Lyne et al., "Identification of Compounds with Nanomolar Binding Affinity for Checkpoint Kinase-1 using Knowledge-based Virtual Screening", Journal of Medicinal Chemistry, vol. 47. No. 8, 2004, pp. 1962-1968.
Mackay et al., "The *Drosophila melanogaster* Genetic Reference Panel", Nature, vol. 482, Feb. 9, 2012, pp. 173-178.
Maldonado et al., "Molecular Similarity and Diversity in Chemoinformatics: From Theory to Applications", Molecular Diversity, vol. 10, 2006, pp. 39-79.
Mann et al., "Sulfur Volatiles from *Allium* Spp. affect Asian Citrus Psyllid, Diaphorina Citri Kuwayama (Hemiptera: Psyllidae), Response to Citrus Volatiles", Bulletin of Entomological Research, vol. 101, No. 1, Feb. 2011, pp. 89-97.
Masuyama et al., "Mapping Neural Circuits with Activity-Dependent Nuclear Import of a Transcription Factor", J. Neurogenetics, vol. 26, 2012, pp. 89-102.
Mayer et al., "Field Evaluation of Non-Pesticide Chemicals as Honey Bee Repellents", Chemical Abstracts Service, Columbus, Ohio, US; 2001, XP002744301, Database Accession No. 2001:493021, 2 pages. (English Abstract Submitted).
Mboera et al., "The Response of Culex Quinquefasciatus (Diptera: Culicidae) to Traps Baited with Carbon Dioxide, 1-Octen-3-ol, Acetone, Butyric Acid and Human Foot Odour in Tanzania", Bulletin Entomological Research, vol. 90, No. 2, 2000, pp. 155-159.
Meijerink et al., "Identification of Olfactory Stimulants for Anopheles Gambiae from Human Sweat Samples", Journal of Chemical Ecology, vol. 26, No. 6, 2000, pp. 1367-1382.
Mumcuoglu et al., "Repellency of Essential Oils and their Components to the Human Body Louse, Pediculus Humanus Humanus", Entomologia Experimentalis et Applicata, vol. 78, 1996, pp. 309-314.
Nikonov et al., "A Photoaffinity-Labeled Green Leaf Volatile Compound 'Tricks' Highly Selective and Sensitive Insect Olfactory Receptor Neurons", Chem. Senses, vol. 26, 2001, pp. 49-54.
Njiru et al., "Trapping of the Malaria Vector Anopheles Gambiae with Odour-Baited MM-X Traps in Semi-field Conditions in Western Kenya", Malaria Journal, vol. 5, No. 39, 2006, pp. 1-8.

Non-Final Office Action received for U.S. Appl. No. 14/855,024, dated Nov. 22, 2016, 8 pages.
Non-Final Office Action received for U.S. Appl. No. 14/352,483, dated Sep. 24, 2015, 6 pages.
Non-Final Office Action received for U.S. Appl. No. 12/398,164, dated Aug. 12, 2013, 12 pages.
Non-Final Office Action received for U.S. Appl. No. 12/398,164, dated Jun. 23, 2011, 10 pages.
Non-Final Office Action received for U.S. Appl. No. 13/641,065, dated Aug. 15, 2014, 9 pages.
Notice of Allowance received for U.S. Appl. No. 12/398,164, dated Sep. 26, 2014, 11 pages.
Notice of Allowance received for U.S. Appl. No. 14/352,483, dated Jul. 1, 2016, 7 pages.
Notice of Allowance received for U.S. Appl. No. 14/540,908, dated Dec. 4, 2015, 8 pages.
"Organic Synthesis, vol. III", E.C.Horning, Science Press, Aug. 31, 1981. (See Communication under 37 CFR § 1.98(a) (3)).
Paluch et al., "Mosquito Repellents: A Review of Chemical Structural Diversity and Olfaction", Pest Manag Sci, vol. 66, 2010, pp. 925-935.
Patt et al., "Responses of the Asian Citrus Psyllid to Volatiles Emitted by the Flushing Shoots of Its Rutaceous Host Plants", Environmental Entomology, vol. 39, No. 2, Apr. 2010, pp. 618-624.
Pellegrino et al., "A Natural Polymorphism Alters Odour and DEET Sensitivity in an Insect Odorant Receptor", Nature, vol. 478, No. 7370, Sep. 21, 2011, pp. 511-514.
Pitts et al., "Transcriptome Profiling of Chemosensory Appendages in the Malaria Vector Anopheles Gambiae Reveals Tissue- and Sex-Specific Signatures of Odor Coding", BMC Genomics, vol. 12, vol. 271, 2011, pp. 1-17.
Praag et al., "Steam Volatile Aroma Constituents of Roasted Cocoa Beans", Journal of Agricultural and Food Chemistry, vol. 16, No. 6, Nov.-Dec. 1968, pp. 1005-1008.
Pub, Chem, "(Pentyl-2 Aminobenzoate, Mar. 26, 2005 CID 100495", Available at : <https://pubchem.ncbi.nlm.nih.gov/compound/100495#section=Top>.
Qiu et al., "Attractiveness of MM-X Traps Baited with Human or Synthetic Odor to Mosquitoes (*Diptera: Culicidae*) in the Gambia", Journal of Medical Entomology, vol. 44, No. 6, Nov. 2007, pp. 970-983.
Qiu et al., "Olfactory Coding in Antennal Neurons of the Malaria Mosquito, *Anopheles gambiae*", Chem. Senses, vol. 31, 2006, pp. 845-863.
Ràmia et al., "PopDrowser: The Population *Drosophila* Browser", Bioinformatics, vol. 28, No. 4, 2012, pp. 595-596.
Ramirez et al., "Repellents Inhibit P450 Enzymes in Stegomyia (Aedes) Aegypti", Plos One, vol. 7, No. 11, e48698, Nov. 2012, pp. 1-8.
Reeder, "Isolation of a Deet-Insensitive Mutant of *Drosophila melanogaster* (Diptera: Drosophilidae)", Journal of Economic Entomology, vol. 94, No. 6, Dec. 2001, pp. 1584-1588.
Rehr et al., "L-Dopa in Legume Seeds: A Chemical Barrier to Insect Attack", Science, vol. 181, Jul. 6, 1973, pp. 81-82.
Robertson et al., "Evolution of the Gene Lineage Encoding the Carbon Dioxide Receptor in Insects", Journal of Insect Science, vol. 9, No. 19, 2009, pp. 1-14.
Saito et al., "Odor Coding by a Mammalian Receptor Repertoire", Science Signaling, vol. 2, No. 60, Mar. 3, 2009, pp. 1-14.
Schmuker et al., "Predicting Olfactory Receptor Neuron Responses from Odorant Structure", Chemistry Central Journal, vol. 1, No. 11, 2007, pp. 1-10.
Scognamiglio, "Fragrance Material Review on Cyclopentanone", Food and Chemical Toxicology, vol. 50, 2012, pp. S608-S612.
Silbering et al., "Complementary Function and Integrated Wiring of the Evolutionarily Distinct *Drosophila* Olfactory Subsystems", The Journal of Neuroscience, vol. 31, No. 38, Sep. 21, 2011, pp. 13357-13375.
Silbering et al., "Ir40a Neurons are not DEET Detectors", Nature, vol. 534, Jun. 23, 2016, pp. E5-E7.
Singer, Allen W., "Topical Hazard Evaluation Program of Candidate Insect", Database accession No. 1980:141441, 1979, 2 pages. (English Abstract Submitted).

(56) References Cited

OTHER PUBLICATIONS

Skinner et al., "Topical Mosquito Repellents IX: Quinolines, Isoquinolines, and Quinoxalines", Journal of Pharmaceutical Sciences, vol. 65, No. 9, Sep. 1976, pp. 1404-1407.
Smagghe et al., "Insect Cell Culture and Applications to Research and Pest Management", In Vitro Cellular & Developmental Biology—Animal, vol. 45, 2009, pp. 93-105.
Smallegange et al., "Effectiveness of Synthetic Versus Natural Human Volatiles as Attractants for Anopheles Gambiae (Diptera: Culicidae) Sensu Stricto", Journal of Medical Entomology, vol. 47, No. 3, May 2010, pp. 338-344.
Smallegange et al., "Host-Seeking Behaviour of Mosquitoes: Responses to Olfactory Stimuli in the Laboratory", Olfaction in Vector-Host Interactions, Ch. 7, 2010, pp. 143-180.
Smallegange et al., "Synergism Between Ammonia, Lactic Acid and Carboxylic Acids as Kairomones in the Host-seeking Behaviour of the Malaria Mosquito Anopheles Gambiae Sensu Stricto (Diptera: Culicidae)", Chem. Senses, vol. 30, No. 2, 2005, pp. 145-152.
Smith et al., "Effectiveness of Repellents Applied to Clothing for Protection against Salt-Marsh Mosquitoes", Journal of Economic Entomology, vol. 42, 1949, pp. 439-444. (English Abstract Submitted).
Stanczyk et al., "Behavioral Insensitivity to DEET in Aedes Aegypti is a Genetically Determined Trait Residing in Changes in Sensillum Function", PNAS, vol. 107, No. 19, May 11, 2010, pp. 8575-8580.
Su et al., "Non-Synaptic Inhibition between Grouped Neurons in an Olfactory Circuit", Nature, vol. 492, No. 7427, Dec. 6, 2012, pp. 66-71.
Svirbely et al., "Physical Properties of Some Organic Insect Repellents", Journal of the American Chemical Society, vol. 71, Feb. 1949, pp. 507-509.
Sweeney et al., "Targeted Expression of Tetanus Toxin Light Chain in *Drosophila* Specifically Eliminated Synaptic Transmission and Causes Behavioral Defects", Neuron, vol. 14, Feb. 1995, pp. 341-351.
Syed et al., "Acute Olfactory Response of Culex Mosquitoes to a Human- and Bird-Derived Attractant", PNAS, vol. 106, No. 44, Nov. 3, 2009, pp. 18803-18808.
Syed et al., "Generic Insect Repellent Detector from the Fruit Fly *Drosophila melanogaster*", Plos One, vol. 6, No. 3, e17705, 2011, pp. 1-6.
Syed et al., "Maxillary Palps are Broad Spectrum Odorant Detectors in Culex Quinquefasciatus", Chem. Senses, vol. 32, 2007, pp. 727-738.
Syed et al., "Mosquitoes Smell and Avoid the Insect Repellent DEET", PNAS, vol. 105, No. 36, Sep. 9, 2008, pp. 13598-13603.
Tanaka et al., "Allyl Derivatives as Cockroach Repellents", Chemical Abstracts Service, Columbus, Ohio, US; Aug. 20, 1975 (Aug. 20, 1975),XP0027 44424, retrieved from STN Database Accession No. 1976:70350 ; & JP S50 105821 A (Taisho Pharmaceutical Co., I to., Japan; Takasago Perfumery Co.,Ltd.) Aug. 20, 1975. (English Abstract Submitted).
Tanaka et al., "Highly Selective Tuning of a Silkworm Olfactory Receptor to a Key Mulberry Leaf Volatile", Current Biology, vol. 19, No. 11, Jun. 9, 2009, pp. 881-890.
Tentschert et al., "2,3-Dimethyl-5-(2-Methylpropyl)Pyrazine, A Trail Pheromone Component of Eutetramorium Mocquerysi Emery (1899) (Hymenoptera: Formicidae)", Naturwissenschaften, vol. 87, 2000, pp. 377-380.
Turner et al., "Modification of $CO_2$ Avoidance Behaviour in *Drosophila* by Inhibitory Odorants", Nature, vol. 461, Sep. 2009, pp. 277-281.
Turner et al., "Ultra-Prolonged Activation of $CO_2$-Sensing Neurons Disorients Mosquitoes", Nature, vol. 474, No. 7349, Jun. 2, 2011, pp. 87-91.
Verhulst et al., "Chemical Ecology of Interactions Between Human Skin Microbiota and Mosquitoes", FEMS Microbiol Ecol, vol. 74, 2010, pp. 1-9.
Verhulst et al., "Differential Attraction of Malaria Mosquitoes to Volatile Blends Produced by Human Skin Bacteria", PLoS One, vol. 5, No. 12, e15829, Dec. 2010, pp. 1-9.
Viktorov-Nabokov et al., "Effect of Substituents in a Series of Benzoic Acid Esters and Amides on Repellence with Respect to Blood-Sucking Mosquitoes", Fiziologicheski Aktivnye Veshchestva, vol. 12, 1980, 1 page (Abstract only).
Walker et al., "Quantitative Structure-Activity Relationships for Predicting Percutaneous Absorption Rates", Environmental Toxicology and Chemistry, vol. 22, No. 8, 2003, pp. 1870-1884.
Wang et al., "Molecular Basis of Odor Coding in the Malaria Vector Mosquito Anopheles Gambiae", PNAS, vol. 107, No. 9, Mar. 2, 2010, pp. 4418-4423.
Wang et al., "QSAR Study of Mosquito Repellents from Terpenoid with a Six-Member-Ring", Bioorganic & Medicinal Chemistry Letters, vol. 18, 2008, pp. 2854-2859.
Weeks et al., "Topical Hazard Evaluation Program of Candidate Insect Repellent AI3-36706 Pentyl 2-Aminobenzoate", Database Accession No. 1978:1227, Study No. 51-0847-77, Dec. 1977, 13 pages. (English Abstract Submitted).
Weiss et al., "The Molecular and Cellular Basis of Bitter Taste in *Drosophila*", Neuron, vol. 69, No. 2, Jan. 27, 2011, pp. 258-272.
Whitney, A. W., "A Direct Method of Nonparametric Measurement Selection", IEEE Transactions on Computers, vol. 20, No. 9, Sep. 1971, pp. 1100-1103.
Xia et al., "The Molecular and Cellular Basis of Olfactory-Driven Behavior in Anopheles Gambiae Larvae", PNAS, vol. 105, No. 17, Apr. 29, 2008, pp. 6433-6438.
Xu et al., "Mosquito Odorant Receptor for DEET and Methyl Jasmonate", Proceedings of the National Academy of Sciences, vol. 111, No. 46, Nov. 18, 2014, pp. 16592-16597.
Xue et al., "Field Evaluation of CDC and Mosquito Magnet X Traps Baited with Dry Ice, CO2 Sachet, and Octenol against Mosquitoes", Journal of the American Mosquito Control Association, vol. 24, No. 2, Jun. 2008, pp. 249-252.
Zhu, Song-Nian, "Research on a Repellent for Ants and Rats for Plastics", Chemical Abstracts Service, Columbus, Ohio, US; 2004, XP002744300, Database Accession No. 2004:1027260. (English Abstract Submitted).
Zwiebel et al., "Olfactory regulation of mosquito-host interactions", Insect Biochem Mol Biol. vol. 34, No. 7, 2004, pp. 645-652.

\* cited by examiner

SEQUENCE LISTING

```
<160> NUMBER OF SEQ ID NOS: 51

<210> SEQ ID NO 1
<211> LENGTH: 765
<212> TYPE: PRT
<213> ORGANISM: Drosophila melenogaster

<400> SEQUENCE: 1

Met His Lys Phe Leu Ala Leu Gly Leu Leu Pro Tyr Leu Leu Gly Leu
1               5                   10                  15

Leu Asn Ser Thr Arg Leu Thr Phe Ile Gly Asn Asp Glu Ser Asp Thr
            20                  25                  30

Ala Ile Ala Leu Thr Gln Ile Val Arg Gly Leu Gln Gln Ser Ser Leu
        35                  40                  45

Ala Ile Leu Ala Leu Pro Ser Leu Ala Leu Ser Asp Gly Val Cys Gln
    50                  55                  60

Lys Glu Arg Asn Val Tyr Leu Asp Asp Phe Leu Gln Arg Leu His Arg
65                  70                  75                  80

Ser Asn Tyr Lys Ser Val Val Phe Ser Gln Thr Glu Leu Phe Phe Gln
                85                  90                  95

His Ile Glu Glu Asn Leu Gln Gly Ala Asn Glu Cys Ile Ser Leu Ile
            100                 105                 110

Leu Asp Glu Pro Asn Gln Leu Leu Asn Ser Leu His Asp Arg His Leu
        115                 120                 125

Gly His Arg Leu Ser Leu Phe Ile Phe Tyr Trp Gly Ala Arg Trp Pro
    130                 135                 140

Pro Ser Ser Arg Val Ile Arg Phe Arg Glu Pro Leu Arg Val Val Val
145                 150                 155                 160

Val Thr Arg Pro Arg Lys Lys Ala Phe Arg Ile Tyr Tyr Asn Gln Ala
                165                 170                 175

Arg Pro Cys Ser Asp Ser Gln Leu Gln Leu Val Asn Trp Tyr Asp Gly
            180                 185                 190
```

```
Asp Asn Leu Gly Leu Gln Arg Ile Pro Leu Pro Thr Ala Leu Ser
    195                 200                 205

Val Tyr Ala Asn Phe Lys Gly Arg Thr Phe Arg Val Pro Val Phe His
    210                 215                 220

Ser Pro Pro Trp Phe Trp Val Thr Tyr Cys Asn Asn Ser Phe Glu Glu
225                 230                 235                 240

Asp Glu Glu Phe Asn Ser Leu Asp Ser Ile Glu Lys Arg Lys Val Arg
                245                 250                 255

Val Thr Gly Gly Arg Asp His Arg Leu Leu Met Leu Leu Ser Lys His
                260                 265                 270

Met Asn Phe Arg Phe Lys Tyr Ile Glu Ala Pro Gly Arg Thr Gln Gly
            275                 280                 285

Ser Met Arg Ser Glu Asp Gly Lys Asp Ser Asn Asp Ser Phe Thr Gly
            290                 295                 300

Gly Ile Gly Leu Leu Gln Ser Gly Gln Gln Ala Asp Phe Phe Leu Gly
305                 310                 315                 320

Asp Val Gly Leu Ser Trp Glu Arg Arg Lys Ala Ile Glu Phe Ser Phe
                325                 330                 335

Phe Thr Leu Ala Asp Ser Gly Ala Phe Ala Thr His Ala Pro Arg Arg
                340                 345                 350

Leu Asn Glu Ala Leu Ala Ile Met Arg Pro Phe Lys Gln Asp Ile Trp
            355                 360                 365

Pro His Leu Ile Leu Thr Ile Phe Ser Gly Pro Ile Phe Tyr Gly
            370                 375                 380

Ile Ile Ala Leu Pro Tyr Ile Trp Arg Arg Trp Ala Asn Ser Asp
385                 390                 395                 400

Val Glu His Leu Gly Glu Leu Tyr Ile His Met Thr Tyr Leu Lys Glu
                405                 410                 415

Ile Thr Pro Arg Leu Leu Lys Leu Lys Pro Arg Thr Val Leu Ser Ala
                420                 425                 430

His Gln Met Pro His Gln Leu Phe Gln Lys Cys Ile Trp Phe Thr Leu
            435                 440                 445

Arg Leu Phe Leu Lys Gln Ser Cys Asn Glu Leu His Asn Gly Tyr Arg
            450                 455                 460

Ala Lys Phe Leu Thr Ile Val Tyr Trp Ile Ala Ala Thr Tyr Val Leu
465                 470                 475                 480

Ala Asp Val Tyr Ser Ala Gln Leu Thr Ser Gln Phe Ala Arg Pro Ala
                485                 490                 495

Arg Glu Pro Pro Ile Asn Thr Leu Gln Arg Leu Gln Ala Ala Met Ile
                500                 505                 510

His Asp Gly Tyr Arg Leu Tyr Val Glu Lys Glu Ser Ser Ser Leu Glu
            515                 520                 525

Met Leu Glu Asn Gly Thr Glu Leu Phe Arg Gln Leu Tyr Ala Leu Met
530                 535                 540

Arg Gln Gln Val Ile Asn Asp Pro Gln Gly Phe Phe Ile Asp Ser Val
545                 550                 555                 560

Glu Ala Gly Ile Lys Leu Ile Ala Glu Gly Gly Glu Asp Lys Ala Val
                565                 570                 575

Leu Gly Gly Arg Glu Thr Leu Phe Phe Asn Val Gln Tyr Gly Ser
            580                 585                 590

Asn Asn Phe Gln Leu Ser Gln Lys Leu Tyr Thr Arg Tyr Ser Ala Val
            595                 600                 605
```

```
Ala Val Gln Ile Gly Cys Pro Phe Leu Gly Ser Leu Asn Asn Val Leu
610                 615                 620

Met Gln Leu Phe Glu Ser Gly Ile Leu Asp Lys Met Thr Ala Ala Glu
625                 630                 635                 640

Tyr Ala Lys Gln Tyr Gln Glu Val Glu Ala Thr Arg Ile Tyr Lys Gly
                645                 650                 655

Ser Val Gln Ala Lys Asn Ser Glu Ala Tyr Ser Arg Thr Glu Ser Tyr
            660                 665                 670

Asp Ser Thr Val Ile Ser Pro Leu Asn Leu Arg Met Leu Gln Gly Ala
        675                 680                 685

Phe Ile Ala Leu Gly Val Gly Ser Leu Ala Ala Ala Leu Asn Asn
690                 695                 700

Thr Ile Asn Val Arg Ser Leu Asn Ser Arg Asp Lys Phe Ile Cys Gly
705                 710                 715                 720

Gly Pro Val Lys Ile Trp Tyr Tyr Leu Val Leu Leu Trp Tyr Tyr
                725                 730                 735

Phe Asn Arg Gly Leu Val Gly Ile Tyr Gln Leu Trp His Lys Thr Ser
                740                 745                 750

Ile Arg Asn Thr Gly Lys Gly Met Pro Phe Leu Gly Glu
            755                 760                 765

<210> SEQ ID NO 2
<211> LENGTH: 812
<212> TYPE: PRT
<213> ORGANISM: Aedes aegypti

<400> SEQUENCE: 2

Met Asn Lys Val Leu Ala Thr Pro Ala Ser Lys Ala Asp Lys Leu Glu
1               5                   10                  15

Ser Leu Ile Ser Ile Gly Leu Val Val Gln Asn Leu Cys Ser Gln Leu
                20                  25                  30

Gln Ser Met Arg Met Glu Ala His Leu Ser Asn Pro Ser Leu Leu Gln
            35                  40                  45

Glu Leu Val Asp Lys Leu Pro Ala Asn Ile Lys Leu His Trp Ala Leu
50                  55                  60

His Gln Arg Gln Val Pro Val Val Asp Phe Arg Ala Phe Thr Tyr His
65                  70                  75                  80

Ala His Leu Ala Pro Leu Pro Asp Leu Ser Asn His Ser Gly Met Val
                85                  90                  95

Leu Gly Leu Ser Glu Met Ile Asn Leu Leu Ala Pro Lys Thr Leu Ala
            100                 105                 110

Ile Leu Val Leu Lys Glu Thr Lys Ile Asp Lys Ile Asp Arg Leu Thr
        115                 120                 125

Val Met Ile His His His Asn Ile Pro Thr Cys Ile Phe Asn Asn Gln
130                 135                 140

Asp Glu Tyr Phe Gln Tyr Ile Gly Asn Asn Leu Lys Lys Ser Leu Glu
145                 150                 155                 160

Thr Thr Ser Leu Leu Phe Cys His Pro Glu Glu Met Leu Gly Glu Leu
                165                 170                 175

Ile Asp Arg Arg Leu Ala His Arg Leu Ser Leu Tyr Ile Phe Tyr Trp
            180                 185                 190

Gly Ala Arg Lys Ala Pro Thr Asn Leu Asp Arg Ser Leu Met Arg Glu
        195                 200                 205

Pro Leu Arg Val Ala Val Ile Thr Asn Pro Arg Lys Asn Ile Phe Arg
210                 215                 220
```

-continued

```
Ile Phe Tyr Asn Gln Ala Lys Pro Asn Asn Arg Gly Glu Leu Leu Ser
225                 230                 235                 240

Ala Asn Trp Phe Asp Gly Asn Asp Met Thr Phe Gln Lys Val Pro Leu
            245                 250                 255

Leu Pro Thr Pro Thr Thr Val Tyr Lys Asn Phe Glu Gly Arg Val Phe
        260                 265                 270

Thr Ile Pro Val Ile His Lys Pro Pro Trp His Phe Val Thr Tyr Arg
    275                 280                 285

Lys Val Asn Glu Ser Ser Leu Asn Glu Thr Asp Val Asp Gln Leu Glu
290                 295                 300

Leu Ser Ala Asn Gly Thr Asp Asn Glu Gln Leu Glu Val Phe Glu Val
305                 310                 315                 320

Thr Gly Gly Arg Asp His Asn Leu Ile Gln Leu Ile Ala His Arg Met
            325                 330                 335

Asn Phe Ser Phe Lys Tyr Val Asp Gln Glu Asp Arg Ile Gln Gly Thr
        340                 345                 350

Ala Val Gly Pro Pro Glu Asn Ala Ile Phe Thr Gly Ala Leu Gly Met
    355                 360                 365

Leu Gln Arg Arg Glu Val Asp Leu Phe Leu Gly Asp Val Ala Val Thr
370                 375                 380

Trp Glu Arg Met Gln Ala Val Glu Phe Ser Phe Phe Thr Leu Ala Asp
385                 390                 395                 400

Ser Ala Ala Phe Val Thr His Ala Pro Arg Lys Leu Ser Glu Ala Leu
            405                 410                 415

Ala Leu Val Arg Pro Phe Gln Val Ala Val Trp Pro Leu Val Leu Leu
        420                 425                 430

Thr Ile Met Met Ser Gly Pro Ile Leu Tyr Met Ile Ile Ala Met Pro
    435                 440                 445

Tyr Arg Leu Glu Asp Trp Ala Arg Gly Thr Met Ala Arg Arg Arg Arg
450                 455                 460

Phe Lys Val Gln Arg Gly Pro Ala Phe Tyr His Met Gln Tyr Ile Gln
465                 470                 475                 480

Glu Met Asn Tyr Gly Thr Leu Pro Gly Gly Thr Glu Ile Ala Gly Thr
            485                 490                 495

Pro Arg His Pro Ser Leu Asp Arg Cys Ile Trp Tyr Thr Ile Asn Val
        500                 505                 510

Tyr Leu Arg Gln Ser Ala Thr Ile Pro Tyr Asn Gly His Val Ser Arg
    515                 520                 525

Phe Phe Ser Ile Leu Leu Trp Leu Cys Ala Thr Tyr Val Leu Gly Asp
530                 535                 540

Val Tyr Ser Ala Gln Leu Thr Ser Gln Leu Ala Arg Pro Ala Arg Glu
545                 550                 555                 560

Gly Pro Ile Asp Thr Leu Gly Lys Leu Glu Val Phe Met Glu Arg Asp
            565                 570                 575

Gly Tyr Gln Leu Leu Val Glu Arg Gln Ser Ala Phe Gln Ala Ala Leu
        580                 585                 590

Val Asn Ser Thr Gly Ile Leu Gln Arg Leu Tyr Arg Ile Thr Gln Arg
    595                 600                 605

Gln Ser His Asn Glu Ser Tyr Leu Val Ser Val Glu Glu Gly Ile
610                 615                 620

Arg Ile Leu Val Asp Asn Ser Lys Arg Ala Val Phe Gly Gly Arg Glu
625                 630                 635                 640
```

```
Thr Leu Tyr Phe Asn Thr Lys Arg Tyr Gly Ala His Arg Phe Gln Leu
                645                 650                 655

Ser Glu Lys Leu Tyr Thr Arg Tyr Ser Ala Val Ala Val Gln Phe Gly
            660                 665                 670

Ser Pro Phe Leu Asp Ser Leu Asn Glu Val Ile Met Arg Leu Phe Glu
        675                 680                 685

Ala Gly Ile Ile Glu Lys Ile Thr Ile Ala Glu Tyr Glu Arg Met Phe
    690                 695                 700

Gly Ser Gln Leu Gly Gln Phe Gly Asp Glu Ser Ala Lys Thr Thr Lys
705                 710                 715                 720

Pro Glu Ser Ser Glu Thr Glu Gly Gly Lys Ser Lys Ser Thr Glu
                725                 730                 735

Ser Asn Glu Lys Leu Gln Pro Met Asn Leu Arg Met Leu Gln Gly Ala
            740                 745                 750

Phe Leu Ala Leu Ala Cys Gly His Leu Leu Gly Val Leu Thr Leu Val
        755                 760                 765

Leu Glu Asn Lys Thr Lys Cys Ile Gln Ile Ser Phe Gly Trp Ile Lys
    770                 775                 780

Ala Trp Leu His Arg Ile Gly Leu Ile Phe Cys Lys Leu Gly Lys Ala
785                 790                 795                 800

Val Trp Arg Ser Trp Arg Arg Leu His Asn Asp Asp
                805                 810

<210> SEQ ID NO 3
<211> LENGTH: 779
<212> TYPE: PRT
<213> ORGANISM: Anopheles gambiae

<400> SEQUENCE: 3

Met Gly Val Gly Ser Asn Ser Lys Tyr Ile Leu Ala Leu Val Leu Leu
 1               5                  10                  15

Arg Val Ala Leu Val Trp Gly Ala Phe Pro Thr Gln Arg Asn Leu Ile
            20                  25                  30

Ala Leu Tyr Glu Arg Ser Asn Gln Ser Gly Met Ile Arg Gly Ile Ser
        35                  40                  45

Glu Met Val Asn Leu Leu Ala Pro Lys Ser Leu Val Ile Leu Val Gln
    50                  55                  60

Asn Glu Thr Lys Ile Asp Arg Leu Asp Lys Leu Thr Val Met Ile His
65                  70                  75                  80

His His Asn Ile Pro Thr Cys Val Tyr Tyr Asp Leu Glu Ala Tyr Phe
                85                  90                  95

Ser Leu Ile Glu Glu Asn Leu Lys Lys Ser Leu Glu Ile Thr Ser Leu
            100                 105                 110

Ile Phe Cys His Pro Glu Asp Met Leu Gln Asp Ile Thr Asp Arg Arg
        115                 120                 125

Leu Ala His Arg Leu Ser Leu Phe Ile Phe Tyr Trp Gly Ala Ala Gln
    130                 135                 140

Leu Pro Pro Thr Leu Asn Pro Asn Leu Leu Met Glu Pro Phe Arg Val
145                 150                 155                 160

Ala Ile Ile Thr Asn Pro Arg Arg Asn Ile Phe Arg Ile Phe Tyr Asn
                165                 170                 175

Gln Ala Lys Pro Asn Asn Arg Gly Asp Met Leu Ser Val Asn Trp Phe
            180                 185                 190

Asp Gly Asn Asp Met Thr Phe Lys Arg Val Pro Leu Leu Pro Ser Pro
        195                 200                 205
```

```
Thr Glu Val Tyr Lys Asn Phe Glu Gly Arg Ile Phe Thr Ile Pro Val
    210                 215                 220
Ile His Lys Pro Pro Trp His Phe Ile Val Tyr Gly Asn Gly Ser Ala
225                 230                 235                 240
Ser Val Gly Asp Asn Gln Asn Ser Ser Ser Asp Ala Ala Gly Gly
                245                 250                 255
Phe Glu Leu Glu Leu Asp Glu Asn Val Thr Val Glu Ser Asp Asp Thr
            260                 265                 270
Tyr Phe Thr Val Lys Gly Gly Arg Asp His Asn Leu Met Gln Leu Ile
        275                 280                 285
Ala Glu Arg Met Asn Phe Thr Phe Gln Tyr Val Glu Pro Pro Glu Lys
290                 295                 300
Ile Gln Gly Ile Ala Leu Gly Ser Glu Asp Asn Ala Ser Phe Ser Gly
305                 310                 315                 320
Ala Leu Gly Met Leu Gln Arg Arg Glu Val Glu Leu Tyr Leu Gly Asp
                325                 330                 335
Val Ala Val Thr Trp Glu Arg Met Lys Ala Val Glu Phe Ser Phe Phe
            340                 345                 350
Thr Leu Ala Asp Ser Ala Ala Phe Val Thr His Ala Pro Arg Lys Leu
        355                 360                 365
Asn Glu Ala Leu Ala Leu Val Arg Pro Phe Gln Ile Thr Val Trp Pro
370                 375                 380
Pro Val Ile Ile Thr Ile Leu Ile Ser Gly Pro Ile Leu Tyr Ile Ile
385                 390                 395                 400
Ile Ser Thr Pro Tyr Arg Trp Arg Ser Ala Gln Thr Val His Ala Arg
                405                 410                 415
Asn Ala Arg Trp Arg Pro Thr Arg Ser Arg Leu Arg Lys Pro Ala Phe
            420                 425                 430
Tyr Asn Leu Arg Tyr Ile Glu Glu Met Ser Tyr Thr Arg Phe Arg Ala
        435                 440                 445
Glu Arg Thr Ser Leu Ile Asn Asn His His Ser Arg Gly Gln Asp
450                 455                 460
Tyr Pro Ser Leu Asp Arg Cys Ile Trp Tyr Thr Ile Asn Val Tyr Leu
465                 470                 475                 480
Arg Gln Ser Ala Asn Ile Pro Phe Asp Gly His Leu Ala Arg Phe Phe
                485                 490                 495
Ser Ile Leu Leu Trp Leu Cys Ala Thr Tyr Val Leu Gly Asp Val Tyr
            500                 505                 510
Ser Ala Gln Leu Thr Ser Gln Leu Ala Arg Pro Ala Arg Glu Ser Pro
        515                 520                 525
Ile Asn Thr Leu Gly Arg Leu Glu Asn Arg Met Asn Arg Glu Gly Tyr
530                 535                 540
Gln Leu Leu Val Glu Arg Gln Ser Ala Phe His Ala Ala Leu Val Asn
545                 550                 555                 560
Ser Thr Gly Val Leu Gln Arg Leu Tyr Arg Leu Thr Arg Gln Arg Ser
                565                 570                 575
Val Asn Asp Ser Phe Leu Val Lys Ser Val Glu Glu Gly Ile Arg Val
            580                 585                 590
Leu Gln Ala Asp Pro Lys Tyr Ala Val Phe Gly Gly Arg Glu Thr Leu
        595                 600                 605
Tyr Phe Asn Thr Lys Arg Tyr Gly Ala Asn Arg Phe Gln Leu Ser Glu
610                 615                 620
```

-continued

```
Lys Leu Tyr Thr Arg Tyr Ser Ala Val Ala Val Gln Ile Gly Cys Pro
625                 630                 635                 640

Phe Leu Asp Ser Leu Asn Glu Val Ile Met Arg Leu Phe Glu Ala Gly
            645                 650                 655

Ile Val Glu Lys Ile Thr Ile Ala Glu Tyr Glu Gln Met Phe Gly Arg
        660                 665                 670

Gln Lys Gly Gly Val Ser His Ala Glu Glu Thr Val Arg Thr Val Lys
    675                 680                 685

Ser Thr Asn Ser Glu Cys Asp Thr Asp Gly Thr Gly Ser Gly Lys Arg
690                 695                 700

Lys Thr Asp Ser Asn Asp Lys Leu Gln Pro Met Asn Leu Arg Met Leu
705                 710                 715                 720

Gln Gly Ala Phe Leu Val Leu Ala Cys Gly His Leu Leu Gly Gly Ile
            725                 730                 735

Cys Leu Phe Ile Glu Arg His Met Gly Met Ile Asn Pro Cys Gly Asp
        740                 745                 750

Thr Leu Arg Gln Gly Trp Arg His Leu Asn Arg Val Val Arg Lys Leu
    755                 760                 765

Gly Arg Gly Gly Ser Phe Lys Thr Gln Ser Asn
770                 775

<210> SEQ ID NO 4
<211> LENGTH: 740
<212> TYPE: PRT
<213> ORGANISM: Culex quinquefasciatus

<400> SEQUENCE: 4

Met Lys Val Gly Ile Val Trp Cys Leu Phe Val Leu Leu Gly Arg Ser
1               5                   10                  15

Phe Val Gln Ala Tyr His Ser Gln Leu Val Pro Ile Ala Asp Pro Ser
            20                  25                  30

Asn His Ser Gly Met Val Thr Gly Leu Ser Glu Met Ile Asn Leu Leu
        35                  40                  45

Ser Pro Lys Thr Leu Val Leu Val Leu Asn Glu Thr Lys Ile His
50                  55                  60

Lys Ile Asp Arg Leu Thr Val Ala Ile His Ser Tyr Asn Ile Pro Thr
65                  70                  75                  80

Cys Ile Phe Tyr Asp Leu Glu Gln Tyr Phe Glu Tyr Ile Ala Asn Asn
                85                  90                  95

Leu Lys Asn Ser Leu Asp Thr Thr Ser Leu Leu Leu Cys His Pro Ala
            100                 105                 110

Asp Met Leu Val Asp Leu Val Asp Arg Arg Leu Ala His Arg Leu Ser
        115                 120                 125

Leu Tyr Ile Phe Tyr Trp Gly Ala Arg Arg Leu Pro Ala Gly Phe Asp
    130                 135                 140

Arg Ala Leu Leu Arg Glu Pro Leu Arg Val Ala Val Ile Thr Asn Pro
145                 150                 155                 160

Lys Lys Lys Ile Phe Arg Ile Phe Tyr Asn Gln Ala Lys Pro Asn Asn
                165                 170                 175

Leu Gly Glu Leu Leu Ser Ala Asn Trp Phe Asp Gly Ser Asp Met Thr
            180                 185                 190

Phe Lys Arg Val Pro Leu Leu Pro Thr Pro Thr Glu Val Tyr Lys Asn
        195                 200                 205

Phe Glu Gly Arg Val Phe Thr Ile Pro Val Ile His Lys Pro Pro Trp
    210                 215                 220
```

```
His Phe Leu Thr Tyr Thr Asn Leu Asn Glu Ser Cys Asn Asp Thr Asp
225                 230                 235                 240

Thr Glu Phe Asp Met Ala Asn Val Thr Ser Phe Gln Val Thr Gly Gly
                245                 250                 255

Arg Asp His Asn Leu Met Gln Leu Ile Ala Ala Arg Met Asn Phe Thr
            260                 265                 270

Phe Arg Tyr Ile Glu Pro Glu Lys Ile Gln Gly Thr Ala Met Gly
        275                 280                 285

Ser Gly Asp Asn Val Ser Ile Ser Gly Ala Leu Gly Met Leu Gln Arg
    290                 295                 300

Arg Glu Val Asp Leu Phe Leu Gly Asp Val Ala Val Thr Trp Glu Arg
305                 310                 315                 320

Met Gln Ala Val Glu Phe Ser Phe Phe Thr Leu Ala Asp Ser Ala Ala
                325                 330                 335

Phe Val Thr His Ala Pro Arg Lys Leu Ser Glu Ala Leu Ala Leu Val
            340                 345                 350

Arg Pro Phe Gln Val Thr Val Trp Pro Leu Val Ile Phe Thr Ile Ile
        355                 360                 365

Leu Ser Gly Pro Val Leu Tyr Leu Ile Ile Ala Met Pro Phe Arg Leu
370                 375                 380

Glu Asp Trp Met Lys Gly Thr Leu Asp Lys Ala Arg Arg Leu Gln Val
385                 390                 395                 400

Arg Arg Gly Pro Pro Phe Tyr Asp Met Gln Tyr Ile Arg Glu Met Gly
                405                 410                 415

Tyr Gly Leu Val Pro Arg Ala Asp Ile Ala Gly Thr Pro Gln His Pro
            420                 425                 430

Ser Leu Asn Arg Cys Val Trp Tyr Thr Ile Asn Val Tyr Leu Arg Gln
        435                 440                 445

Ser Ala Thr Ile Pro Tyr Asn Gly His Val Ala Arg Phe Phe Ser Ile
450                 455                 460

Leu Leu Trp Leu Cys Ala Thr Tyr Val Leu Gly Asp Val Tyr Ser Ala
465                 470                 475                 480

Gln Leu Thr Ser Gln Leu Ala Arg Pro Ala Arg Glu Gly Pro Ile Asn
                485                 490                 495

Thr Leu Gly Lys Leu Glu Glu Leu Met Glu Ser Pro Gly Gly Gly Tyr
            500                 505                 510

Gln Leu Leu Val Glu Arg Gln Ser Ala Phe Gln Val Ala Leu Ala Asn
        515                 520                 525

Ser Thr Gly Ile Leu Gln Arg Leu Tyr Arg Ile Thr Gln Arg His Pro
530                 535                 540

Asp Asn Glu Ser Tyr Leu Val Gly Ser Val Glu Glu Gly Ile Gln Ile
545                 550                 555                 560

Leu Leu Val Asn Ser Lys Arg Ala Val Phe Gly Gly Arg Glu Thr Leu
                565                 570                 575

Tyr Phe Asn Thr Lys Arg Tyr Gly Ala His Arg Phe Gln Leu Ser Asp
            580                 585                 590

Asn Leu Tyr Thr Arg Tyr Ser Ala Val Ala Val Gln Phe Gly Ser Pro
        595                 600                 605

Phe Leu Asp Ser Leu Asn Glu Val Ile Met Arg Leu Phe Glu Ala Gly
610                 615                 620

Ile Ile Gly Lys Ile Thr Val Ala Glu Tyr Glu Arg Met Phe Gly Ser
625                 630                 635                 640
```

```
Lys Ser Gly Gly Gln Phe Ala Asp Glu Thr Val Glu Ser Thr Lys Ser
                645                 650                 655

Asp Asp Gly Val Asp Ala Thr Gly Lys Ala Lys Lys Ser Ala Glu Ser
            660                 665                 670

Ser Glu Lys Leu Gln Pro Met Asn Leu Arg Met Leu Gln Gly Ala Phe
        675                 680                 685

Leu Ala Leu Gly Phe Gly His Ser Val Gly Ala Ile Ile Leu Leu Val
690                 695                 700

Glu Asn Gln Leu Lys Gly Ile Lys Ser Val Tyr Gln Arg Val Leu Gly
705                 710                 715                 720

Val Leu Thr Arg Thr Gly Arg Val Val Arg Lys Ile Trp Thr Ala Ile
                725                 730                 735

Arg Arg Ser Leu
            740

<210> SEQ ID NO 5
<211> LENGTH: 663
<212> TYPE: PRT
<213> ORGANISM: Acyrthosiphon pisum
<220> FEATURE:
<221> NAME/KEY: VARIANT
<222> LOCATION: 42
<223> OTHER INFORMATION: Xaa = Any Amino Acid

<400> SEQUENCE: 5

Ile Tyr Ile Phe Phe Leu Ile Arg Ser Thr Ile Tyr Tyr Val Ser Phe
1               5                   10                  15

Ser Gly Arg Asp Ile Phe Lys Asn Thr Val Ala Ser Ala Ile Cys Asn
            20                  25                  30

Glu Tyr Ser Ile Val Val Leu Thr Asn Xaa Asn Ala Asn Ile Ile Met
        35                  40                  45

Leu Ile Leu Ile Asn Ile Ile Phe Ile Ser Leu Tyr Leu Ser Ser Ser
50                  55                  60

Ile Ile Leu Ile Asp Tyr Asn Thr Tyr Leu Ile Ile Gln Asn Leu Leu
65                  70                  75                  80

Val Asn Val Thr Ile Tyr Ile Asn Ile Tyr Arg Leu Leu Gly Leu His
                85                  90                  95

Arg Asp Gly Asp Phe Leu Phe Phe Thr Gln Ile Arg Arg Ser Asn Leu
            100                 105                 110

Met Ser Arg Asn Val Val Tyr Val Phe Leu Trp Leu Arg Ser Ser Val
        115                 120                 125

Ser Arg Thr Phe Lys Ala Asp Ile Leu Glu Ala Met Arg Val Cys Val
130                 135                 140

Ile Thr Ser Pro Arg Pro Gly Phe Tyr Gln Ile Tyr Tyr Ser Gln Ala
145                 150                 155                 160

Ser Ala Arg Pro Gly Tyr Gly Ser Ser Leu Lys Met Val Asn Trp Trp
                165                 170                 175

Ser Ala Met Asp Gly Leu Val Arg Phe Pro Leu Leu Pro Pro Pro Lys
            180                 185                 190

Gln Val Tyr Lys Asn Phe Glu Gly Arg Tyr Phe Asn Val Pro Val Leu
        195                 200                 205

His Lys Pro Pro Trp Thr Phe Val Glu Tyr Leu Asn Asp Ser Phe Arg
210                 215                 220

Val Glu Gly Gly Arg Asp Asp Lys Leu Ile Asn Leu Leu Ala Asp Lys
225                 230                 235                 240

Leu His Phe Gln Phe Lys Tyr Ile Asp Pro Pro Asp Arg Thr Gln Gly
```

```
                    245                 250                 255
Ser Gly Leu Asp Arg Gly Ser Ser Met Gln Gly Val Leu Gly Leu Ile
                260                 265                 270
Trp Gln Arg Glu Ala Asp Trp Phe Val Gly Asp Leu Ser Ile Thr Tyr
                275                 280                 285
Glu Arg Asn Leu Val Val Asp Phe Ser Phe Leu Thr Leu Val Asp Asn
            290                 295                 300
Glu Ala Phe Leu Thr His Ala Pro Gly Arg Leu Asn Glu Ala Phe Ser
305                 310                 315                 320
Leu Ile Arg Pro Phe His Trp Ser Val Trp Pro Leu Leu Ile Thr
                325                 330                 335
Val Ile Phe Ala Gly Pro Ile Leu Tyr Ile Leu Val Asp Thr Thr Asp
                340                 345                 350
Gly His Pro Gln Gly Lys Ser Met Leu Tyr Trp Lys Cys Val Trp Trp
                355                 360                 365
Ser Val Thr Val Phe Leu Gln Gln Ala Ala Ile Ile Pro Ser Glu Asn
            370                 375                 380
Asn Lys Ile Arg Phe Val Ala Gly Leu Leu Met Leu Ser Val Thr Tyr
385                 390                 395                 400
Val Ile Gly Asp Met Tyr Ser Ala Ser Leu Thr Ser Ile Leu Ala Arg
                405                 410                 415
Pro Pro Lys Glu Pro Pro Ile Asn Thr Leu Lys Glu Leu Ser Glu Ala
                420                 425                 430
Met Arg Asp Ser Gly Leu Gln Leu Leu Val Glu Val Gln Ser Ala Ser
                435                 440                 445
Gln Ala Met Leu Glu Asn Gly Thr Gly Val Tyr Glu Glu Leu Ser Gln
            450                 455                 460
Leu Val Thr Arg Gln Arg Glu Tyr Leu Ile Gly Ser Thr Glu Lys Gly
465                 470                 475                 480
Met Gln Leu Val Arg Asp Asn Lys Asn Tyr Ala Val Ile Gly Gly Arg
                485                 490                 495
Glu Thr Phe Tyr Tyr Asp Ile Lys Arg Phe Gly Ala Gln His Phe His
                500                 505                 510
Leu Ser Glu Lys Leu Asn Thr Arg Tyr Ser Ala Ile Ala Phe Gln Arg
            515                 520                 525
Ala Cys Pro Tyr Arg Asp Asn Phe Asp Asp Val Leu Met Arg Leu Phe
                530                 535                 540
Glu Gly Gly Ile Leu Ser Lys Ile Thr Glu Glu Tyr Gln Lys Leu
545                 550                 555                 560
Asn Asp Lys Leu Met Gly Ser Glu Glu Phe Asp Ser Thr Ser Val Val
                565                 570                 575
Ile Glu Pro Val Leu Glu Gly Ser Glu Pro Arg Gln Glu Asp Asp Asp
                580                 585                 590
Lys Gln Leu Thr Ile Ala Met Ser Met Lys Thr Leu Gln Gly Ala Phe
            595                 600                 605
Tyr Val Leu Ala Ile Gly Ser Ile Leu Ala Gly Leu Leu Leu Ile
                610                 615                 620
Glu Met Arg Ser His Asp Lys Leu Glu Lys Asp Lys Val Ile Lys Leu
625                 630                 635                 640
Val Glu Ala Pro Phe Val Tyr Lys Arg Lys Val Pro Asn Lys Phe Gln
                645                 650                 655
Asn Arg Leu Tyr Asp Leu Lys
                660
```

<210> SEQ ID NO 6
<211> LENGTH: 677
<212> TYPE: PRT
<213> ORGANISM: Bombyx mori

<400> SEQUENCE: 6

```
Met Thr Lys Leu Pro Lys Asp Phe Asn Val Ala Ile Lys Asp Ile Ala
 1               5                  10                  15

Glu Ser Leu Pro Ser Lys Glu Met Thr Val Val Arg Gly Asn Ser Thr
            20                  25                  30

Asn Ile Arg Ser Gln Asp Val Phe Glu Leu Leu Arg Leu Leu Cys Gln
        35                  40                  45

His Asn Ile Gln Val Val Asn Leu Asp Ile Ala Ala Met Glu Asn Lys
    50                  55                  60

Glu Met Tyr Tyr Gly Tyr Leu Lys Lys Ala Leu Asp Val Ser Asp Glu
65                  70                  75                  80

Arg Thr Asn Leu Ile Leu Cys Glu Pro Tyr Glu Cys Glu Asn Leu Leu
                85                  90                  95

Leu Glu Leu Arg Glu Asn Asn Leu Ile His Arg Thr Ile Leu Tyr Ile
            100                 105                 110

Phe Phe Trp Pro Tyr Gly Ser Val Ser Asp Arg Phe Leu Asn Thr Met
        115                 120                 125

Val Glu Ala Met Arg Val Ala Val Ile Thr Asn Pro Arg Glu Ser Val
    130                 135                 140

Phe Arg Ile Tyr Tyr Asn Gln Ala Thr Pro Asn Arg Leu Asn His Leu
145                 150                 155                 160

Ser Leu Val Asn Trp Trp Ala Phe Arg Leu Tyr Lys Ser Pro Leu Leu
                165                 170                 175

Pro Ser Ala Asp Lys Val Tyr Lys Asn Phe Arg Gly Arg Val Phe Asp
            180                 185                 190

Val Pro Val Leu His Ala Pro Pro Trp His Phe Val Lys Tyr Asn Asn
        195                 200                 205

Asp Ser Ser Ile Asn Val Thr Gly Gly Arg Asp Asp Lys Leu Leu Lys
    210                 215                 220

Leu Ile Ala Asn Lys Leu Asn Phe Arg Tyr Arg Tyr Tyr Asp Pro Pro
225                 230                 235                 240

Asp Arg Ser Gln Gly Ser Gly Ile Ile Gly Asn Gly Thr Phe Lys Gly
                245                 250                 255

Thr Leu Gly Leu Ile Trp Lys Arg Gln Ala Asp Phe Phe Leu Gly Asp
            260                 265                 270

Val Thr Met Thr Trp Glu Arg Leu Gln Ala Val Glu Phe Ser Phe Leu
        275                 280                 285

Thr Leu Ala Asp Ser Gly Ala Phe Leu Thr His Ala Pro Ala Lys Leu
    290                 295                 300

Ser Glu Thr Leu Ala Ile Ile Arg Pro Phe Arg Trp Glu Val Trp Pro
305                 310                 315                 320

Leu Val Cys Ala Thr Leu Phe Ile Thr Gly Pro Ala Leu Trp Ile Val
                325                 330                 335

Ile Ala Ala Pro Ser Leu Trp Gln Arg Lys Arg Asp Gln Met Gly
            340                 345                 350

Leu Leu Asn Asn Cys Cys Trp Phe Thr Val Thr Leu Phe Leu Arg Gln
        355                 360                 365

Ser Ser Thr Lys Glu Pro Ser Ser Thr His Lys Ala Arg Leu Val Thr
```

```
            370                 375                 380
Val Leu Ile Ser Leu Gly Ala Thr Tyr Val Ile Gly Asp Met Tyr Ser
385                 390                 395                 400

Ala Asn Leu Thr Ser Leu Leu Ala Arg Pro Ala Lys Glu Pro Pro Ile
                405                 410                 415

Gly Thr Leu Pro Ala Leu Glu Glu Ala Met Arg Glu His Gly Tyr Glu
                420                 425                 430

Leu Val Val Glu Ser His Ser Ser Leu Ser Ile Leu Glu Asn Gly
                435                 440                 445

Thr Gly Val Tyr Gly Arg Leu Ala Lys Leu Met Lys Arg Gln Arg Val
        450                 455                 460

Gln Arg Val His Asn Val Glu Ala Gly Val Arg Leu Val Leu Asn Arg
465                 470                 475                 480

Arg Arg Val Ala Val Leu Gly Gly Arg Glu Thr Leu Tyr Tyr Asp Thr
                485                 490                 495

Glu Arg Phe Gly Ser His Asn Phe His Leu Ser Glu Lys Leu Tyr Thr
                500                 505                 510

Arg Tyr Ser Ala Ile Ala Phe Gln Ile Gly Ser Pro Tyr Leu Glu Thr
        515                 520                 525

Ile Asn Asn Val Val Met Thr Leu Phe Glu Ala Gly Ile Leu Gly Lys
530                 535                 540

Met Thr Thr Asp Glu Tyr Lys Asn Leu Pro Glu Gln Ser Arg Arg Ser
545                 550                 555                 560

Glu Pro Val Thr Glu Ser Glu Asn Leu Ser Thr Glu Lys Thr Gly Glu
                565                 570                 575

Thr Ala Ala Val Thr Gln Ile Gln Asn Glu Thr Ser Lys Gly Leu Glu
                580                 585                 590

Pro Val Ser Leu Thr Met Leu Arg Gly Ala Phe Cys Leu Leu Gly Ile
        595                 600                 605

Gly His Leu Leu Ala Gly Val Thr Leu Leu Ile Glu Ile Gln Leu Tyr
610                 615                 620

Arg Arg Ala Arg Lys Arg Ala Leu Pro Pro Gln Thr Arg Asn Pro Thr
625                 630                 635                 640

Asn Thr Phe Lys Ala Lys Ala Lys Lys Cys Ile Leu Arg Gly Trp Arg
                645                 650                 655

Arg Ile Lys Ala Ala Ala Ile Leu Ala Ile Asp Arg Ala Leu Ala Pro
        660                 665                 670

Asp Arg Gly Ile Asp
        675

<210> SEQ ID NO 7
<211> LENGTH: 680
<212> TYPE: PRT
<213> ORGANISM: Tribolium castenium

<400> SEQUENCE: 7

Met Arg Arg Asp His Gly Gly Asp Leu Val Ser Ala Ser Phe Asp Ile
1               5                   10                  15

Val Ala Gly Phe Leu Phe Glu Glu Ile Cys Ile Cys Phe Asp Lys Asn
                20                  25                  30

Thr Asn Ile Asn Phe Leu Gln His Leu Leu Val Arg Phe Val Ser Asn
        35                  40                  45

Asn Ile Ala Ile Lys Leu Phe Asn Ile Thr Thr Val Glu Val Gln Asp
50                  55                  60
```

-continued

```
Lys Tyr Phe Ala Phe Leu Asn Tyr Gln Val Thr Asn His Leu Gly Ala
 65                  70                  75                  80

Asn Thr Ile Phe Phe Ser Ser His Lys Phe Tyr Glu His Val Leu Leu
                 85                  90                  95

Glu Ile Asn Glu Arg Asp Phe Ile Arg Arg Asn Leu Ile Tyr Ile Phe
            100                 105                 110

Asn Trp Gly Arg Arg Pro Phe Ser Arg Tyr Phe Val Arg Asn Ile Ile
        115                 120                 125

Asn Val Met Lys Val Phe Val Ile Thr Asn Pro Arg Asn Asp Thr Phe
    130                 135                 140

Arg Ile Phe Tyr Asn Gln Ala Val Pro Tyr Lys Lys His His Leu Glu
145                 150                 155                 160

Met Val Asn Trp Trp Gln His Gly Val Gly Leu Phe Asn His Pro Thr
                165                 170                 175

Leu Pro Ala Lys Tyr Asn Asn Val Phe Lys Asp Phe Lys Glu Asn Val
            180                 185                 190

Phe Lys Ile Pro Val Ile His Lys Pro Pro Trp His Phe Val Gln Tyr
        195                 200                 205

Gly Asn Asp Ser Ile Lys Val Thr Gly Gly Arg Asp Asp Arg Ile Leu
    210                 215                 220

Ser Leu Leu Ser Lys Lys Leu Asn Phe Arg Tyr Asp Tyr Phe Asp Pro
225                 230                 235                 240

Pro Glu Arg Ile Gln Gly Ser Ser Ala Ser Glu Asn Gly Thr Phe Lys
                245                 250                 255

Gly Val Leu Gly Leu Ile Trp Lys Arg Gln Ala Glu Phe Phe Ile Gly
            260                 265                 270

Asp Val Ala Leu Ser His Glu Arg Ala Asn Tyr Val Glu Phe Ser Phe
        275                 280                 285

Ile Thr Leu Ala Asp Ser Gly Ala Phe Ile Thr His Ala Pro Ser Lys
    290                 295                 300

Leu Asn Glu Ala Leu Ala Leu Leu Arg Pro Phe Gln Trp Gln Val Trp
305                 310                 315                 320

Pro Ala Ile Gly Val Thr Phe Val Val Val Gly Pro Val Leu Tyr Ala
                325                 330                 335

Ile Ile Ala Leu Pro Asn Ala Trp Arg Pro Arg Phe Arg Val Arg Ser
            340                 345                 350

His Ala Arg Leu Phe Phe Asp Cys Thr Trp Phe Thr Thr Val Leu
        355                 360                 365

Leu Lys Gln Thr Gly Lys Glu Pro Ser Ser His Lys Ala Arg Phe
370                 375                 380

Phe Ile Ile Ile Leu Ser Ile Ser Ser Thr Tyr Val Ile Asn Asp Met
385                 390                 395                 400

Tyr Ser Ala Asn Leu Thr Ser Leu Leu Ala Lys Pro Gly Arg Glu Lys
            405                 410                 415

Ala Ile Asn Asn Leu Asn Gln Leu Glu Lys Ala Met Ala Thr Arg Gly
        420                 425                 430

Tyr Asp Leu Tyr Val Glu Arg His Ser Ser Ser Tyr Ser Leu Phe Glu
    435                 440                 445

Asn Gly Thr Gly Ile Tyr Ser Arg Leu Trp Gln Met Met Asn Arg Arg
                450                 455                 460

Gln Thr His Phe Leu Leu Glu Ser Val Glu Glu Gly Val Gln Leu Val
465                 470                 475                 480

Arg Asp Ser Thr Asn Lys Ala Val Ile Ala Gly Arg Glu Thr Leu Phe
```

```
                    485                 490                 495
Phe Asp Ile Gln Arg Phe Gly Ala Ser Asn Phe His Leu Ser Glu Lys
                500                 505                 510

Leu Asn Thr Ala Tyr Ser Ala Ile Ala Leu Gln Leu Gly Cys Pro Tyr
            515                 520                 525

Ile Glu Glu Ile Asn Lys Ile Leu Met Ala Ile Phe Glu Ala Gly Ile
        530                 535                 540

Ile Thr Lys Met Thr Glu Asn Glu Tyr Glu Gln Leu Gly Lys Lys Lys
545                 550                 555                 560

Gln Thr Thr Ser Glu Thr Glu Lys Glu Leu Ile Pro Gly Val Lys Lys
                565                 570                 575

Glu Asn Arg Arg Val Ala Lys Val Ser Glu Asp Asn Glu Lys Leu Gln
            580                 585                 590

Pro Ile Ser Ile Lys Met Leu Gln Gly Thr Phe Tyr Leu Leu Cys Ile
        595                 600                 605

Gly Asn Ile Phe Ser Gly Phe Ile Leu Leu Ala Glu Ile Leu Val Tyr
        610                 615                 620

Lys His Arg Lys Thr Tyr Lys His Lys Lys Arg Arg His Arg Phe Val
625                 630                 635                 640

Tyr Leu Arg Lys Ile Arg His Ser Val Ala Ser Lys Phe Gly Ala Val
                645                 650                 655

Val Asp Ala Val Arg Arg Val Tyr Arg Arg Ala Met His Asp Ala Phe
            660                 665                 670

Val Ala Thr Leu Glu Tyr Leu Glu
        675                 680

<210> SEQ ID NO 8
<211> LENGTH: 610
<212> TYPE: PRT
<213> ORGANISM: Pediculus humanus

<400> SEQUENCE: 8

Thr Pro Thr Phe Cys Phe Ser Tyr Met Lys Ile Phe Phe Phe Leu Phe
1               5                   10                  15

Asn Phe Gly Gly Ile Ile Arg Gly His His Leu Thr Glu Asn Asp
            20                  25                  30

Phe Asp Asp Asp Glu Asp Met Met Met Ser Leu Ser Leu Ala Val Lys
        35                  40                  45

Asp Ile Ile Ile Gly Leu Pro Ser Ser His Val Thr Leu Leu Phe Glu
    50                  55                  60

Asn Ile Thr Asp Ser Thr Phe Pro Met Ile Leu Ser Lys Thr Leu Gln
65                  70                  75                  80

Lys Ser Leu Ile Thr Thr Ser Ile Tyr Thr Ile Glu Lys Gly Glu Asn
                85                  90                  95

Gln Lys Glu Val Glu Gln Glu Asp Leu Met His Arg Lys Ile Leu Tyr
            100                 105                 110

Ile Leu Tyr Arg Asp His Asn Leu Arg Asp Asn Asp Phe Phe Ser Gly
        115                 120                 125

Gln Phe Glu Ala Met Arg Ile Ser Leu Leu Thr Lys Thr Gln Asn Gly
    130                 135                 140

Met Phe Val Arg Tyr Lys Phe Phe Leu Lys Ile Phe Phe Phe Phe
145                 150                 155                 160

Phe Leu Glu Asn Leu Ile Tyr Asn Arg Ser Thr Arg Phe Phe Ser Asp
                165                 170                 175
```

```
Asp Lys Leu Leu Thr Ile Ile Ala Gln Lys Leu Asn Phe Arg Tyr Lys
            180                 185                 190

Tyr Val Asp Pro Pro Glu Arg Leu Gln Gly Thr Gly Ile Phe Thr Asn
        195                 200                 205

Gly Thr Phe Ser Gly Val Leu Gly Gln Val Trp Gln Arg Glu Phe Asp
    210                 215                 220

Phe Phe Met Gly Asp Val Thr Ile Thr Tyr Asp Arg Ala Lys Thr Val
225                 230                 235                 240

Glu Phe Thr Phe Thr Leu Val Asp Ser Glu Ala Phe Val Thr His
                245                 250                 255

Arg Pro Ser Lys Leu Asn Glu Ala Phe Ala Leu Ile Arg Pro Phe Gln
            260                 265                 270

Trp Gln Val Trp Pro Pro Ile Leu Cys Thr Phe Thr Ile Tyr Gly Pro
        275                 280                 285

Ile Leu Phe Phe Ile Ile Glu Ser Gln Asn Tyr Leu Met Lys Ile Lys
    290                 295                 300

Arg Asp Ser Lys Glu Arg Lys Lys Leu Phe Phe His Cys Val Trp Phe
305                 310                 315                 320

Ser Ile Ser Thr Phe Leu Lys Gln Gly Gly Ile Tyr Pro Ser Lys Ser
                325                 330                 335

His Lys Val Arg Leu Leu Leu Ile Ile Val Thr Leu Ala Ala Thr Tyr
            340                 345                 350

Val Ile Gly Asp Met Tyr Ser Ala Asn Leu Thr Ser Leu Leu Ala Arg
        355                 360                 365

Pro Gly Arg Glu Lys Pro Ile Thr Val Leu Glu Gln Leu Asp Thr Ala
    370                 375                 380

Met Glu Thr Arg Gly Tyr Gln Leu Leu Val Glu Lys His Ser Ser Ser
385                 390                 395                 400

Leu Thr Thr Leu Gln Asn Gly Thr Gly Ile Tyr Glu Lys Ile Trp Glu
                405                 410                 415

Lys Met Lys Asn Gln Lys Asn Tyr Leu Ile Glu Ser Val Glu Ser Gly
            420                 425                 430

Met Lys Met Val Arg Lys Asn Lys Asn Ile Val Ile Leu Gly Gly Arg
        435                 440                 445

Glu Thr Leu Tyr Phe Asp Ser Arg Arg Phe Gly Ser Tyr Asn Phe Gln
    450                 455                 460

Met Ser Glu Lys Leu Asn Thr Arg Tyr Ala Gly Ile Ala Met Gln Leu
465                 470                 475                 480

Gly Cys Pro Tyr Ile Glu Asn Phe Asn Lys Ile Leu Met Gln Leu Phe
                485                 490                 495

Glu Gly Gly Ile Leu Thr Lys Met Thr Val Glu Glu Tyr Glu Arg Leu
            500                 505                 510

Gly Glu Glu Gln Arg Ala Glu Phe Glu Asn Val Lys Lys Lys Asn
        515                 520                 525

Val Ser Gln Ile Lys Asn Glu Asp Ile Gln Val Ser Thr Thr His Ala
    530                 535                 540

Leu Gln Pro Leu Asn Thr Lys Met Leu Gln Gly Ala Phe Tyr Ile Leu
545                 550                 555                 560

Phe Ile Gly Tyr Leu Leu Ser Gly Phe Thr Leu Phe Leu Glu Ile Gln
                565                 570                 575

Phe Glu Asn Ile Cys Arg Phe Leu Lys Leu Ile Lys Cys His Pro Phe
            580                 585                 590

Ile Lys Ser Ile Lys Phe Asn Lys Phe Phe Asn Lys Ile Tyr Arg Lys
```

-continued

```
                595                 600                 605

Lys Phe
    610

<210> SEQ ID NO 9
<211> LENGTH: 730
<212> TYPE: PRT
<213> ORGANISM: Phlebotomus papatasi

<400> SEQUENCE: 9

Met Cys Tyr Leu Ser Glu Asn Ser Asp Gln Glu Asn Glu Leu Met Ile
  1               5                  10                  15

Gly Leu Val Glu Ile Val Lys Ser Leu Asp Ile Lys Asn Leu Val Ile
             20                  25                  30

Phe Leu Pro Thr Glu Asn Ser Thr Tyr Asp Ile Asp Lys Phe Ile Met
         35                  40                  45

Arg Val His Glu Arg Gln Leu Gln Ser Val Ile Phe Phe Asn Pro Asp
     50                  55                  60

Asp Tyr Tyr Asn His Ile Ala Gln Cys Lys Ser Asp Ser Val Glu Thr
 65                  70                  75                  80

Thr Ser Leu Ile Phe Ser Glu Pro Arg Glu Ile Val Arg Glu Ile Gln
                 85                  90                  95

Glu Arg Ile Leu Asp His Arg Leu Asn Leu Phe Met Phe Tyr Trp Gly
            100                 105                 110

Ser His Gly Leu Pro Lys Arg Gly Gln Leu Cys Leu Lys Glu Pro Met
        115                 120                 125

Lys Val Val Ile Leu Thr Thr Pro Arg Gln Asn Ile Tyr Tyr Asn Gln
130                 135                 140

Ala Thr Pro Asp Gly Asn Gly Thr Leu Thr Leu Val Asn Trp Tyr Asp
145                 150                 155                 160

Gly Asn Ser Leu Gly Leu Phe Lys Val Pro Val Leu Pro Ser Pro Ser
                165                 170                 175

Gln Val Tyr Gln Asn Phe Arg Glu Arg Val Phe Tyr Ile Pro Val Ile
            180                 185                 190

His Ser Pro Pro Trp His Phe Val Ile Tyr Arg Asn Glu Ser Ser Asp
        195                 200                 205

Asn Glu Thr Phe Pro Met Glu Glu Tyr Asp Asp Met Asp Ile Ser Phe
    210                 215                 220

Lys Val Ile Gly Gly Arg Asp Asp Ser Leu Leu Gln Leu Leu Ala Lys
225                 230                 235                 240

Lys Met Asn Phe Lys Tyr Glu Tyr Ile Asp Pro Pro Glu Arg Thr Gln
                245                 250                 255

Gly Ser Ala Phe Gly Ser Asn Asp Asn Leu Ser Phe Ser Gly Gly Leu
            260                 265                 270

Gly Leu Leu Gln Arg Arg Glu Ala Asn Leu Leu Leu Gly Asp Ile Ala
        275                 280                 285

Ile Thr Ser Glu Arg Ser Lys Ala Val Glu Phe Ser Phe Phe Thr Leu
    290                 295                 300

Val Asp Ser Gly Ala Phe Val Thr His Ala Pro Arg Arg Leu Ser Glu
305                 310                 315                 320

Ala Leu Ala Leu Val Arg Pro Phe Arg Leu Asn Val Trp Pro Ala Leu
                325                 330                 335

Ile Ile Thr Ser Leu Ser Gly Pro Val Leu Tyr Leu Val Ile Ile Met
            340                 345                 350
```

Pro Gln Trp Trp Arg Lys Ser Gln Lys Glu Lys Glu Asn Arg Asp
           355                 360                 365

Ser Phe His His Ile Asp Tyr Ile Glu Met Asn Tyr Gly Val Pro
    370                 375                 380

Arg Arg Arg Ile Gln Ala Met Lys Phe Thr Lys Arg Lys Glu Leu Pro
385                 390                 395                 400

Gln Asn Leu Leu Gly Arg Gln Phe Leu Val Asp Arg Cys Val Trp Phe
                405                 410                 415

Thr Ile Asn Leu Phe Leu Lys Gln Ser Ala Cys Leu Pro Tyr Gly Gly
            420                 425                 430

Asn Arg Ala Arg Phe Val Ser Ser Ile Leu Trp Leu Ser Ala Thr Tyr
            435                 440                 445

Ile Leu Gly Asp Phe Tyr Ser Ala Gln Leu Thr Ser Gln Leu Ala Arg
            450                 455                 460

Pro Ala Arg Glu Ala Pro Ile Asn Asp Leu Tyr Arg Leu Glu Ala Ala
465                 470                 475                 480

Met Lys Trp Lys Gly Tyr Glu Leu Tyr Val Glu Arg Gln Ser Ala Ser
                485                 490                 495

Leu Ala Ile Leu Glu Asn Gly Thr Glu Ile Phe His Arg Leu His Leu
            500                 505                 510

Met Met Met Ala Gln Asn Arg Lys Ser Asn Glu Ser Tyr Leu Ile Ser
            515                 520                 525

Ser Ile Glu Glu Gly Val His Met Val Met Gly Asp Arg Lys Val
            530                 535                 540

Val Leu Gly Gly Arg Glu Thr Leu Phe Phe Asn Ile Lys Arg Tyr Gly
545                 550                 555                 560

Met Lys Lys Phe Gln Leu Ser Glu Lys Leu Tyr Thr Arg Tyr Ser Ala
                565                 570                 575

Val Ala Val Pro Asn Gly Cys Pro Phe Leu Asp Ser Leu Asn Lys Val
            580                 585                 590

Tyr Val Thr Phe Phe His Lys Ile Met His Leu Phe Glu Gly Gly
            595                 600                 605

Ile Leu Asp Arg Met Thr Asn Glu Glu Tyr Glu Lys Met Phe Asn Ser
610                 615                 620

Ile Lys Phe Lys Thr Pro Lys Glu Val Asp Lys Thr Thr Lys Lys
625                 630                 635                 640

Ser Asn Lys Glu Val Pro Gln Glu Glu His Leu Leu Lys Pro Val Ser
                645                 650                 655

Leu Lys Leu Leu Gln Gly Ala Phe Tyr Thr Leu Leu Ile Gly Tyr Ile
            660                 665                 670

Leu Ser Gly Ile Val Leu Leu Leu Glu Ser Gly Lys Ser Pro Glu Gly
            675                 680                 685

Ile Ala Gln Arg Gln Leu Pro Gly Ala Ile Ser Val Cys Ile Tyr Met
            690                 695                 700

Lys Ile Ile Ile Ala Lys Cys Phe Ser Phe Ile Ala Glu Glu Ile Tyr
705                 710                 715                 720

Asp Cys Phe Lys Asp Asp Glu Asp Glu
                725                 730

<210> SEQ ID NO 10
<211> LENGTH: 838
<212> TYPE: PRT
<213> ORGANISM: Drosophila melenogaster

<400> SEQUENCE: 10

```
Met Asn Pro Gly Glu Met Arg Pro Ser Ala Cys Leu Leu Leu Ala
 1               5                  10                  15

Gly Leu Gln Leu Ser Ile Leu Val Pro Thr Glu Ala Asn Asp Phe Ser
             20                  25                  30

Ser Phe Leu Ser Ala Asn Ala Ser Leu Ala Val Val Asp His Glu
         35                  40                  45

Tyr Met Thr Val His Gly Glu Asn Ile Leu Ala His Phe Glu Lys Ile
     50                  55                  60

Leu Ser Asp Val Ile Arg Glu Asn Leu Arg Asn Gly Gly Ile Asn Val
 65                  70                  75                  80

Lys Tyr Phe Ser Trp Asn Ala Val Arg Leu Lys Lys Asp Phe Leu Ala
             85                  90                  95

Ala Ile Thr Val Thr Asp Cys Glu Asn Thr Trp Asn Phe Tyr Lys Asn
             100                 105                 110

Thr Gln Glu Thr Ser Ile Leu Leu Ile Ala Ile Thr Asp Ser Asp Cys
         115                 120                 125

Pro Arg Leu Pro Leu Asn Arg Ala Leu Met Val Pro Ile Val Glu Asn
     130                 135                 140

Val Glu Glu Asn Ala Leu Leu Val Lys Ser Ile Val His Glu Ser Ile
145                 150                 155                 160

Thr Asn His Ile Thr Pro Ile Ser Leu Ile Leu Tyr Glu Ile Asn Asp
             165                 170                 175

Ser Leu Arg Gly Gln Gln Lys Arg Val Ala Leu Arg Gln Ala Leu Ser
         180                 185                 190

Gln Phe Ala Pro Lys Lys His Glu Glu Met Arg Gln Phe Leu Val
     195                 200                 205

Ile Ser Ala Phe His Glu Asp Ile Ile Glu Ile Ala Glu Thr Leu Asn
     210                 215                 220

Met Phe His Val Gly Asn Gln Trp Met Ile Phe Val Leu Asp Met Val
225                 230                 235                 240

Ala Arg Asp Phe Asp Ala Gly Thr Val Thr Ile Asn Leu Asp Glu Gly
             245                 250                 255

Ala Asn Ile Ala Phe Ala Leu Asn Glu Thr Asp Pro Asn Cys Gln Asp
         260                 265                 270

Ser Leu Asn Cys Thr Ile Ser Glu Ile Ser Leu Ala Leu Val Asn Ala
     275                 280                 285

Ile Ser Lys Ile Thr Val Glu Glu Glu Ser Ile Tyr Gly Glu Ile Ser
     290                 295                 300

Asp Glu Glu Trp Glu Ala Ile Arg Phe Thr Lys Gln Glu Lys Gln Ala
305                 310                 315                 320

Glu Ile Leu Glu Tyr Met Lys Glu Phe Leu Lys Thr Asn Ala Lys Cys
             325                 330                 335

Ser Ser Cys Ala Arg Trp Arg Val Glu Thr Ala Ile Thr Trp Gly Lys
         340                 345                 350

Ser Gln Glu Asn Arg Lys Phe Arg Ser Thr Pro Gln Arg Asp Ala Lys
     355                 360                 365

Asn Arg Asn Phe Glu Phe Ile Asn Ile Gly Tyr Trp Thr Pro Val Leu
     370                 375                 380

Gly Phe Val Cys Gln Glu Leu Ala Phe Pro His Ile Glu His Phe
385                 390                 395                 400

Arg Asn Ile Thr Met Asp Ile Leu Thr Val His Asn Pro Pro Trp Gln
             405                 410                 415
```

-continued

```
Ile Leu Thr Lys Asn Ser Asn Gly Val Ile Val Glu His Lys Gly Ile
            420                 425                 430

Val Met Glu Ile Val Lys Glu Leu Ser Arg Ala Leu Asn Phe Ser Tyr
            435                 440                 445

Tyr Leu His Glu Ala Ser Ala Trp Lys Glu Asp Ser Leu Ser Thr
450                 455                 460

Ser Ala Gly Gly Asn Glu Ser Asp Glu Leu Val Gly Ser Met Thr Phe
465                 470                 475                 480

Arg Ile Pro Tyr Arg Val Val Glu Met Val Gln Gly Asn Gln Phe Phe
            485                 490                 495

Ile Ala Ala Val Ala Ala Thr Val Glu Asp Pro Asp Gln Lys Pro Phe
            500                 505                 510

Asn Tyr Thr Gln Pro Ile Ser Val Gln Lys Tyr Ser Phe Ile Thr Arg
            515                 520                 525

Lys Pro Asp Glu Val Ser Arg Ile Tyr Leu Phe Thr Ala Pro Phe Thr
            530                 535                 540

Val Glu Thr Trp Phe Cys Leu Met Gly Ile Ile Leu Leu Thr Ala Pro
545                 550                 555                 560

Thr Leu Tyr Ala Ile Asn Arg Leu Ala Pro Leu Lys Glu Met Arg Ile
            565                 570                 575

Val Gly Leu Ser Thr Val Lys Ser Cys Phe Trp Tyr Ile Phe Gly Ala
            580                 585                 590

Leu Leu Gln Gln Gly Gly Met Tyr Leu Pro Thr Ala Asp Ser Gly Arg
            595                 600                 605

Leu Val Val Gly Phe Trp Trp Ile Val Val Ile Val Leu Val Thr Thr
            610                 615                 620

Tyr Cys Gly Asn Leu Val Ala Phe Leu Thr Phe Pro Lys Phe Gln Pro
625                 630                 635                 640

Gly Val Asp Tyr Leu Asn Gln Leu Glu Asp His Lys Asp Ile Val Gln
            645                 650                 655

Tyr Gly Leu Arg Asn Gly Thr Phe Phe Glu Arg Tyr Val Gln Ser Thr
            660                 665                 670

Thr Arg Glu Asp Phe Lys His Tyr Leu Glu Arg Ala Lys Ile Tyr Gly
            675                 680                 685

Ser Ala Gln Glu Glu Asp Ile Glu Ala Val Lys Arg Gly Glu Arg Ile
690                 695                 700

Asn Ile Asp Trp Arg Ile Asn Leu Gln Leu Ile Val Gln Arg His Phe
705                 710                 715                 720

Glu Arg Glu Lys Glu Cys His Phe Ala Leu Gly Arg Glu Ser Phe Val
            725                 730                 735

Asp Glu Gln Ile Ala Met Ile Val Pro Ala Gln Ser Ala Tyr Leu His
            740                 745                 750

Leu Val Asn Arg His Ile Lys Ser Met Phe Arg Met Gly Phe Ile Glu
            755                 760                 765

Arg Trp His Gln Met Asn Leu Pro Ser Ala Gly Lys Cys Asn Gly Lys
            770                 775                 780

Ser Ala Gln Arg Gln Val Thr Asn His Lys Val Asn Met Asp Asp Met
785                 790                 795                 800

Gln Gly Cys Phe Leu Val Leu Leu Leu Gly Phe Thr Leu Ala Leu Leu
            805                 810                 815

Ile Val Cys Gly Glu Phe Trp Tyr Arg Arg Phe Arg Ala Ser Arg Lys
            820                 825                 830

Arg Arg Gln Phe Thr Asn
```

-continued

835

<210> SEQ ID NO 11
<211> LENGTH: 830
<212> TYPE: PRT
<213> ORGANISM: Aedes aegypti

<400> SEQUENCE: 11

```
Met Leu Pro Arg Leu Lys Trp Leu Val Leu Val Val Cys Lys
 1               5                  10                  15

Leu Asp His Ser Arg Gly Asp Asp Phe Pro Ser Leu Ile Ser Ala Asn
            20                  25                  30

Ala Ser Ile Ala Val Ile Leu Asp Arg Glu Tyr Leu Asp Ala Gln Tyr
        35                  40                  45

Asp Asp Ile Leu Glu Gly Thr Lys Arg Leu Phe Glu Arg Ile Leu Arg
    50                  55                  60

Asp Asn Phe Arg Asn Gly Gly Leu Ile Val Lys Tyr Phe Ser Trp Thr
65                  70                  75                  80

Ser Ile Asn Leu Arg Arg Asp Phe Thr Ala Val Leu Ser Ile Ser Asn
                85                  90                  95

Cys Glu Asn Thr Trp Asp Val Tyr Lys Asn Ala Ala Lys Glu Asn Leu
            100                 105                 110

Val Ile Met Ser Ile Thr Asp Ser Asp Cys Leu Arg Leu Pro Leu Asn
        115                 120                 125

Asn Ala Ile Met Val Asn Leu Lys Ser Ile Val Ala Leu Ser Lys Glu
    130                 135                 140

Ser Glu Asp Val Arg Pro Leu Ser Leu Ser Leu Phe Arg Ile Glu Ser
145                 150                 155                 160

His Thr His Met Trp Glu Lys Arg Lys Ala Ile Arg Lys Val Leu Val
                165                 170                 175

Asn Leu Pro Thr Arg Tyr Ile Gly Arg Asn Phe Ile Ala Ile Ile Thr
            180                 185                 190

Thr Gln Thr Met Glu Leu Val Met Glu Ile Ala Lys Glu Leu Arg Met
        195                 200                 205

Val Thr Pro Leu Ala Gln Trp Leu Tyr Val Val Ser Asp Thr Ser Ala
    210                 215                 220

Asp Arg Asn Asn Ile Ser Ala Val His Pro Ile Ile Ser Glu Gly Asp
225                 230                 235                 240

Asn Ile Ala Phe Val Tyr Asn Leu Arg Arg Asn Ala Gln Ser Cys Glu
                245                 250                 255

Ser His Met Leu Cys Tyr Val Glu Asn Leu Ile Thr Ser Leu Val His
            260                 265                 270

Gly Leu Ser Lys Leu Ile Arg Glu Lys Ala Val Tyr Gly Gln Ile
        275                 280                 285

Ala Asp Glu Glu Trp Glu Val Ile Arg Met Thr Lys Ala Glu Arg Lys
    290                 295                 300

Asp Glu Ile Leu Lys Ile Met Arg Ser Asp Leu Ile Gly Lys Asp Ser
305                 310                 315                 320

Cys Asn Glu Cys Ser Met Trp Lys Val Glu Ala Gly Glu Thr Trp Gly
                325                 330                 335

Tyr Thr Tyr Gln Ser Ala Ala Asp Glu Leu Leu Thr Gly Val Met Ser
            340                 345                 350

Thr His Arg Lys Gln Ile Ser Leu Leu Asp Val Gly Tyr Trp Thr Pro
        355                 360                 365
```

-continued

```
Gln Asp Gly Phe Val Met Arg Asp Asn Met Phe Pro His Val Ala Asp
        370                 375                 380
Gly Phe Arg Gly Val His Leu Asn Phe Tyr Ser Tyr His Asn Pro Pro
385                 390                 395                 400
Trp Gln Phe Val Thr Tyr Asn Glu Ser Gly His Leu Ser Leu Ser Arg
                405                 410                 415
Gly Val Val Met Asp Ile Leu Thr Glu Leu Ser Arg Lys Leu Asn Phe
                420                 425                 430
Thr Phe Asn Ile Leu Ile Ser Gln Thr Asn Leu Glu Tyr Ile Gly Asn
            435                 440                 445
Met Thr Asp Asp Ala Asn Asn Thr Ile Asn Arg Asp Ala His Ser Ile
450                 455                 460
Thr Thr Asp Ile Pro Asn Glu Ile Leu Arg Ser Leu Met Asp Asn Lys
465                 470                 475                 480
Ile Leu Leu Ala Ala Val Gly Ala Thr Val Ser Pro Lys Gln Lys Lys
                485                 490                 495
Tyr Val Asn Phe Thr Thr Pro Ile Ser Ile Gln Thr Tyr Ser Phe Ile
                500                 505                 510
Val Ser Arg Pro Lys Glu Leu Ser Arg Val Phe Leu Phe Leu Ser Pro
            515                 520                 525
Phe Thr Ile Asp Thr Trp Leu Cys Leu Ser Ala Thr Val Leu Leu Met
530                 535                 540
Gly Pro Phe Leu Tyr Val Val Asn Arg Leu Ser Pro Phe Tyr Glu His
545                 550                 555                 560
His Gly Arg Ser Asn Thr Ile Gly Leu Gly Lys Leu Tyr Asn Cys Phe
                565                 570                 575
Trp Tyr Ile Tyr Gly Ala Leu Leu Gln Gln Gly Gly Leu Tyr Leu Pro
                580                 585                 590
Tyr Ala Asp Ser Gly Arg Ile Ile Ile Gly Thr Trp Trp Leu Val Val
                595                 600                 605
Leu Val Ile Val Thr Thr Tyr Cys Gly Asn Leu Val Ala Phe Leu Thr
            610                 615                 620
Phe Pro Lys Ile Ala Ile Pro Ile Thr Thr Val Asn Gln Leu Ile Arg
625                 630                 635                 640
Asn Glu Gln Gly Val Ser Trp Ser Ile Arg Arg Gly Thr Phe Leu Glu
                645                 650                 655
Gln Phe Leu Gln Glu Thr Asp Asp Pro Lys Tyr Ile Lys Leu His Asn
            660                 665                 670
His Ala Gly Tyr Val Ser Glu Glu Ser Glu Gln Met Val Glu Arg Ile
            675                 680                 685
Arg Thr Gly Arg His Val His Ile Asp Trp Arg Thr Asn Leu Lys Tyr
690                 695                 700
Leu Met Lys Lys Glu Phe Leu Lys Asn Asp Arg Cys Asp Phe Ala Leu
705                 710                 715                 720
Ser Val Asp Glu Phe Leu Asp Glu Gln Ile Ala Leu Ala Met Pro Lys
                725                 730                 735
Asn Ser Pro Tyr Leu Glu Leu Ile Asn Ala Glu Leu Thr Lys Met His
                740                 745                 750
Gln Phe Gly Phe Ile Gln Arg Trp Leu Gly Ser Tyr Met Pro Ser Glu
            755                 760                 765
Asp Lys Cys Ser Asn Ala Arg Lys Ser Thr Glu Val Glu Asn His Thr
770                 775                 780
Val Asn Asn Asp Asp Met Ala Gly Ser Tyr Tyr Val Leu Met Ile Gly
```

```
                785                 790                 795                 800
Phe Ser Met Gly Leu Phe Met Phe Val Leu Glu Tyr Gly Trp Arg Trp
                    805                 810                 815
Tyr Lys Arg Ser Lys Glu Glu Thr Leu Gln Pro Phe Thr Glu
                820                 825                 830

<210> SEQ ID NO 12
<211> LENGTH: 857
<212> TYPE: PRT
<213> ORGANISM: Anopheles gambiae

<400> SEQUENCE: 12

Met Val Leu Arg Leu Val Gly Leu Trp Ser Ile Leu Leu Leu Leu Leu
1               5                   10                  15

Leu Leu Leu Val Leu Arg Pro Asp Pro Ala Val Gly Asp Asp Phe Pro
            20                  25                  30

Ser Leu Leu Ser Thr Asn Ala Ser Met Gly Lys Leu Asn Ile Thr Pro
        35                  40                  45

Leu Leu Ser Ile Ile Leu Asp Arg Glu Tyr Leu Gly Ala Asp Tyr Glu
    50                  55                  60

Arg Thr Leu Asp Glu Thr Lys Asn Val Val Glu Lys Leu Ile Arg Glu
65                  70                  75                  80

His Leu Lys Asn Gly Gly Leu Ile Val Lys Tyr Tyr Ser Trp Thr Ser
                85                  90                  95

Ile Asn Leu Lys Arg Asp Phe Ser Ala Val Leu Ser Val Ser Ser Cys
            100                 105                 110

Lys Asn Thr Trp Asp Ile Tyr Gln Glu Ala Val Arg Glu Arg Leu Val
        115                 120                 125

Met Leu Ser Ile Thr Asp Pro Asp Cys Pro Arg Leu Pro Thr Asn Asn
    130                 135                 140

Ala Ile Met Ile Pro Arg Ser Asp Gly Ser Gly Ser Asn Ala Phe Asp
145                 150                 155                 160

Glu Val Ser Gln Ile Ile Leu Asp Met Lys Ser Ser Arg Ala Ile Asn
                165                 170                 175

Trp His Thr Ala Thr Leu Leu Tyr Asp Gln Val Tyr Asp Ala Glu Ile
            180                 185                 190

Ser Arg Cys Ile Leu Ser Leu Leu Glu Asp Arg Glu Gly Ile Lys Pro
        195                 200                 205

Leu Thr Leu Thr Glu Phe Lys Ile Asn Ala Pro Thr His Ser Trp Glu
    210                 215                 220

Lys Arg Lys Glu Ile Arg Arg Thr Leu Leu Gly Ile Pro Thr Ala Tyr
225                 230                 235                 240

Thr Gly Arg Asn Phe Ile Ala Ile Val Asn Ile Ala Thr Leu Thr Leu
                245                 250                 255

Leu Met Glu Ile Ser Lys Asp Leu Lys Leu Val Asn Pro Phe Ala Gln
            260                 265                 270

Trp Leu Tyr Leu Ile Pro Asn Thr Glu Lys Ala Asn Ser Asn Phe Thr
        275                 280                 285

Thr Arg Ser Thr Leu Ile Asn Glu Gly Asp Asn Val Ala Phe Val Tyr
    290                 295                 300

Asn Ser Gly Ser Lys Ala Gln Asn Cys Thr Val Ser Val Leu Cys Tyr
305                 310                 315                 320

Ile Glu Ser Tyr Leu Leu His Phe Ile Arg Ser Leu Ser Lys Leu Ile
                325                 330                 335
```

-continued

```
Arg Glu Glu Gln Val Val Phe Gly Gln Ile Ser Asp Glu Glu Trp Glu
                340                 345                 350
Ile Ile Arg Pro Ser Lys Gln Glu Arg Lys Thr Lys Phe Leu Gln Met
        355                 360                 365
Ile Lys Ala Ala Ile Thr Ser Lys Asp Glu Cys Asn Lys Cys Ser Gln
    370                 375                 380
Trp Lys Ile Gln Ser Ala Glu Thr Trp Gly Tyr Val Tyr Arg Thr Asp
385                 390                 395                 400
Phe Leu Thr Asp Gly Ala Asp Leu Gln Glu Arg Arg Lys Tyr Thr Met
                405                 410                 415
Leu Asp Ile Gly Tyr Trp Ser Pro Gln Asp Gly Phe Met Leu Thr Asp
            420                 425                 430
Ala Leu Phe Pro His Thr Gln Tyr Gly Phe Arg Gly Val Gln Leu Ile
        435                 440                 445
Phe Tyr Ser Tyr His Asn Pro Pro Trp Gln Phe Val Ala Tyr Asn Asp
    450                 455                 460
Ser Gly Ser Pro Val Ile Ser Ser Gly Val Val Tyr Asp Ile Leu Asn
465                 470                 475                 480
Glu Leu Ser Arg Lys Leu Asn Phe Thr Tyr Thr Met Val Ile Ser Gln
                485                 490                 495
Pro Ala Glu Ile Asn Gly Ser Leu Val Glu Gly Asn Thr Ser Ser Val
            500                 505                 510
Tyr Asp Leu Lys Thr Ile Ser Ser Asp Ile Pro Gln Glu Ile Phe Ser
        515                 520                 525
Thr Leu Val Asn Asn Lys Ile Leu Leu Ala Ala Val Gly Ala Thr Val
    530                 535                 540
Asn Glu Lys Gln Lys Lys Phe Val Ser Phe Thr Asp Pro Ile Ser Ile
545                 550                 555                 560
Gln Thr Tyr Ser Phe Val Ile Ser Arg Pro Arg Pro Tyr Tyr Glu Val
                565                 570                 575
His Asn Lys Pro Thr Asp Thr Gly Leu Gly Lys Val Asn Asn Cys Phe
            580                 585                 590
Trp Tyr Ile Tyr Gly Ala Leu Leu Gln Gln Gly Leu Tyr Leu Pro Tyr
        595                 600                 605
Ala Asp Ser Gly Arg Ile Ile Ile Gly Thr Trp Trp Leu Val Val Leu
    610                 615                 620
Val Ile Val Thr Thr Tyr Cys Gly Asn Leu Val Ala Phe Leu Thr Phe
625                 630                 635                 640
Pro Lys Ile Asp Ile Pro Val Asn Arg Val Met Gln Leu Leu Arg Asn
                645                 650                 655
Asp Arg Gly Met Thr Trp Ser Ile Arg Arg Gly Thr Phe Leu Glu Glu
            660                 665                 670
Met Leu Met Val Gln Val Ile Ser Ser Pro Ile Ile Tyr Asp Ser Thr
        675                 680                 685
Glu Pro Lys Tyr Met Gln Leu Tyr Lys Gly Ser Gln Ile Ile Gly Glu
    690                 695                 700
Leu Thr Asp Glu Leu Val Glu Arg Ile Glu Ala Gly Gln His Val His
705                 710                 715                 720
Ile Asp Trp Arg Asn Asn Leu Arg Tyr Leu Met Lys Arg Gln Phe Leu
                725                 730                 735
Arg Thr Asp Arg Cys Asp Phe Ala Leu Ser Thr Asp Glu Phe Leu Asp
            740                 745                 750
Glu Gln Ile Ala Leu Val Met Pro Lys Asp Ser Pro Tyr Leu Glu Leu
```

```
            755                 760                 765
Val Asn Glu Ile Lys Arg Met His Gln Phe Gly Phe Ile Gln Arg
770                 775                 780

Trp Val Ala Gln Tyr Leu Pro Ala Lys Asp Lys Cys Ser Gly Thr Gly
785                 790                 795                 800

Arg Val Met Asp Val Gln Asn His Thr Val Asn Ser Ser Asp Met Ala
                805                 810                 815

Gly Ser Tyr Trp Ile Leu Leu Leu Gly Phe Val Ser Gly Leu Phe Val
                820                 825                 830

Phe Val Cys Glu Phe Ala Val Ala Trp Tyr Arg Lys His Arg Ala Ala
                835                 840                 845

Arg Ala Ala Thr Val Ala Tyr Arg Asp
850                 855

<210> SEQ ID NO 13
<211> LENGTH: 840
<212> TYPE: PRT
<213> ORGANISM: Culex quinquefasciatus

<400> SEQUENCE: 13

Met Ala Ala Val Ile Leu Asp Arg Glu Tyr Leu Asp Asn Gln Tyr Glu
1               5                   10                  15

Ala Leu Leu Glu Asn Thr Lys Arg Thr Phe Glu Gln Ile Leu Arg Asp
                20                  25                  30

Asn Phe Lys Asn Gly Gly Leu Ile Val Lys Tyr Phe Ser Trp Thr Ser
            35                  40                  45

Ile Asn Leu Arg Arg Asp Phe Thr Ala Val Leu Ser Val Ser Asn Cys
    50                  55                  60

Glu Asn Thr Trp Asp Val Tyr Arg Asn Ala Ala Lys Glu Asn Leu Val
65                  70                  75                  80

Ile Met Ala Ile Thr Asp Thr Asp Cys Pro Arg Leu Pro Ser His Asn
                85                  90                  95

Ala Ile Met Ile Pro Lys Ser Ile Pro Ala Ser Gly Ile Phe Glu Glu
                100                 105                 110

Leu Pro Gln Val Ile Met Asp Met Lys Thr Met Lys Ala Phe Ser Trp
            115                 120                 125

Lys Ser Ala Ile Leu Leu Tyr Asp Asp Ser Phe Asp Arg Asp Ile Val
    130                 135                 140

Ala Arg Ser Val Leu Ala Leu Ser Lys Glu Ser Glu Asp Val Leu Pro
145                 150                 155                 160

Leu Ser Leu Ser Leu Phe Arg Ile Glu Ser His Thr His Met Trp Glu
                165                 170                 175

Lys Arg Lys Ala Val Arg Lys Val Leu Leu Gly Leu Pro Thr Arg Tyr
                180                 185                 190

Ile Gly Thr Asn Phe Ile Ala Ile Val Thr Ala Thr Thr Met Glu Leu
            195                 200                 205

Val Met Asp Ile Ala Lys Glu Leu Lys Met Val Asn Pro Leu Ala Gln
    210                 215                 220

Trp Leu Tyr Val Ile Ser Asp Thr Thr Ala Glu Gln Asn Asn Ile Ser
225                 230                 235                 240

Ser Val His Ser Ile Ile Ser Glu Gly Asp Asn Ile Ala Phe Val Tyr
                245                 250                 255

Asn Met Arg Lys Thr Ala Ala Ser Cys Glu Ser Gln Ser Thr Leu Cys Tyr
                260                 265                 270
```

```
Ile Glu Asn Leu Val Asn Ala Leu Val Lys Gly Leu Ser Lys Leu Ile
            275                 280                 285

Arg Glu Glu Lys Ala Val Tyr Gly Gln Ile Ala Asp Glu Glu Trp Glu
        290                 295                 300

Val Ile Arg Met Thr Lys Val Glu Arg Lys Asn Asp Ile Leu Gln Ile
305                 310                 315                 320

Ile Lys Glu Glu Arg Val Gly Lys Asp Thr Cys Asn Glu Cys Ser Met
                325                 330                 335

Trp Lys Val Gln Ser Gly Glu Thr Trp Gly Tyr Thr Tyr Gln Leu Pro
            340                 345                 350

Ala Asp Asp Val Leu Ser Gly Thr Ala Val Gly Arg Arg Lys Gln Val
        355                 360                 365

Glu Met Leu Asp Val Gly Tyr Trp Thr Pro Gln Asp Gly Phe Val Met
370                 375                 380

Ala Asp Phe Leu Phe Pro His Ile Ser His Gly Phe Arg Gly Ile His
385                 390                 395                 400

Leu Asn Phe Tyr Thr Tyr His Asn Pro Pro Trp Gln Phe Val Ser Phe
                405                 410                 415

Asn Glu Ser Gly His Pro Thr Leu Ser Gly Gly Val Val Met Asp Ile
            420                 425                 430

Leu Glu Glu Leu Ser Arg Lys Leu Asn Phe Thr Tyr Thr Val Ile Val
        435                 440                 445

Ala Gln Thr Asn Ile Glu Tyr Val Gly Asn Leu Thr Glu Asp Gly Asn
    450                 455                 460

Asn Thr Ser Ile Arg Glu Ile His Thr Val Thr Thr Asp Ile Pro Ser
465                 470                 475                 480

Glu Ile Met Lys Ser Leu Ile Asp Asn Lys Ile Leu Leu Ala Ala Val
                485                 490                 495

Gly Ala Thr Val Ser Glu Lys Gln Lys Lys Phe Ile Asn Phe Thr Val
            500                 505                 510

Pro Ile Ser Ile Gln Thr Tyr Ser Phe Ile Val Ser Arg Pro Lys Glu
        515                 520                 525

Leu Ser Arg Val Phe Leu Phe Leu Ser Pro Phe Thr Val Asp Thr Trp
530                 535                 540

Met Cys Leu Gly Leu Thr Ile Leu Met Met Ala Pro Leu Leu Tyr Val
545                 550                 555                 560

Val Asn Arg Val Ser Pro Phe Tyr Glu His His Gly Lys Ser Asn Lys
                565                 570                 575

Leu Gly Leu Gly Lys Leu Asn Asn Cys Phe Trp Tyr Leu Tyr Gly Ala
            580                 585                 590

Leu Leu Gln Gln Gly Gly Leu Tyr Leu Pro Tyr Ala Asp Ser Gly Arg
        595                 600                 605

Ile Ile Ile Gly Thr Trp Trp Leu Val Val Leu Val Ile Val Thr Thr
610                 615                 620

Tyr Cys Gly Asn Leu Val Ala Phe Leu Thr Phe Pro Lys Ile Ala Val
625                 630                 635                 640

Pro Ile Thr Thr Ile Ser Gln Leu Val Arg Asn Asn Glu Gly Ile Thr
                645                 650                 655

Trp Ser Ile Arg Lys Gly Thr Phe Leu Glu Gln Phe Leu Arg Glu Thr
            660                 665                 670

Asp Asp Ala Lys Tyr Leu Lys Leu Ser His Gly Ala Thr Phe Ile Ser
        675                 680                 685

Asp Glu Ser Asp Ser Met Val Gln Ser Ile Arg Asn Gly His His Val
```

```
                690              695                700
His Ile Asp Trp Arg Thr Asn Leu Lys Tyr Leu Leu Lys Arg Glu Phe
705                 710                 715                 720

Leu Lys Asn Asp Arg Cys Asp Phe Ala Leu Ser Leu Asp Glu Phe Leu
                725                 730                 735

Asp Glu Gln Ile Ala Leu Ala Leu Pro Lys Ala Ser Pro Tyr Leu Asp
            740                 745                 750

Val Ile Asn Ala Glu Ile Thr Lys Met His Gln Phe Gly Phe Ile His
        755                 760                 765

Lys Trp Leu Ser Asn Tyr Met Pro Ser Glu Asp Lys Cys Ser Lys Ala
    770                 775                 780

Arg Lys Asn Thr Asp Val Glu Asn His Thr Val Asn Asn Asp Asp Met
785                 790                 795                 800

Ala Gly Ser Tyr Tyr Val Leu Leu Ile Gly Phe Ser Ser Gly Met Phe
                805                 810                 815

Leu Phe Leu Ile Glu Phe Gly Trp Arg Phe Tyr Lys Lys Ser Lys Glu
            820                 825                 830

Gln Ser Leu Gln Pro Phe Thr Asp
        835                 840

<210> SEQ ID NO 14
<211> LENGTH: 743
<212> TYPE: PRT
<213> ORGANISM: Acyrthosiphon pisum

<400> SEQUENCE: 14

Met Thr Gly Tyr Asn Thr Asp Cys Pro Arg Leu Pro Thr Asp Glu Ala
 1               5                  10                  15

Ile Thr Ile Pro Leu Thr Val His His Ser Glu Leu Ser Gln Met Ile
             20                  25                  30

Leu Asp Leu Arg Met Ser Asn Ala Phe Ser Trp Lys Ser Ala Val Leu
         35                  40                  45

Met His Asp Asn Ser Ile Gly Asp Ser Val Leu Gln His Ile Val Thr
     50                  55                  60

Ser Leu Thr Lys Tyr Tyr Pro Ser Asn Ile Met Ser Pro Ser Ile Thr
 65                  70                  75                  80

Ile Phe Glu Ile Tyr Thr Gln Gly Ser Glu Trp Lys Arg Arg Lys Leu
                 85                  90                  95

Phe Met Glu Asp Leu Gln His Phe Leu Lys Met Ser Glu Ile Asn Ser
            100                 105                 110

Asn Tyr Ile Cys Ile Val Ser Ile Leu Tyr Val Pro Leu Ile Leu Asp
        115                 120                 125

Val Ala Lys Ser Leu Asn Leu Met Thr Ala Glu Asn Ser Trp Leu Ile
    130                 135                 140

Ile Ile Pro Asp Ile Asp Ser Ser Arg Asn Asn Thr Ser Ser Phe Thr
145                 150                 155                 160

Asn Leu Leu Ser Glu Gly Glu Asn Ile Ser Phe Ile Tyr Asn Ser Thr
                165                 170                 175

Lys Thr Gly Ser Lys Cys Ile Gly Gly Ile Leu Cys Leu Val Asp Glu
            180                 185                 190

Leu Met Ser Val Phe Ile Met Ala Phe Ser Ala Leu Ile Gln Gln Glu
        195                 200                 205

Ile Glu Leu Ser Gln Arg Val Ser Glu Glu Glu Trp Asp Glu Ile Arg
    210                 215                 220
```

-continued

Pro Ser Lys Ile Asp Arg Arg Gln Ser Met Val Ser Phe Ile Lys Phe
225                 230                 235                 240

Arg Leu Asn Glu Ser Gly Val Cys Glu Thr Cys Pro Leu Trp Gln Ile
            245                 250                 255

Asp Ser Gly Val Thr Trp Gly Gln Glu His Phe Gly Gln Gly Cys Tyr
        260                 265                 270

Ile Leu Pro Val Gly Asn Trp Asn Thr Lys Thr Gly Leu Lys Leu Thr
    275                 280                 285

Glu Pro Leu Phe Leu His Leu Ala Asn Gly Phe Arg Gly Ile Ala Leu
290                 295                 300

Pro Ile Ala Thr Phe Asn Phe Pro Pro Trp Gln Ile Val Asn Phe Asn
305                 310                 315                 320

Arg Ser Gly His Leu Ile Gly Tyr Ser Gly Leu Val Phe Asp Ile Ile
            325                 330                 335

Asn Gln Leu Ala Lys Thr Leu Asn Phe Thr Tyr Asn Val Ile Val Ile
        340                 345                 350

Ser Asn Thr Glu Gln Met Asn Thr Thr Arg Thr Leu Phe Met Gln Asn
    355                 360                 365

Asn Val Leu Gly Glu His Asp Ala Val Val Ser Lys Pro Leu Trp Asp
370                 375                 380

Lys Met Ile Asp Leu Val Arg Ser Glu Lys Val Phe Ile Ala Ala Ala
385                 390                 395                 400

Ala Phe Ala Val Lys Glu Ala Asn Gln Ile Leu Val Asn Tyr Thr Thr
            405                 410                 415

His Ile Ser Leu Glu Pro His Gln Ile Leu Val Ala Arg Pro Lys Glu
        420                 425                 430

Leu Ser Arg Ala Leu Leu Phe Thr Ala Pro Phe Thr Leu Leu Thr Trp
    435                 440                 445

Leu Cys Ile Ala Ile Val Val Gly Leu Met Gly Pro Leu Leu Asn Val
450                 455                 460

Phe His Val Leu Ser Pro Tyr Tyr Glu Tyr His Asn Ile Pro Arg Lys
465                 470                 475                 480

Gly Gly Leu Asn Ser Pro Leu Asn Cys Phe Trp Tyr Val Tyr Gly Ala
            485                 490                 495

Leu Leu Gln Gln Gly Gly Ala His Leu Pro Asp Ala Asp Ser Gly Arg
        500                 505                 510

Leu Val Val Gly Thr Trp Trp Leu Phe Val Leu Val Ile Val Thr Thr
    515                 520                 525

Tyr Ser Gly Asn Leu Val Ala Tyr Leu Thr Phe Pro Gln Met Asp Ser
530                 535                 540

Met Val Ser Asn Val Ala Asp Leu Met Ala Arg Lys Pro Gln Gly Tyr
545                 550                 555                 560

Ser Trp Gly Ile Pro Lys Thr Ser Asn Leu His Ser Leu Leu Thr Val
            565                 570                 575

Asn Asp Thr Met Val Lys Glu Leu Ile Lys Asn Ala Glu His His Glu
        580                 585                 590

Glu Leu Ser Arg Ser Ile Ile Glu Arg Val Arg Ser Gly Lys His Ala
    595                 600                 605

Phe Ile His Arg Arg Thr Asn Leu Met Tyr Ile Met Lys Asn Asp Phe
610                 615                 620

Leu Lys Thr Asn Arg Cys Asp Phe Ala Ile Gly Asn Glu Asp Phe Ala
625                 630                 635                 640

Glu Glu Lys Leu Ala Met Met Leu Ser Lys Glu Ser Pro Tyr Leu Ser

-continued

```
                645                 650                 655
Arg Ile Asn Arg Glu Ile Glu Lys Met His Lys Val Gly Leu Ile Asn
            660                 665                 670

Lys Trp Leu Val Asp Thr Leu Pro Lys Lys Asp Gln Cys Trp Thr Asn
        675                 680                 685

Thr Gln Leu Glu Val Thr Asn His Lys Val Asn Leu Asp Asp Met Gln
    690                 695                 700

Gly Ser Phe Ile Val Leu Leu Gly Val Leu Ser Ser Leu Val Ser
705                 710                 715                 720

Phe Val Phe Glu Tyr Ile Leu His Lys Tyr Ile Asn Arg Arg Gln Ile
                725                 730                 735

Val Ile Thr Pro Phe Ile Asn
            740

<210> SEQ ID NO 15
<211> LENGTH: 782
<212> TYPE: PRT
<213> ORGANISM: Bombyx mori

<400> SEQUENCE: 15

Met Lys Ile Trp Val Leu Gly Val Leu Cys Leu Ala Ile Ser Val Gln
  1               5                  10                  15

Gly Glu Asp Phe Pro Ser Leu Ile Thr Ala Asn Ala Ser Ile Ala Val
            20                  25                  30

Ile Leu Asp Arg Gln Tyr Leu Gly Asp Lys Tyr Gln Thr Val Leu Asp
        35                  40                  45

Glu Leu Lys Asp Tyr Ile Lys Glu Leu Ala Arg Val Glu Leu Lys His
    50                  55                  60

Gly Gly Val Leu Val His Tyr Tyr Ser Trp Thr Asn Ile Ser Leu Asn
65                  70                  75                  80

Lys Gly Phe Leu Ala Val Phe Ser Ile Ala Ser Cys Glu Asp Thr Trp
                85                  90                  95

Glu Leu Phe Ser Arg Thr Glu Glu Asp Leu Leu Leu Phe Ala Leu
            100                 105                 110

Thr Glu Val Asp Cys Pro Arg Leu Pro Gln Arg Ser Ala Ile Thr Val
        115                 120                 125

Thr Tyr Ser Glu Pro Gly Glu Glu Leu Pro Gln Leu Leu Leu Asp Leu
    130                 135                 140

Arg Ser Ser Asn Ala Ile Ser Trp Lys Ser Ala Val Ile Leu His Asp
145                 150                 155                 160

Asp Thr Leu Gly Arg Asp Met Val Ser Arg Val Val Gln Ser Leu Thr
                165                 170                 175

Ser Gln Ile Asp Glu Glu Ser Ala Arg Pro Val Ser Val Thr Val Phe
            180                 185                 190

Lys Met Lys His Glu Met Asn Glu Tyr Leu Arg Arg Lys Glu Met His
        195                 200                 205

Arg Val Leu Ser Lys Leu Pro Val Lys Tyr Ile Gly Glu Asn Phe Ile
    210                 215                 220

Ala Ile Val Thr Ser Asp Val Met Thr Thr Met Ala Glu Ile Ala Arg
225                 230                 235                 240

Glu Leu Leu Met Ser His Thr Met Ala Gln Trp Leu Tyr Val Ile Ser
                245                 250                 255

Asp Thr Asn Ala His Ala Ser Asn Leu Ser Gly Phe Ile Asn Thr Leu
            260                 265                 270
```

-continued

```
Asn Glu Gly Glu Asn Val Ala Phe Ile Tyr Asn Ile Thr Glu Asn Gly
                275                 280                 285
Pro Asp Cys Lys Asn Gly Leu Met Cys Tyr Ser Gln Glu Met Met Ser
            290                 295                 300
Ala Phe Ile Ser Ala Leu Asp Ala Ala Ile Gln Ala Glu Phe Asp Val
305                 310                 315                 320
Ala Ala Gln Val Ser Asp Glu Trp Glu Ala Ile Arg Pro Ser Lys
                325                 330                 335
Val Gln Arg Arg Asp Ile Leu Leu Lys His Met Gln Gln Tyr Ile Leu
                340                 345                 350
Ala Lys Ser Val Cys Gly Asn Cys Thr Leu Trp Arg Ala Leu Ala Ala
            355                 360                 365
Asp Thr Trp Gly Val Thr Tyr Arg Gln Asn Asp Val Pro Glu Gln Ile
370                 375                 380
Asn Glu His Ala Asn Gly Ser Thr Gly Val Ile Glu His Leu Glu Leu
385                 390                 395                 400
Met Asn Val Gly Ile Trp Arg Pro Ile Asp Ala Met Thr Phe Ala Asp
                405                 410                 415
Leu Leu Phe Pro His Val His His Gly Phe Arg Gly Lys Glu Leu Pro
                420                 425                 430
Ile Ile Thr Tyr His Asn Pro Pro Trp Thr Phe Leu Gln Ala Asn Glu
                435                 440                 445
Ser Gly Ala Ile Val Lys Tyr Ser Gly Leu Met Phe Asp Ile Val Asn
            450                 455                 460
Gln Leu Ala Lys Asn Lys Asn Phe Thr Pro Arg Glu Leu Ser Arg Ala
465                 470                 475                 480
Leu Leu Phe Leu Leu Pro Phe Thr Thr Asp Thr Trp Leu Cys Leu Gly
                485                 490                 495
Phe Ala Val Ile Leu Met Gly Pro Met Leu Tyr Ile Val His Arg Leu
                500                 505                 510
Ser Pro Tyr Tyr Glu Ala Met Glu Ile Thr Arg Glu Gly Gly Leu Ala
            515                 520                 525
Thr Ile His Asn Cys Leu Trp Tyr Ile Tyr Gly Ala Leu Leu Gln Gln
            530                 535                 540
Gly Gly Met Tyr Leu Pro Arg Ala Asp Ser Gly Arg Leu Val Ile Gly
545                 550                 555                 560
Thr Trp Trp Leu Val Val Leu Val Ile Val Thr Thr Tyr Ser Gly Asn
                565                 570                 575
Leu Val Ala Phe Leu Thr Phe Pro Lys Leu Glu Ala Pro Val Thr Thr
            580                 585                 590
Ile Ser Glu Leu Leu Lys Asn Ser Asp Ala Tyr Thr Trp Ser Val Thr
            595                 600                 605
Lys Gly Ser Tyr Leu Glu Met Glu Leu Lys Asn Ser Glu Glu Pro Lys
        610                 615                 620
Tyr Lys Arg Leu Ile Lys Glu Ala Glu Leu Leu Lys Glu Thr Gly Gly
625                 630                 635                 640
Ile Glu Gly Thr Ile His Ala Ala Arg Gly Thr Leu Asp Arg Val Arg
                645                 650                 655
Gly Gln Arg His Leu Ile Phe Asp Trp Arg Leu Arg Leu Thr Tyr Leu
            660                 665                 670
Met Ser Ala Asp His Ile Ala Thr Glu Thr Cys Asp Phe Ala Leu Ala
            675                 680                 685
Val Glu Asp Phe Met Glu Glu Gln Val Ala Met Ile Val Pro Ala Gly
```

```
            690                 695                 700
Ser Pro Tyr Leu Pro Val Ile Asn Lys Glu Ile Asn Arg Met His Lys
705                 710                 715                 720

Ala Gly Leu Ile Ser Lys Trp Leu Ser Ala Tyr Leu Pro Lys Pro Asn
                725                 730                 735

Arg Cys Leu Lys Ile Ser Thr Val Thr Gln Glu Val Ser Asn His Thr
                740                 745                 750

Val Asn Leu Ser Asp Met Gln Gly Ser Phe Phe Val Leu Phe Leu Gly
                755                 760                 765

Asn Asp Lys Ile Tyr Val Tyr Met Tyr Ile Ala Glu Leu Ile
                770                 775                 780

<210> SEQ ID NO 16
<211> LENGTH: 834
<212> TYPE: PRT
<213> ORGANISM: Tribolium castenium

<400> SEQUENCE: 16

Met Leu Leu Glu Leu Val Leu Ser Ser Ala Phe Val Cys Val Ile Arg
1               5                   10                  15

Ala Val Ile Ile Asp Arg Glu Phe Leu Ser Asn Glu Tyr Glu Val Ile
                20                  25                  30

Lys His Ala Ile Glu Ser Tyr Leu Val Phe Ala Lys Arg Glu Ile Leu
            35                  40                  45

Lys His Gly Gly Val Asn Val Gln Tyr Tyr Ser Trp Thr Thr Ile Asn
        50                  55                  60

Ile Lys Lys Asp Val Thr Ala Ile Phe Ser Ile Ala Ser Cys Pro Asp
65                  70                  75                  80

Thr Trp Arg Leu Phe Arg Gln Ala Arg Asp Ala Asn Leu Leu His Met
                85                  90                  95

Ala Ile Ser Glu Ser Asp Cys Pro Arg Leu Pro Pro Asp Glu Ala Ile
            100                 105                 110

Thr Val Pro Leu Ile Thr Arg Gly Glu Leu Pro Gln Leu Leu Leu
        115                 120                 125

Asp Leu Arg Thr Arg Gln Thr Tyr Asn Trp Asn Ser Ala Phe Ile Leu
    130                 135                 140

Tyr Asp Asp Thr Leu Ser Arg Asp Gln Val Thr Arg Val Val Lys Ser
145                 150                 155                 160

Ile Thr Ala Gln Tyr Ser Asn Leu Arg Val Asn Ala Ala Ile Ser
                165                 170                 175

Phe Val Lys Leu Glu Thr Arg Leu Pro Met Asp Glu Ile Arg Arg Gln
            180                 185                 190

Val Lys Glu Ile Leu Ser Ser Val Ser Ile Lys Thr Val Gly Gly Asn
        195                 200                 205

Phe Leu Ala Ile Ile Gly Tyr Glu Leu Val Glu Leu Leu Met Glu Tyr
    210                 215                 220

Ala Lys Met Phe Gly Leu Val Asn Thr Arg Thr Gln Trp Leu Tyr Ile
225                 230                 235                 240

Ile Ser Asn Thr His Phe Arg His Lys Asp Ile Asn Arg Phe Arg Gln
                245                 250                 255

Leu Leu Ser Glu Gly Asp Asn Ile Ala Phe Leu Tyr Asn Asn Thr Val
            260                 265                 270

Asn Asn Asp Thr Cys Thr Gly Gly Ile Gln Cys His Cys Glu Glu Ile
        275                 280                 285
```

Leu Ser Gly Phe Thr Arg Ala Leu Asp Glu Ala Ile Leu Phe Glu Trp
290                 295                 300

Glu Thr Ser Ser Gln Val Ser Asp Glu Trp Glu Ala Ile Arg Pro
305                 310                 315                 320

Ser Lys Leu Asp Arg Arg Asn Ser Leu Leu Gln Gly Ile Lys Thr Phe
                325                 330                 335

Leu Leu Gln Arg Gly Gln Cys Asp Asn Cys Thr Ser Trp Leu Met Lys
                340                 345                 350

Thr Gly Asp Thr Trp Gly Arg Glu Tyr Gln Gln Asn Gly Thr Asp Ser
                355                 360                 365

Gly Gly Leu Ile Ser Val Gly Asn Trp Arg Pro Ser Asp Gly Pro Ser
370                 375                 380

Met Ser Asp Glu Leu Phe Pro His Ile Val His Gly Phe Arg Lys Arg
385                 390                 395                 400

Asn Leu Pro Ile Val Thr Phe His Asn Pro Pro Trp Gln Ile Ile Arg
                405                 410                 415

Ser Asn Glu Ser Gly Ala Val Ser Glu Tyr Ala Gly Val Ile Phe Glu
                420                 425                 430

Leu Ile Lys Glu Leu Ser Lys Asn Leu Asn Phe Thr Tyr Thr Val Glu
                435                 440                 445

Leu Ala Lys Ile Gly Gln Glu Phe Ser Ala Asn Leu Thr Lys Asn Glu
                450                 455                 460

Ala Gln Val Val Thr Asn Phe Ile Pro Asp Ser Ile Leu Asp Met Ile
465                 470                 475                 480

Arg Asn Lys Ser Val Ala Phe Gly Ala Cys Ala Phe Thr Val Thr Glu
                485                 490                 495

Glu Ser Lys Arg Leu Ile Asn Phe Thr Ser Pro Ile Ser Thr Gln Thr
                500                 505                 510

Tyr Thr Phe Leu Val Ser Arg Pro Arg Glu Leu Ser Arg Ala Leu Leu
                515                 520                 525

Phe Met Ser Pro Phe Thr Gly Asp Thr Trp Leu Cys Leu Ser Ala Ser
530                 535                 540

Ile Val Ser Met Gly Pro Ile Leu Tyr Tyr Ile His Lys Tyr Ser Pro
545                 550                 555                 560

Val Tyr Glu Tyr Lys Gly Leu Ser Lys Arg Gly Leu Ser Ser Val Gln
                565                 570                 575

Asn Cys Ile Trp Tyr Met Tyr Gly Ala Leu Leu Gln Gln Gly Gly Met
                580                 585                 590

His Leu Pro Gln Ala Asp Ser Ala Arg Ile Ile Val Gly Ala Trp Trp
                595                 600                 605

Leu Val Val Leu Val Leu Ala Thr Thr Tyr Cys Gly Asn Leu Val Ala
610                 615                 620

Phe Leu Thr Phe Pro Lys Ile Asp Ile Pro Ile Thr Thr Ile Asp Glu
625                 630                 635                 640

Leu Leu Ala His Ser Gly Thr Val Thr Trp Ser Met Pro Lys Gly Ser
                645                 650                 655

Tyr Leu Glu Arg Thr Leu Lys Tyr Thr Thr Glu Pro Arg Phe Arg Tyr
                660                 665                 670

Leu Phe Asp Lys Lys Val Glu Val Gly Asn Phe Lys Asn Met Ile Glu
                675                 680                 685

Asp Ile Glu Asn Gly Lys His Val His Ile Asp Trp Lys Ile Lys Leu
690                 695                 700

Gln Tyr Ile Met Lys Gln Gln Tyr Leu Asp Ser Asp Arg Cys Asp Leu

```
                705                 710                 715                 720
Ala Leu Gly Leu Asp Glu Phe Leu Asn Glu Gln Leu Ala Met Val Val
                    725                 730                 735

Ser Gln Asp Thr Pro Tyr Leu Glu Ile Ile Asn Asp Glu Ile Lys Lys
                740                 745                 750

Leu His Gln Val Gly Leu Ile Gln Lys Trp Leu Thr Asp Tyr Leu Pro
                755                 760                 765

Lys Lys Asp Arg Cys Trp Lys Asn Asn Arg His Ile Val Glu Val Asn
                770                 775                 780

Asn His Thr Val Asn Met Asp Asp Met Gln Gly Ser Phe Phe Val Leu
785                 790                 795                 800

Phe Leu Gly Phe Leu Leu Ser Phe Phe Ile Thr Ile Gly Glu Lys Leu
                    805                 810                 815

Trp His Lys Tyr Val Thr Lys Lys Lys Met Lys Ile Ile Gln Pro Phe
                820                 825                 830

Thr Thr

<210> SEQ ID NO 17
<211> LENGTH: 861
<212> TYPE: PRT
<213> ORGANISM: Pediculus humanus

<400> SEQUENCE: 17

Met Leu Leu Phe Ile Phe Arg Ile Val Phe Leu Ile Ile Phe Cys
1               5                   10                  15

Lys Lys Thr Gly Gly Asn Tyr Phe Ser Asp Ser His Asn Val Thr Leu
                20                  25                  30

Ala Val Ile Val Glu Gln Lys Phe Ala Ser Lys Asp Asp Leu Ser Phe
                35                  40                  45

Val Ile Lys Asn Leu Ile Ser Asp Ala Arg Lys Lys Phe Val Lys Asn
            50                  55                  60

Gly Asp Leu Thr Val Gln Tyr His Thr Asn Thr Asn Thr Ile Pro Lys
65                  70                  75                  80

Lys Asn Leu Ile Ala Val Leu Ser Ile Ala Ser Cys Glu Asn Thr Trp
                85                  90                  95

Lys Ile Phe Arg Asn Ala Glu Asp Asp Ser Ile Leu His Leu Ala Ile
                100                 105                 110

Thr Glu Ala Asp Cys Pro Arg Leu Pro Phe Glu Glu Ala Ile Thr Val
                115                 120                 125

Pro Leu Ile Arg Glu Gly Gly Glu Ile Ser Gln Ile Ile Leu Asp Ile
            130                 135                 140

Arg Thr Ile His Gly Ile Asp Trp Lys Ser Ala Val Ile Phe Tyr Asp
145                 150                 155                 160

Thr Ser Ala Ile Asp Gly Glu Glu Ile Gln Gly Ile Thr Ser Ala Leu
                165                 170                 175

Ser Met Ser Val Pro Ile His Ser Val Asp Pro Ala Ser Val Ser Ile
                180                 185                 190

Phe Lys Leu Glu Arg Lys Lys Asn Glu Trp Ser Arg Arg Lys Gln Ile
                195                 200                 205

Arg Asn Ile Leu Thr Asn Phe Pro Ser Lys Ile Leu Gly Ser Asn Phe
            210                 215                 220

Leu Val Ile Ala Lys Arg Asp Leu Val Gly Val Ile Met Glu Val Ala
225                 230                 235                 240

Lys Ser Thr Gly Leu Val His Pro Leu Ser Gln Trp Leu Tyr Ile Ile
```

```
                    245                 250                 255
Pro Asp Thr Asn Val Ile Arg Asp Asn Ile Thr Ala Leu Ser Thr Leu
                260                 265                 270

Leu Met Glu Gly Asp Asn Val Ser Phe Ile Tyr Asn Gly Thr Ser Asp
            275                 280                 285

Asn Pro Asp Cys Ile Val Arg Leu Ile Cys His Val Asp Glu Leu Ile
        290                 295                 300

Lys Ser Phe Thr Val Ser Leu Asn Glu Leu Ile Arg Glu Ile Glu
305                 310                 315                 320

Leu Ser Ser Gln Val Ser Asp Glu Glu Trp Glu Thr Ile Lys Pro Thr
                325                 330                 335

Lys Leu Asp Arg Arg Ile Ser Leu Leu Ser His Ile Lys Thr Lys Leu
            340                 345                 350

Ser Glu Ser Gly Gly Cys Asp Lys Cys Val Thr Trp Leu Leu Lys Ala
        355                 360                 365

Gly Glu Thr Trp Gly Lys Glu Phe Glu Ile Arg Lys Lys Gly Glu Ser
    370                 375                 380

Arg Tyr Asp Asp Phe Leu Gln Asp Val Gly Leu Trp His Pro Arg Ser
385                 390                 395                 400

Gly His Val Met Lys Asp Ile Leu Phe Pro His Ile Val His Gly Phe
                405                 410                 415

Arg Gly Arg Ser Leu Pro Leu Ile Ser Phe Asn His Pro Pro Trp Gln
            420                 425                 430

Ile Ile Asn His Asn Glu Ser Gly Gln Phe Val Glu Phe Lys Gly Leu
        435                 440                 445

Val Phe Glu Ile Val Asn Glu Leu Ala Lys Ser Leu Asn Phe Ser Tyr
    450                 455                 460

Ser Val Ile Tyr Pro Gln Lys Asp Lys Gln Asn Phe Phe Asn Asp
465                 470                 475                 480

Ser Ala Lys Tyr Glu Gly Leu Asn Gly Thr Gln Asp Phe Ser Thr Ile
                485                 490                 495

Ala Ala Asn Trp Glu Ile Ile Ile Glu Ala Ile Lys Asn Lys Lys Val
            500                 505                 510

Phe Leu Gly Ala Val Ala Phe Ile Val Ser Pro Glu His Lys Arg Phe
        515                 520                 525

Ile Asn Phe Thr Thr Pro Ile Gly Ile Glu Pro Tyr Thr Phe Leu Val
    530                 535                 540

Ala Arg Pro Gln Glu Leu Ser Arg Ala Leu Leu Phe Leu Ser Pro Phe
545                 550                 555                 560

Gly Gly Asp Thr Trp Leu Cys Ile Ala Leu Ala Val Ala Ile Val Gly
                565                 570                 575

Pro Leu Leu Asn Trp Phe His Arg Ser Thr Pro Tyr Tyr Asp Tyr Phe
            580                 585                 590

Asn Thr Arg Thr Ser Gly Gly Leu Gln Thr Val Thr Asn Cys Leu Trp
        595                 600                 605

Tyr Met Tyr Gly Ala Leu Leu Gln Gln Gly Gly Ile His Leu Pro Met
    610                 615                 620

Ala Asp Ser Gly Arg Ile Ile Val Gly Ala Trp Trp Leu Phe Val Leu
625                 630                 635                 640

Val Ile Val Thr Thr Tyr Ser Gly Asn Leu Val Ala Phe Leu Thr Phe
                645                 650                 655

Pro Lys Met Asp Val Pro Ile Asn Thr Ile Gln Glu Leu Leu Leu Arg
            660                 665                 670
```

Lys Asn Ser Leu Asn Trp Gly Phe Val Arg Gly Ser Pro Val Asp Leu
            675                 680                 685

Arg Leu Lys Asn Asn Val Asp Pro Lys Tyr Lys Glu Leu Tyr Asp Asn
690                 695                 700

Ala Gln Leu Tyr Arg Lys Leu Glu Ser Glu Thr Ile Glu Lys Ile Arg
705                 710                 715                 720

Lys Gly Glu His Val Tyr Met Asp Trp Lys Thr Asn Met Leu Phe Leu
            725                 730                 735

Thr Lys Lys Gln Tyr Val Glu Thr Gly Thr Cys Asp Phe Thr Phe Gly
            740                 745                 750

Thr Glu Glu Phe Leu Glu Glu Gln Leu Ala Met Val Ile Ala Gln Gly
            755                 760                 765

Asn Pro Tyr Leu Pro Arg Ile Asp Gln Glu Ile Arg Arg Ile His Arg
770                 775                 780

Val Gly Leu Ile Tyr Lys Trp Leu Gln Asp Tyr Leu Pro Lys Lys Asp
785                 790                 795                 800

Lys Cys Trp Ser Thr Asn Arg Leu Thr Glu Val Thr Ser His Thr Val
            805                 810                 815

Asn Met Arg Asp Met Gln Gly Ser Phe Phe Val Leu Phe Leu Gly Ile
            820                 825                 830

Ile Leu Ser Thr Ile Leu Ile Leu Thr Glu Tyr Phe Tyr Lys Lys Lys
            835                 840                 845

Thr Asp Arg Glu Lys Asn Val Ile Lys Pro Phe Thr Thr
850                 855                 860

<210> SEQ ID NO 18
<211> LENGTH: 659
<212> TYPE: PRT
<213> ORGANISM: Ixodes scapularis

<400> SEQUENCE: 18

Met Asn Asn Lys Asn Met Met Thr Phe His Arg Glu Phe Val Ser Val
1               5                   10                  15

Val Thr Gln Pro Ile Asp Asp Asp Phe Gln Lys Leu Val Gly Phe
            20                  25                  30

Pro Asp Gly Ala Asn Val Leu Ala Ala Tyr Pro Glu Ile Ala Asp Asn
            35                  40                  45

Asp Cys Pro Val Glu Pro Gly Cys Gln Leu Pro Leu Ala Met Glu Thr
50                  55                  60

Val Ala Lys Thr Ile Gly Asp Lys Leu Glu Lys Gly Thr Tyr Arg Thr
65                  70                  75                  80

Thr Glu Phe Phe Thr Thr Lys Phe Ile Phe Ser Asn Thr Ser Lys Ser
            85                  90                  95

Leu Leu Leu Ala Ser Gly Lys Cys Gly Gln Cys Ala Arg Phe Ile Ile
            100                 105                 110

Arg Ser Val Ala Lys Val Gln Gly Ile Gln Glu Phe Leu Lys Ile Gly
            115                 120                 125

Glu Trp Thr Pro Ala Val Gly Leu Lys Met Thr His Lys Gln Phe Phe
            130                 135                 140

Pro Gly Ile Met Gly Asn Leu Gly Gly Ile Arg Leu Thr Ile Gly Val
145                 150                 155                 160

Ile Asn Asp Pro Pro Met Ser Val Val Glu Met Ser Pro Asp Arg Lys
            165                 170                 175

Thr Val Lys Asn Val Thr Gly Thr Met Ala Asp Met Val Glu Ala Leu

```
            180                 185                 190
Ala Lys Gly Leu Asn Phe Thr Tyr Thr Trp Lys Val Pro Lys Glu Glu
            195                 200                 205

Ile Pro Gly Ser Lys Glu Asn Gly Asn Trp Asn Gly Leu Ile Gly Met
            210                 215                 220

Leu Ala Thr Gly Glu Ala Asp Leu Gly Ala Tyr Gly Phe Ser Val Thr
225                 230                 235                 240

Lys Glu Arg Ser Glu Val Val Asn Phe Thr Ser Ala Tyr Asp Glu Ser
                245                 250                 255

Pro Tyr Lys Ile Leu Val Pro Lys Pro Arg Ala Asn Tyr Lys Tyr Leu
            260                 265                 270

Phe Leu Asp Pro Phe Thr Trp Asp Thr Trp Val Ala Leu Val Ser
            275                 280                 285

Leu Val Leu Ile Gly Pro Ile Leu Trp Gly Ile His Cys Ala Ser Pro
            290                 295                 300

Phe Tyr Asp Tyr His Gly Leu Arg Asp Asn Lys Gly Leu Phe Leu Leu
305                 310                 315                 320

Gln Asn Cys Glu Trp Tyr Cys Phe Gly Ala Ile Ile Gln Gln Gly Gly
                325                 330                 335

Ile His Leu Pro Glu Ala Ile Ser Gly Arg Ile Leu Val Gly Phe Trp
            340                 345                 350

Trp Leu Phe Val Ile Val Thr Leu Thr Thr Tyr Ser Gly Asn Leu Val
            355                 360                 365

Ala Asp Leu Thr Phe Pro Lys Ile Arg Asn Pro Val Asp Ser Val Glu
370                 375                 380

Asn Leu Val Ala His Arg Gly Tyr Met Arg Trp Gly Ala Phe Lys Gly
385                 390                 395                 400

Gln Ala Val Phe Glu Leu Leu Lys Ser Gln Glu Gln Gly Pro Leu Lys
                405                 410                 415

Val Leu Ser Asp Arg Met Asn Val Phe Glu Pro Asn His Glu Met Trp
            420                 425                 430

Val Leu Asp Gln Val Arg Leu Gly Tyr Met Ala Leu Ile Gly Ser Glu
            435                 440                 445

Val Asn Met Phe His Tyr Leu Gly Arg Glu Leu Asn Arg Thr Gly Glu
            450                 455                 460

Cys Asp Phe Ala Val Ala Arg Gly Glu Val Ile Arg Asp Val Lys Ser
465                 470                 475                 480

Leu Ala Val Ala Pro Asn Phe Ala Phe Leu Glu Arg Leu Asn Asn Glu
                485                 490                 495

Pro Asp His Asp Gly Arg Pro Pro Arg Leu Lys Arg Leu Val
            500                 505                 510

Glu Ser Gly Leu Val Met Arg Trp Lys Lys Tyr Trp Pro Gln Asp
            515                 520                 525

Asn Glu Cys Thr Val Glu Ser Lys Pro Gln Ala Gly Asp Ile Arg Lys
            530                 535                 540

Ile Thr Leu Arg His Met Thr Gly Ser Phe Trp Val Leu Gly Val Gly
545                 550                 555                 560

Phe Phe Ser Ser Phe Ala Ala Leu Phe Val Glu Phe Arg Arg Lys
                565                 570                 575

Arg Glu Leu Thr Ala Pro Pro Thr His Lys Pro Pro Thr Val Ile His
            580                 585                 590

Thr Lys Ser Pro Phe Phe Thr Arg Thr Glu Tyr Ser Gly Lys Asp Thr
            595                 600                 605
```

```
Leu Thr Thr Asp Arg Phe Ala Thr Asp Tyr Gly Gly Arg Gly Pro Arg
            610                 615                 620

Asp Asn Ala Gly Phe Ala Phe Ser Pro Pro Asn Ser Pro Phe Arg Tyr
625                 630                 635                 640

Asn Gly Tyr Pro Asn Asn Arg Ser Asp Leu Ile Pro Tyr Asn Tyr Pro
            645                 650                 655

Ala Arg Arg

<210> SEQ ID NO 19
<211> LENGTH: 656
<212> TYPE: PRT
<213> ORGANISM: Heliconius melpomene

<400> SEQUENCE: 19

Met Lys Leu Trp Met Val Ala Cys Val Ile Trp Ser Ser Leu Gln Tyr
 1               5                  10                  15

Gly Gln Ala Glu Asp Phe Pro Ser Leu Ile Thr Ala Asn Ala Ser Ile
            20                  25                  30

Ala Val Val Leu Asp Arg Gln Phe Leu Gly Asp Glu Tyr Gln Thr Thr
        35                  40                  45

Leu Asp Glu Ile Lys Asp Tyr Ile Lys Glu Leu Ala Arg Val Glu Leu
50                  55                  60

Lys His Gly Gly Val Asn Val His Tyr Phe Ser Trp Thr Ala Ile Ser
65                  70                  75                  80

Leu Lys Lys Gly Tyr Leu Ala Val Phe Ser Val Ala Ser Cys Glu Gly
                85                  90                  95

Thr Trp Ser Leu Phe Gln Lys Thr Glu Glu Glu Leu Leu Leu Leu Phe
            100                 105                 110

Ala Leu Thr Glu Val Asp Cys Pro Arg Leu Pro Thr Ser Ala Ile
        115                 120                 125

Thr Val Thr Tyr Ala Ala Val Gly Gln Glu Leu Pro Gln Leu Phe Leu
    130                 135                 140

Asp Leu Arg Thr Gln Lys Gly Met Asn Trp Lys Ser Ala Ile Ile Leu
145                 150                 155                 160

His Asp Asp Thr Leu Asn Leu Cys Tyr Ile Phe Leu Leu Leu Arg Arg
                165                 170                 175

Leu Ile His Lys Lys Gln Glu Asn Leu Glu Ser Leu Ser Phe Tyr Leu
            180                 185                 190

Leu Asn His Asp Asp Val Pro Ser Ile Ser Val Thr Val Phe Lys
        195                 200                 205

Met Lys His Glu Val Asn Glu Tyr Leu Arg Arg Lys Glu Val Asn Arg
    210                 215                 220

Val Leu Ser Lys Leu Pro Val Lys Tyr Ile Gly Glu Lys Phe Ile Ala
225                 230                 235                 240

Ile Val Thr Thr Ala Val Met Ala Thr Ile Ala Glu Ala Ala Arg Glu
                245                 250                 255

Leu Leu Met Ser His Thr Gln Ala Gln Trp Leu Tyr Val Ile Ser Asp
            260                 265                 270

Thr Ser Gly Arg Gly Asn Phe Ser Asn Leu Ile Asn Asp Leu Tyr Glu
        275                 280                 285

Gly Glu Asn Val Ala Tyr Ile Tyr Asn Val Thr Glu Asn Asp Glu Gly
    290                 295                 300

Cys Lys Asn Gly Leu Ile Cys Tyr Ala Lys Glu Met Met Ser Ala Phe
305                 310                 315                 320
```

Ile Ser Glu Leu Asp Ser Ala Val Gln Glu Glu Phe Asp Val Ala Ala
            325                 330                 335

Gln Gln Tyr Ile Met Val Lys Ser Glu Cys Gly Asn Cys Ser Trp Trp
        340                 345                 350

Arg Ala Leu Ala Ala Asp Thr Trp Gly Ala Thr Tyr Arg Glu Lys Thr
    355                 360                 365

Tyr Glu Thr Lys Arg Asn Val Thr Ser Ile Val Ile Glu His Val Glu
370                 375                 380

Leu Leu Asn Thr Trp Leu Cys Leu Gly Phe Ala Val Ile Leu Met Gly
385                 390                 395                 400

Pro Thr Leu Tyr Ile Ile His Arg Leu Ser Pro Tyr Tyr Asp Ala Met
                405                 410                 415

Glu Ile Thr Arg Glu Gly Gly Leu Ser Thr Ile His Asn Cys Leu Trp
            420                 425                 430

Tyr Ile Tyr Gly Ala Leu Leu Gln Gln Gly Gly Met Tyr Leu Pro Arg
        435                 440                 445

Ala Asp Ser Gly Arg Leu Val Val Gly Thr Trp Trp Ile Val Val Leu
    450                 455                 460

Val Val Val Thr Thr Tyr Ser Gly Asn Leu Val Ala Phe Leu Thr Phe
465                 470                 475                 480

Pro Lys Leu Glu Ile Pro Val Thr Thr Ile Ser Glu Leu Leu Glu Ser
                485                 490                 495

Lys Thr Tyr Thr Trp Ser Ile Ser Lys Gly Ser Phe Leu Glu Met Gln
            500                 505                 510

Leu Lys Ser Ser Asp Glu Pro Lys Tyr Lys Ala Leu Val Lys Gly Ala
        515                 520                 525

Glu Val Thr Gly Gly Ile Asn Val Val Glu Gly Ser Leu Val Ser Gly
    530                 535                 540

Ser Glu Ile Leu Asn Arg Val Arg Asn Gln Arg His Ala Leu Ile Asp
545                 550                 555                 560

Trp Arg Leu Arg Leu Ser Tyr Leu Met Arg Ala Glu Thr Val Lys Thr
                565                 570                 575

Asp Thr Cys Asp Phe Ala Leu Ser Ala Glu Glu Phe Met Asp Glu Gln
            580                 585                 590

Ile Ala Met Ile Val Pro Ala Gly Ser Pro Leu Asn Arg Met His Lys
        595                 600                 605

Ala Gly Leu Ile Thr Lys Trp Leu Ser Ala Tyr Leu Pro Lys Arg Asp
    610                 615                 620

Arg Cys Trp Lys Thr Ser Thr Val Glu Val Asn Asn His Thr Val
625                 630                 635                 640

Asn Leu Ser Asp Met Gln Gly Ser Phe Phe Val Leu Phe Leu Glu Lys
                645                 650                 655

<210> SEQ ID NO 20
<211> LENGTH: 817
<212> TYPE: PRT
<213> ORGANISM: Manduca sexta

<400> SEQUENCE: 20

Met Arg Leu Lys Leu Val Gly Phe Leu Cys Leu Val Cys Arg Val Ser
 1               5                  10                  15

Gly Glu Glu Phe Pro Ser Leu Ile Thr Ala Asn Ala Ser Ile Ala Val
            20                  25                  30

Val Leu Asp Arg Gln Tyr Leu Gly Asp Lys Tyr Gln Ala Val Leu Asp

```
               35                  40                  45
Glu Leu Lys Asp Tyr Ile Lys Glu Leu Ala Arg Val Asp Leu Thr His
 50                  55                  60
Gly Gly Val Val Val His Tyr Tyr Ser Trp Thr Ser Ile Ser Leu Asn
 65                      70                  75                  80
Lys Gly Phe Leu Ala Val Phe Ser Val Ala Ser Cys Leu Asp Thr Trp
                     85                  90                  95
Asp Leu Phe Ser Arg Thr Glu Glu Glu Leu Leu Leu Phe Ala Leu
                100                 105                 110
Thr Glu Val Asp Cys Pro Arg Leu Pro Leu Arg Ser Ala Ile Thr Val
                115                 120                 125
Thr Tyr Ala Glu Ala Gly Glu Leu Pro Gln Leu Leu Leu Asp Leu
130                 135                 140
Arg Thr Ser Asn Ala Phe Lys Trp Lys Ser Ala Val Ile Leu His Asp
145                 150                 155                 160
Asp Thr Leu Asn Arg Asp Met Val Ser Arg Val Val Gln Ser Leu Thr
                165                 170                 175
Ser Gln Ile Asp Asp Glu Ser Ala Ser Pro Val Ser Val Ser Val Phe
                180                 185                 190
Lys Met Lys His Glu Ile Asn Glu Tyr Leu Arg Lys Lys Glu Met His
                195                 200                 205
Arg Val Leu Ser Lys Leu Pro Val Lys Thr Val Gly Glu Asn Phe Ile
210                 215                 220
Ala Ile Val Thr Ser Asp Val Met Thr Thr Met Ala Asp Thr Ala Arg
225                 230                 235                 240
Glu Leu Leu Met Ser His Thr Met Ala Gln Trp Leu Tyr Val Ile Ser
                245                 250                 255
Asp Thr Asn Ile His Asn Ser Asn Leu Ser Gly Leu Ile Arg Ala Leu
                260                 265                 270
Tyr Glu Gly Glu Asn Val Ala Phe Ile Tyr Asn Gln Thr Asp Asn Ser
                275                 280                 285
Pro Asp Cys Lys Asn Gly Ile Met Cys Tyr Cys Gln Glu Ile Met Asn
290                 295                 300
Ala Phe Ile Ser Ala Leu Asp Ala Ala Ile Gln Asp Glu Phe Asp Val
305                 310                 315                 320
Ala Ala Gln Val Ser Asp Glu Glu Trp Glu Ala Ile Arg Pro Asn Lys
                325                 330                 335
Ile Gln Arg Arg Asp Met Leu Leu Lys His Met Gln Gln His Ile Ser
                340                 345                 350
Thr Lys Ser Arg Cys Gly Asn Cys Thr Thr Trp Arg Ala Leu Ala Ala
                355                 360                 365
Asp Thr Trp Gly Ala Thr Tyr Arg His Phe Thr Glu Asp Ile Leu
                370                 375                 380
Lys Glu Asn Asp Asn Gly Thr Glu Ala Thr Gly Val Ile Glu Lys Val
385                 390                 395                 400
Thr Leu Leu Asp Val Gly Phe Trp Arg Pro Ile Asp Ala Met Thr Phe
                405                 410                 415
Phe Asp Val Leu Phe Pro His Val Gln His Gly Phe Arg Gly Lys Glu
                420                 425                 430
Leu Pro Val Ile Thr Tyr His Asn Pro Pro Trp Thr Ile Leu His Thr
                435                 440                 445
Asn Glu Ser Gly Ala Ile Val Lys Tyr Gly Gly Leu Met Phe Asp Ile
450                 455                 460
```

```
Val Asn Gln Leu Ala Lys Asn Lys Asn Phe Thr Ile Lys Ile Leu Leu
465                 470                 475                 480

Pro Gly Asn Val Lys Asn Glu Ile Ser Asn Glu Thr Asp Ala Leu His
                485                 490                 495

Ser Arg Arg Ala Met Leu Ala Leu Ala Ala Ile Ala Lys Gly Gln Ala
            500                 505                 510

Ala Leu Ala Ala Ala Ser Phe Thr Ile Leu Pro Asn Pro Thr Pro Gly
        515                 520                 525

Ile Asn Tyr Thr Ile Pro Val Ser Thr Gln Pro Tyr Ala Phe Leu Val
    530                 535                 540

Ala Arg Pro Arg Ala Leu Ser Arg Ala Met Leu Phe Phe Leu Pro Phe
545                 550                 555                 560

Thr Ala Asp Thr Trp Leu Cys Leu Gly Leu Ala Val Ile Thr Met Gly
                565                 570                 575

Pro Val Leu Tyr Ile Ile His Arg Met Ser Pro Tyr Tyr Glu Ala Met
            580                 585                 590

Lys Ile Thr Arg Gln Gly Gly Leu Ala Thr Ile His Asn Cys Leu Trp
        595                 600                 605

Tyr Ile Tyr Gly Ala Leu Leu Gln Gln Gly Gly Met Tyr Leu Pro Arg
    610                 615                 620

Ala Asp Ser Gly Arg Leu Val Val Gly Thr Trp Trp Leu Val Val Leu
625                 630                 635                 640

Val Val Val Thr Thr Tyr Ser Gly Asn Leu Val Ala Phe Leu Thr Phe
                645                 650                 655

Pro Lys Leu Glu Ile Pro Val Thr Ser Ile Ala Glu Leu Ile Glu Asn
            660                 665                 670

Arg Ala Leu Tyr Thr Trp Ser Ile Asn Lys Gly Ser Tyr Leu Glu Met
        675                 680                 685

Glu Leu Lys Asn Ser Glu Glu Pro Lys Tyr Lys Ala Leu Leu Lys Gly
    690                 695                 700

Ala Glu Leu Thr Lys Pro Thr His Ser Ser Glu Thr Asn Ala His Ala
705                 710                 715                 720

Gly Val Glu Asp Phe Met Asp Glu Arg Val Ala Met Ile Val Pro Ala
                725                 730                 735

Gly Ser Pro Tyr Leu Ala Leu Leu Asn Lys Glu Ile Asn Arg Met His
            740                 745                 750

Lys Ala Gly Leu Ile Thr Lys Trp Leu Ser Ala Tyr Leu Pro Lys Arg
        755                 760                 765

Asp Arg Cys Tyr Ser Met Ser Ser Met Ala Ala Glu Val Asn Asn His
    770                 775                 780

Thr Val Asn Leu Asn Asp Met Gln Gly Ser Phe Phe Val Leu Leu Leu
785                 790                 795                 800

Gly Asp Phe Phe Phe Ile Val Leu Asn Asp Glu Thr Ser Leu Pro Phe
                805                 810                 815

Val

<210> SEQ ID NO 21
<211> LENGTH: 383
<212> TYPE: PRT
<213> ORGANISM: Mayetiola destructor

<400> SEQUENCE: 21

Met Met Leu Arg Ala His Ser Cys Leu Thr Leu Cys Ala Val Leu Val
 1               5                  10                  15
```

Val Ser Ile Asn Gln Ser Glu Ala Asn Asp Phe Pro Ser Leu Leu Val
            20                  25                  30

Ala Asn Ala Thr Met Gly Val Ile Ile Asp His Gly Tyr Leu Gly Asp
         35                  40                  45

Arg Tyr Glu Ser Thr Leu Asp Thr Met Lys Gln Ile Ile Glu Arg Val
 50                  55                  60

Ile Arg Glu Asp Leu Arg Gly Ala Gly Leu Phe Val Lys Tyr Phe Ser
 65                  70                  75                  80

Trp Ser Arg Ile Asn Phe Asn Lys Asp Leu Thr Val Ile Phe Ser Ile
                 85                  90                  95

Ala Ser Cys Lys Ser Thr Trp Glu Thr Phe Phe His Ala Arg Arg Glu
            100                 105                 110

Arg Leu Leu Leu Leu Ala Ile Thr Asp Pro Asp Cys Pro Arg Leu Pro
        115                 120                 125

Ser His Glu Ala Leu Thr Ile Pro Arg Ile Lys Val Gly Met Glu Leu
    130                 135                 140

Pro Gln Ile Ile Leu Asp Ile Arg Thr Ser Lys Ser Val Asn Trp Lys
145                 150                 155                 160

Thr Val Ala Ile Leu Tyr Asp Asp Ile Phe Asp Arg Asp Thr Ile Ser
                165                 170                 175

Arg Val Ala Thr Ala Leu Thr Val Glu Ser Ser Ser Met Ala Met Ser
            180                 185                 190

Ile Ser Leu Leu Lys Leu Asn Ser Ser Thr Asp Ser Phe Glu Arg Arg
        195                 200                 205

Glu Asn Ile Lys Arg Ser Leu Leu Ser Phe Pro Asn Arg Phe Ile Gly
    210                 215                 220

Lys Asn Tyr Leu Val Val Ala Thr Ile Pro Thr Thr Ile Leu Glu Ile
225                 230                 235                 240

Ala Thr Glu Met Asn Met Ile Asp Ser Lys Ser Gln Trp Leu Phe Leu
                245                 250                 255

Val Ser Asn Pro Lys Lys Thr Asn Ile Ser Thr Leu Leu Pro Phe Ile
            260                 265                 270

Lys Glu Gly Gly Asn Val Ala Ile Ala Thr Asn Thr Ala Asn Asp
        275                 280                 285

Asp Asn Asn Cys Ala Lys Thr Asp Glu Cys Leu Tyr His Glu Leu Ile
    290                 295                 300

Lys Tyr Val Ala Leu Ser Leu Ser Lys Leu Leu Arg Glu Glu Glu Ala
305                 310                 315                 320

Ile Tyr Gly Gln Ile Ser Asp Glu Glu Trp Glu Ala Ile Arg Leu Thr
                325                 330                 335

Lys Arg Glu Arg Arg Asp Ser Met Leu Glu Tyr Ile Gln Asp Lys Leu
            340                 345                 350

Lys Asn Ser Pro Ile Cys Thr Pro Cys Val Lys Trp Lys Phe Glu Ala
        355                 360                 365

Ala Glu Thr Trp Gly Leu Arg Phe Asn Asn Ile Gln Gly Phe Ala
    370                 375                 380

<210> SEQ ID NO 22
<211> LENGTH: 693
<212> TYPE: PRT
<213> ORGANISM: Atta cephalotes

<400> SEQUENCE: 22

Met Trp Ser Leu His Asp Ala Ala Arg Lys Glu Glu Leu Val His Leu

-continued

```
  1               5                  10                 15
Ala Ile Thr Asp Glu Asp Cys Pro Arg Leu Pro Asp Ser Glu Gly Val
                 20                 25                 30

Ser Ile Pro Leu Ile Leu Pro Gly Lys Glu Leu Ser Gln Ile Phe Phe
                 35                 40                 45

Asp Met Arg Ser Ile Asp Ala Leu Leu Trp Asn Asn Val Asn Ile Leu
 50                                 55                 60

His Asp Asp Thr Phe Asp Arg Asp Thr Ile Gly Arg Val Thr Lys Ala
 65                                 70                 75                 80

Leu Ser Thr Ser Leu Pro Asn Lys Lys Phe Asn Leu Val Ser Arg Thr
                 85                 90                 95

Leu Phe Thr Phe Lys His Ala Asn Ser Glu Arg Asn Arg Arg Tyr Asp
                100                105                110

Ile Lys Asn Met Leu Glu Ser Phe His Val Glu Gln Leu Gly Lys Cys
                115                120                125

Phe Leu Val Ile Val Thr Ile Asp Thr Ala Ala Asp Val Met Glu Val
130                                135                140

Ala Lys Ser Leu Asn Met Ala Leu Pro Asp Ser Gln Trp Leu Tyr Ile
145                                150                155                160

Ile Thr Asp Ser Val Val Arg Asn Ser Thr Asn Ile Thr Ser Phe Ala
                                   165                170                175

Asp Leu Leu Thr Glu Gly Ser Asn Val Ala Phe Ile Tyr Asn Val Thr
                180                185                190

Asp Ser Asp Thr Tyr Cys Asn Glu Leu Val Ser Ala Leu Ala Asn Ala
                195                200                205

Leu Lys Met Ser Leu Met Thr Glu Ile Glu Leu Tyr Ser His Met Thr
210                                215                220

Asp Glu Glu Phe Glu Leu Ile Arg Leu Asn Lys Gln Glu Arg Arg Gln
225                                230                235                240

Glu Ile Leu Lys Ser Ile Lys Ile Gln Leu Ile Glu Asp Thr Phe Ser
                245                250                255

Thr Asn Gly Val Cys Gly Lys Cys Leu Phe Trp Arg Phe Ala Ser Ala
                260                265                270

Ile Thr Trp Gly Asn Phe Phe Ile His Gly Lys Asn Val Ala His Leu
                275                280                285

Ile Glu Ser Gly Thr Trp Ile Pro Val Leu Gly Ala Asn Phe Thr Asp
                290                295                300

Val Leu Phe Pro His Val Met His Gly Phe Arg Gly Ile Asn Val Pro
305                                310                315                320

Ile Ala Thr Tyr His Asn Pro Pro Trp Gln Thr Ile Ser Leu Thr Asn
                                   325                330                335

Ser Gly Glu Lys Glu Tyr Gly Gly Leu Leu Phe Asp Val Val Arg Tyr
                340                345                350

Leu Gly Lys Lys Leu Asn Phe Thr Tyr Asn Val Leu Ser Pro Ala Ile
                355                360                365

Asn Arg Thr Lys Phe Thr Arg Asn Ala Thr Val Ala Asn Val Val Leu
                370                375                380

Thr Ser Thr Thr Arg Glu Met Pro Ser Gln Ile Ile Asp Met Ile Leu
385                                390                395                400

Glu Lys Lys Val Leu Phe Ala Ala Cys Ala Tyr Thr Val Asn Asp His
                                   405                410                415

Gly Arg Lys Gln Ile Asn Phe Thr Leu Pro Ile Phe Met Gln Thr Tyr
                420                425                430
```

Ser Phe Leu Thr Ala Lys Pro Gly Gln Leu Ser Arg Ala Leu Leu Phe
            435                 440                 445

Thr Ala Pro Phe Thr Lys Glu Thr Trp Ala Cys Leu Ala Ala Ser Ile
450                 455                 460

Ile Ile Met Gly Pro Val Leu Tyr Leu Ile His Lys Tyr Ser Pro Ser
465                 470                 475                 480

Ser Thr Lys Thr Ser Gly Leu Asn Ser Cys Trp Gln Cys Val Trp Tyr
            485                 490                 495

Ile Tyr Gly Ala Leu Leu Gln Gln Gly Gly Met Tyr Leu Pro His Ser
            500                 505                 510

Asp Ser Ala Arg Leu Leu Val Gly Val Trp Trp Leu Val Val Met Val
            515                 520                 525

Leu Val Ala Thr Tyr Ser Gly Ser Leu Val Ala Phe Leu Thr Phe Pro
            530                 535                 540

Asn Thr Asp Thr Ala Ile Leu Thr Val Asp Asp Leu Ile Ala His Lys
545                 550                 555                 560

Asn Lys Leu Thr Trp Gly Phe Pro Asn Gly Ser Phe Leu Glu Glu Tyr
            565                 570                 575

Leu Lys Asn Val Glu Glu Lys Tyr His Ile Leu Leu Glu Arg Ala
            580                 585                 590

Ile Ile His Asn Ala Thr Gln Glu Ala Asp Met Val Glu Gln Ile Lys
            595                 600                 605

Met Gly Lys His Val Leu Ile Asp Trp Arg Ser Thr Leu Arg Leu His
            610                 615                 620

Arg Met His Glu Ser Gly Leu Met Asn Lys Trp Ile Ala Glu Gln Ile
625                 630                 635                 640

Pro Val Lys Asp Lys Cys Ser Asp Ser Phe Ala Asn Gln Val Val Glu
            645                 650                 655

Glu Arg Lys Val Asn Val Thr Asp Met Gln Gly Ile Phe Phe Val Leu
            660                 665                 670

Phe Met Gly Asn Val Phe Phe Ala Ile Pro Ser Phe Gly Glu Cys Asn
            675                 680                 685

Asn Ile Ser Trp Glu
            690

<210> SEQ ID NO 23
<211> LENGTH: 728
<212> TYPE: PRT
<213> ORGANISM: Acromyrmex echinatior

<400> SEQUENCE: 23

Met Asn Met Ile Ser Phe Phe Phe Leu Ala Trp Ile Leu Asn Ser Gly
1               5                   10                  15

Asp Ala Phe Ser Asp Phe Pro Ser Leu Met Ser Thr Asn Ala Ser Met
            20                  25                  30

Ala Val Val Ile Asp Lys Ser Phe Phe Asp Asn Lys Ala Glu Tyr Arg
            35                  40                  45

Asp Thr Val Lys Asn Ile Tyr Asn Phe Ile Thr Ala Ile Thr Arg Lys
50                  55                  60

Glu Ile His Met Ala Asp Ile Asp Val His Ile Phe Glu Gly Thr Lys
65                  70                  75                  80

Val His Asn Leu Arg Asp Phe Thr Val Leu Leu Ser Val Thr Ser Cys
            85                  90                  95

Tyr Gln Met Trp Ser Leu His Asp Ala Ala Arg Lys Glu Asp Leu Val

-continued

```
                100                 105                 110
His Leu Ala Ile Thr Asp Gln Asp Cys Pro Arg Leu Pro Asp Ser Glu
            115                 120                 125
Gly Val Ser Ile Pro Leu Ile Leu Pro Gly Lys Glu Leu Ser Gln Ile
        130                 135                 140
Phe Phe Asp Met Arg Ser Ile Asp Ala Leu Leu Trp Asn Asn Val Asn
145                 150                 155                 160
Ile Leu His Asp Asp Thr Phe Asp Arg Asp Thr Ile Gly Arg Val Thr
                165                 170                 175
Lys Ala Leu Ser Ile Ser Leu Pro Asn Lys Lys Phe Asn Leu Val Ser
            180                 185                 190
Arg Ala Leu Phe Ala Phe Lys His Ala Asn Ser Glu Arg Asn Arg Arg
        195                 200                 205
Tyr Tyr Ile Lys Asn Met Leu Glu Ser Phe His Val Glu Gln Leu Gly
    210                 215                 220
Lys Cys Phe Leu Val Ile Val Thr Ile Asp Thr Ala Ala Asp Val Met
225                 230                 235                 240
Glu Val Ala Lys Ser Leu Asn Met Ala Leu Pro Asp Ser Gln Trp Leu
                245                 250                 255
Tyr Ile Ile Thr Asp Ser Val Val Arg Asn Ser Thr Asn Ile Thr Ser
            260                 265                 270
Phe Ile Asp Leu Leu Thr Glu Gly Ser Asn Val Ala Phe Ile Tyr Asn
        275                 280                 285
Met Thr Asp Ser Asp Thr Tyr Cys Asn Val Ser Leu Lys Cys Tyr Ile
    290                 295                 300
Gln Glu Leu Val Ser Thr Leu Ala Asn Ala Leu Lys Met Ser Leu Met
305                 310                 315                 320
Thr Glu Ile Glu Leu Tyr Ser His Met Thr Glu Glu Phe Glu Leu
                325                 330                 335
Ile Arg Leu Asn Lys Gln Glu Arg Arg Gln Glu Ile Leu Lys Ser Ile
            340                 345                 350
Lys Ile Gln Leu Ile Glu Asp Thr Phe Ser Thr Ser Gly Val Cys Gly
        355                 360                 365
Lys Cys Leu Phe Trp Arg Phe Ala Ser Ala Ile Thr Trp Gly Asn Phe
    370                 375                 380
Phe Val Arg Gly Lys Asn Val Ala His Leu Ile Asp Ser Gly Thr Trp
385                 390                 395                 400
Ile Pro Val Leu Gly Ala Asn Phe Thr Asp Val Leu Phe Pro His Val
                405                 410                 415
Val His Gly Phe Arg Gly Ile Arg Ile Pro Ile Ala Thr Tyr His Asn
            420                 425                 430
Pro Pro Trp Gln Thr Ile Ser Leu Thr Asn Ser Gly Glu Lys Glu Tyr
        435                 440                 445
Gly Gly Leu Leu Phe Asp Val Val Lys Tyr Leu Gly Lys Lys Leu Asn
    450                 455                 460
Phe Thr Tyr Asn Val Leu Ser Pro Ala Ile Asn Gln Thr Lys Phe Thr
465                 470                 475                 480
Arg Asn Ala Thr Val Ala Asn Val Leu Thr Ser Thr Thr Arg Glu
                485                 490                 495
Met Pro Ser Gln Ile Ile Asp Met Ile Leu Glu Lys Lys Val Leu Leu
            500                 505                 510
Ala Ala Cys Ala Tyr Thr Val Asn Asp Tyr Gly Lys Lys Gln Ile Asn
        515                 520                 525
```

-continued

```
Phe Thr Leu Pro Ile Phe Ile Gln Thr Tyr Ser Phe Leu Thr Ser Lys
            530                 535                 540

Pro Gly Gln Leu Ser Arg Ala Leu Leu Phe Thr Ala Pro Phe Thr Lys
545                 550                 555                 560

Glu Thr Trp Ala Cys Val Ala Ala Ser Ile Ile Met Gly Pro Ile
                565                 570                 575

Leu Tyr Leu Ile His Lys Tyr Ser Pro Ser Ser Thr Lys Thr Ser Gly
            580                 585                 590

Leu Asn Ser Cys Trp Gln Cys Val Trp Tyr Ile Tyr Gly Ala Leu Leu
            595                 600                 605

Gln Gln Gly Gly Met Tyr Leu Pro His Ser Asp Ser Ala Arg Leu Leu
            610                 615                 620

Val Gly Val Trp Trp Leu Val Val Met Val Leu Val Ala Thr Tyr Ser
625                 630                 635                 640

Gly Ser Leu Val Ala Phe Leu Thr Phe Pro Asn Thr Asp Ile Ala Ile
                645                 650                 655

Leu Thr Val Asn Asp Leu Ile Ala His Lys Asn Lys Leu Thr Trp Gly
            660                 665                 670

Phe Pro Asn Gly Ser Phe Leu Glu Glu Tyr Leu Lys Asn Ala Glu Glu
            675                 680                 685

Glu Lys Tyr His Ile Leu Leu Glu Arg Ala Ile Ile His Asn Ala Thr
690                 695                 700

Gln Glu Ala Asp Met Ile Glu Gln Ile Lys Met Gly Lys His Val Leu
705                 710                 715                 720

Ile Asp Trp Arg Ser Thr Leu Arg
                725

<210> SEQ ID NO 24
<211> LENGTH: 726
<212> TYPE: PRT
<213> ORGANISM: Solenopsis invicta

<400> SEQUENCE: 24

Cys Leu Asn Leu Ala Ala Val Ile Ile Asp Lys Asn Phe Phe Asp Asp
1               5                   10                  15

Lys Val Glu Tyr Arg Asp Val Met Lys Asn Ile His Gly Leu Ile Ala
            20                  25                  30

Ser Ile Thr Arg Glu Glu Ile His Thr Ile Asp Ile Asp Ile Gln Ile
            35                  40                  45

Ile Arg Gly Thr Lys Ile Asn Phe Arg Asp Tyr Thr Val Leu Leu Ser
50                  55                  60

Val Thr Thr Cys His Gln Met Trp Ser Leu His Asp Ala Ala Arg Lys
65                  70                  75                  80

Glu Glu Leu Ile His Leu Ala Ile Thr Asp Glu Asp Cys Pro Arg Leu
                85                  90                  95

Pro Asp Thr Glu Gly Val Ser Ile Pro Ile Leu Pro Gly Gln Glu
            100                 105                 110

Leu Ala Gln Ile Phe Phe Asp Ile Arg Ser Thr Asp Ala Leu Leu Trp
            115                 120                 125

Asn Asn Val Asn Ile Ile His Asp Asp Thr Phe Asp Arg Asp Thr Ile
130                 135                 140

Gly Arg Val Thr Lys Ala Leu Ser Thr Ala Leu Pro Asn Lys Lys Phe
145                 150                 155                 160

Asn Met Val Ser Arg Ala Leu Phe Thr Phe Lys Tyr Ser Asp Ser Ala
```

-continued

```
            165                 170                 175
Thr Thr Arg Arg Tyr Tyr Ile Lys Asp Ser Leu Glu Asn Phe His Val
                180                 185                 190
Asp Gln Leu Gly Arg Cys Phe Leu Val Ile Val Thr Ile Asp Thr Ala
            195                 200                 205
Ser Asp Val Met Glu Val Thr Lys Thr Leu Asn Met Ala Leu Pro Asp
            210                 215                 220
Ser Gln Trp Leu Tyr Ile Ile Thr Asp Ser Val Val Arg Asn Ser Thr
225                 230                 235                 240
Asn Ile Thr Ile Leu Thr Asp Leu Leu Ser Glu Gly Ser Asn Met Ala
                245                 250                 255
Phe Ile Tyr Asn Ala Thr Asp Asn Asp Thr Tyr Cys Asn Val Ser Leu
                260                 265                 270
Lys Cys His Ile Gln Glu Leu Val Ala Ala Phe Val Asn Ala Leu Lys
                275                 280                 285
Ile Ser Leu Met Thr Glu Ile Glu Leu Phe Ser His Leu Ser Asp Glu
                290                 295                 300
Glu Phe Glu Leu Val Arg Leu Asn Lys Ala Glu Arg Arg Glu Ile
305                 310                 315                 320
Leu Lys Asn Ile Arg Ile Lys Leu Ile Asp Glu Asn Phe Ala Thr Gly
                325                 330                 335
Gly Val Cys Gly Lys Cys Leu Phe Trp Arg Phe Ala Ser Ala Ile Thr
                340                 345                 350
Trp Gly Asn Phe Phe Leu His Ser Lys Asn Val Ala His Leu Ile Glu
                355                 360                 365
Ser Gly Thr Trp Ile Pro Gly Leu Gly Leu Asn Leu Thr Asp Glu Ile
                370                 375                 380
Phe Pro His Val Val His Gly Phe Arg Gly Ile Ser Leu Pro Ile Ala
385                 390                 395                 400
Thr Tyr Asn Val Cys Lys Tyr Val Pro Phe Ser Leu Ser Thr Ile Lys
                405                 410                 415
Phe Val Arg Phe Asp Phe Phe Phe Gln Asn Pro Pro Trp Gln Thr Ile
                420                 425                 430
Ser Leu Asn Asn Ala Gly Glu Lys Glu Tyr Gly Gly Leu Val Phe Asp
                435                 440                 445
Val Ile Lys Tyr Leu Gly Lys Lys Leu Asn Phe Thr Tyr Thr Val Leu
                450                 455                 460
Thr Pro Ala Ser Asn Arg Ala Val Lys Phe Ile Arg Asn Glu Thr Ala
465                 470                 475                 480
Asp Val Val Leu Ala Ser Thr Thr Arg Glu Met Pro Pro Gln Ile Ile
                485                 490                 495
Asp Met Val Leu Glu Lys Lys Val Leu Leu Ala Ala Cys Ala Tyr Thr
                500                 505                 510
Val Asn Asn Phe Gly Arg Gly Lys Val Asn Phe Thr Leu Pro Ile Phe
                515                 520                 525
Met Gln Thr Tyr Ser Phe Met Thr Ala Lys Pro Gly Gln Leu Ser Arg
                530                 535                 540
Ala Leu Leu Phe Thr Ala Pro Phe Ala Lys Glu Thr Trp Ala Cys Leu
545                 550                 555                 560
Ala Ser Ser Ile Ile Ile Met Gly Pro Ile Leu Tyr Leu Ile Arg Lys
                565                 570                 575
Tyr Ser Pro Asp Asn Thr Glu Thr Ser Gly Leu Asn Ser Cys Trp Gln
                580                 585                 590
```

```
Cys Met Trp Tyr Val Tyr Gly Ala Leu Leu Gln Gln Val Pro Met Ile
        595                 600                 605

Leu Gly Gly Met Tyr Leu Pro His Ser Asp Ser Ala Arg Leu Leu Ile
610                 615                 620

Ala Val Trp Trp Leu Ile Val Met Val Val Ala Thr Tyr Ser Gly
625                 630                 635                 640

Ser Leu Val Ala Phe Leu Thr Phe Pro Asn Met Asp Ala Ala Ile Leu
                645                 650                 655

Thr Val Asp Asp Leu Ile Ala His Lys Asn Arg Ile Thr Trp Gly Phe
                660                 665                 670

Pro Asn Gly Ser Phe Leu Glu Glu Tyr Leu Lys Asn Ser Glu Glu Glu
                675                 680                 685

Lys Tyr His Ile Leu Leu Glu Arg Ser Ile His Asn Glu Thr Thr
        690                 695                 700

Ala Ser Lys Val Ile Glu Lys Val Lys Ala Gly Lys His Ala Leu Ile
705                 710                 715                 720

Asp Trp Arg Ser Thr Leu
                725

<210> SEQ ID NO 25
<211> LENGTH: 1497
<212> TYPE: PRT
<213> ORGANISM: Pogonomyrmex barbatus

<400> SEQUENCE: 25

Met Leu Gln Tyr Asp Leu Ser Leu Asp Met Ile Ser Ile Phe Phe Leu
1               5                   10                  15

Ala Trp Ile Leu Asn Ser Gly Asp Ala Phe Gly Asp Phe Pro Ser Leu
                20                  25                  30

Val Ser Ala Asn Thr Ser Met Ala Val Val Ile Asp Lys Ser Phe Phe
            35                  40                  45

Asp Asn Lys Ala Glu Tyr Arg Asp Ile Val Arg Asn Ile Tyr Asn Tyr
        50                  55                  60

Ile Ala Thr Val Thr Lys Glu Glu Thr Asn Thr Ile Asp Ile Asp Val
65                  70                  75                  80

His Ile Phe Arg Gly Thr Arg Val Asn Asn Leu Arg Asp Tyr Thr Val
                85                  90                  95

Leu Leu Ser Val Ala Thr Cys His Gln Met Trp Ser Leu His Asp Ala
            100                 105                 110

Ala Arg Lys Glu Glu Leu Val His Leu Ala Ile Thr Asp His Asp Cys
        115                 120                 125

Pro Arg Leu Pro Asp Ser Glu Gly Val Ser Ile Pro Leu Val Ser Pro
    130                 135                 140

Gly Glu Glu Leu Ser Gln Ile Ile Phe Asp Ile Arg Glu Ile Asp Ala
145                 150                 155                 160

Phe Ala Trp Thr Asn Val Asn Ile Leu His Asp Thr Phe Asp Arg
                165                 170                 175

Asp Thr Ile Asn Arg Val Thr Lys Ala Ile Ser Arg Ser Leu Pro Asn
            180                 185                 190

Lys Lys Phe Asn Leu Ile Ser Arg Ala Leu Phe Ala Phe Lys Asn Ala
        195                 200                 205

Asp Ser Glu Arg Ser Arg Arg Tyr Tyr Ile Lys His Val Leu Glu Asn
    210                 215                 220

Tyr Arg Val Asp Gln Leu Gly Arg Cys Phe Leu Val Ile Val Thr Ile
```

```
            225                 230                 235                 240
        Asp Ala Ala Asp Val Met Glu Val Ala Lys Ser Leu Asn Met Ala
                        245                 250                 255
        Leu Pro Asp Ser Gln Trp Leu Tyr Ile Ile Thr Asp Ser Val Met Arg
                        260                 265                 270
        Asn Ser Thr Asn Ile Thr Ser Phe Val Asn Leu Leu Thr Glu Gly Ser
                    275                 280                 285
        Asn Val Ala Phe Ile Tyr Asn Thr Thr Asp Ser Asp Thr Tyr Cys Asn
                290                 295                 300
        Val Ser Leu Lys Cys His Ile Gln Glu Leu Val Gly Ala Leu Ile Asn
        305                 310                 315                 320
        Ala Leu Lys Leu Ser Phe Met Ile Glu Ile Glu Leu Tyr Ser His Met
                        325                 330                 335
        Ser Asp Glu Glu Phe Glu Leu Ile Lys Leu Ile Glu Asp Thr Phe Ala
                        340                 345                 350
        Thr Gly Gly Val Cys Gly Lys Cys Leu Phe Trp Arg Leu Ala Ser Ala
                    355                 360                 365
        Ile Thr Trp Gly Asn Phe Phe Val His Gly Lys Asn Thr Ala His Leu
                370                 375                 380
        Ile Asp Ser Gly Thr Trp Met Pro Asn Leu Gly Ala Asn Leu Thr Gly
        385                 390                 395                 400
        Pro Ile Phe Pro His Val Val His Gly Phe Arg Gly Ile Ser Val Pro
                        405                 410                 415
        Ile Ala Thr Tyr His Asn Pro Pro Trp Gln Thr Ile Ser Leu Ser Asp
                        420                 425                 430
        Ser Gly Glu Lys Glu Tyr Gly Gly Leu Val Phe Asp Val Val Lys Tyr
                    435                 440                 445
        Leu Gly Arg Lys Leu Asn Phe Thr Tyr Ser Val Ile Ser Pro Ala Ser
                450                 455                 460
        Asn Arg Ile Val Lys Phe Thr Arg Asn Ala Thr Thr Asp Met Ile Leu
        465                 470                 475                 480
        Thr Ser Thr Thr Arg Glu Met Pro Ser Gln Ile Ile Asp Met Ile Leu
                        485                 490                 495
        Glu Lys Lys Ile Leu Leu Ala Ala Cys Ala Tyr Thr Val Asn Gly Lys
                        500                 505                 510
        Gly Lys Gly His Ile Asn Phe Thr Leu Pro Ile Phe Met Gln Thr Tyr
                    515                 520                 525
        Ser Phe Leu Thr Ala Lys Pro Ser Gln Leu Ser Arg Ala Leu Leu Phe
                530                 535                 540
        Thr Ala Pro Phe Ala Lys Glu Thr Trp Ala Cys Leu Ala Ala Ser Ile
        545                 550                 555                 560
        Ile Ile Met Gly Pro Ile Leu Tyr Leu Ile His Lys Tyr Ser Pro Ser
                        565                 570                 575
        Asn Thr Arg Lys Ser Gly Leu Asn Ser Ser Trp Gln Cys Ile Trp Tyr
                        580                 585                 590
        Val Tyr Gly Ala Leu Leu Gln Gln Gly Gly Met Tyr Leu Pro His Ser
                    595                 600                 605
        Asp Ser Ala Arg Leu Met Val Ala Val Trp Trp Leu Val Val Met Val
                610                 615                 620
        Leu Val Ala Thr Tyr Ser Gly Ser Leu Val Ala Phe Leu Thr Phe Pro
        625                 630                 635                 640
        Asn Met Asp Ile Thr Ile Leu Thr Val Glu Asp Leu Ile Thr His Lys
                        645                 650                 655
```

```
Asp Arg Leu Thr Trp Gly Phe Pro Asn Gly Ser Phe Leu Glu Glu Tyr
        660                 665                 670

Leu Lys Asn Ala Glu Glu Lys Tyr His Thr Leu Leu Glu Lys Ala
        675                 680                 685

Ile Ile His Asn Ala Thr Gln Glu Ala Glu Val Ile Lys Lys Val Lys
        690                 695                 700

Ala Gly Lys His Ala Leu Ile Asp Trp Arg Ser Thr Leu Arg Ile Thr
705                 710                 715                 720

Ile Thr Met His Cys Pro Ser Arg Phe Leu Met Arg Asn Asp Met Leu
                    725                 730                 735

Thr Thr Asp Glu Cys Ala Phe Ala Leu Ser Thr Asp Glu Phe Met Asp
            740                 745                 750

Glu Pro Ile Ala Met Ile Ile Ser Glu Asn Ser Pro Tyr Leu Asn Ile
        755                 760                 765

Ile Asn Ala Glu Leu His Arg Met His Glu Ser Gly Leu Met Asn Lys
        770                 775                 780

Trp Thr Ser Glu Gln Ile Pro Leu Lys Asp Lys Cys Ser Glu Ser Leu
785                 790                 795                 800

Thr Asn Gln Ala Val Val Glu Arg Lys Val Asn Val Ala Asp Met Gln
                    805                 810                 815

Gly Ile Phe Phe Val Leu Phe Met Ala Val Ser Ser Ala Phe Ala Tyr
            820                 825                 830

Arg Tyr Asp Pro Trp Tyr Arg Ala Asp Thr Gln Arg Pro Val Asp Val
        835                 840                 845

Ile Thr Asp Val Ile Asn Glu Leu Gly Val Arg Ile Leu Gln Gln Tyr
        850                 855                 860

Ser Thr Arg Gly Asn Val Ala Phe Ser Pro Thr Gly Val Ala Phe Val
865                 870                 875                 880

Leu Ala Ala Leu Tyr Glu Gly Ser Ala Gly Arg Gly Ser Gln Gln Ile
                    885                 890                 895

Ala Gln Ala Leu Gly Leu Pro Ala Asn Arg Asp Val Thr Arg Ile Gly
            900                 905                 910

Phe Arg Asp Ile His Arg Arg Leu Arg Ser Tyr Leu Asn Ala Asp Gly
        915                 920                 925

Phe Leu Gly Gly Leu Thr Leu Ser Arg Glu Asn Thr Arg Leu Arg Pro
        930                 935                 940

Glu Tyr Glu Asp Ile Leu Arg Phe Tyr Gly Phe Asp Leu Ser Ser Ile
945                 950                 955                 960

Glu Gln Glu Ala Asn Val Thr Val Ser Thr Gly Asp Ser Ser Gly Thr
                    965                 970                 975

Thr Lys Leu Pro Thr Ser Thr Val Gly Val Thr Thr Leu Pro Thr Glu
            980                 985                 990

Thr Thr Asn Thr Gly Ser Val Pro Asp Met Thr Thr Thr Thr Thr Met
        995                 1000                1005

Met Ser Thr Asp Val Gly Thr Thr Leu Pro Pro Ser Gly Ala Glu Thr
        1010                1015                1020

Met Ile Pro Ser Thr Val Thr Asp Ala Ser Thr Gln Gln Pro Leu Thr
1025                1030                1035                1040

Met Val Pro Thr Gly Ala Thr Asp Val Pro Ser Thr Leu Ala Pro Val
                    1045                1050                1055

Thr Gly Asp Gly Ala Ala Val Gln Asn Ala Ser Pro Thr Gln Ser Ala
            1060                1065                1070
```

```
Asn Ser Thr Thr Ala Val Thr Ser Gly Glu Ser Val Gln Ser Thr Thr
        1075                1080                1085

Ser Ala Gly Ala Glu Ser Val Ala Gly Ser Pro Asn Thr Ile Thr Pro
    1090                1095                1100

Ala Val Asn Ala Asp Ser Gln Thr Thr Pro Thr Thr Val Ala Gly Ala
1105                1110                1115                1120

Gly Asp Gln Ser Pro Gln Thr Ser Pro Thr Val Ala Ala Asp Gly Val
                1125                1130                1135

Gly Thr Gly Glu Ile Val Thr Ser Thr Ile Val Pro Asp Ala Thr Ala
            1140                1145                1150

Ala Asp Val Thr Ala Ala Ala Thr Asp Ala Ala Gly Gly Met Val
        1155                1160                1165

Ser Thr Ser Thr Gln Ala Gln Val Ser Ser Thr Val Ala Thr Ser Thr
    1170                1175                1180

Glu Ala Pro Met Thr Thr Asn Thr Pro Ser Ser Ala Ala Met Ile Ile
1185                1190                1195                1200

Ala Asn Thr Asp Ser Leu Ala Ala Ile Asp Val Asn Val Thr Pro
                1205                1210                1215

Ala Asn Val Thr Ser Pro Ser Glu Ala Ile Leu Asn Thr Val Thr Thr
            1220                1225                1230

Asn Ser Leu Thr Thr Val Ala Ile Ala Asn Val Ala Asn Val Thr Ile
        1235                1240                1245

Pro Ser Pro Val Thr Glu Thr Thr Ala Asp Ser Val Val Ser Gln Pro
    1250                1255                1260

Ser Thr Leu Ala Asp Thr Pro Ala Thr Thr Asp Ile Pro Gly Ser Thr
1265                1270                1275                1280

Ala Thr Asn Asn Leu Ala Met Thr Thr Met Thr Asn Ile Asp Gly Ala
                1285                1290                1295

Ala Ala Thr Thr Ala Ser Leu Val Asp Glu Asn Thr Ile Ser Met Asn
            1300                1305                1310

Arg Lys Lys Lys Asp Leu Thr Asp Val Arg Ile Asn Asp Asn Thr Val
        1315                1320                1325

Lys Gln Glu Ser Thr Asn Glu Ser Leu Asn Val Arg Lys Arg Lys Ala
    1330                1335                1340

Arg Ser Pro Arg Gly Tyr Phe Ser Ser Tyr Pro Asp Glu Gly Ile Trp
1345                1350                1355                1360

Met Gln Asp Leu Glu Ile Trp Lys Ser Tyr Asn Thr Val Asn Pro Gly
                1365                1370                1375

Asp Ser Ser Ala Gly Asp Ser Ala Glu Ile Ser Phe Leu Val Asn
            1380                1385                1390

Gly Cys Asp Val Ser Ser Val Ser Ala Ser Arg Tyr Ile Ala Val Leu
        1395                1400                1405

Pro Phe Ala Tyr Phe Pro Ser Leu Gln Ala Val Ala Leu Glu Phe Pro
    1410                1415                1420

Leu Asp Asp Pro Arg Tyr Asn Ile Ile Leu Phe Met Pro Thr Asp Lys
1425                1430                1435                1440

Thr Asp Thr His Arg Leu Ala Arg Asp Leu Ser Gly Lys Ser Leu Arg
                1445                1450                1455

Leu Leu Arg Lys Arg Leu Gln Pro Thr Trp Val Arg Ala Thr Ile Pro
            1460                1465                1470

Ser Phe Met Leu Arg Gly Phe Val Thr Leu Thr Ser Phe Leu Gln Arg
        1475                1480                1485

Glu Lys Glu Thr Glu Ile Glu Glu Gly
```

<210> SEQ ID NO 26
<211> LENGTH: 801
<212> TYPE: PRT
<213> ORGANISM: Camponotus floridanus

<400> SEQUENCE: 26

```
Met Asp Met Ile Ser Val Phe Phe Leu Val Trp Ile Leu Asn Ser Val
1               5                   10                  15

Asp Ala Phe Asn Asp Phe Pro Ser Leu Val Ser Asn Asn Ala Ser Met
            20                  25                  30

Ala Ile Ile Ile Glu Lys Ser Phe Phe Asp Asn Lys Ala Glu Tyr Arg
        35                  40                  45

Ser Val Val Ser Asn Ile Tyr Asn Phe Ile Ser Asn Ile Thr Ser Asp
    50                  55                  60

Ile Glu Val His Val Phe His Asp Thr Lys Ile Asp Ser Phe Gln Asp
65                  70                  75                  80

Tyr Thr Val Leu Leu Ser Val Thr Thr Cys Asp Gln Thr Trp Asn Leu
                85                  90                  95

Tyr Asn Ala Val Arg Lys Asp Glu Ile Ile His Leu Ala Ile Thr Glu
            100                 105                 110

Gln Asp Cys Pro Arg Leu Pro Glu Gly Val Ser Ile Pro Leu Ile Leu
        115                 120                 125

Pro Gly Lys Glu Leu Ser Gln Ile Phe Phe Asp Ile Arg Met Ala Asp
    130                 135                 140

Ala Leu Leu Trp Asn Asn Val Asn Ile Leu His Asp Asp Thr Phe Asp
145                 150                 155                 160

Arg Asp Thr Ile Asn Arg Val Thr Lys Ala Ile Ser Ile Ala Leu Pro
                165                 170                 175

Asn Lys Lys Phe Asn Leu Val Ser Arg Ser Leu Phe Val Phe Lys His
            180                 185                 190

Ala Asp Ser Glu Arg Asn Lys Arg Tyr Tyr Ile Lys Glu Met Leu Glu
        195                 200                 205

Ser Phe His Val Asp Gln Leu Gly Lys Cys Phe Leu Val Ile Val Thr
    210                 215                 220

Ile Asp Thr Val Ala Asp Val Met Glu Ala Ala Lys Met Leu Asn Met
225                 230                 235                 240

Val Gln Pro Asp Ser Gln Trp Leu Tyr Val Ile Thr Asp Ile Val Lys
                245                 250                 255

Asn Asn Ser Thr Asn Ile Thr Ser Leu Ile Asp Leu Leu Ser Glu Gly
            260                 265                 270

Ser Asn Val Ala Phe Ile Tyr Asn Ala Thr Asp Asn Asn Thr Tyr Cys
        275                 280                 285

Asn Asn Asn Leu Ile Cys His Ile Gln Glu Leu Thr Met Ala Leu Asn
    290                 295                 300

Asn Ala Leu Lys Ile Ser Leu Met Thr Glu Ile Glu Leu Tyr Asn His
305                 310                 315                 320

Val Ser Asn Glu Glu Phe Glu Ile Val Arg Leu Asn Lys Arg Glu Arg
                325                 330                 335

Arg Arg Glu Ile Leu Lys Phe Ile Arg Thr Lys Leu Ala Gln Asp Asn
            340                 345                 350

Phe Ala Thr Gly Gly Ile Cys Gly Lys Cys Leu Phe Trp Arg Phe Ala
        355                 360                 365
```

```
Ser Ala Ile Thr Trp Gly Asn Phe Phe Ile Arg Asp Lys Ser Thr Ala
370                 375                 380

His Leu Ile Asp Ser Gly Ser Trp Ile Pro Thr Leu Gly Met Asn Leu
385                 390                 395                 400

Thr Asp Val Ile Phe Pro His Val His Gly Phe Arg Gly Ile Asn
                405                 410                 415

Leu Pro Ile Ala Thr Tyr His Asn Pro Pro Trp Gln Ile Ile Ser Met
                420                 425                 430

Thr Asn Ser Gly Glu Lys Glu Tyr Gly Gly Leu Leu Phe Asp Val Val
                435                 440                 445

Lys Tyr Leu Gly Asn Lys Leu Asn Phe Thr Tyr Ser Val Leu Ser Pro
450                 455                 460

Val Ser Asn Arg Thr Ile Lys Phe Thr Gln Asn Glu Thr Gln Ala Asp
465                 470                 475                 480

Met Thr Tyr Ser Phe Leu Thr Ala Lys Pro Gly Gln Leu Ser Arg Ala
                485                 490                 495

Leu Leu Phe Thr Ala Pro Phe Ala Lys Glu Thr Trp Ala Cys Leu Ala
                500                 505                 510

Ser Ser Ile Ile Ile Met Gly Pro Ser Leu Tyr Leu Ile His Lys Tyr
                515                 520                 525

Gly Pro Thr Ser Thr Lys Thr Ser Gly Leu Asn Ser Ser Trp Gln Cys
530                 535                 540

Ile Trp Tyr Val Tyr Gly Ala Leu Leu Gln Gln Gly Gly Met Tyr Leu
545                 550                 555                 560

Pro Tyr Ser Asp Ser Ala Arg Leu Leu Ile Gly Ile Trp Trp Leu Ile
                565                 570                 575

Val Met Val Val Val Ala Thr Tyr Ser Gly Ser Leu Val Ala Phe Leu
                580                 585                 590

Thr Phe Pro Asn Met Asp Ser Ser Ile Leu Thr Ile Asp Ala Leu Leu
                595                 600                 605

Ala Asn Lys Asn Arg Leu Thr Trp Gly Phe Pro Asn Gly Ser Tyr Leu
610                 615                 620

Glu Glu Tyr Leu Lys Asn Ala Glu Glu Glu Lys Tyr His Ile Met Leu
625                 630                 635                 640

Lys Arg Ala Lys Ile Tyr Asn Ala Thr Gln Glu Ala Glu Val Ile Glu
                645                 650                 655

Lys Val Lys Ala Gly Lys Tyr Ala Leu Ile Asp Trp Arg Ser Thr Leu
                660                 665                 670

Arg Phe Leu Met Arg Thr Asp Met Leu Thr Thr Gly Arg Cys Ser Phe
                675                 680                 685

Ser Leu Ser Thr Asp Glu Phe Met Asp Glu Pro Ile Ala Met Ile Ile
                690                 695                 700

Asn Gln Asp Asn Pro Tyr Ile Lys Ile Ile Asn Ala Glu Leu His Arg
705                 710                 715                 720

Met His Glu Ser Gly Leu Met Asn Lys Trp Val Thr Glu Gln Ile Pro
                725                 730                 735

Met Lys Asp Lys Cys Ser Asp Ile Leu Ala Asn Gln Ala Val Asn Glu
                740                 745                 750

Arg Lys Val Asn Val Ala Asp Met Gln Gly Ile Phe Phe Val Leu Phe
                755                 760                 765

Met Gly Val Ala Gly Ser Ile Phe Leu Cys Cys Glu Phe Tyr Trp
770                 775                 780

His Lys Arg Gln Val Ala Lys Arg Arg Lys Leu Ile Gln Pro Phe Leu
```

785         790         795         800

Ser

<210> SEQ ID NO 27
<211> LENGTH: 741
<212> TYPE: PRT
<213> ORGANISM: Linepithema humile

<400> SEQUENCE: 27

Met Asn Thr Arg Cys Leu Asn Ala Ile Val Ile Asp Lys Ser Phe Phe
1               5                   10                  15

Asp Asn Lys Ile Glu Tyr Arg Asp Thr Val Arg Asn Ile Val Asp Phe
            20                  25                  30

Ile Thr Asn Val Thr Asn Glu Glu Ala His Met Ser Asp Ile Asn Met
        35                  40                  45

His Ile Phe Arg Asp Thr Asn Val Asn Asn Leu Arg Asp Tyr Thr Val
    50                  55                  60

Leu Leu Ser Val Ala Thr Cys Tyr Gln Thr Trp Ser Leu His Asp Val
65                  70                  75                  80

Ala Arg Lys Glu Glu Leu Val His Leu Ala Ile Thr Asn Gln Asp Cys
                85                  90                  95

Pro Arg Phe Ser Asp Ser Glu Gly Val Ile Ile Pro Leu Ile Pro Met
            100                 105                 110

Gly Asp Glu Leu Ser Gln Ile Phe Phe Asp Ile Arg Thr Ala Asp Ala
        115                 120                 125

Leu Phe Trp Asn Ser Val Asn Ile Leu His Asp Asp Thr Phe Asp Lys
    130                 135                 140

Asn Thr Ile Ser Arg Val Thr Lys Ala Ile Ser Thr Ala Leu Pro Asn
145                 150                 155                 160

Lys Lys Phe Asn Leu Val Ser Arg Ser Leu Phe Val Phe Lys His Ala
                165                 170                 175

Asn Ser Asp Arg Ser Arg Arg Tyr Tyr Ile Lys Asp Met Leu Glu Thr
            180                 185                 190

Phe His Val Glu Gln Leu Gly Lys Cys Phe Leu Ile Ile Val Thr Ile
        195                 200                 205

Asp Ala Ala Asp Val Met Glu Val Ala Lys Thr Leu Asp Met Val
    210                 215                 220

Gln Pro Asp Ser Gln Trp Leu Tyr Ile Ile Thr Asp Ser Val Ile Arg
225                 230                 235                 240

Asn Ser Thr Asn Ile Thr Thr Phe Ile Asp Leu Leu Thr Glu Gly Ser
                245                 250                 255

Asn Val Ala Phe Ile Tyr Asn Ala Thr Asp Ser Asp Ala Tyr Cys Asn
            260                 265                 270

Val Thr Leu Met Cys His Val Gln Glu Leu Ile Ala Ala Leu Ser Asn
        275                 280                 285

Ala Leu Lys Leu Ser Leu Met Thr Glu Met Glu Leu Tyr Asn Arg Met
    290                 295                 300

Ser Glu Glu Glu Phe Glu Leu Ile Arg Leu Asn Lys Asn Glu Arg Arg
305                 310                 315                 320

Gln Glu Ile Leu Lys Asn Ile Lys Ile Lys Leu Val Glu Asp Thr Phe
                325                 330                 335

Ala Thr Gly Gly Thr Cys Gly Lys Cys Leu Phe Trp Arg Phe Ala Ser
            340                 345                 350

Ala Ile Thr Trp Gly Asn Phe Phe Ile His Gly Lys Thr Ser Ala His

```
                    355                 360                 365
Leu Ile Asn Ser Gly Thr Trp Ile Pro Thr Leu Gly Val Asn Leu Thr
370                 375                 380

Asp Ala Ile Phe Pro His Ile Val His Gly Phe Arg Gly Ile Asn Leu
385                 390                 395                 400

Pro Ile Ala Thr Tyr His Asn Pro Pro Trp Gln Thr Ile Ser Leu Thr
                405                 410                 415

Asn Thr Gly Glu Lys Glu Tyr Gly Gly Leu Val Phe Asp Val Ile Arg
                420                 425                 430

Tyr Leu Gly Lys Lys Leu Asn Phe Thr Tyr Thr Val His Ser Pro Arg
            435                 440                 445

Ser Asn Arg Thr Val Lys Phe Ile Arg Asn Glu Ser Asp Ile Glu Val
        450                 455                 460

Val Leu Thr Ser Thr Thr Arg Lys Ile Pro Pro Glu Ile Val Asp Met
465                 470                 475                 480

Val Ala Glu Lys Lys Val Leu Leu Ala Ala Cys Ala Tyr Thr Val Asn
                485                 490                 495

Asp Arg Gly Arg Gly Lys Ile Asn Phe Thr Leu Pro Ile Phe Met Gln
                500                 505                 510

Thr Tyr Ser Phe Leu Thr Ala Lys Pro Gly Gln Leu Ser Arg Ala Leu
            515                 520                 525

Leu Phe Thr Ala Pro Phe Thr Lys Glu Thr Trp Ala Cys Leu Ala Ala
        530                 535                 540

Ser Ile Ile Met Gly Pro Ile Leu Tyr Leu Ile His Lys Tyr Ser
545                 550                 555                 560

Pro Ser Ser Thr Arg Thr Ser Gly Leu Asn Ser Pro Trp Gln Cys Ile
                565                 570                 575

Trp Tyr Val Tyr Gly Ala Leu Leu Gln Gln Glu Lys Cys Asp Glu Lys
                580                 585                 590

Met Phe Leu Gly Gly Met Tyr Leu Pro His Ser Asp Ser Ala Arg Leu
            595                 600                 605

Leu Val Gly Val Trp Trp Leu Val Val Met Val Leu Val Ala Thr Tyr
        610                 615                 620

Ser Gly Ser Leu Val Ala Phe Leu Thr Phe Pro Asn Met Asp Thr Ala
625                 630                 635                 640

Ile Leu Thr Val Asp Asp Leu Ile Ala His Lys Ser Gln Leu Thr Trp
                645                 650                 655

Gly Phe Pro Asn Gly Ser Phe Leu Glu Glu Tyr Leu Lys Asn Ala Glu
                660                 665                 670

Glu Glu Lys Tyr His Ile Leu Leu Glu Arg Ser Ile Ile His Asn Thr
            675                 680                 685

Thr Gln Glu Ala Glu Val Ile Lys Lys Val Lys Ala Gly Lys His Val
        690                 695                 700

Leu Ile Asp Trp Arg Ser Thr Leu Ile Arg Leu Ile Ser Thr Ser Asp
705                 710                 715                 720

Lys Asn Asp Asp Asn Asp Ile Leu Leu Glu Gln Val Cys Asp Glu Lys
                725                 730                 735

Arg Ser Val Ile Asn
            740

<210> SEQ ID NO 28
<211> LENGTH: 766
<212> TYPE: PRT
<213> ORGANISM: Harpegnathos saltator
```

<400> SEQUENCE: 28

```
Met Ile Ser Val Leu Phe Leu Ala Trp Ile Leu Asn Phe Gly Asn Ala
 1               5                  10                  15

Phe Asn Glu Phe Pro Ser Leu Met Ser Ala Asn Ala Ser Met Ala Val
            20                  25                  30

Val Ile Asp Lys Ser Phe Phe Asp Lys Lys His Glu Tyr Ile Asp Val
        35                  40                  45

Thr Lys Arg Ile His Glu Tyr Ile Thr Asn Ile Ala Arg Glu Glu Met
 50                  55                  60

His Met Gly Asp Ile Asn Val Arg Val Phe Arg Asn Ala Lys Ile Asn
 65                  70                  75                  80

Asn Leu Arg Glu Gln Asp Cys Pro Arg Phe Pro Asp Thr Asp Gly Val
                85                  90                  95

Ser Ile Pro Leu Val Val Ala Gly Gln Glu Leu Ser Gln Ile Phe Tyr
            100                 105                 110

Asp Leu Arg Ser Tyr Asp Val Leu Asn Trp Asn Asn Ile Asn Ile Leu
        115                 120                 125

His Asp Asp Thr Phe Asp Arg Asp Thr Ile Ser Arg Val Thr Lys Ala
130                 135                 140

Val Ser Thr Pro Leu Pro Asn Lys Lys Phe Asn Met Val Ser Arg Ser
145                 150                 155                 160

Leu Phe Ala Phe Lys His Ala Asn Ser Glu Arg Ser Lys Lys Tyr Tyr
                165                 170                 175

Ile Lys Glu Ile Leu Glu Lys Phe His Val Asp Gln Leu Gly Lys Cys
            180                 185                 190

Phe Leu Val Ile Val Thr Thr Asp Val Ala Phe Asp Val Met Glu Val
        195                 200                 205

Pro Asp Ser Gln Trp Leu Tyr Val Ile Ala Asp Ser Met Val Arg Asn
210                 215                 220

Ala Thr Asn Ile Thr Ser Phe Thr Glu Tyr Leu Ser Glu Gly Ala Asn
225                 230                 235                 240

Val Ala Phe Ala Tyr Asn Ser Thr Asp Asn Asp Thr Tyr Cys Asp Ala
                245                 250                 255

Lys Leu Leu Cys Arg Val Gln Glu Leu Ile Gly Ser Leu Ala Asn Ala
            260                 265                 270

Leu Lys Leu Ser Leu Met Ile Glu Ile Glu Leu Tyr Asn Arg Val Ser
        275                 280                 285

Glu Glu Glu Phe Glu Phe Ile Arg Leu Asn Lys Arg Glu Arg Arg Arg
290                 295                 300

Glu Ile Leu Lys Asn Ile Gln Ile Lys Leu Thr Asp Asp Thr Phe Ala
305                 310                 315                 320

Ser Gly Gly Gly Cys Gly Lys Cys Leu Phe Trp Arg Phe Ala Ser Ala
                325                 330                 335

Ile Thr Trp Gly Asn Phe Phe Leu Arg Gly Lys Asn Ile Ala His Leu
            340                 345                 350

Ile Asp Ser Gly Met Trp Ile Pro Ser Leu Gly Ala Asn Leu Thr Asp
        355                 360                 365

Val Ile Phe Pro His Ile Ser His Gly Phe Arg Gly Ile Ser Leu Pro
370                 375                 380

Val Ala Thr Tyr His Asn Pro Pro Trp Gln Ser Ile Ser Leu Thr Asn
385                 390                 395                 400

Ser Gly Glu Lys Glu Tyr Gly Gly Leu Ile Phe Asp Val Ile Lys Tyr
```

```
            405                 410                 415
Leu Gly Lys Lys Leu Asn Phe Thr Tyr Thr Val Leu Ser Pro Thr Ser
            420                 425                 430

Asn Arg Thr Val Lys Phe Thr Gln Asn Glu Thr Gln Ala Asp Val Thr
            435                 440                 445

Tyr Ser Phe Leu Thr Ala Lys Pro Asn Gln Leu Ser Arg Ala Leu Leu
            450                 455                 460

Phe Thr Ala Pro Phe Ala Lys Glu Thr Trp Ala Cys Leu Ala Ala Ser
465                 470                 475                 480

Ile Ile Ile Met Gly Pro Ile Leu Tyr Leu Ile His Lys Tyr Ser Pro
            485                 490                 495

Gly Thr Lys Thr Ser Gly Leu Asn Ser Ser Trp Gln Cys Val Trp Tyr
            500                 505                 510

Val Tyr Gly Ala Leu Leu Gln Gln Gly Gly Met Tyr Leu Pro Arg Cys
            515                 520                 525

Asp Ser Ala Arg Leu Leu Val Gly Val Trp Trp Leu Val Val Met Val
            530                 535                 540

Leu Val Ala Thr Tyr Ser Gly Ser Leu Val Ala Phe Leu Thr Phe Pro
545                 550                 555                 560

Asn Met Asp Val Ala Ile Leu Thr Val Asp Asp Leu Ile Ala His Lys
            565                 570                 575

Gly Arg Val Thr Trp Gly Phe Pro Asn Gly Ser Phe Leu Glu Glu Tyr
            580                 585                 590

Leu Lys Asn Ala Glu Glu Lys Tyr His Ile Met Trp Glu Arg Ser
            595                 600                 605

Glu Ile Tyr Asn Ser Thr Gln Glu Val Glu Val Ile Glu Lys Val Lys
            610                 615                 620

Thr Gly Lys His Val Leu Ile Asp Trp Arg Ser Thr Leu Arg Phe Leu
625                 630                 635                 640

Met Arg Asn Asp Leu Leu Ser Thr Gly Gly Cys Ser Phe Ser Leu Ser
            645                 650                 655

Thr Asp Glu Phe Met Asp Glu Pro Ile Ala Met Ile Ile Ser Gln Asp
            660                 665                 670

Ser Pro Tyr Thr Lys Ile Ile Asn Ala Glu Leu His Arg Met His Glu
            675                 680                 685

Ser Gly Leu Met Thr Lys Trp Ile Thr Glu Gln Ile Pro Met Lys Asp
            690                 695                 700

Lys Cys Ser Asp Ser Ser Gly Lys Gln Gly Val Asp Glu Arg Lys Val
705                 710                 715                 720

Asn Val Leu Asp Met Gln Gly Ile Phe Phe Val Leu Phe Met Gly Val
            725                 730                 735

Val Gly Ser Ile Phe Leu Leu Cys Cys Glu Phe Tyr Trp His Arg Arg
            740                 745                 750

Gln Ile Thr Arg Arg Ser Lys Leu Ile Gln Pro Phe Leu Ser
            755                 760                 765

<210> SEQ ID NO 29
<211> LENGTH: 959
<212> TYPE: PRT
<213> ORGANISM: Anopheles darlingi

<400> SEQUENCE: 29

Met Ser Pro Glu Glu Gly Lys Asn Gly Gln Lys Ile Asn Gln Thr Cys
1               5                   10                  15
```

```
Gln Pro Val Glu Glu Ser Thr Tyr Ala Pro Asp Ser Asn Glu Met Asn
             20                  25                  30

Ser Ser Asn Asp Ala Glu Lys Asp His Glu Met Gln Ser Asn Ile Gln
         35                  40                  45

Tyr Val Met Asp Ile Leu Pro His Leu Asp Pro Tyr Tyr Val Arg Arg
     50                  55                  60

Ile Ile Glu His Phe Asp Ser Val Glu Lys Ala Leu Ala Ile Leu Leu
65                   70                  75                  80

Glu Gly Asn Glu Asp Ala Gln Ser Lys Asp Ser Arg Lys Asp Ile Asn
                 85                  90                  95

Gly Glu Ile Val Pro Glu Asp Pro Leu Asp Ser Phe Tyr Leu Gln Thr
            100                 105                 110

Gly Ile Asp Arg Leu Asn Ile Phe Asp Gly Asp Glu Phe Asp Val Met
            115                 120                 125

Ser Lys Ser His Val Lys Gly Thr Ile Lys Lys Gly Lys Gly Met Pro
130                 135                 140

Gly Asn Pro Lys Ser Phe Lys Ala Leu Leu Asp Asp Lys Ser His Val
145                 150                 155                 160

Asn Glu Met Arg His Val Tyr Arg Gln Tyr Ser Thr Leu Ala Asp Met
                165                 170                 175

Asp Asp Asp Glu Tyr Asp Asp Thr Phe Glu Ala Met Ala Glu Ser Glu
            180                 185                 190

Ser Arg His Ile Lys Phe Ala Lys Gly Thr Arg Ile Ser Gly Ile Glu
        195                 200                 205

Glu Ser Asp Asp Asp Asp Glu Ser Asp Thr Glu Asp Ser Asp Pro Glu
210                 215                 220

Ala Glu Pro His Lys Met Ala Gly Phe Glu Phe Cys Glu Asn Pro Glu
225                 230                 235                 240

Ile Thr Arg Lys Arg Tyr Glu Glu Arg Leu Ile Ser Lys Gly Val Lys
                245                 250                 255

Pro Gln Ala Pro Lys Glu Thr Ala Asp Val Arg Gly Asn Pro Lys Ala
            260                 265                 270

Ser Asn Asp Ala Asn Asn Asp Lys Val Ile Lys Thr Arg Asp Leu Tyr
        275                 280                 285

Arg Ser Gly His Leu Pro Asp Glu Thr Cys Val Lys Lys Leu Cys Pro
290                 295                 300

Ser Asn Gly Thr Asp Val Thr Leu Leu Ile Leu Val Thr Ser Ala Pro
305                 310                 315                 320

Thr His Arg Glu Gln Arg Leu Ala Ile Arg Gln Ser Trp Gly Tyr Tyr
                325                 330                 335

Gly Ser Arg Arg Asp Ile Ser Ile Gly Phe Ile Val Gly Gln Thr Asp
            340                 345                 350

Glu Ser Arg Ile Glu Asp Gln Leu Ala Ala Glu Ser Tyr Met Tyr Ser
        355                 360                 365

Asp Leu Ile Arg Gly Asn Phe Ile Asp Ser Tyr Lys Asn Leu Thr Leu
370                 375                 380

Lys Thr Ile Ser Leu Leu Glu Trp Thr Lys Leu His Cys Ser Asn Ala
385                 390                 395                 400

Ser Phe Leu Leu Lys Thr Asp Asp Asp Met Phe Ile Asn Val Pro Lys
                405                 410                 415

Leu Leu Gln Phe Met Glu Val His Asn Gln Arg Arg Thr Ile Phe
            420                 425                 430

Gly Arg Leu Ala Lys Lys Trp Lys Pro Ile Arg Asn Lys Lys Ser Lys
```

-continued

```
            435                 440                 445
Tyr Tyr Val Arg Pro Ala Tyr Leu Leu Thr Ala Asp Ile Ile Ser Glu
450                 455                 460

Leu Phe Glu Lys Ser Leu Ser Gln Thr Tyr Leu Lys Leu Glu Asp Val
465                 470                 475                 480

Tyr Thr Thr Gly Ile Val Ala Gln Leu Leu Asn Ile Arg Arg Thr Asn
                485                 490                 495

Val Lys Glu Phe Leu Asn Arg Arg Ile Ala Phe Asn Gln Cys Ser Ile
                500                 505                 510

Lys Lys Ala Ile Ser Ile His Met Val Lys Asn Glu Gln Leu Asp
            515                 520                 525

Leu Trp Lys Lys Leu Ile Asp Val Asn Ile Leu Cys Tyr Ile Glu Ser
530                 535                 540

Phe Leu Val His Phe Ile Arg Ser Leu Ser Lys Leu Ile Arg Glu Glu
545                 550                 555                 560

Gln Val Val Phe Gly Gln Ile Ser Asp Glu Glu Trp Glu Ile Ile Arg
                565                 570                 575

Pro Ser Lys Val Glu Arg Lys Lys Met Leu Gln Met Ile Gln Asn
            580                 585                 590

Pro Pro Trp Gln Phe Val Ser Tyr Asn Glu Ser Gly Ser Pro Val Ile
                595                 600                 605

Thr Gly Gly Val Ile Tyr Asp Val Leu Ser Glu Leu Ser Arg Lys Leu
610                 615                 620

Asn Phe Thr Tyr Thr Leu Val Ile Thr Gln Gly Ala Ser Glu Gln Asn
625                 630                 635                 640

Gly Ser Leu Ile Asp Asp Asn Ser Thr Val Ser Asp Gly Asn Ser Met
                645                 650                 655

Val Ile Ser Arg Leu Arg Phe Phe Met Lys Cys Phe Cys Leu Leu Gln
                660                 665                 670

Thr Leu Tyr Glu Thr Asn Gly Leu Thr Ser Asp Ile Pro Gln Glu Ile
                675                 680                 685

Tyr Ser Thr Leu Val Asn Asn Lys Ile Leu Leu Ala Ala Ile Gly Thr
690                 695                 700

Thr Val Thr Glu Lys Arg Lys Lys Tyr Ile Ser Phe Thr Asp Pro Ile
705                 710                 715                 720

Ser Ile Gln Thr Tyr Ser Phe Ile Asp Ile Pro Val Asn Arg Ile Met
                725                 730                 735

Gln Leu Leu Arg Asn Glu Arg Gly Met Thr Trp Ser Ile Arg Lys Gly
                740                 745                 750

Thr Phe Leu Glu Glu Val Leu Met Val Arg Gln His Tyr Arg Gln Gln
                755                 760                 765

Leu Gln Leu His Leu Ala Asn Arg Met Ser Phe Pro Ser Pro Val Trp
                770                 775                 780

Thr Gln Glu Ser Asp Glu Asn Lys Tyr Ile Glu Leu Tyr Arg Gly Ser
785                 790                 795                 800

Gln Val Ile Thr Glu Leu Thr Asp Asp Leu Val Arg Arg Ile Glu Ala
                805                 810                 815

Gly Gln His Val His Ile Asp Trp Arg Asn Asn Leu Lys Tyr Leu Ile
                820                 825                 830

Lys Lys Gln Phe Leu Ala Thr Asp Arg Cys Asp Phe Ala Leu Ser Thr
                835                 840                 845

Asp Glu Phe Leu Asp Glu Gln Ile Ala Leu Val Met Pro Lys Asp Ser
850                 855                 860
```

```
Pro Tyr Leu Glu Leu Val Asn Asp Glu Ile Arg Arg Met His Gln Phe
865                 870                 875                 880

Gly Phe Ile Gln Arg Trp Ile Ser Gln Tyr Leu Pro Ser Lys Asp Arg
            885                 890                 895

Cys Ser Gly Thr Ser Asn Lys Ala Met Asp Val Gln Asn His Thr Val
            900                 905                 910

Asn Ser Ser Asp Met Ala Gly Ser Tyr Trp Ile Leu Leu Gly Phe
        915                 920                 925

Ser Ser Gly Leu Ile Ile Phe Ile Gly Glu Phe Ala Ile His Trp Tyr
930                 935                 940

Arg Gln Arg Arg Leu Ala Lys Ala Val Val Thr Ser Tyr Ser Ser
945                 950                 955
```

<210> SEQ ID NO 30
<211> LENGTH: 1402
<212> TYPE: PRT
<213> ORGANISM: Anopheles

<400> SEQUENCE: 30

```
Met Ile Ser Val Leu Leu Leu Val Trp Cys Ile Asn Tyr Gly Ser Ser
1               5                   10                  15

Tyr Asn Asp Phe Pro Ser Leu Ile Thr Ser Asn Ala Thr Met Asp Pro
            20                  25                  30

Asp Cys Pro Arg Ile Pro Asp Thr Asp Gly Ile Thr Val Pro Ser Ile
        35                  40                  45

Val Pro Gly Glu Glu Leu Ser Gln Ile Phe Leu Asp Leu Arg Met Thr
50                  55                  60

Asp Ile Leu Ser Trp Asn Val Ile Asn Ile Leu His Asp Asp Thr Phe
65                  70                  75                  80

Gly Asp Lys Ala Thr Ser Ser Asn Asp Asn Val Thr Ile Leu Leu Ser
                85                  90                  95

Asn Ala Asn Thr Ser Ile Phe Ser Leu Arg His Gly Asn Thr Gly Gly
            100                 105                 110

Gly Arg Lys Ser Ser Val Lys Lys Thr Leu Asn Asp Phe His Val Asp
        115                 120                 125

Gln Leu Gly His Cys Phe Leu Val Ile Ala Thr Val Asp Met Val Ala
130                 135                 140

Asp Val Met Thr Val Ala Asn Ser Leu Asn Met Val His Pro Gly Ser
145                 150                 155                 160

Gln Trp Leu Tyr Val Ile Thr Asn Ser Val Ser Gly Asn Leu Ile Asn
                165                 170                 175

Thr Thr Phe Ile Asn Leu Leu Ala Glu Gly Gly Asn Val Ala Phe Met
            180                 185                 190

Tyr Asn Ala Thr Asn Leu Asp Gly Phe Tyr Lys Ile Lys Leu Lys Cys
        195                 200                 205

Tyr Ile Lys Asn Leu Ile Glu Ala Leu Ala Lys Ala Leu Glu Tyr Ser
210                 215                 220

Leu Thr Asn Glu Ile Glu Leu Phe Lys Arg Met Asn Glu Asp Glu Phe
225                 230                 235                 240

Glu Met Ile Arg Leu Thr Lys Ser Lys Arg Arg Thr Glu Leu Leu Lys
                245                 250                 255

Asn Val Arg Asn Pro Pro Trp Gln Ile Ile Ser Met Ser Lys Thr Gly
            260                 265                 270

Lys Lys Leu Tyr Glu Gly Leu Ile Phe Asp Ala Ile Asn Tyr Leu Ser
```

```
            275                 280                 285
Met Lys Leu Asn Phe Thr Tyr Thr Val Ile Met Pro Glu Thr Ser Gln
290                 295                 300

Ile Ser Arg Ser Trp Asn Thr Ser Gln Phe Ala Lys Leu Gly Glu Lys
305                 310                 315                 320

Ile Lys Glu Met Thr Met Ser Thr Thr Lys Val Pro Leu Glu Ile
                325                 330                 335

Ile Asp Leu Val Arg Gln Lys Val Leu Ala Ala Cys Ala Leu
                340                 345                 350

Thr Val Asn Glu Cys Gly Asn Thr Thr Phe Asn Tyr Thr Val Pro Ile
                355                 360                 365

Phe Val Gln Thr Tyr Ser Phe Leu Thr Ala Lys Pro Ser Gln Leu Ser
370                 375                 380

Arg Val Leu Leu Phe Ala Ser Pro Phe Thr Lys Glu Thr Trp Ala Cys
385                 390                 395                 400

Leu Ala Val Ser Ile Ile Met Gly Pro Ile Leu Tyr Leu Ile His
                405                 410                 415

Lys Tyr Ser Pro Tyr Ser Thr Lys Ala Ser Gly Leu Asn Ser Ser Trp
                420                 425                 430

Gln Cys Val Trp Tyr Val Tyr Gly Ala Leu Leu Gln Gln Gly Gly Met
                435                 440                 445

Tyr Leu Pro His Asn Asp Ser Ala Arg Ile Leu Ile Gly Ile Trp Trp
450                 455                 460

Leu Val Val Met Val Leu Val Ala Thr Tyr Ser Gly Ser Leu Val Ala
465                 470                 475                 480

Phe Leu Thr Phe Pro Arg Met Asp Thr Ser Ile Leu Ser Val Glu Asp
                485                 490                 495

Leu Ile Ala His Lys Asp Arg Ile Ser Trp Gly Phe Pro Asn Gly Ser
                500                 505                 510

Phe Leu Glu Met Tyr Leu Gln Asn Ala Glu Glu Pro Lys Tyr His Val
                515                 520                 525

Leu Leu Ser Arg Ala Glu Arg His Asn Asp Thr Glu Glu Arg Leu
530                 535                 540

Val Gly Arg Val Lys Glu Gly Lys His Ala Leu Ile Asp Trp Arg Ser
545                 550                 555                 560

Ser Leu Arg Phe Leu Met Arg Lys Asp Phe Leu Leu Thr Gly Ser Cys
                565                 570                 575

His Phe Ser Leu Ser Met Asp Glu Phe Leu Asp Glu Pro Ile Ala Met
                580                 585                 590

Ile Ile Pro Tyr Gly Ser Pro Tyr Leu Pro Val Ile Asn Ala Glu Leu
                595                 600                 605

His Arg Met Leu Glu Ser Gly Leu Met Asn Lys Trp Ile Thr Glu Arg
                610                 615                 620

Met Pro Met Lys Asp Lys Cys Trp Glu Ala Pro Gly Ser Asn Gln Ala
625                 630                 635                 640

Val Asn Lys Arg Lys Val Asn Val Ala Asp Met Gln Gly Ile Phe Phe
                645                 650                 655

Val Leu Phe Ile Val Ser Ser Val Phe Val His Gly Tyr Asp Asn Val
                660                 665                 670

Gly Phe Asp Gly Trp Tyr Gln Pro Gln Tyr Thr Ala His Gly Asn Val
                675                 680                 685

Ala Phe Ser Pro Thr Gly Val Gly Phe Val Leu Ala Ala Leu Tyr Glu
                690                 695                 700
```

-continued

Gly Ser Ala Gly Arg Gly Arg Gln Gln Ile Val Asp Ala Leu Gly Leu
705                 710                 715                 720

Pro Arg Asp Arg Asp Ile Thr Arg Ile Gly Phe Arg Asp Ile His Arg
            725                 730                 735

Arg Leu Arg Thr Tyr Leu Asn Ala Asp Gly Phe Leu Gly Gly Leu Thr
        740                 745                 750

Leu Asn His Glu Asn Thr Arg Leu Arg Pro Glu Tyr Glu Asp Ile Leu
    755                 760                 765

Arg Phe Tyr Gly Phe Asp Leu Ser Ile Pro Glu Glu Glu Met Asn Glu
770                 775                 780

Thr Thr Phe Ala Pro Glu Thr Thr Ser Ser Val Ala Ile Glu Gln Ser
785                 790                 795                 800

Thr Thr Glu Thr Lys Thr Val Ile Pro Asp Glu Ile Thr Thr Gln Ser
            805                 810                 815

Ile Thr Thr Gln Gly Ile Gln Ser Phe Glu Thr Ile Thr Asn Ser Gly
        820                 825                 830

Thr Pro Ile Ser Thr Thr Ser Ser Val Glu Leu Thr Gly Ile Val Thr
    835                 840                 845

Ser Ser Thr Ile Glu Gln Asp Lys Leu Thr Gln Thr Thr Pro Ala Ala
850                 855                 860

Ser Val Leu Thr Asn Asn Pro Asn Ala Ala Met Thr Thr Val Ser Ser
865                 870                 875                 880

Ser Ile Val Val Thr Ser Ser Thr Glu Thr Thr Thr Ser Ser
            885                 890                 895

Ile Pro Thr Ile Ile Asn Pro Asn Leu Ile Thr Thr Ser Ser Ser Glu
        900                 905                 910

Ile Val Thr Thr Thr Pro Ser Val Thr Ser Thr Pro Pro Ser Thr Ile
    915                 920                 925

Pro Ser Thr Thr Pro Ile Ile Ile Ile Thr Thr Val Ala Ser Thr Ile
930                 935                 940

Ser Glu Glu Pro Gln Thr Thr Ile Ala Asn Leu Thr Gln Pro Ile Thr
945                 950                 955                 960

Thr Val Thr Leu Ser Asn Gln Ser Pro Ser Ile Glu Glu Ser Thr Ser
            965                 970                 975

Thr Leu Ser Thr Ser Thr Ser Thr Ser Thr Pro Phe Thr Thr Thr
        980                 985                 990

Thr Thr Thr Ser Thr Thr Thr Ser Thr Ser Ile Pro Ser Ser Thr
    995                 1000                1005

Ser Glu Thr Pro Leu Pro Pro Thr Thr Leu Ile Ile Val Glu Thr Pro
    1010                1015                1020

Glu Ser Thr Thr Ile Ser Thr Gly Gln Thr Thr Lys Glu Ser Val Val
1025                1030                1035                1040

Met Thr Glu Ser Ile Pro Glu Ser Thr Ile Met Pro Pro Thr Met Ser
            1045                1050                1055

Ala Pro Ile Asn Ala Gly Ala Thr Val Thr Glu Val Ser Thr Thr Leu
        1060                1065                1070

Pro Val Asn Ile Thr Glu Ile Ser Thr Asn Ser Thr Ile Pro Thr Thr
    1075                1080                1085

Ile Gln Thr Asn Glu Met Ser Ile Asn Glu Thr Ser Arg Phe Thr Asn
    1090                1095                1100

Lys Pro Asp Asp Glu Asn Thr Ile Ser Val Asp Ser Leu Asn Asn Gln
1105                1110                1115                1120

-continued

Ser Ser Ile Ser Asn Glu Met Glu Ser Thr Glu Leu Pro Val Thr Ile
            1125                1130                1135

Val Ala Gly Glu Ile Gly Ser Thr Ile Gly Gln Lys Thr Ile Thr Thr
        1140                1145                1150

Thr Val Ser Ser Asn Thr Met Met Asn Arg Arg Lys Arg Ser Asp Arg
    1155                1160                1165

Ser Pro Arg Gly Phe Phe Ser Ser Tyr Pro Asp Glu Gly Ile Trp Met
1170                1175                1180

Gln Asp Leu Gly Ile Trp Lys Pro Tyr Ser Thr Ser Leu Asn Glu Ala
1185                1190                1195                1200

Ser Val Arg Asp Ser Thr Glu Ile Ser Phe Leu Val Asn Gly Cys Asp
        1205                1210                1215

Val Ser Ser Val Thr Ala Ser Arg Tyr Phe Ala Val Leu Pro Phe Ala
        1220                1225                1230

Tyr Phe Pro Ser Leu His Ala Val Ala Leu Glu Phe Pro Leu Asp Asp
            1235                1240                1245

Pro Arg Tyr Asn Ile Ile Leu Met Met Ala Thr Asp Arg Arg Asp Thr
    1250                1255                1260

Tyr Arg Leu Ala Arg Asp Leu Gly Gly Lys Ser Leu Arg Leu Leu Arg
1265                1270                1275                1280

Lys Gln Leu Gln Ala Thr Trp Val Arg Ala Thr Ile Pro Ser Phe Met
            1285                1290                1295

Leu Arg Gly Phe Val Thr Leu Thr Ser Phe Leu Gln Arg Leu Gly Ile
        1300                1305                1310

Leu Asp Val Phe Glu Pro Arg Thr Ala Asp Leu Ser Pro Met Thr Pro
        1315                1320                1325

Asp Leu Gly Val Tyr Ala Arg Asp Val Gln Gln Ser Ile Gly Val Asn
    1330                1335                1340

Ile Arg Asn Tyr Met Lys Pro Asp Arg Thr His Ser Arg Asn Gly Leu
1345                1350                1355                1360

Phe Glu Arg Ala Gly Pro Val Pro Phe Thr Val Val His Pro Phe Leu
            1365                1370                1375

Tyr Phe Ile Val Asp Ala Glu Thr Ser Val Val Leu Ile Ala Gly Arg
        1380                1385                1390

Val Asn Asp Pro Leu Asn Ser Arg Ile Leu
        1395                1400

<210> SEQ ID NO 31
<211> LENGTH: 818
<212> TYPE: PRT
<213> ORGANISM: Bombyx

<400> SEQUENCE: 31

Met Ile Ser Val Leu Leu Leu Leu Trp Cys Val Asn Tyr Gly Asp Ser
  1               5                  10                  15

Tyr Asn Asn Phe Pro Ser Leu Ile Thr Thr Asn Ala Thr Met Ala Val
             20                  25                  30

Ile Ile Asp Lys Ser Phe Phe Asp Asn Asn Gly Glu His Arg Asn Val
         35                  40                  45

Met Gly Val Val His Asp Leu Ile Asn Thr Val Lys Lys Glu Met
     50                  55                  60

His Ile Gly Gly Ile Val Val Arg Ile Phe Arg Asp Ala Asp Val Asn
 65                  70                  75                  80

Leu Trp Gln Gly Tyr Thr Ile Leu Leu Ser Val Ala Ser Cys Cys Ile
                 85                  90                  95

```
Thr Trp Arg Leu His Glu Val Ala Arg Lys Glu Leu Ile His Leu
            100                 105                 110

Ala Ile Thr Asp Pro Asp Cys Pro Arg Ile Pro Glu Thr Asp Gly Met
            115                 120                 125

Ser Met Pro Val Val Pro Gly Glu Glu Leu Ser Gln Ile Phe Leu
130             135                 140

Asp Leu Arg Met Met Asn Ile Leu Pro Trp Asn Val Ile Asn Ile Leu
145                 150                 155                 160

His Asp Asp Thr Phe Gly Arg Asp Thr Ile Ser Arg Val Met Thr Ala
                165                 170                 175

Ile Ser Asp Lys Leu Pro Asn Lys Gln Val Asn Leu Ile Ser Arg Ser
            180                 185                 190

Ile Phe Thr Leu Lys His Glu Thr Thr Arg Ser Glu Arg Lys Ser Ser
            195                 200                 205

Val Lys Lys Thr Leu Asn Asp Phe His Val Glu Gln Leu Gly His Cys
210                 215                 220

Phe Leu Val Ile Ala Thr Val Asp Met Ile Ala Asp Val Met Gly Val
225                 230                 235                 240

Ala Arg Ser Leu Lys Met Val His Pro Gly Ser Gln Trp Leu Tyr Val
                245                 250                 255

Ile Thr Asp Ser Ala Thr Lys Asn Met Thr Asn Met Thr Ala Phe Val
            260                 265                 270

Asp Leu Leu Ala Glu Gly Gly Asn Val Ala Phe Met Tyr Asn Ala Thr
            275                 280                 285

Asn Leu Ser Asn Tyr Cys Glu Ile Lys Leu Ile Cys Tyr Val Glu Lys
            290                 295                 300

Leu Ile Gln Ala Leu Ala Lys Ala Leu Glu Tyr Ser Leu Thr Asn Glu
305                 310                 315                 320

Ile Asp Leu Phe Lys Ser Met Glu Glu Glu Lys Phe Glu Met Ile Arg
                325                 330                 335

Leu Thr Lys Arg Glu Arg Arg Ala Glu Leu Leu Lys Asn Ile Arg Ile
            340                 345                 350

His Leu Ser Gln Asn Ala Phe Ala Ser Glu Gly Phe Cys Gly Arg Cys
            355                 360                 365

Leu Leu Trp Arg Phe Ser Ser Ser Ile Thr Trp Gly Asn Phe Phe Ser
370                 375                 380

Arg Gly Arg Asn Met Ala His Leu Leu Asp Ile Gly Thr Trp Ser Pro
385                 390                 395                 400

Gly Phe Gly Val Asn Leu Thr Asp Val Ile Phe Pro His Ile Ala His
                405                 410                 415

Gly Phe Arg Gly Thr Asn Leu Pro Ile Ala Thr Tyr His Asn Pro Pro
            420                 425                 430

Trp Gln Ile Ile Ser Val Ser Lys Thr Gly Gln Lys Leu Tyr Glu Gly
            435                 440                 445

Leu Val Phe Asp Ala Ile Asn Tyr Leu Gly Ser Lys Leu Asn Phe Ser
450                 455                 460

Tyr Thr Ala Ile Thr Pro Glu Val Thr Arg Asn Ser Asn Phe Thr Val
465                 470                 475                 480

Asn Glu Asn Lys Lys Asp Ala Ile Asn Phe Thr Val Pro Ile Phe Val
                485                 490                 495

Gln Thr Tyr Ser Phe Leu Thr Ser Arg Pro Lys Gln Leu Ser Arg Ala
            500                 505                 510
```

```
Leu Leu Phe Ala Ser Pro Phe Thr Lys Glu Thr Trp Ala Cys Leu Ala
            515                 520                 525

Val Ser Ile Ile Val Met Gly Pro Ile Leu Tyr Leu Val His Lys Tyr
        530                 535                 540

Ser Pro Tyr Ser Ile Lys Thr Ser Gly Leu Lys Ser Ser Phe Gln Cys
545                 550                 555                 560

Val Trp Tyr Val Tyr Gly Ala Leu Leu Gln Gln Gly Met Tyr Leu
                565                 570                 575

Pro His Cys Asp Ser Ala Arg Ile Leu Ile Gly Val Trp Trp Leu Ile
                580                 585                 590

Val Met Val Val Ala Thr Tyr Ser Gly Ser Leu Val Ala Phe Leu
        595                 600                 605

Thr Phe Pro Arg Met Asp Ala Ser Ile Leu Thr Val Asp Asp Leu Leu
            610                 615                 620

Ala Arg Lys Asp Gly Ile Thr Trp Ser Phe Pro Asn Gly Ser Phe Leu
625                 630                 635                 640

Glu Met Tyr Leu Gln Glu Thr Asp Glu Pro Lys Tyr His Thr Leu Leu
                645                 650                 655

Ser Arg Ala Glu Ser His Asn Asp Thr Glu Glu Lys Leu Val Glu
                660                 665                 670

Arg Val Lys Asp Gly Lys His Ala Leu Ile Asp Trp Arg Ser Ser Leu
            675                 680                 685

Arg Phe Leu Met Arg Lys Asp Leu Leu Thr Gly Val Cys His Phe
                690                 695                 700

Ser Leu Ser Met Asp Glu Phe Leu Asp Glu Pro Ile Ala Met Ile Ile
705                 710                 715                 720

Pro His Asp Ser Pro Tyr Leu Pro Val Ile Asn Ala Glu Leu His Arg
                725                 730                 735

Met Leu Glu Ser Gly Met Met Asn Lys Trp Ile Thr Glu Arg Met Pro
                740                 745                 750

Ile Lys Asp Lys Cys Trp Glu Val Pro Gly Ser Asn Gln Ala Val Asn
            755                 760                 765

Lys Arg Lys Val Asn Val Thr Asp Met Gln Gly Ile Phe Phe Val Leu
            770                 775                 780

Phe Met Gly Ile Ile Leu Ala Phe Phe Leu Phe Cys Glu Cys Tyr
785                 790                 795                 800

Cys His Arg Arg Lys Ile Ser Lys Glu Arg Lys Leu Ile His Pro Phe
                805                 810                 815

Val Ser

<210> SEQ ID NO 32
<211> LENGTH: 818
<212> TYPE: PRT
<213> ORGANISM: Bombyx

<400> SEQUENCE: 32

Met Ile Ser Val Leu Leu Leu Trp Cys Val Asn Tyr Gly Asp Ser
1               5                   10                  15

Tyr Asn Asn Phe Pro Ser Leu Ile Thr Thr Asn Ala Thr Met Ala Val
                20                  25                  30

Ile Ile Asp Lys Ser Phe Phe Asp Asn Asn Gly Asp His Arg Asn Val
            35                  40                  45

Met Gly Val Val His Asp Leu Ile Ile Asn Thr Val Lys Lys Glu Met
        50                  55                  60
```

-continued

His Ile Gly Gly Ile Val Arg Ile Phe Arg Asp Ala Asp Val Asn
65                  70                  75                  80

Leu Trp Gln Gly Tyr Thr Ile Leu Leu Ser Val Ala Ser Cys Cys Ile
                85                  90                  95

Thr Trp Arg Leu His Glu Val Ala Arg Lys Glu Glu Leu Ile His Leu
            100                 105                 110

Ala Ile Thr Asp Pro Asp Cys Pro Arg Ile Pro Glu Thr Asp Gly Met
            115                 120                 125

Ser Met Pro Val Val Pro Gly Glu Glu Leu Ser Gln Ile Phe Leu
130                 135                 140

Asp Leu Arg Met Met Asn Ile Leu Pro Trp Asn Val Ile Asn Ile Leu
145                 150                 155                 160

His Asp Asp Thr Phe Asp Arg Asp Thr Ile Ser Arg Val Met Thr Ala
                165                 170                 175

Ile Ser Asp Lys Leu Pro Asn Lys Gln Val Asn Leu Ile Ser Arg Ser
            180                 185                 190

Ile Phe Thr Leu Lys His Glu Thr Thr Arg Ser Glu Arg Lys Ser Ser
            195                 200                 205

Val Lys Lys Thr Leu Asn Asp Phe His Val Glu Gln Leu Gly His Cys
210                 215                 220

Phe Leu Val Ile Ala Thr Val Asp Met Ile Ala Asp Val Met Gly Val
225                 230                 235                 240

Ala Arg Ser Leu Lys Met Val His Pro Gly Ser Gln Trp Leu Tyr Val
                245                 250                 255

Ile Thr Asp Ser Ala Ser Lys Asn Met Thr Asn Met Thr Ala Phe Val
            260                 265                 270

Asp Leu Leu Ala Glu Gly Gly Asn Val Ala Phe Met Tyr Asn Ala Thr
            275                 280                 285

Asn Leu Ser Asn Tyr Cys Glu Ile Lys Leu Ile Cys Tyr Val Glu Glu
290                 295                 300

Leu Ile Gln Ala Leu Ala Lys Ala Leu Glu Tyr Ser Leu Thr Ser Glu
305                 310                 315                 320

Ile Asp Leu Phe Lys Ser Met Glu Glu Glu Lys Phe Glu Met Ile Arg
                325                 330                 335

Leu Thr Lys Arg Glu Arg Arg Ala Glu Leu Leu Lys Asn Ile Arg Ile
            340                 345                 350

His Leu Ser Gln Asn Ala Phe Ala Ser Glu Gly Phe Cys Gly Arg Cys
            355                 360                 365

Leu Leu Trp Arg Phe Ser Ser Ser Ile Thr Trp Gly Asn Phe Phe Ser
370                 375                 380

Arg Gly Arg Asn Met Ala His Leu Leu Asp Ile Gly Thr Trp Ser Pro
385                 390                 395                 400

Gly Phe Gly Val Asn Leu Thr Asp Val Ile Phe Pro His Ile Ala His
                405                 410                 415

Gly Phe Arg Gly Thr Asn Leu Pro Ile Ala Thr Tyr His Asn Pro Pro
            420                 425                 430

Trp Gln Ile Ile Ser Val Ser Lys Thr Gly Gln Lys Leu Tyr Glu Gly
            435                 440                 445

Leu Val Phe Asp Ala Ile Asn Tyr Leu Gly Ser Lys Leu Asn Phe Ser
450                 455                 460

Tyr Thr Ala Ile Thr Pro Glu Val Thr Arg Asn Ser Asn Phe Thr Val
465                 470                 475                 480

Asn Glu Asn Lys Lys Asp Ala Ile Asn Phe Thr Val Pro Ile Phe Val

```
                485                 490                 495
Gln Thr Tyr Ser Phe Leu Thr Ser Arg Pro Lys Gln Leu Ser Arg Ala
            500                 505                 510
Leu Leu Phe Ala Ser Pro Phe Thr Lys Glu Thr Trp Ala Cys Leu Ala
        515                 520                 525
Val Ser Ile Ile Val Met Gly Pro Ile Leu Tyr Leu Val His Lys Tyr
    530                 535                 540
Ser Pro Tyr Ser Ile Lys Thr Ser Gly Leu Lys Ser Ser Phe Gln Cys
545                 550                 555                 560
Val Trp Tyr Val Tyr Gly Ala Leu Leu Gln Gln Gly Gly Met Tyr Leu
                565                 570                 575
Pro His Cys Asp Ser Ala Arg Ile Leu Ile Gly Val Trp Trp Leu Ile
            580                 585                 590
Val Met Val Val Val Ala Thr Tyr Ser Gly Ser Leu Val Ala Phe Leu
        595                 600                 605
Thr Phe Pro Arg Met Asp Ala Ser Ile Leu Thr Val Asp Asp Leu Leu
    610                 615                 620
Ala Arg Lys Asp Gly Ile Thr Trp Ser Phe Pro Asn Gly Ser Phe Leu
625                 630                 635                 640
Glu Met Tyr Met Gln Glu Thr Asp Glu Pro Lys Tyr His Thr Leu Leu
                645                 650                 655
Ser Arg Ala Glu Ser His Asn Asp Thr Glu Glu Lys Leu Val Glu
            660                 665                 670
Arg Val Lys Asp Gly Lys His Ala Leu Ile Asp Trp Arg Ser Ser Leu
        675                 680                 685
Arg Phe Leu Met Arg Lys Asp Leu Leu Leu Thr Gly Val Cys His Phe
    690                 695                 700
Ser Leu Ser Met Asp Glu Phe Leu Asp Glu Pro Ile Ala Met Ile Ile
705                 710                 715                 720
Pro His Asp Ser Pro Tyr Leu Pro Val Ile Asn Ala Glu Leu His Arg
                725                 730                 735
Met Leu Glu Ser Gly Met Met Asn Lys Trp Ile Thr Glu Arg Met Pro
            740                 745                 750
Ile Lys Asp Lys Cys Trp Glu Val Pro Gly Ser Asn Gln Ala Val Asn
        755                 760                 765
Lys Arg Lys Val Asn Val Thr Asp Met Gln Gly Ile Phe Phe Val Leu
    770                 775                 780
Phe Met Gly Ile Ile Leu Ala Phe Phe Phe Leu Phe Cys Glu Cys Tyr
785                 790                 795                 800
Cys His Arg Arg Lys Ile Ser Lys Glu Arg Lys Leu Ile His Pro Phe
                805                 810                 815
Val Ser

<210> SEQ ID NO 33
<211> LENGTH: 519
<212> TYPE: PRT
<213> ORGANISM: Drosophila

<400> SEQUENCE: 33

Met Lys Asp Tyr Leu Lys Ala Asn Ser Lys Cys Ala Ser Cys Ala Arg
 1               5                  10                  15

Trp Gln Ile Glu Thr Ala Ile Thr Trp Gly Lys Ser Gln Glu Asn Arg
            20                  25                  30

Lys Phe Arg Ala Ala Pro Thr Arg Asp Ala Lys Asn Gln Asn Phe Glu
```

```
                35                  40                  45
Phe Ile Asn Ile Gly Tyr Trp Ser Pro Leu Leu Gly Phe Val Cys Gln
 50                  55                  60
Glu Leu Thr Phe Pro His Ile Asp His His Phe Arg Asn Ile Thr Met
 65                      70                  75                  80
Asp Val Val Thr Val His Asn Pro Pro Trp Gln Ile Leu Thr Lys Asp
                     85                  90                  95
Ser His Gly Val Ile Leu Glu His Lys Gly Ile Val Met Glu Leu Leu
               100                 105                 110
Lys Glu Leu Ser Arg Ala Leu Asn Phe Ser Tyr Tyr Leu His Glu Ala
               115                 120                 125
Ser Asn Trp Lys Asp Asp Tyr Ser Ile Thr Thr Ser Thr Ser Ser Asn
130                 135                 140
Glu Ser Asp Glu Leu Ala Gly Ser Met Thr Phe Arg Ile Pro Tyr Arg
145                 150                 155                 160
Leu Val Glu Met Val Gln Gly Asn Gln Phe Phe Met Ala Ala Val Ala
                    165                 170                 175
Ala Thr Val Glu Asp Pro Asp His Lys Pro Phe Asn Tyr Thr Leu Pro
                180                 185                 190
Ile Ser Val Gln Lys Tyr Ser Phe Ile Thr Arg Gln Pro Asp Glu Val
                    195                 200                 205
Ser Arg Ile Tyr Leu Phe Thr Ala Pro Phe Thr Thr Glu Thr Trp Ala
210                 215                 220
Cys Leu Val Gly Ile Ile Leu Leu Thr Ala Pro Met Leu Tyr Ala Ile
225                 230                 235                 240
Asn Arg Leu Ala Pro Leu Gln Glu Met Gln Ile Ile Gly Leu Ser Thr
                    245                 250                 255
Val Lys Ser Cys Phe Trp Tyr Ile Phe Gly Ala Leu Leu Gln Gln Gly
                260                 265                 270
Gly Met Tyr Leu Pro Arg Ala Asp Ser Gly Arg Leu Val Val Gly Phe
                275                 280                 285
Trp Trp Ile Val Val Ile Val Leu Val Thr Thr Tyr Cys Gly Asn Leu
                290                 295                 300
Val Ala Phe Leu Thr Phe Pro Lys Phe Gln Pro Gly Val Asp Tyr Leu
305                 310                 315                 320
Ser Gln Leu Pro Arg His Lys Glu Ile Ser Gln Tyr Gly Leu Arg Asn
                    325                 330                 335
Gly Thr Phe Phe Glu Arg Tyr Val Gln Thr Thr Thr Arg Asp Asp Phe
                340                 345                 350
Lys His Tyr Met Ala Arg Ala Gln Ile Tyr Gly Asn Ser Gln Glu Glu
                355                 360                 365
Asn Ile Glu Ala Val Lys Gln Gly His Arg Ile Asn Ile Asp Trp Arg
370                 375                 380
Ile Asn Leu Gln Leu Ile Val Gln Gln His Phe Glu Arg Asp Lys Glu
385                 390                 395                 400
Cys Arg Phe Ala Leu Gly Lys Glu Ser Phe Val Asp Glu Gln Ile Ala
                    405                 410                 415
Met Ile Val Pro Ser His Ser Val Pro Tyr Leu His Leu Ile Asn Ser
                420                 425                 430
His Ile Asp Arg Leu Phe Arg Met Gly Phe Met Glu Arg Trp His Gln
                435                 440                 445
Met Asn Leu Pro Ser Ala Asp Lys Cys Thr Gly Lys Ser Ser Leu Arg
450                 455                 460
```

Gln Val Thr Asn His Lys Val Asn Met Asp Asp Met Gln Gly Cys Phe
465                 470                 475                 480

Leu Val Leu Leu Leu Gly Phe Met Val Ala Phe Ala Ile Gly Cys Gly
                485                 490                 495

Glu Phe Trp Tyr His His Leu Tyr Val His Lys Thr Ser Arg Gln Pro
                500                 505                 510

Pro Ser Ser Val Phe Thr Thr
            515

<210> SEQ ID NO 34
<211> LENGTH: 637
<212> TYPE: PRT
<213> ORGANISM: Drosophila

<400> SEQUENCE: 34

Met Arg Gln Gln Phe Leu Val Ile Ser Ala Phe His Glu Asp Ile Ile
1               5                   10                  15

Glu Ile Ala Glu Thr Leu Asn Met Phe His Val Gly Asn Gln Trp Met
                20                  25                  30

Ile Phe Val Leu Asp Met Val Gly Arg Asp Phe Asp Ala Gly Thr Ala
            35                  40                  45

Thr Ile Asn Leu Asp Glu Gly Ala Asn Ile Ala Phe Ala Leu Asn Glu
        50                  55                  60

Thr Asp Pro Asn Cys Gln Asp Ser Leu Asn Cys Thr Ile Ser Glu Ile
65                  70                  75                  80

Ser Leu Ala Leu Val Thr Ser Ile Ser Lys Ile Thr Val Glu Glu Glu
                85                  90                  95

Ser Ile Tyr Gly Glu Ile Ser Asp Glu Glu Trp Glu Ala Ile Arg Phe
                100                 105                 110

Thr Lys Gln Glu Lys Gln Ala Glu Ile Leu Glu Tyr Met Lys Glu Ser
            115                 120                 125

Leu Lys Thr Asn Ala Lys Cys Ser Ser Cys Ala Arg Trp Arg Val Glu
        130                 135                 140

Thr Ala Ile Thr Trp Gly Lys Ser Gln Glu Asn Arg Lys Phe Arg Ser
145                 150                 155                 160

Ile Pro Ser Arg Asp Ala Lys Asn Arg Asn Phe Glu Phe Ile Asn Ile
                165                 170                 175

Gly Tyr Trp Thr Pro Leu Leu Gly Phe Val Cys Gln Glu Leu Ala Phe
                180                 185                 190

Pro His Ile Glu His His Phe Arg Asn Ile Thr Met Asp Ile Leu Thr
            195                 200                 205

Val His Asn Pro Pro Trp Gln Ile Leu Thr Lys Asn Ser His Gly Val
        210                 215                 220

Ile Val Glu His Lys Gly Ile Val Met Glu Ile Val Lys Glu Leu Ser
225                 230                 235                 240

Arg Ala Leu Asn Phe Ser Tyr Tyr Leu His Glu Ala Ser Ser Trp Lys
                245                 250                 255

Glu Glu Tyr Ser Val Ser Thr Ser Ala Gly Ser Asn Glu Ser Asp Glu
                260                 265                 270

Leu Val Gly Ser Met Thr Phe Arg Ile Pro Tyr Arg Val Val Glu Met
            275                 280                 285

Val Gln Gly Asn Gln Phe Phe Ile Ala Ala Val Ala Ala Thr Val Glu
        290                 295                 300

Asp Phe Asp Gln Lys Pro Phe Asn Tyr Thr Val Pro Ile Ser Val Gln

```
            305                 310                 315                 320

Lys Tyr Ser Phe Ile Thr Arg Lys Pro Asp Glu Val Ser Arg Ile Tyr
                325                 330                 335

Leu Phe Thr Ala Pro Phe Thr Met Glu Thr Trp Phe Cys Leu Met Gly
                340                 345                 350

Ile Ile Leu Leu Thr Ala Pro Thr Leu Tyr Ala Ile Asn Arg Leu Ala
                355                 360                 365

Pro Leu Lys Glu Met Arg Ile Val Gly Leu Ser Thr Val Lys Ser Cys
            370                 375                 380

Phe Trp Tyr Ile Phe Gly Ala Leu Leu Gln Gln Gly Met Tyr Leu
385                 390                 395                 400

Pro Thr Ala Asp Ser Gly Arg Leu Val Val Gly Phe Trp Ile Val
                405                 410                 415

Val Ile Val Leu Val Thr Thr Tyr Cys Gly Asn Leu Val Ala Phe Leu
                420                 425                 430

Thr Phe Pro Lys Phe Gln Pro Gly Val Asp Tyr Leu Asn Gln Leu Glu
                435                 440                 445

His His Lys Asp Ile Val Gln Tyr Gly Leu Arg Asn Gly Thr Phe Phe
            450                 455                 460

Glu Arg Tyr Val Gln Ser Ser Thr Arg Glu Asp Phe Lys Arg Tyr Leu
465                 470                 475                 480

Glu Arg Ala Arg Ile Tyr Gly Ser Ala Gln Glu Asp Ile Glu Ala
                485                 490                 495

Val Lys Arg Gly Glu Arg Ile Asn Ile Asp Trp Arg Ile Asn Leu Gln
                500                 505                 510

Leu Ile Val Gln Arg His Phe Glu Arg Asp Lys Glu Cys Arg Phe Ala
            515                 520                 525

Leu Gly Lys Glu Ser Phe Val Asp Glu Gln Ile Ala Met Ile Val Pro
            530                 535                 540

Ala Gln Ser Ala Tyr Leu His Leu Val Asn Arg His Ile Asn Ser Met
545                 550                 555                 560

Phe Arg Met Gly Phe Ile Glu Arg Trp His Gln Met Asn Leu Pro Ser
                565                 570                 575

Ala Gly Lys Cys Asn Gly Lys Ser Ala Gln Arg Gln Val Thr Asn His
                580                 585                 590

Lys Val Asn Met Asp Asp Met Gln Gly Cys Phe Leu Val Leu Leu
            595                 600                 605

Gly Phe Thr Val Ala Leu Leu Ile Val Cys Gly Glu Phe Trp Tyr Arg
            610                 615                 620

Arg Phe Arg Ala Ser Lys Gln Arg Gln Phe Thr Asn
625                 630                 635

<210> SEQ ID NO 35
<211> LENGTH: 662
<212> TYPE: PRT
<213> ORGANISM: Drosophila

<400> SEQUENCE: 35

Met Arg Gly Gln Gln Lys Arg Ile Ser Leu Arg Lys Ala Leu Ile Gln
1               5                   10                  15

Phe Ala Pro Thr Lys His Glu Leu Arg Arg Gln Gln Phe Leu Val Leu
                20                  25                  30

Ser Arg Phe His Glu Asp Ile Ile Glu Ile Ala Glu Thr Leu Ser Met
            35                  40                  45
```

```
Phe His Val Asn Asn Gln Trp Met Phe Phe Val Leu Glu Asp Pro His
 50                  55                  60

Asn Glu Phe Asp Ala Asn Thr Val Thr Ile Asn Leu Asp Glu Gly Ala
 65                  70                  75                  80

Asn Ile Ala Phe Ala Leu Asn Glu Thr Asn Phe Asn Cys Val Asp Thr
                 85                  90                  95

Leu Asn Cys Thr Ile Thr Glu Val Ser Met Ala Leu Val Thr Ser Leu
            100                 105                 110

Ser Arg Met Ile Leu Glu Glu Ser Ile Tyr Gly Glu Ile Ser Asp
            115                 120                 125

Glu Glu Trp Glu Ser Ile Arg Phe Thr Lys Gln Glu Lys Gln Asp Glu
            130                 135                 140

Met Leu Glu Tyr Met Lys Asp Tyr Leu Lys Thr Asn Ser Lys Cys Ala
145                 150                 155                 160

Ser Cys Ala Arg Trp Arg Phe Glu Thr Ala Ile Thr Trp Gly Lys Ser
                165                 170                 175

Gln Glu Asn Arg Lys Phe Arg Ala Ala Pro Thr Arg Asp Ala Lys Asn
            180                 185                 190

Arg Asn Phe Asp Phe Ile Asn Ile Gly Tyr Trp Ser Pro Leu Leu Gly
            195                 200                 205

Phe Val Cys His Glu Leu Ile Phe Pro His Ile Glu His His Phe Arg
210                 215                 220

Asn Ile Thr Met Asp Ile Val Thr Glu His Asn Pro Pro Trp Gln Ile
225                 230                 235                 240

Leu Thr Lys Asp Ser Arg Gly Val Ile Val Glu His Asn Gly Ile Val
                245                 250                 255

Met Glu Ile Leu Lys Glu Leu Ser Arg Ala Leu Asn Phe Ser Tyr Tyr
            260                 265                 270

Leu His Asp Ala Thr Ala Gln Asp Tyr Asp Asn Gln Leu Gly Pro Ser
            275                 280                 285

Thr Asn Glu Ser Asp Glu Leu Met Gly Ser Met Thr Phe Arg Ile Pro
290                 295                 300

Tyr Arg Val Val Glu Met Val Gln Gly Asn Glu Phe Phe Met Ala Ala
305                 310                 315                 320

Val Ala Ala Thr Ile Asp Glu Gln His Lys Lys Arg Phe Asn Tyr Thr
                325                 330                 335

Gln Pro Ile Ser Val Gln Lys Tyr Thr Phe Ile Leu Arg Gln Pro Asp
            340                 345                 350

Glu Val Ser Arg Ile Tyr Leu Phe Thr Ala Pro Phe Thr Ile Glu Thr
            355                 360                 365

Trp Ala Cys Leu Ala Gly Ile Leu Met Val Thr Ala Pro Met Leu Tyr
370                 375                 380

Ile Val Asn Arg Leu Val Pro Leu Gln Glu Leu Gln Ile Arg Gly Leu
385                 390                 395                 400

Ser Thr Val Lys Asn Cys Phe Trp Tyr Ile Tyr Gly Ala Leu Leu Gln
                405                 410                 415

Gln Gly Gly Met Tyr Leu Pro Arg Ala Asp Ser Gly Arg Leu Val Val
            420                 425                 430

Gly Phe Trp Trp Ile Val Val Ile Leu Val Thr Thr Tyr Cys Gly
            435                 440                 445

Asn Leu Val Ala Phe Leu Thr Phe Pro Lys Phe Gln Pro Gly Ile Asp
450                 455                 460

Tyr Leu Asn Gln Leu Phe Gly His Thr Glu Ile Lys Gln Tyr Gly Leu
```

```
                465                 470                 475                 480
Arg Asn Gly Thr Phe Phe Glu Lys Tyr Val Glu Thr Thr Thr Arg Pro
                    485                 490                 495

Glu Phe Lys Arg Phe Ile Glu Arg Ala Thr Ile Tyr Ser Ser Val Gln
                500                 505                 510

Ser Glu Asn Ile Ala Ala Val Lys His Gly Asp Arg Ile Asn Ile Asp
            515                 520                 525

Trp Arg Ile Asn Leu Gln Leu Ile Val Gln Gln His Phe Asp Lys Asp
        530                 535                 540

Lys Glu Cys Arg Phe Ala Leu Gly Lys Glu Asp Phe Val Asp Glu Gln
545                 550                 555                 560

Ile Gly Leu Ile Val Pro Thr Ser Ser Ala Tyr Leu His Leu Ile Asn
                565                 570                 575

Gln His Leu Asp Lys Leu Phe Arg Met Gly Phe Ile Glu Arg Trp His
                580                 585                 590

Lys Thr Asn Leu Pro Ser Met Asp Lys Cys Asn Gly Arg Asn Val Gln
                595                 600                 605

Arg Gln Ile Ala Asn His Lys Val Asn Met Asp Asp Met Gln Gly Cys
            610                 615                 620

Phe Met Val Leu Leu Phe Gly Ile Ile Leu Ala Leu Phe Ile Ser Cys
625                 630                 635                 640

Ile Glu Phe Trp Tyr Tyr Arg Phe Phe Val Val Gly Arg Asp Arg Lys
                645                 650                 655

Ser Ile Ala Phe Ala Asn
                660

<210> SEQ ID NO 36
<211> LENGTH: 514
<212> TYPE: PRT
<213> ORGANISM: Drosophila

<400> SEQUENCE: 36

Met Lys Glu Tyr Leu Lys Ala Asn Ser Lys Cys Ala Ser Cys Ala Arg
1               5                   10                  15

Trp Arg Ile Glu Thr Ala Ile Thr Trp Gly Lys Ser Gln Glu Asn Arg
            20                  25                  30

Lys Phe Arg Thr Thr Pro Thr Arg Asp Ala Lys Asn Arg Asn Phe Glu
        35                  40                  45

Phe Ile Asn Ile Gly Tyr Trp Thr Pro Leu Leu Gly Phe Met Cys His
    50                  55                  60

Glu Leu Thr Phe Pro His Ile Asp His His Phe Arg Asn Ile Thr Met
65                  70                  75                  80

Asp Ile Val Thr Val His Asn Pro Pro Trp Gln Ile Leu Thr Lys Asp
                85                  90                  95

Ser Arg Gly Val Ile Val Glu His Ser Gly Ile Val Met Glu Ile Leu
            100                 105                 110

Lys Glu Leu Ser Arg Ala Leu Asn Phe Ser Tyr Tyr Leu His Glu Gly
        115                 120                 125

His Ser Ser Asp Thr Asp Asp Thr Ile Arg Gln Asn Met Asn Asp Ser
    130                 135                 140

Asp Glu Leu Met Gly Ser Met Thr Tyr Arg Ile Pro Tyr Arg Val Val
145                 150                 155                 160

Glu Leu Met Gln Ser Asn Ala Tyr Phe Met Gly Ala Val Ala Ala Thr
                165                 170                 175
```

```
Ile Asp Glu Pro Ser Lys Lys His Phe Asn Tyr Thr Gln Pro Ile Ser
            180                 185                 190

Ile Gln Lys Tyr Thr Phe Ile Leu Arg Gln Pro Asp Glu Val Ser Arg
        195                 200                 205

Ile Tyr Leu Phe Thr Ala Pro Phe Thr Leu Glu Thr Trp Gly Cys Leu
        210                 215                 220

Ala Gly Ile Leu Leu Phe Thr Ala Pro Ile Leu Tyr Phe Val Asn Arg
225                 230                 235                 240

Leu Met Pro Leu Pro Glu Leu Arg Ile His Gly Leu Ser Thr Val Lys
                245                 250                 255

Asn Cys Phe Trp Tyr Ile Tyr Gly Ala Leu Leu Gln Gln Gly Gly Met
            260                 265                 270

Tyr Leu Pro Arg Ala Asp Ser Gly Arg Leu Val Val Gly Phe Trp Trp
        275                 280                 285

Leu Val Val Ile Val Leu Val Thr Thr Tyr Cys Gly Asn Leu Val Ala
        290                 295                 300

Phe Leu Thr Phe Pro Lys Phe Gln Pro Gly Val Asp Tyr Leu His Gln
305                 310                 315                 320

Leu Phe Ala His Lys Glu Ile Lys Gln Tyr Gly Leu Arg Asn Gly Thr
                325                 330                 335

Phe Phe Glu Lys Tyr Val Glu Ala Thr Thr Arg Glu Asp Phe Lys Arg
            340                 345                 350

Phe Ile Ala Arg Ser Ser Ile Tyr Asn Ser Val Gln Ser Glu Asn Ile
        355                 360                 365

Asp Ala Val Lys His Gly Asp Arg Ile Asn Ile Asp Trp Arg Ile Asn
370                 375                 380

Leu Gln Leu Ile Val Gln Gln His Phe Glu Leu Asp Lys Glu Cys Arg
385                 390                 395                 400

Phe Ala Leu Gly Lys Glu Asp Phe Val Asp Glu Gln Ile Gly Leu Met
                405                 410                 415

Val Pro Thr Gly Ser Ala Tyr Leu His Leu Ile Asn His His Ile Asp
            420                 425                 430

Arg Leu Phe Arg Met Gly Phe Ile Asp Arg Trp His Lys Thr Asn Leu
        435                 440                 445

Pro Ser Met Asp Lys Cys Asn Gly Lys Asn Met Gln Arg Gln Ile Ala
450                 455                 460

Asn His Lys Val Asn Met Asp Asp Met Gln Gly Cys Phe Met Val Leu
465                 470                 475                 480

Leu Phe Gly Val Ile Leu Ala Thr Ile Val Ser Cys Phe Glu Phe Trp
                485                 490                 495

Tyr His Arg Phe Phe Val Val Ser Arg Glu Arg Lys Arg Val Pro Phe
            500                 505                 510

Ser Asn

<210> SEQ ID NO 37
<211> LENGTH: 617
<212> TYPE: PRT
<213> ORGANISM: Drosophila

<400> SEQUENCE: 37

Met Asn Met Phe His Val Gly Asn Gln Trp Met Phe Val Phe Glu
1               5                   10                  15

Thr Met Arg Gln Asp Phe Asp Ala Ser Thr Val Thr Ile Asn Leu Ala
            20                  25                  30
```

```
Glu Gly Ala Asn Ile Ala Phe Ala Leu Asn Glu Thr Asn Thr Asp Cys
             35                  40                  45

Met Asp Thr Leu Asn Cys Thr Ile Ser Glu Ile Ser Met Ala Leu Val
 50                  55                  60

Thr Ala Ile Ser Lys Met Thr Val Asp Glu Gln Ser Ile Tyr Gly Glu
 65                  70                  75                  80

Ile Ser Asp Glu Glu Trp Glu Ser Ile Arg Phe Thr Lys Gln Glu Lys
                 85                  90                  95

Gln Tyr Glu Ile Leu Met Tyr Met Lys Glu Tyr Leu Lys Thr Asn Ser
             100                 105                 110

Lys Cys Ala Ser Cys Ala Lys Trp Arg Phe Glu Thr Ala Ile Thr Trp
             115                 120                 125

Gly Lys Ser Gln Gln Asn Arg Gln Phe Arg Thr Ala Pro Thr Arg Asp
130                 135                 140

Ala Arg Asn Gln Asn Phe Glu Phe Val Asp Ile Gly Tyr Trp Ser Pro
145                 150                 155                 160

Leu Leu Gly Phe Val Cys Gln Glu Leu Thr Phe Pro His Ile Ala Gln
                 165                 170                 175

His Phe Arg Asn Ile Thr Met Asp Ile Val Thr Met His Asn Pro Pro
             180                 185                 190

Trp Gln Ile Leu Thr Lys Asn Ser His Gly Val Ile Val Glu His Lys
             195                 200                 205

Gly Ile Thr Leu Glu Ile Leu Lys Glu Leu Ser Arg Ala Leu Asn Phe
             210                 215                 220

Ser Tyr Tyr Leu His Glu Ala Lys Thr Tyr Asp Asp Glu Phe Pro Leu
225                 230                 235                 240

Asn Gln Ser Thr Asn Glu Ser Asp Glu Leu Leu Gly Ser Met Thr Tyr
                 245                 250                 255

Gly Ile Pro Tyr Arg Val Val Glu Met Val Gln Gly Asn Gln Phe Phe
             260                 265                 270

Met Ala Ala Val Ala Ala Thr Val Glu Asp Pro Asp Lys Lys Ala Phe
             275                 280                 285

Asn Tyr Thr Gln Pro Val Ser Val Gln Lys Tyr Ser Phe Ile Thr Arg
             290                 295                 300

Gln Pro Asp Glu Val Ser Arg Ile Tyr Leu Phe Thr Ala Pro Phe Thr
305                 310                 315                 320

Thr Glu Thr Trp Gly Cys Leu Val Gly Ile Phe Leu Thr Ala Pro
                 325                 330                 335

Met Leu Tyr Ala Ile Asn Arg Leu Ala Pro Leu Gln Glu Leu Gln Ile
             340                 345                 350

His Gly Leu Ser Ser Val Lys Ser Cys Phe Trp Tyr Ile Phe Gly Ala
             355                 360                 365

Leu Leu Gln Gln Gly Gly Met Tyr Leu Pro Arg Ala Asp Ser Gly Arg
             370                 375                 380

Leu Val Val Gly Phe Trp Trp Ile Val Ile Val Leu Val Thr Thr
385                 390                 395                 400

Tyr Cys Gly Asn Leu Val Ala Phe Leu Thr Phe Pro Lys Phe Gln Pro
                 405                 410                 415

Gly Val Asp Tyr Leu Asn Gln Leu His Arg His Thr Glu Ile Ser Gln
             420                 425                 430

Tyr Gly Leu Arg Asn Gly Thr Phe Phe Glu Lys Tyr Val Gln Arg Thr
             435                 440                 445

Thr Arg Asp Asp Phe Lys Gln Tyr Val Ala Lys Ala Ile Ile Tyr Asn
```

```
                    450                 455                 460
Asn Gly Gln Gly Glu Asp Ile Glu Ala Val Lys Asp Gly Gln Arg Ile
465                 470                 475                 480

Asn Ile Asp Trp Arg Ile Asn Leu Gln Leu Val Val Gln Gln His Phe
                485                 490                 495

Glu Arg Asp Lys Glu Cys Arg Phe Ala Leu Gly Lys Glu Ser Phe Val
                500                 505                 510

Asp Glu Gln Ile Ala Leu Ile Val Pro Ser Gln Ser Ala Tyr Leu His
                515                 520                 525

Leu Ile Asn Gln His Ile Asp Arg Met Phe Arg Met Gly Phe Ile Glu
                530                 535                 540

Arg Trp His Arg Thr Asn Leu Pro Ser Ala Asp Lys Cys Asn Gly Lys
545                 550                 555                 560

Ser Ile Leu Arg Gln Ile Thr Asn His Lys Val Asn Met Asp Asp Met
                565                 570                 575

Gln Gly Cys Phe Leu Val Leu Leu Gly Phe Ile Leu Ala Val Phe
                580                 585                 590

Val Gly Cys Ile Glu Tyr Trp Phe Tyr Arg Leu Tyr Val Gln Ser Asp
                595                 600                 605

Ser Arg Lys Pro Thr Val Phe Thr Asn
610                 615

<210> SEQ ID NO 38
<211> LENGTH: 940
<212> TYPE: PRT
<213> ORGANISM: Drosophila

<400> SEQUENCE: 38

Met Glu Thr Val Val Leu Asp His Gln Phe Leu Gly Asp Glu Tyr Gln
1               5                   10                  15

Met Met Leu Glu Asp Leu Glu Asp Tyr Ile Lys Glu Leu Val Arg Val
                20                  25                  30

Glu Leu Lys His Gly Gly Ile Asn Val His Tyr Tyr Ser Trp Thr Ser
            35                  40                  45

Ile Asn Leu Lys Lys Gly Phe Leu Ala Ile Phe Ser Ile Ala Ser Cys
        50                  55                  60

Glu Asp Thr Trp Ser Leu Phe Leu Arg Ala Glu Glu Asp Leu Leu
65                  70                  75                  80

His Ile Ala Val Thr Glu Val Asp Cys Pro Arg Leu Pro Ser Asp Ser
                85                  90                  95

Ala Ile Thr Val Thr Phe Ala Asp Pro Gly Gln Glu Leu Pro Gln Leu
                100                 105                 110

Val Leu Asp Leu Arg Thr Arg Lys Ala Phe Asn Trp Lys Ser Ala Ile
                115                 120                 125

Ile Leu His Asp Glu Thr Leu Asn Arg Asp Met Val Ser Arg Val Val
                130                 135                 140

Glu Ser Leu Thr Ser Gln Ile Asp Asp Ile Ser Ser Ile Ser Val Ser
145                 150                 155                 160

Val Tyr Lys Met Arg His Glu Asn Asn Glu Tyr Leu Arg Arg Lys Glu
                165                 170                 175

Val Tyr Arg Val Leu Lys Lys Leu Pro Val Lys Tyr Ile Gly Glu Asn
                180                 185                 190

Phe Ile Ala Ile Val Thr Thr Asp Val Met Ala Thr Ile Ala Glu Ile
                195                 200                 205
```

-continued

Ala Arg Glu Leu Arg Met Ser His Thr Gln Ala Gln Trp Leu Tyr Leu
210             215                 220

Val Pro Asp Thr Asp Ser His Thr Gly Asn Val Thr Asn Leu Ile Asn
225             230                 235                 240

Asp Leu Tyr Glu Gly Glu Asn Ile Ala Tyr Ile Phe Asn Phe Thr Asp
                245                 250                 255

Asp Arg Gly Cys Lys Asn Gly Leu Lys Cys Tyr Ala His Glu Val Leu
                260                 265                 270

Asp Ser Phe Ile Ser Ala Leu Glu Ala Val Leu Asp Glu Leu Glu
                275                 280                 285

Ala Ala Leu Gln Val Ser Asp Glu Glu Trp Glu Ala Val Arg Pro Thr
290             295                 300

Lys Leu Gln Arg Arg Asn Ser Leu Leu Trp His Met Gln Gln Tyr Leu
305             310                 315                 320

Ser Thr Arg Ser Val Cys Gly Asn Cys Ser Ser Trp Arg Ala Leu Ser
                325                 330                 335

Ala Asp Thr Trp Gly Ala Thr Tyr Asp Arg Ala Asp Glu Asn Thr Ser
                340                 345                 350

Ser Leu Ile Glu Gln Val His Leu Val Gln Val Gly Phe Trp Arg Pro
                355                 360                 365

Ile Asp Gly Val Thr Phe Glu Asp Val Leu Phe Pro His Ile Gln His
                370                 375                 380

Gly Phe Arg Gly Lys Gln Leu Pro Ile Met Thr Tyr His Ser Pro Pro
385             390                 395                 400

Trp Thr Ile Val Thr Tyr Asn Ala Ser Gly Ala Val Thr Ser Tyr Gly
                405                 410                 415

Gly Leu Leu Phe Asp Ile Val Asn Gln Leu Ala Lys Asn Lys Asn Phe
                420                 425                 430

Thr Tyr Ala Ile Tyr Ile Leu Leu Ala Glu Asn Leu Arg Leu Asn
                435                 440                 445

Tyr Thr Asn Glu Thr Thr Thr Asp Thr Leu Tyr Asn Thr Asn Arg Gln
                450                 455                 460

Leu Ile Leu Ser Ala Ile Ala Lys Gly His Ala Ala Leu Val Ala Ala
465             470                 475                 480

Pro Phe Thr Val Ser Pro Asp Thr His Pro Gly Val Asn Phe Thr Val
                485                 490                 495

Pro Val Ser Thr Gln Ser Tyr Ser Phe Ile Ile Ala Arg Pro Arg Glu
                500                 505                 510

Leu Asn Arg Ala Leu Leu Phe Leu Pro Phe Thr Thr Asp Thr Trp
                515                 520                 525

Leu Cys Ile Ala Phe Ala Val Val Leu Met Gly Pro Thr Leu Tyr Val
530             535                 540

Val His Arg Val Ser Pro Tyr Glu Ala Met Glu Ile Thr Arg Glu
545             550                 555                 560

Gly Gly Leu Ser Thr Ile Tyr Asn Cys Leu Trp Tyr Ile Tyr Gly Ala
                565                 570                 575

Leu Leu Gln Gln Gly Gly Met Tyr Leu Pro Arg Ala Asp Ser Gly Arg
                580                 585                 590

Leu Val Val Gly Thr Trp Trp Leu Val Leu Val Val Thr Thr
                595                 600                 605

Tyr Ser Gly Asn Leu Val Val Phe Leu Thr Phe Pro Lys Leu Glu Ile
                610                 615                 620

Pro Val Thr Thr Val Ser Glu Leu Leu Asp Ser Gly Thr Tyr Ser Trp

```
            625                 630                 635                 640
Ser Ile Arg Ser Gly Ser Phe Leu Glu Ser Gln Leu Lys Asn Ser Asn
                    645                 650                 655

Glu Pro Lys Tyr Glu Ala Leu Leu Lys Arg Ala Glu Leu Thr Ser Pro
                660                 665                 670

Ser Asp Gly Ala Glu Asn Asp Ala Ile Val Glu Arg Val Arg Phe Ser
            675                 680                 685

His His Ala Leu Phe Asp Trp Lys Leu Arg Leu Arg Tyr Leu Met Arg
        690                 695                 700

Ala Asp Thr Glu Gln Thr Asp Ser Cys Asp Phe Ala Leu Ser Thr Glu
705                 710                 715                 720

Glu Phe Met Asp Glu Gln Val Ala Met Ile Leu Pro Ala Gly Ser Pro
                725                 730                 735

Tyr Leu Pro Val Ile Asn Lys Glu Ile Asn Arg Met Lys Lys Ala Gly
                740                 745                 750

Leu Ile Thr Lys Trp Leu Ser Ala Tyr Leu Pro Lys Arg Asp Arg Cys
            755                 760                 765

Trp Lys Thr Ser Ala Ile Thr Gln Glu Val Asn Asn His Thr Val Asn
        770                 775                 780

Leu Ser Asp Met Gln Gly Ser Phe Leu Val Leu Phe Leu Ala Ile Val
785                 790                 795                 800

Glu Arg Val Arg Phe Ser His His Ala Leu Phe Asp Trp Lys Leu Arg
                805                 810                 815

Leu Arg Tyr Leu Met Arg Ala Asp Thr Glu Gln Thr Asp Ser Cys Asp
            820                 825                 830

Phe Ala Leu Ser Thr Glu Glu Phe Met Asp Glu Gln Val Ala Met Ile
        835                 840                 845

Leu Pro Ala Gly Ser Pro Tyr Leu Pro Val Ile Asn Lys Glu Ile Asn
    850                 855                 860

Arg Met Lys Lys Ala Gly Leu Ile Thr Lys Trp Leu Ser Ala Tyr Leu
865                 870                 875                 880

Pro Lys Arg Asp Arg Cys Trp Lys Thr Ser Ala Ile Thr Gln Glu Val
                885                 890                 895

Asn Asn His Thr Val Asn Leu Ser Asp Met Gln Gly Ser Phe Leu Val
            900                 905                 910

Leu Phe Leu Asp Ser Gln Lys Thr Cys Ala Pro Glu Lys Ala Val Val
        915                 920                 925

Glu Leu Thr Pro Gly Thr Val Trp Ser Thr Arg Tyr
    930                 935                 940

<210> SEQ ID NO 39
<211> LENGTH: 867
<212> TYPE: PRT
<213> ORGANISM: Drosophila

<400> SEQUENCE: 39

Met Arg Ser Ser Gly Cys Leu Leu Leu Phe Gly Phe Gln Leu Tyr
1               5                   10                  15

Phe Leu Ser Trp Pro Met Ala Val Glu Gly Asn Asp Phe Ser Ser Phe
                20                  25                  30

Leu Ser Ala Asn Ala Ser Leu Ala Val Val Val Asp His Glu Tyr Met
            35                  40                  45

Thr Arg His Gly Gln Asn Ile Met Ala His Phe Glu Lys Ile Leu Ser
        50                  55                  60
```

-continued

```
Asp Ile Ile Arg Glu Asn Leu Lys Asn Gly Ile Asn Val Arg Tyr
 65                  70                  75                  80

Phe Arg Trp Asn Ala Val Arg Leu Lys Lys Asp Phe Leu Ala Ile
                 85                  90                  95

Thr Val Thr Asp Cys Ala Asn Thr Trp Asn Phe Tyr Arg Ser Thr Gln
                100                 105                 110

Glu Thr Ser Val Leu Leu Ile Ala Ile Thr Asp Ser Asp Cys Pro Arg
                115                 120                 125

Leu Pro Leu Asn Lys Ala Leu Met Ala Pro Met Val Glu His Gly Asp
130                 135                 140

Glu Leu Pro Gln Ile Ile Leu Asp Ala Lys Val Gln Gln Ile Leu Asn
145                 150                 155                 160

Trp Lys Thr Ala Val Val Leu Val Asp Gln Asn Ile Leu Asp Asn Asn
                165                 170                 175

Ser Glu Leu Val Lys Ala Ile Val His Glu Ser Thr Thr Asn His Ile
                180                 185                 190

Ala Pro Ile Ser Leu Ile Leu Tyr Lys Ile Asp Asp Ser Leu Arg Gly
                195                 200                 205

Gln Lys Lys Arg Ala Ala Leu Arg His Ala Leu Ser His Phe Ser Pro
210                 215                 220

Ile Asn His Glu Gln Lys Asn Gln Gln Phe Leu Val Leu Ser Lys Phe
225                 230                 235                 240

His Asp Asp Ile Ile Glu Ile Gly Glu Thr Met Asn Met Phe His Val
                245                 250                 255

Gly Asn Gln Trp Met Phe Phe Val Phe Glu Thr Met Arg Gln Asp Phe
                260                 265                 270

Asp Ala Ser Thr Val Thr Ile Asn Leu Ala Glu Gly Ala Asn Ile Ala
                275                 280                 285

Phe Ala Leu Asn Glu Thr Asn Thr Asp Cys Met Asp Thr Leu Asn Cys
290                 295                 300

Thr Ile Ser Glu Ile Ser Met Ala Leu Val Thr Ala Ile Ser Lys Met
305                 310                 315                 320

Thr Val Glu Glu Gln Ser Ile Tyr Gly Glu Ile Ser Asp Glu Trp
                325                 330                 335

Glu Ser Ile Arg Phe Thr Lys Gln Glu Lys Gln Tyr Glu Ile Leu Lys
                340                 345                 350

Tyr Met Lys Glu Tyr Leu Lys Thr Asn Ser Lys Cys Ala Ser Cys Ala
                355                 360                 365

Lys Trp Arg Phe Glu Thr Ala Ile Thr Trp Gly Lys Ser Gln Gln Asn
370                 375                 380

Arg Gln Phe Arg Thr Ala Pro Thr Arg Asp Ala Arg Asn Gln Asn Phe
385                 390                 395                 400

Glu Phe Val Asp Ile Gly Tyr Trp Ser Pro Leu Leu Gly Phe Val Cys
                405                 410                 415

Gln Glu Leu Thr Phe Pro His Ile Ala Gln His Phe Arg Asn Ile Thr
                420                 425                 430

Met Asp Ile Val Thr Met His Asn Pro Pro Trp Gln Ile Leu Thr Lys
                435                 440                 445

Asn Ser Asp Gly Val Ile Val Glu His Lys Gly Ile Thr Leu Glu Ile
                450                 455                 460

Leu Lys Glu Leu Ser Arg Ala Leu Asn Phe Ser Tyr Tyr Leu His Glu
465                 470                 475                 480

Ala Lys Thr Tyr Asp Asp Glu Phe Pro Leu Asn Gln Ser Thr Asn Glu
```

```
                    485                 490                 495

Ser Asp Glu Leu Leu Gly Ser Met Thr Tyr Gly Ile Pro Tyr Arg Val
                500                 505                 510

Val Glu Met Val Gln Gly Asn Arg Phe Phe Met Ala Ala Val Ala Ala
            515                 520                 525

Thr Val Glu Asp Pro Asp Lys Lys Ala Phe Asn Tyr Thr Gln Pro Val
        530                 535                 540

Ser Val Gln Lys Tyr Ser Phe Ile Thr Arg Gln Pro Asp Glu Val Ser
545                 550                 555                 560

Arg Ile Tyr Leu Phe Thr Ala Pro Phe Thr Thr Glu Thr Trp Gly Cys
                565                 570                 575

Leu Val Gly Ile Ile Phe Leu Thr Ala Pro Met Leu Tyr Ala Ile Asn
            580                 585                 590

Arg Leu Ala Pro Leu Gln Glu Leu Gln Ile His Gly Leu Ser Ser Val
        595                 600                 605

Lys Ser Cys Phe Trp Tyr Ile Phe Gly Ala Leu Leu Gln Gln Gly Gly
    610                 615                 620

Met Tyr Leu Pro Arg Ala Asp Ser Gly Arg Leu Val Val Gly Phe Trp
625                 630                 635                 640

Trp Ile Val Val Ile Val Leu Val Thr Thr Tyr Cys Gly Asn Leu Val
                645                 650                 655

Ala Phe Leu Thr Phe Pro Lys Phe Gln Pro Gly Val Asp Tyr Leu Asn
            660                 665                 670

Gln Leu His Arg His Thr Glu Ile Ser Gln Tyr Gly Leu Arg Asn Gly
        675                 680                 685

Thr Phe Phe Glu Lys Tyr Val Gln Arg Thr Thr Arg Asp Asp Phe Lys
    690                 695                 700

Gln Tyr Val Ala Lys Ala Ile Ile Tyr Asn Asn Gly Gln Gly Glu Asp
705                 710                 715                 720

Ile Glu Ala Val Lys Asp Gly Gln Arg Ile Asn Ile Asp Trp Arg Ile
                725                 730                 735

Asn Leu Gln Leu Val Val Gln Gln His Phe Glu Arg Asp Lys Glu Cys
            740                 745                 750

Arg Phe Ala Leu Gly Lys Glu Ser Phe Val Asp Glu Gln Ile Ala Leu
        755                 760                 765

Ile Val Pro Ser Glu Ser Ala Tyr Leu His Leu Ile Asn Gln His Ile
    770                 775                 780

Asp Arg Met Phe Arg Met Gly Phe Ile Glu Arg Trp His Arg Thr Asn
785                 790                 795                 800

Leu Pro Ser Ala Asp Lys Cys Asn Gly Lys Ser Ile Leu Arg Gln Ile
                805                 810                 815

Thr Asn His Lys Val Asn Met Asp Asp Met Gln Gly Cys Phe Leu Val
            820                 825                 830

Leu Leu Leu Gly Phe Ile Leu Ala Val Phe Val Gly Cys Ile Glu Tyr
        835                 840                 845

Trp Phe Tyr Arg Leu Tyr Val Gln Ser Asp Ser Arg Lys Pro Thr Val
    850                 855                 860

Phe Thr Asn
865

<210> SEQ ID NO 40
<211> LENGTH: 630
<212> TYPE: PRT
<213> ORGANISM: Drosophila
```

<400> SEQUENCE: 40

```
Met Met Gln His Leu Gly Ala Asn Trp Ser Gln Trp Ala Asn Ile Phe
  1               5                  10                  15

Asn Gln Val Pro Ala Phe Ser Asn Leu Trp Glu Pro Ile Gly His Lys
             20                  25                  30

Trp Asp Asn Ile Phe Asn Gln Val Pro Leu Ser Asn His Trp Glu Leu
         35                  40                  45

Ile Gly His Lys Trp Asp Asn Ile Phe Asn Gln Val Pro Phe Ser Asn
 50                  55                  60

His Trp Glu Leu Ile Gly His Lys Thr Thr Phe Thr Arg Ile Asn Pro
 65                  70                  75                  80

Asp Thr Lys Phe Leu Asp Asp Glu Asp Val Glu Gly Val His Leu Val
                 85                  90                  95

His Asp Phe Asp Leu Val Arg Glu Met Gln Val Arg Leu Gly Lys Phe
            100                 105                 110

Ala Lys Gly Gln Ala Val Phe Phe Pro Val Met Trp Ser Val Ser Leu
        115                 120                 125

Ser Met Lys Asn Val Gln Ser Leu Ala Ser Lys Pro Tyr Val Val Gly
130                 135                 140

Pro Lys Pro Ser Gly Pro Arg Phe Leu Leu Tyr Ile Asp Ser Ser Gly
145                 150                 155                 160

Asp Ile Phe Leu Glu Asn Met Thr Gln His Ile Phe Arg Val Asp Glu
                165                 170                 175

Asp His Ala Ile Lys Ile Glu Thr Phe Glu Gly Lys Pro Ile Thr Asp
            180                 185                 190

Thr Val Leu Asp Gly Val Ile Thr Arg Glu Lys Ser Asp Asp Asp Ala
        195                 200                 205

Ser Cys Asn Gly Asn Ile Lys Glu Asp Gly Thr Thr Gly Lys Leu Lys
210                 215                 220

Phe Val Ile Leu Asp Ala Ile Arg Cys Ser Gly Asn Asp Leu Thr Gly
225                 230                 235                 240

Leu Asn Ile Leu Glu Arg Ile Ala Phe Val Arg Glu Glu Ile Ile Ile
                245                 250                 255

Pro Met Thr Pro Thr Glu Ala Glu Leu His Val Gly Gly Pro Lys Thr
            260                 265                 270

Lys Phe Glu Ile Lys Tyr Asp Met Ile Arg Leu Thr Asp Glu Met Lys
        275                 280                 285

Met Leu Asp Gly Cys Ile Ile Asp Cys Arg Tyr Phe Asp His Gln Trp
290                 295                 300

Ile Phe Ile Lys Gln Arg His Asp Arg Asn His Pro Asn Gly Ser Glu
305                 310                 315                 320

Ala Val Lys Glu Thr Thr Ala Asn Ala Asn Ser Ser Ser Glu Arg Val
                325                 330                 335

Asn Asp Leu Ser Cys Tyr Thr Ser Asn Leu Leu Gln Val Tyr Val Lys
            340                 345                 350

Ala Leu His Gln Val Ile Arg Glu Glu Glu Thr His Tyr Phe Gln Thr
        355                 360                 365

Thr Glu Asp Asp Trp Asn Arg Ser Lys Pro Ser Ala Gly Asp Arg Arg
            370                 375                 380

Asn Asn Ile Phe Arg Thr Leu Gln Asn Met Trp Lys Asp Ala Thr Lys
385                 390                 395                 400

Trp Ser Ser Trp Leu Asn Trp Ala Leu Lys Ala Val Glu Ile Lys Glu
```

```
                405                 410                 415
Thr Arg Lys Pro Thr Leu Leu Asp Val Gly Val Trp Asp Ala Ala His
            420                 425                 430

Gly Leu Val Val Tyr Asp Asp Phe Pro His Phe Thr Gly Gly Leu
            435                 440                 445

Arg Gln Arg Val Ile Ser Val Thr Thr Met Glu Phe Pro Pro Trp Gln
            450                 455                 460

Ile Phe Glu Arg Asn Ser Gln Gly Lys Val Val Arg His Thr Gly Leu
465                 470                 475                 480

Val Leu Glu Leu Thr Lys Glu Leu Gly Asn Leu Ser Met Leu Trp Asn
            485                 490                 495

His Val Glu Pro Ala Asp Gly Lys Trp Gly Ser Arg Leu Ser Phe Ser
            500                 505                 510

Arg Trp Thr Gly Met Val Glu Gln Val Arg Thr Gly Ser Val Ala Phe
            515                 520                 525

Ala Ala Ala Gly Cys Thr Val Thr Ala Asp Arg Met Ser Ala Val Asn
            530                 535                 540

Phe Ser Met Ser Leu Asp Ala Gln Pro Tyr Thr Phe Met Phe Ala Arg
545                 550                 555                 560

Pro Lys Gln Leu Ser Arg Ala Tyr Leu Phe Ile Gln Pro Tyr Thr Pro
                565                 570                 575

Asn Ala Trp Ile Thr Ile Phe Ala Met Thr Ile Gly Ala Gly Ser Leu
            580                 585                 590

Ile Trp Ser Phe Asn Asn Ile Thr Pro Phe Tyr Asp Phe Tyr Pro Asp
            595                 600                 605

Arg Pro Gly Ser Pro Ile Phe Ser Ile Trp Pro Tyr Phe Tyr Ala Lys
            610                 615                 620

Glu Lys Cys Leu Ser Leu
625                 630

<210> SEQ ID NO 41
<211> LENGTH: 897
<212> TYPE: PRT
<213> ORGANISM: Drosophila

<400> SEQUENCE: 41

Met Leu Leu Arg Val Leu Leu Val Leu Ala Ser Ala Phe Ile His Val
1               5                   10                  15

Gln Ser Ala His Tyr Glu Leu Tyr Ser Glu Leu Arg Pro Asp Glu Arg
            20                  25                  30

Trp Phe Leu Asp Asp Thr Lys Leu Ile Pro Val Ser Cys Glu Asn Gly
            35                  40                  45

Asp Cys Ser Ala Leu Phe Asn Lys His Asn Lys His Lys Ile Ala Lys
50                  55                  60

Arg Ala Ala Val Gln Val Glu Thr Met Lys Asp Tyr Ile Lys Phe Leu
65                  70                  75                  80

Leu Arg Gly Asn Lys Thr Lys Asp Asp Thr Asn Thr Asp Pro Tyr
                85                  90                  95

Arg Thr Ala Asn Ile Thr Leu Gly Val Val Met Asp Lys Asn Leu Ile
            100                 105                 110

Gly Asn Leu Gln Thr Phe Thr Asn Ile Phe Asp Val Ala Asn Met Pro
            115                 120                 125

Ser Asn Pro Glu Ile Asp Tyr Leu Arg Leu Gln Lys Phe Asn Val Thr
            130                 135                 140
```

```
Tyr Leu Asn Pro Gln Asp Lys Leu Pro Ser Asn Ile Asn Ala Val Leu
145                 150                 155                 160

Ser Ile Leu Pro Cys Asp Val Leu Thr Arg Phe Asp Lys Asn Leu Ala
                165                 170                 175

Ser Leu Pro Ile Leu His Ile Ala Ile Thr Ser Asp Asn Cys Pro Arg
            180                 185                 190

Ile Thr Arg Trp Ala Val Leu Met Val Pro Val Val Lys Thr Gly Ala
        195                 200                 205

Glu Leu Pro Gln Ile Phe Thr Asp Leu Arg Leu Ser Asp Thr Leu Asn
    210                 215                 220

Trp Lys Glu Ala Val Val Ile Ala Glu His Ala Asn Lys Glu Leu
225                 230                 235                 240

Phe Asp Gly Leu Val Asp Ser Leu Ser Arg Pro Val His Lys Lys Asp
                245                 250                 255

Pro Leu Ala Leu Thr Val Val Lys Leu His Gly Pro Val Ala Leu Arg
            260                 265                 270

Lys Lys Asn Phe Glu Ser Gln Leu Leu Asn Leu Gln Val Arg Pro Lys
        275                 280                 285

Gly Arg Asn Phe Ile Leu Val Ser Lys Gln Asp Thr Ala Leu Trp Ala
    290                 295                 300

Phe Asp Ala Ala Ser His Val Gly Leu Val Asn Pro Tyr Ser Gln Trp
305                 310                 315                 320

Leu Phe Leu Ile Thr Asp Ser Thr Asp Pro Ala Ile Phe Leu Pro Asn
                325                 330                 335

Val Glu Asp Gly Gln Asn Ile Ser Phe Leu Tyr Asn Ile Ser Asp Ile
            340                 345                 350

Glu Thr Thr Ala Asn Ala Asn Ser Ser Ser Glu Arg Val Asn Asp Leu
        355                 360                 365

Pro Cys Tyr Thr Ser Asn Leu Leu Gln Val Tyr Val Lys Ala Leu His
    370                 375                 380

Gln Leu Ile Arg Glu Glu Thr His Tyr Phe Gln Thr Thr Glu Asp
385                 390                 395                 400

Asp Trp Ile Arg Ser Lys Pro Ser Ala Gly Asp Arg Arg Asn Asn Ile
                405                 410                 415

Phe Arg Thr Leu Gln Asn Met Trp Lys Asp Ala Thr Lys Cys Ser Ser
            420                 425                 430

Trp Leu Asn Trp Ala Met Lys Ala Val Glu Ile Lys Glu Thr Arg Lys
        435                 440                 445

Pro Thr Leu Leu Asp Val Gly Val Trp Asp Ala Ala His Gly Leu Val
450                 455                 460

Val Tyr Asp Asp Phe Phe Pro His Phe Thr Gly Gly Leu Arg Gln Arg
465                 470                 475                 480

Val Ile Asn Val Thr Thr Met Glu Phe Pro Pro Trp Gln Ile Phe Glu
                485                 490                 495

Arg Asn Ser His Gly Lys Val Val Arg His Thr Gly Leu Val Leu Glu
            500                 505                 510

Leu Thr Lys Glu Leu Gly Asn Arg Leu Asn Phe Ser Val Asn Val Val
        515                 520                 525

Glu Pro Ala Asp Gly Lys Trp Gly Ser Arg Leu Ser Phe Ser Arg Trp
    530                 535                 540

Thr Gly Met Val Glu Gln Val Arg Thr Gly Ser Val Ala Phe Ala Ala
545                 550                 555                 560

Ala Gly Phe Thr Val Thr Ala Asp Arg Met Ser Ala Val Asn Phe Ser
```

Met Ser Leu Asp Ala Gln Pro Tyr Thr Phe Met Phe Ala Arg Pro Lys
            580                 585                 590

Gln Leu Ser Arg Ala Tyr Leu Phe Ile Gln Pro Tyr Thr Pro Asn Ala
            595                 600                 605

Trp Ile Thr Ile Phe Ala Met Thr Ile Gly Ala Gly Pro Leu Ile Trp
610                 615                 620

Ala Phe Asn Lys Ile Thr Pro Phe Tyr Asp Phe Tyr Pro Asp Arg Pro
625                 630                 635                 640

Gly Ser Pro Ile Phe Ser Ile Trp Tyr Asn Ile Trp Tyr Cys Ile Gly
                645                 650                 655

Ala Leu Leu Phe Gln Gly Gln Arg Glu Met Pro Ile Ala Leu Ser Gly
            660                 665                 670

Arg Met Val Val Gly Phe Phe Trp Leu Phe Val Ile Val Val Leu Thr
                675                 680                 685

Ala Tyr Ser Gly Asn Leu Val Ala Phe Leu Thr Phe Pro Thr Tyr Thr
        690                 695                 700

Asn Pro Ile Asn Thr Leu Gln Asp Leu Ile Asp Asn Lys Gly Ser Leu
705                 710                 715                 720

Thr Trp Gly Ile Leu Arg Gly Thr Ala Leu Glu Asp Tyr Leu Lys Thr
                    725                 730                 735

Ser Asp Glu Lys Met Tyr Arg Glu Leu Tyr Glu Gly Ala Ile Leu His
            740                 745                 750

Asp Thr Ala Asp Asp Val Leu Leu Asp Met Ile Arg Asn Gln Gln His
            755                 760                 765

Val Tyr Ile Glu Trp Lys Thr Asn Leu Gln Trp Leu Met Lys Gln Asp
770                 775                 780

Phe Met Lys Thr Asn Ser Cys Asp Phe Ser Leu Gly Thr Glu Asn Phe
785                 790                 795                 800

Phe Leu Gln Gln Val Ala Leu Ala Phe Pro Arg Asp Ser Pro Ile Leu
                    805                 810                 815

Glu Arg Val Asn Leu Glu Ile Ile Tyr Met Gln Arg Gly Gly Leu Ile
            820                 825                 830

Glu His Trp Arg Gln Glu Phe Trp Pro Ser Ala Asp Arg Cys Ser Glu
            835                 840                 845

Thr Ala Thr Gly Gly Ser Asp Gly Asp Thr Ile Gln Ala Ile Ser Val
        850                 855                 860

Ala Asp Met Gln Gly Ser Phe Tyr Val Leu Phe Phe Gly Lys Thr Lys
865                 870                 875                 880

Asn Leu Gly Thr Leu Tyr Asn Leu Phe Ile Asn Gly Lys Phe Met Tyr
                    885                 890                 895

Glu

<210> SEQ ID NO 42
<211> LENGTH: 637
<212> TYPE: PRT
<213> ORGANISM: Drosophila

<400> SEQUENCE: 42

Met Arg Gln Gln Phe Leu Val Ile Ser Ala Phe His Glu Asp Ile Ile
1               5                   10                  15

Glu Ile Ala Glu Thr Leu Asn Met Phe His Val Gly Asn Gln Trp Met
            20                  25                  30

Ile Phe Val Leu Asp Met Val Ala Arg Asp Phe Asp Ala Gly Thr Val

```
                    35                  40                  45
Thr Ile Asn Leu Asp Glu Gly Ala Asn Ile Ala Phe Ala Leu Asn Glu
                50                  55                  60
Thr Glu Pro Asn Cys Gln Asp Ser Leu Asn Cys Thr Ile Ser Glu Ile
 65                 70                  75                  80
Ser Leu Ala Leu Val Asp Ala Ile Ser Lys Ile Thr Val Glu Glu Glu
                    85                  90                  95
Ser Ile Tyr Gly Glu Ile Ser Asp Glu Glu Trp Glu Ala Ile Arg Phe
               100                 105                 110
Thr Lys Gln Glu Lys Gln Ser Glu Ile Leu Gly Tyr Met Lys Glu Phe
               115                 120                 125
Leu Lys Thr Asn Ala Lys Cys Ser Ser Cys Ala Arg Trp Arg Val Glu
           130                 135                 140
Thr Ala Ile Thr Trp Gly Lys Ser Gln Glu Asn Arg Lys Phe Arg Ser
145                 150                 155                 160
Thr Pro Gln Arg Asp Ala Lys Asn Arg Asn Phe Glu Phe Ile Asn Ile
                165                 170                 175
Gly Tyr Trp Thr Pro Val Leu Gly Phe Val Cys Gln Glu Leu Ala Phe
            180                 185                 190
Pro His Ile Glu His His Phe Arg Asn Ile Thr Met Asp Ile Leu Thr
        195                 200                 205
Val His Asn Pro Pro Trp Gln Ile Leu Thr Lys Asn Ser Asn Gly Asp
210                 215                 220
Ile Val Glu His Lys Gly Ile Val Met Glu Ile Val Lys Glu Leu Ser
225                 230                 235                 240
Arg Ala Leu Asn Phe Ser Tyr Tyr Leu His Glu Ala Ser Ser Trp Lys
                245                 250                 255
Glu Glu Asp Ser Leu Ser Thr Ser Ala Gly Gly Asn Glu Ser Asp Glu
            260                 265                 270
Leu Val Gly Ser Met Thr Phe Arg Ile Pro Tyr Arg Val Val Glu Met
        275                 280                 285
Val Gln Gly Asn Gln Phe Phe Ile Ala Ala Val Ala Ala Thr Leu Glu
290                 295                 300
Asp Pro Asp Gln Lys Pro Phe Asn Tyr Thr Gln Pro Ile Ser Val Gln
305                 310                 315                 320
Lys Tyr Ser Phe Ile Thr Arg Lys Pro Asp Glu Val Ser Arg Ile Tyr
                325                 330                 335
Leu Phe Thr Ala Pro Phe Thr Val Glu Thr Trp Phe Cys Leu Met Gly
            340                 345                 350
Ile Ile Leu Leu Thr Ala Pro Thr Leu Tyr Ala Ile Asn Arg Leu Ala
        355                 360                 365
Pro Leu Lys Glu Met Arg Ile Val Gly Leu Ser Thr Val Lys Ser Cys
    370                 375                 380
Phe Trp Tyr Ile Phe Gly Ala Leu Leu Gln Gln Gly Met Tyr Leu
385                 390                 395                 400
Pro Thr Ala Asp Ser Gly Arg Leu Val Val Gly Phe Trp Trp Ile Val
                405                 410                 415
Val Ile Val Leu Val Thr Thr Tyr Cys Gly Asn Leu Val Ala Phe Leu
            420                 425                 430
Thr Phe Pro Lys Phe Gln Pro Gly Val Asp Tyr Leu Asn Gln Leu Glu
        435                 440                 445
Asp His Lys Asp Ile Val Gln Tyr Gly Leu Arg Asn Gly Thr Phe Phe
    450                 455                 460
```

```
Glu Arg Tyr Val Gln Ser Thr Thr Arg Glu Asp Phe Lys His Tyr Leu
465                 470                 475                 480

Glu Arg Ala Lys Ile Tyr Gly Ser Ala Gln Glu Asp Ile Glu Ala
            485                 490                 495

Val Lys Arg Gly Glu Arg Ile Asn Ile Asp Trp Arg Ile Asn Leu Gln
            500                 505                 510

Leu Ile Val Gln Arg His Phe Glu Arg Asp Lys Glu Cys Arg Phe Ala
            515                 520                 525

Leu Gly Arg Glu Ser Phe Val Asp Glu Gln Ile Ala Met Ile Val Pro
            530                 535                 540

Ala Gln Ser Ala Tyr Leu His Leu Val Asn Arg His Ile Lys Ser Met
545                 550                 555                 560

Phe Arg Met Gly Phe Ile Glu Arg Trp His Gln Met Asn Leu Pro Ser
                565                 570                 575

Ala Gly Lys Cys Asn Gly Lys Ser Ala Gln Arg Gln Val Thr Asn His
            580                 585                 590

Lys Val Asn Met Asp Asp Met Leu Gly Cys Phe Leu Val Leu Leu Leu
            595                 600                 605

Gly Phe Thr Phe Ala Leu Leu Ile Val Cys Gly Glu Phe Trp Tyr Arg
            610                 615                 620

Arg Phe Pro Ala Ser Arg Lys Arg Gln Phe Thr Asn
625                 630                 635

<210> SEQ ID NO 43
<211> LENGTH: 637
<212> TYPE: PRT
<213> ORGANISM: Drosophila

<400> SEQUENCE: 43

Met Arg Gln Gln Phe Leu Val Ile Ser Ala Phe His Glu Asp Ile Ile
1               5                   10                  15

Glu Ile Ala Glu Thr Leu Asn Met Phe His Val Gly Asn Gln Trp Met
            20                  25                  30

Ile Phe Val Leu Asp Met Val Ala Arg Asp Phe Asp Ala Gly Thr Val
            35                  40                  45

Thr Ile Asn Leu Asp Glu Gly Ala Asn Ile Ala Phe Ala Leu Asn Glu
50                  55                  60

Thr Glu Pro Asn Cys Gln Asp Ser Leu Asn Cys Thr Ile Ser Glu Ile
65                  70                  75                  80

Ser Leu Ala Leu Val Asp Ala Ile Ser Lys Ile Thr Val Glu Glu Glu
                85                  90                  95

Ser Ile Tyr Gly Glu Ile Ser Asp Glu Glu Trp Glu Ala Ile Arg Phe
            100                 105                 110

Thr Lys Gln Glu Lys Gln Ser Glu Ile Leu Gly Tyr Met Lys Glu Phe
            115                 120                 125

Leu Lys Thr Asn Ala Lys Cys Ser Ser Cys Ala Arg Trp Arg Val Glu
            130                 135                 140

Thr Ala Ile Thr Trp Gly Lys Ser Gln Glu Asn Arg Lys Phe Arg Ser
145                 150                 155                 160

Thr Pro Gln Arg Asp Ala Lys Asn Arg Asn Phe Glu Phe Ile Asn Ile
                165                 170                 175

Gly Tyr Trp Thr Pro Val Leu Gly Phe Val Cys Gln Glu Leu Ala Phe
            180                 185                 190

Pro His Ile Glu His His Phe Arg Asn Ile Thr Met Asp Ile Leu Thr
```

-continued

```
                195                 200                 205
Val His Asn Pro Pro Trp Gln Ile Leu Thr Lys Asn Ser Asn Gly Asp
210                 215                 220

Ile Val Glu His Lys Gly Ile Val Met Glu Ile Val Lys Glu Leu Ser
225                 230                 235                 240

Arg Ala Leu Asn Phe Ser Tyr Tyr Leu His Glu Ala Ser Ser Trp Lys
                245                 250                 255

Glu Glu Asp Ser Leu Ser Thr Ser Ala Gly Asn Glu Ser Asp Glu
                260                 265                 270

Leu Val Gly Ser Met Thr Phe Arg Ile Pro Tyr Arg Val Val Glu Met
                275                 280                 285

Val Gln Gly Asn Gln Phe Phe Ile Ala Ala Val Ala Ala Thr Leu Asp
290                 295                 300

Asp Pro Asp Gln Lys Pro Phe Asn Tyr Thr Gln Pro Ile Ser Val Gln
305                 310                 315                 320

Lys Tyr Ser Phe Ile Thr Arg Lys Pro Asp Glu Val Ser Arg Ile Tyr
                325                 330                 335

Leu Phe Thr Ala Pro Phe Thr Val Glu Thr Trp Phe Cys Leu Met Gly
                340                 345                 350

Ile Ile Leu Leu Thr Ala Pro Thr Leu Tyr Ala Ile Asn Arg Leu Ala
                355                 360                 365

Pro Leu Lys Glu Met Arg Ile Val Gly Leu Ser Thr Val Lys Ser Cys
370                 375                 380

Phe Trp Tyr Ile Phe Gly Ala Leu Leu Gln Gln Gly Met Tyr Leu
385                 390                 395                 400

Pro Thr Ala Asp Ser Gly Arg Leu Val Val Gly Phe Trp Trp Ile Val
                405                 410                 415

Val Ile Val Leu Val Thr Thr Tyr Cys Gly Asn Leu Val Ala Phe Leu
                420                 425                 430

Thr Phe Pro Lys Phe Gln Pro Gly Val Asp Tyr Leu Asn Gln Leu Glu
                435                 440                 445

Asp His Lys Asp Ile Val Gln Tyr Gly Leu Arg Asn Gly Thr Phe Phe
450                 455                 460

Glu Arg Tyr Val Gln Ser Thr Thr Arg Glu Asp Phe Lys His Tyr Leu
465                 470                 475                 480

Glu Arg Ala Lys Ile Tyr Gly Ser Ala Gln Glu Glu Asp Ile Glu Ala
                485                 490                 495

Val Lys Arg Gly Glu Arg Ile Asn Ile Asp Trp Arg Ile Asn Leu Gln
                500                 505                 510

Leu Ile Val Gln Arg His Phe Glu Arg Asp Lys Glu Cys Arg Phe Ala
                515                 520                 525

Leu Gly Arg Glu Ser Phe Val Asp Glu Gln Ile Ala Met Ile Val Pro
                530                 535                 540

Ala Gln Ser Ala Tyr Leu His Leu Val Asn Arg His Ile Lys Ser Met
545                 550                 555                 560

Phe Arg Met Gly Phe Ile Glu Arg Trp His Gln Met Asn Leu Pro Ser
                565                 570                 575

Ala Gly Lys Cys Asn Gly Lys Ser Ala Gln Arg Gln Val Thr Asn His
                580                 585                 590

Lys Val Asn Met Asp Asp Met Gln Gly Cys Phe Leu Val Leu Leu Leu
                595                 600                 605

Gly Phe Thr Phe Ala Leu Leu Ile Val Cys Gly Glu Phe Trp Tyr Arg
610                 615                 620
```

Arg Phe Arg Ala Ser Arg Lys Arg Gln Phe Thr Asn
625                 630                 635

<210> SEQ ID NO 44
<211> LENGTH: 513
<212> TYPE: PRT
<213> ORGANISM: Drosophila

<400> SEQUENCE: 44

Met Lys Glu Tyr Leu Lys Ala Asn Ser Lys Cys Ala Ser Cys Ala Lys
 1               5                  10                  15

Trp Arg Phe Glu Thr Ala Ile Thr Trp Gly Lys Ser Gln Glu Asn Arg
            20                  25                  30

Lys Phe Arg Met Ala Pro Thr Arg Asp Thr Lys Asn Arg Asn Phe Glu
        35                  40                  45

Phe Ile Asn Ile Gly Tyr Trp Ser Pro Leu Leu Gly Phe Val Cys His
    50                  55                  60

Glu Leu Ala Phe Pro His Ile Asp Gln His Phe Arg Asn Ile Thr Met
65                  70                  75                  80

Asp Ile Val Thr Val His Asn Pro Pro Trp Gln Ile Leu Thr Lys Asp
                85                  90                  95

Ser Arg Gly Ala Ile Val Glu His Thr Gly Ile Val Met Glu Ile Leu
            100                 105                 110

Lys Glu Leu Ser Arg Ala Leu Asn Phe Ser Tyr Tyr Leu His Glu Ala
        115                 120                 125

Arg Ser Pro Asp Tyr Glu Tyr Ser Leu Ala Gln Ser Thr Asn Glu Ser
    130                 135                 140

Asp Glu Leu Met Gly Ser Met Thr Tyr Arg Ile Pro Tyr Arg Val Val
145                 150                 155                 160

Glu Leu Val Gln Gly Ser Gly Tyr Phe Met Ala Val Ala Ala Thr
                165                 170                 175

Ile Asp Glu Pro His Lys Lys Arg Phe Asn Tyr Thr Gln Pro Ile Ser
            180                 185                 190

Ile Gln Lys Tyr Thr Phe Ile Leu Arg Gln Pro Asp Glu Val Ser Arg
        195                 200                 205

Ile Tyr Leu Phe Thr Ala Pro Phe Thr Leu Glu Thr Trp Gly Cys Leu
    210                 215                 220

Ala Gly Ile Leu Leu Val Thr Ala Pro Met Leu Tyr Ile Val Asn Arg
225                 230                 235                 240

Leu Val Pro Leu Gln Glu Leu Gln Ile Arg Gly Leu Ser Thr Val Lys
                245                 250                 255

Asn Cys Phe Trp Tyr Ile Tyr Gly Ala Leu Leu Gln Gln Gly Gly Met
            260                 265                 270

Tyr Leu Pro Arg Ala Asp Ser Gly Arg Leu Val Val Gly Phe Trp Trp
        275                 280                 285

Leu Val Val Ile Val Leu Val Thr Thr Tyr Cys Gly Asn Leu Val Ala
    290                 295                 300

Phe Leu Thr Phe Pro Lys Phe Gln Pro Gly Ile Asp Tyr Leu Asn Gln
305                 310                 315                 320

Leu Phe Asp His Lys Glu Ile Lys Gln Tyr Gly Leu Arg Asn Gly Thr
                325                 330                 335

Phe Phe Glu Lys Tyr Val His Ser Thr Thr Arg His Asp Phe Lys Arg
            340                 345                 350

Phe Met Glu Arg Ala Leu Val Tyr Asn Ser Ser Gln Ser Glu Asn Ile

```
                355                 360                 365
Ala Ala Val Lys Gln Gly Glu Arg Ile Asn Ile Asp Trp Arg Ile Asn
370                 375                 380

Leu Gln Leu Ile Val Gln Gln His Phe Glu Gln Asp Lys Glu Cys Arg
385                 390                 395                 400

Phe Ala Leu Gly Lys Glu Asp Phe Val Ser Glu Gln Ile Gly Leu Ile
                405                 410                 415

Val Pro Ser Ser Ser Ala Tyr Leu His Leu Ile Asn Gln His Ile Asp
                420                 425                 430

Arg Leu Phe Arg Met Gly Phe Ile Asp Arg Trp His Asp Thr Asn Leu
                435                 440                 445

Pro Ser Met Asp Lys Cys Asn Gly Lys His Met Gln Arg Gln Ile Ala
                450                 455                 460

Asn His Lys Val Asn Met Asp Asp Met Gln Gly Cys Phe Met Val Leu
465                 470                 475                 480

Leu Phe Gly Ile Ile Ala Ala Leu Leu Val Ser Cys Ile Glu Phe Trp
                485                 490                 495

Tyr Tyr Arg Phe Leu Val Leu Asn Lys Gly Gln Ser Ile Ala Phe Ala
                500                 505                 510

Asn

<210> SEQ ID NO 45
<211> LENGTH: 645
<212> TYPE: PRT
<213> ORGANISM: Drosophila

<400> SEQUENCE: 45

Met Pro Lys His Glu Gln Lys His Gln Gln Phe Leu Val Ile Ser Lys
1               5                   10                  15

Phe His Glu Asp Ile Ile Glu Ile Ala Glu Thr Leu Asn Met Phe His
                20                  25                  30

Val Ser Asn Gln Trp Met Phe Phe Val Leu Glu Glu Leu Arg Arg Asp
                35                  40                  45

Phe Asp Ala Ser Thr Val Thr Ile Asn Leu Asp Glu Gly Ala Asn Ile
50                  55                  60

Ala Phe Ala Leu Asn Glu Thr Tyr Pro Asp Cys Gln Asp Thr Leu Asn
65                  70                  75                  80

Cys Thr Ile Ser Glu Val Ser Met Ala Leu Val Thr Ser Ile Ser Lys
                85                  90                  95

Met Ile Ser Glu Glu Gln Ser Ile Tyr Gly Glu Ile Ser Asp Glu Glu
                100                 105                 110

Trp Glu Ser Ile Arg Phe Thr Lys Gln Glu Lys Gln Asp Glu Leu Leu
                115                 120                 125

Glu Tyr Met Lys Asp Tyr Leu Lys Leu Asn Ser Lys Cys Ala Ser Cys
                130                 135                 140

Ala Arg Trp Arg Ile Asp Thr Ala Ile Thr Trp Gly Lys Thr Gln Glu
145                 150                 155                 160

Ser Arg Gln Phe Arg Thr Ala Pro Thr Arg Asp Ala Lys Asn Arg Asn
                165                 170                 175

Phe Asp Phe Ile Asn Ile Gly Tyr Trp Ser Pro Leu Leu Gly Phe Val
                180                 185                 190

Val Gln Glu Leu Thr Phe Pro His Ile Glu His Phe Arg Asn Ile
                195                 200                 205

Thr Met Asp Ile Leu Thr Val His Asn Pro Pro Trp Gln Ile Leu Thr
```

```
            210                 215                 220
Lys Asn Ser Leu Gly His Ile Val Glu Ser Lys Gly Ile Val Met Glu
225                 230                 235                 240

Ile Val Arg Glu Leu Ser Arg Ala Leu Asn Phe Thr Tyr Gln Leu His
                245                 250                 255

Glu Ala Lys Ser Trp Glu Asp Glu Tyr Ala Ile Ser Gln Ser Lys Asn
            260                 265                 270

Glu Ser Glu Met Glu Leu Leu Gly Ser Met Thr Tyr Arg Ile Pro Ser
        275                 280                 285

Arg Val Thr Glu Leu Ala Gln Gly Asn Gln Tyr Phe Leu Ala Ala Val
    290                 295                 300

Ala Ala Thr Ile Tyr Asp Pro Glu Lys Arg Phe Phe Asn Phe Thr Gln
305                 310                 315                 320

Pro Ile Ser Val Gln Lys Tyr Thr Phe Ile Thr Arg Gln Pro Asp Glu
                325                 330                 335

Val Ser Arg Ile Tyr Leu Phe Thr Ala Pro Phe Thr Gln Glu Thr Trp
            340                 345                 350

Gly Cys Leu Val Gly Ile Ile Leu Thr Ala Pro Leu Leu Tyr Gly
        355                 360                 365

Ile Asn Arg Leu Ala Pro Leu Glu Glu Leu Arg Ile Arg Gly Leu Ser
    370                 375                 380

Thr Ile Lys Ser Cys Phe Trp Tyr Val Leu Gly Ala Leu Leu Gln Gln
385                 390                 395                 400

Gly Gly Met Tyr Leu Pro Lys Ala Asp Ser Gly Arg Leu Ile Val Gly
                405                 410                 415

Phe Trp Trp Ile Val Ile Val Leu Val Thr Thr Tyr Cys Gly Asn
            420                 425                 430

Leu Val Ala Phe Leu Thr Phe Pro Lys Tyr Gln Pro Gly Ile Asp Tyr
        435                 440                 445

Leu Thr Gln Leu Ala His His Lys His Ile Ser Gln Tyr Gly Leu Arg
    450                 455                 460

Asn Gly Thr Phe Phe Glu Lys Tyr Thr Lys Thr Thr Arg Lys Asp
465                 470                 475                 480

Phe Lys Arg Phe Met Glu Lys Ala Ile Ile Tyr Asn Asn Ala Glu Ser
                485                 490                 495

Glu Arg Ile Asp Ala Val Lys Ser Gly Gln Arg Ile Asn Ile Asp Trp
            500                 505                 510

Arg Ile Asn Leu Gln Leu Ile Val Gln Gln His Phe Glu Gln Asp Lys
        515                 520                 525

Glu Cys His Phe Ala Leu Gly Lys Glu Asp Phe Val Asp Glu Gln Ile
    530                 535                 540

Gly Leu Val Val Pro Leu Asn Ser Ala Tyr Leu His Leu Ile Asn Leu
545                 550                 555                 560

His Ile Asp Arg Met Phe Arg Met Gly Phe Ile Glu Arg Trp His Gln
                565                 570                 575

Met Asn Leu Pro Asn Ser Asp Lys Cys Asn Gly Lys Ser Val Leu Arg
            580                 585                 590

Gln Ile Thr Asn His Lys Val Asn Met Asn Asp Met Gln Gly Cys Phe
        595                 600                 605

Leu Val Leu Ile Phe Gly Phe Ile Val Ala Val Leu Val Ala Ser Ile
    610                 615                 620

Glu Phe Trp Tyr Tyr Arg Tyr His Leu His Gln Lys Arg Lys Gln
625                 630                 635                 640
```

```
Ser Val Phe Val Asn
            645

<210> SEQ ID NO 46
<211> LENGTH: 637
<212> TYPE: PRT
<213> ORGANISM: Drosophila

<400> SEQUENCE: 46

Met Arg Gln Gln Phe Leu Val Ile Ser Ala Phe His Glu Asp Ile Ile
  1               5                  10                  15

Glu Ile Ala Glu Thr Leu Asn Met Phe His Val Gly Asn Gln Trp Met
             20                  25                  30

Ile Phe Val Leu Gly Met Val Gly Arg Asp Phe Asp Val Gly Ala Ala
         35                  40                  45

Thr Ile Asn Leu Asp Glu Gly Ala Asn Ile Ala Phe Ala Leu Asn Glu
     50                  55                  60

Thr Asp Pro Asn Cys Gln Asp Ser Leu Asn Cys Thr Ile Ser Glu Leu
 65                  70                  75                  80

Ser Leu Ala Leu Val Thr Ser Ile Ser Lys Ile Thr Val Glu Glu Glu
                 85                  90                  95

Ser Ile Tyr Gly Glu Ile Ser Asp Glu Glu Trp Glu Ala Ile Arg Phe
            100                 105                 110

Thr Lys Gln Glu Lys Gln Ala Glu Ile Leu Glu Tyr Met Lys Asp Tyr
        115                 120                 125

Leu Lys Asn Asn Ala Lys Cys Ser Ser Cys Ala Arg Trp Arg Val Glu
130                 135                 140

Thr Ala Thr Thr Trp Gly Lys Ser Gln Glu Asn Arg Lys Phe Arg Ser
145                 150                 155                 160

Thr Pro Leu Arg Asp Ala Lys Asn Arg Asn Phe Glu Phe Ile Asn Ile
                165                 170                 175

Gly Tyr Trp Ser Pro Val Leu Gly Phe Val Cys Gln Glu Leu Ala Phe
            180                 185                 190

Pro His Ile Glu His His Phe Arg Asn Ile Thr Met Asp Ile Leu Thr
        195                 200                 205

Val His Asn Pro Pro Trp Gln Ile Leu Thr Lys Asn Ser His Gly Val
210                 215                 220

Ile Val Glu His Lys Gly Ile Val Met Glu Ile Val Lys Glu Leu Ser
225                 230                 235                 240

Arg Ala Leu Asn Phe Ser Tyr Tyr Leu His Glu Ala Ser Ser Trp Lys
                245                 250                 255

Glu Glu Tyr Ser Leu Ser Thr Ser Ala Gly Ser Asn Glu Ser Asp Glu
            260                 265                 270

Leu Val Gly Ser Met Thr Phe Arg Ile Pro Tyr Arg Val Val Glu Met
        275                 280                 285

Val Gln Gly Asn Gln Phe Phe Ile Ala Ala Val Ala Thr Val Glu
290                 295                 300

Asp Ser Glu Gln Lys Pro Phe Asn Tyr Thr Leu Pro Ile Ser Val Gln
305                 310                 315                 320

Lys Tyr Ser Phe Ile Thr Arg Lys Pro Asp Glu Val Ser Arg Ile Tyr
                325                 330                 335

Leu Phe Thr Ala Pro Phe Thr Val Glu Thr Trp Phe Cys Leu Met Gly
            340                 345                 350

Ile Ile Leu Leu Thr Ala Pro Thr Leu Tyr Ala Ile Asn Arg Leu Ala
```

```
                355                 360                 365
Pro Leu Lys Glu Met Arg Ile Val Gly Leu Ser Thr Val Lys Ser Cys
370                 375                 380

Phe Trp Tyr Ile Phe Gly Ala Leu Leu Gln Gln Gly Gly Met Tyr Leu
385                 390                 395                 400

Pro Thr Ala Asp Ser Ala Arg Leu Val Val Gly Phe Trp Trp Ile Val
                405                 410                 415

Val Ile Val Leu Val Thr Thr Tyr Cys Gly Asn Leu Val Ala Phe Leu
                420                 425                 430

Thr Phe Pro Lys Phe Gln Pro Gly Val Asp Tyr Leu Asn Gln Leu Ala
                435                 440                 445

Asn His Lys Asp Ile Val Gln Tyr Gly Leu Arg Asn Gly Thr Phe Phe
                450                 455                 460

Glu Arg Tyr Val Gln Ser Ser Thr Arg Glu Asp Phe Lys His Tyr Leu
465                 470                 475                 480

Glu Arg Ala Arg Ile Tyr Gly Ser Ala Gln Glu Glu Asp Ile Glu Ala
                485                 490                 495

Val Lys Arg Gly Glu Arg Ile Asn Ile Asp Trp Arg Ile Asn Leu Gln
                500                 505                 510

Leu Ile Val Gln Arg His Phe Glu Arg Asp Lys Glu Cys Arg Phe Ala
                515                 520                 525

Leu Gly Lys Glu Ser Phe Val Asp Glu Gln Ile Ala Met Ile Val Pro
                530                 535                 540

Ala Lys Ser Ala Tyr Leu His Leu Val Asn Arg His Ile Asn Ser Met
545                 550                 555                 560

Phe Arg Met Gly Phe Ile Glu Arg Trp His Gln Met Asn Leu Pro Ser
                565                 570                 575

Ala Gly Lys Cys Asn Gly Lys Ser Ala Gln Arg Gln Val Thr Asn His
                580                 585                 590

Lys Val Asn Met Asp Asp Met Gln Gly Cys Phe Leu Val Leu Leu Leu
                595                 600                 605

Gly Phe Thr Val Ala Leu Leu Ile Val Cys Gly Glu Phe Trp Cys Arg
                610                 615                 620

Arg Phe Arg Ala Ser Arg Glu Arg Arg Gln Phe Ile Asn
625                 630                 635

<210> SEQ ID NO 47
<211> LENGTH: 1444
<212> TYPE: PRT
<213> ORGANISM: Megachili rotundata

<400> SEQUENCE: 47

Met Leu Ser Val Leu Leu Leu Leu Trp Asn Val Asn Tyr Gly Asn Ser
1               5                   10                  15

Phe Asn Asp Phe Pro Ser Leu Ile Ser Thr Asn Val Thr Met Gly Thr
                20                  25                  30

Ser Leu Phe Ser Phe Leu Asn Asp Ser Tyr Tyr Arg Ser Asp Arg Thr
            35                  40                  45

Ile Thr Leu Ile Asn Cys Leu Tyr Tyr Ile Ser Asp Gln Ala Val Val
        50                  55                  60

Val Asp Arg Ser Leu Phe Asp Ser Lys Glu Glu Tyr His Asn Ile Ala
65                  70                  75                  80

Gly Val Ile Tyr Asp Leu Ile Asp Thr Val Lys Lys Glu Met Gln
                85                  90                  95
```

```
Val Gly Gly Ile Val Val Gln Val Phe Arg Asp Gly Asn Val Asn Leu
            100                 105                 110

Arg Gln Asp Tyr Thr Ile Leu Leu Ser Phe Ala Ser Cys Tyr Leu Thr
            115                 120                 125

Trp Arg Leu His Glu Ala Ala Ala Asn Lys Glu Leu Met His Leu Ala
        130                 135                 140

Ile Thr Asp Pro Asp Cys Pro Arg Ile Pro Glu Thr Asp Gly Leu Ser
145                 150                 155                 160

Val Pro Leu Ile Met Pro Gly Lys Glu Leu Ser Gln Ile Phe Leu Asp
                165                 170                 175

Leu Arg Met Thr Asn Ile Leu Ser Trp Asn Val Ile Asn Ile Leu His
            180                 185                 190

Asp Asp Thr Phe Asp Arg Asp Thr Ile Ser Arg Val Met Lys Ala Ile
            195                 200                 205

Ser Asp Lys Leu Pro Asn Arg Gln Leu Ser Leu Val Ser Arg Ser Ile
210                 215                 220

Phe Thr Leu Lys His Glu Asp Thr Glu Met Ala Arg Lys Lys Ala Val
225                 230                 235                 240

Lys Lys Ile Leu Asp Asp Phe His Val Glu Gln Leu Gly His Cys Phe
                245                 250                 255

Leu Val Ile Ala Thr Val Asp Met Ala Arg Ser Leu Arg Met Val His
            260                 265                 270

Pro Gly Ser Gln Trp Leu Tyr Val Thr Asn Thr Ala Pro Asn Arg
            275                 280                 285

Thr Asn Ile Thr Ser Phe Val Glu Leu Leu Ala Glu Gly Gly Asn Val
            290                 295                 300

Ala Phe Ile Tyr Asn Ala Thr Asp Phe Asn Asp Phe Cys Glu Val Lys
305                 310                 315                 320

Val Thr Tyr Tyr Ala Lys Lys Leu Val Gln Ala Leu Ala Lys Ala Leu
                325                 330                 335

Glu Tyr Ser Leu Thr Asn Glu Ile Asp Met Leu Lys Arg Val Gly Gly
            340                 345                 350

Glu Asp Phe Glu Met Ile Arg Leu Thr Lys Arg Glu Arg Lys Glu
            355                 360                 365

Ile Leu Thr Asn Phe Lys Met Tyr Leu Glu Arg Asp Val Leu Asn Ser
370                 375                 380

Glu Thr Val His Gly Arg Cys Val Leu Trp Lys Phe Thr Ser Ser Ile
385                 390                 395                 400

Thr Trp Gly Asn Phe Phe Ser His Gly Lys Asn Val Ala His Leu Leu
                405                 410                 415

Asp Ile Gly Thr Trp Thr Leu Ala Ala Gly Val Ile Thr Val Asn Glu
            420                 425                 430

Lys Gly Glu Arg Ser Tyr Glu Gly Leu Val Phe Asp Val Ile Asn His
            435                 440                 445

Leu Ser Lys Lys Leu Asn Phe Thr Tyr Thr Val Ile Leu Pro Glu Val
450                 455                 460

Asn Ser Thr Lys Pro Trp Ser Ser Ser Arg Phe Ser Lys Leu Gly Asp
465                 470                 475                 480

Lys Ile Asn Glu Met Thr Met Ser Asn Thr Arg Arg Val Pro Lys Glu
                485                 490                 495

Val Ile Lys Leu Val Arg Glu Lys Lys Val Leu Leu Ala Ala Cys Ala
            500                 505                 510

Tyr Thr Val Gln Glu Tyr Glu Asp Thr Ile Asn Phe Thr Val Pro Thr
```

```
            515                 520                 525
Trp Phe Cys Leu Ala Val Thr Val Ile Ile Met Gly Pro Ile Leu Tyr
530                 535                 540

Leu Ile His Lys Tyr Ser Pro Tyr Ser Thr Lys Thr Ser Gly Leu Asn
545                 550                 555                 560

Ser Ser Trp Gln Cys Val Trp Tyr Val Tyr Gly Ala Leu Leu Gln Gln
                    565                 570                 575

Gly Gly Met Tyr Leu Pro Gln Ser Asp Ser Ala Arg Met Leu Ile Gly
                580                 585                 590

Val Trp Trp Leu Ile Val Met Val Val Ala Thr Tyr Ser Gly Ser
                595                 600                 605

Leu Val Ala Phe Leu Thr Phe Pro Lys Met Asp Ala Ser Ile Leu Thr
610                 615                 620

Val Glu Asp Leu Ile Ala Arg Lys Asp Lys Ile Thr Trp Gly Phe Pro
625                 630                 635                 640

Asn Asp Ser Phe Leu Glu Leu Tyr Leu Arg Asn Thr Asp Glu Gln Lys
                645                 650                 655

Tyr Gln Ile Leu Leu Ala Tyr Ser Glu Arg His Asn Asp Thr Glu Glu
                660                 665                 670

Glu Thr Phe Leu Met Arg Lys Asp Leu Leu Leu Thr Gly Gly Cys His
                675                 680                 685

Phe Ser Leu Ser Ala Asp Glu Phe Leu Asp Glu Pro Ile Ala Met Ile
690                 695                 700

Ile Pro Gln Asp Ser Pro Tyr Leu Ala Glu Ser Gly Leu Met Asn Lys
705                 710                 715                 720

Trp Ile Ser Glu Lys Met Pro Met Lys Asp Lys Cys Trp Glu Val Pro
                725                 730                 735

Gly Ser Asn Gln Ala Val Asn Lys Arg Lys Val Asn Val Ala Asp Met
                740                 745                 750

Gln Gly Ile Phe Phe Val Leu Phe Met Val Trp Ser Val Val Val His
                755                 760                 765

Gly Tyr Asp Asn Val Gly Phe Asp Gly Trp Tyr Gln Pro Val Pro His
                770                 775                 780

Arg Pro Val Asp Ile Ile Thr Asp Val Ile Asn Asp Leu Gly Val Arg
785                 790                 795                 800

Ile Leu Gln Gln Tyr Thr Ser His Gly Asn Val Ala Phe Ser Pro Thr
                805                 810                 815

Gly Val Ala Phe Val Leu Ala Ala Leu Tyr Glu Gly Ser Ala Gly Arg
                820                 825                 830

Gly Arg Gln Gln Ile Ala Asp Ala Leu Gly Leu Pro Arg Asp Arg Asp
                835                 840                 845

Ile Thr Arg Ile Gly Phe Arg Asp Ile His Arg Arg Leu Arg Thr Tyr
                850                 855                 860

Leu Asn Ala Asn Gly Phe Leu Gly Gly Leu Thr Leu Asn Gln Glu Asn
865                 870                 875                 880

Thr Asn Leu Arg Pro Glu Tyr Glu Asp Ile Leu Arg Phe Tyr Gly Phe
                885                 890                 895

Asp Leu Ser Ile Pro Glu Asp Met Asn Asp Thr Thr Ile Val Pro Glu
                900                 905                 910

Thr Glu Pro Thr Glu Lys Asn Ile Glu Thr Glu Thr Val Thr Gly Thr
                915                 920                 925

Val Pro Ser Thr Ser Thr Thr Pro Val Glu Thr Leu Gly Thr Met Thr
                930                 935                 940
```

```
Ala Asp Val Gln Asn Arg Phe Thr Gln Thr Thr Leu Pro Ser Ala Met
945                 950                 955                 960

Glu Ser Thr Val Thr Val Glu Ser Thr Gly Ala Gly Glu Thr Asp Val
            965                 970                 975

Pro Glu Val Ser Thr Met Ser Ser Thr Thr Met Ala Ser Val Thr Ser
        980                 985                 990

Pro Thr Thr Val Pro Pro Val Thr Leu Ser Thr Thr Ile Ala Pro Ala
    995                 1000                1005

Thr Ser Pro Thr Thr Ile Thr Pro Val Thr Pro Ile Thr Thr Ile Ser
1010                1015                1020

Pro Val Thr Ser Pro Thr Thr Ile Ser Pro Val Thr Ser Pro Thr Thr
1025                1030                1035                1040

Ile Ser Pro Met Thr Ser Pro Thr Thr Met Ser Ala Ser Thr Glu Pro
                1045                1050                1055

Phe Met Thr Thr Glu Asp Val Leu Ser Thr Leu Thr Ala Asp Asp Gln
                1060                1065                1070

Pro Val Thr Thr Gln Ser Ser Thr Ser Thr Ser Ala Ser Thr Ser Ala
                1075                1080                1085

Thr Thr Ser Ala Leu Pro Met Glu Ser Thr Ile Pro Thr Asp Ser Thr
                1090                1095                1100

Ile Thr Thr Glu Ser Gly Val Thr Glu Leu Pro Glu Ser Thr Thr Thr
1105                1110                1115                1120

Ser Thr Ile Thr Val Pro Thr Thr Val Asn Val Met Glu Thr Ser Thr
                1125                1130                1135

Ser Ser Thr Ile Pro Thr Gln Thr Gly Leu Pro Asp Val Asp Ala Asn
                1140                1145                1150

Thr Val Ser Thr Gly Ser Ser Asn Asn Gln Ser Val Ser Asp Glu Ile
                1155                1160                1165

Gly Ser Thr Asp Ser Pro Ile Thr Thr Ile Ile Asp Thr Gly Glu Thr
                1170                1175                1180

Gly Ser Asn Glu Gln Thr Thr Val Glu Ser Thr Thr Ser Gly Thr Ile
1185                1190                1195                1200

Asn Arg Arg Lys Arg Asn Ile Arg Ala Pro Arg Gly Phe Phe Ser Ser
                1205                1210                1215

Tyr Pro Asp Glu Gly Ile Trp Met Gln Asp Leu Gly Ile Trp Lys Pro
                1220                1225                1230

Tyr Ser Ser Ser Leu Asn Glu Ala Ser Val Arg Asp Ser Thr Glu Ile
                1235                1240                1245

Ser Phe Leu Val Asn Gly Cys Asp Val Ser Ser Val Thr Ala Ser Arg
                1250                1255                1260

Tyr Ile Ala Val Leu Pro Phe Ala Tyr Phe Pro Ser Leu His Ala Val
1265                1270                1275                1280

Ala Leu Glu Phe Pro Leu Asp Val Arg Ile Ile Phe Thr Val His Asn
                1285                1290                1295

Ser Gly Ser Trp Asn Val Ser Asn Leu Ser Phe Gln Asp Pro Arg Tyr
                1300                1305                1310

Asn Ile Leu Leu Met Met Ser Thr Asp Arg Arg Asp Thr Tyr Arg Leu
                1315                1320                1325

Ala Arg Asp Leu Gly Gly Lys Ser Leu Arg Leu Arg Lys Gln Leu
                1330                1335                1340

Gln Ala Thr Trp Val Arg Ala Thr Ile Pro Ser Phe Met Leu Arg Gly
1345                1350                1355                1360
```

```
Phe Leu Gly Ile Leu Asp Val Phe Glu Pro Arg Ala Ala Asp Leu Ser
            1365                1370                1375

Pro Met Thr Pro Asp Leu Gly Val Tyr Ala Arg Asp Val Gln Gln Ser
            1380                1385                1390

Ile Gly Val Asn Ile Arg Asn Tyr Met Lys Pro Asp Arg Thr His Ser
            1395                1400                1405

Arg Asn Gly Leu Phe Glu Arg Ala Gly Pro Val Pro Phe Thr Val Val
            1410                1415                1420

Gln Pro Tyr Leu Tyr Phe Ile Ile Asp Ala Glu Thr Ser Val Thr Leu
1425                1430                1435                1440

Ile Ala Gly Arg

<210> SEQ ID NO 48
<211> LENGTH: 895
<212> TYPE: PRT
<213> ORGANISM: Nassonia vitripennis

<400> SEQUENCE: 48

Met Leu Leu Ala Leu Leu Val Leu Ala Gly Trp Ile Glu Ile Gly
1               5                   10                  15

Thr Gly Tyr Asn Asp Phe Pro Ser Leu Met Thr Ala Asn Ala Thr Met
            20                  25                  30

Ala Val Ile Val Glu Lys Gly Phe Phe Lys Ser Ala Asp Asn Tyr Arg
            35                  40                  45

His Thr Leu Asp Glu Ile Ser Asp Val Ala Asn Ala Val Ile Arg Lys
        50                  55                  60

Asn Met Glu Ile Ser Gly Ile Ala Leu His Val Phe Gly Asp Ala Asp
65                  70                  75                  80

Val Asn Leu Ala Arg Asp Tyr Thr Val Leu Leu Ser Val Ala Ser Cys
                85                  90                  95

Gln Thr Thr Trp His Leu Phe Lys Arg Ala Gln Lys Glu Lys Leu Val
            100                 105                 110

Tyr Leu Ala Val Thr Asp Pro Asp Cys Pro Arg Leu Pro Glu Asp Ala
            115                 120                 125

Gly Ile Ser Leu Pro Leu Thr Asn Pro Gly Glu Leu Pro Gln Ile
        130                 135                 140

Phe Leu Asp Leu Arg Thr Thr Gly Ser Leu Ser Trp Pro Lys Val Asn
145                 150                 155                 160

Leu Ile His Asp Asp Thr Phe Ala Arg Asp Thr Ile Ser Arg Val Val
                165                 170                 175

Lys Ala Leu Ser Leu Glu Leu Pro Asp Lys Arg Val Ser Leu Ser Ala
            180                 185                 190

Gln Ala Leu Phe Ser Thr Arg Phe Glu Lys Asn Glu Asn Ala Met Arg
            195                 200                 205

Gln Arg Val His Arg Ile Leu Ser Asn Tyr His Val Asp Gln Leu Gly
        210                 215                 220

Ser Cys Phe Met Val Val Thr Val Asp Met Val Ser Ile Val Met
225                 230                 235                 240

Glu Val Ala Lys Ser Leu Arg Leu Val His Pro Gly Ser Gln Trp Leu
                245                 250                 255

Tyr Val Ile Ser Asp Ala Ala Gly Arg Glu Ala Lys Val Thr Ser Phe
            260                 265                 270

Ala Glu Leu Leu Ala Glu Gly Glu Asn Val Ala Phe Val His Asn Ala
            275                 280                 285
```

-continued

```
Thr Lys His Val Ala Asn Cys Asn Met Gly Leu Met Cys His Val Lys
    290                 295                 300
Glu Leu Val Arg Ala Leu Ala Ile Ser Leu Glu Asn Ser Leu Leu Asn
305                 310                 315                 320
Glu Leu Glu Leu Tyr Asp Arg Val Thr Glu Glu Phe Glu Val Val
                325                 330                 335
Arg Leu Ser Lys Ala Glu Arg Lys Gln Glu Ile Val Lys Ser Val Asn
                340                 345                 350
Arg Glu Leu Ser Tyr Ala Arg Ala His Thr Ser Ser Cys Gly Lys Cys
                355                 360                 365
Val Asn Trp Arg Phe Ser Ser Ala Ile Thr Trp Gly Thr Ser Phe Ala
370                 375                 380
Ser Ser Glu Glu Lys Gln Arg Arg Glu Ser Glu Lys Arg Arg Arg
385                 390                 395                 400
Glu Asn Ser Lys Arg His Ser Glu Asp Asp Leu Gly Glu Lys Ser Leu
                405                 410                 415
Gly Leu Gly Glu Leu Leu Asp Ala Gly Thr Trp Ser Pro Gly Pro Gly
                420                 425                 430
Val Asn Met Ser Glu Pro Leu Phe Pro His Val Glu His Gly Phe Arg
        435                 440                 445
Gly Arg Ser Leu Pro Val Ser Thr Phe His Asn Pro Pro Trp Gln Ile
    450                 455                 460
Ile Lys Tyr Ser Asn Thr Gly Ala Gln Glu Tyr Gly Gly Leu Ile Phe
465                 470                 475                 480
Asp Val Leu Asn Tyr Leu Ser Leu Lys Leu Asn Phe Thr Tyr Thr Val
                485                 490                 495
Arg Leu Ala Ser Ser Pro Ala Ala Glu Ala Pro Thr Arg Leu Pro Ser
                500                 505                 510
Ala Gly Asp Ser Ser Lys Ser Met Asp Leu Ala Ala Met Ser Val Ala
        515                 520                 525
Gln Lys Val Pro Gln Glu Val Val Glu Leu Val Arg Ser Lys Gln Val
    530                 535                 540
Phe Ile Ala Ala Ser Ala Phe Thr Val Gly Lys Asn Ser Gly Gly Leu
545                 550                 555                 560
Asn Phe Thr Ala Ala Ile Val Met Gln Asn Tyr Ala Leu Leu Ser Ala
                565                 570                 575
Lys Pro Lys Pro Leu Ser Arg Ala Leu Leu Phe Thr Ala Pro Tyr Thr
                580                 585                 590
Asn Glu Thr Trp Ala Cys Leu Thr Ser Val Leu Ile Val Ile Gly Pro
        595                 600                 605
Ile Leu Tyr Leu Thr Val Lys Leu Ser Pro Arg Pro Arg Asp Ile Asp
    610                 615                 620
Asn Ser Leu Ser Leu Ser Thr Thr Trp Gln Cys Ser Trp Tyr Val Tyr
625                 630                 635                 640
Gly Ala Leu Leu Gln Gln Gly Gly Met Ser Leu Pro Lys Ala Asp Ser
                645                 650                 655
Ala Arg Leu Val Ile Gly Thr Trp Trp Leu Val Val Met Ile Val Val
                660                 665                 670
Ala Thr Tyr Ser Gly Asn Leu Ile Ala Phe Leu Thr Phe Pro Arg Ile
                675                 680                 685
Asp Ala Pro Ile Asp Asn Val Asp Asp Leu Leu Ala Arg Ser Asp Ala
        690                 695                 700
Phe His Trp Ser Phe Pro Asn Gly Ser Ala Leu Glu Ser Tyr Leu Ile
```

```
                705                 710                 715                 720
        Ala Ala Val Asn Asp Asp Pro Lys Tyr Lys Gln Leu Leu Asp Gly Ala
                            725                 730                 735

Glu Arg Gln Asp Pro Ser Lys Pro Lys Gln Ile Leu Asp Arg Val Lys
                        740                 745                 750

Ala Gly Asn Gln Val Leu Ile Asp Trp Arg Ile Ser Leu Ala Phe Leu
                    755                 760                 765

Met Arg Glu Asp Leu Ile Asp Thr Gly Gly Cys His Phe His Val Ser
                770                 775                 780

Ala Glu Asp Phe Met His Glu Asn Met Ala Met Ile Ile Ser Gly Asp
        785                 790                 795                 800

Ser Pro Tyr Leu Pro Leu Ile Asn Asp Ala Ile Glu Arg Met His Glu
                            805                 810                 815

Ser Gly Leu Met Lys Lys Trp Ile Thr Glu Lys Met Pro Met Lys Asp
                        820                 825                 830

Lys Cys Trp Glu Ile Ala Lys Thr Asn Gln Glu Ala Thr Asn His Lys
                    835                 840                 845

Val Asp Met Gly Asp Met Gln Gly Ile Phe Phe Val Leu Ala Ile Gly
                850                 855                 860

Phe Val Ile Ala Ala Ile Ala Ile Gly Val Glu Phe Ala Trp His Lys
        865                 870                 875                 880

Arg Lys Glu Ala Phe Glu Arg Ser Leu Ile Arg Pro Phe Val Ser
                            885                 890                 895

<210> SEQ ID NO 49
        <211> LENGTH: 781
        <212> TYPE: PRT
        <213> ORGANISM: Rhodnius prolixus

<400> SEQUENCE: 49

Met Tyr Pro Lys Phe Arg Tyr Phe Glu Asn Lys Leu Lys Glu Ile Val
        1               5                   10                  15

Asn Ser Arg Ile His Lys Phe Leu Asp Asp Gly Ser Leu Ser Val Ile
                    20                  25                  30

Tyr Asn Gly Arg Asp Leu Lys Ser Lys Glu Asp Leu Thr Ala Ile Phe
                35                  40                  45

Ser Ile Thr Ser Cys Glu Glu Met Trp Asn Leu Tyr Ser Asn Phe Thr
        50                  55                  60

Gly Asn Gly Ile Ile Phe Ile Thr Ile Thr Glu Pro Asp Cys Pro Arg
        65                  70                  75                  80

Leu Pro Gln His Val Gly Thr Thr Leu Pro Val Tyr Glu Arg Gly Ser
                        85                  90                  95

Glu Ile Ser Gln Leu Ile Leu Asp Leu Arg Ser Lys Glu Lys Leu Asp
                    100                 105                 110

Trp Gln Ser Val Thr Ile Val His Asp Asn Ser Ile Ser Asp Lys Leu
                115                 120                 125

Val Glu Lys Ile Thr Leu Ala Val Thr Lys Ser Leu Pro Ile Thr Asn
        130                 135                 140

Ser Thr Cys Ala Ile Ser Leu Tyr Lys Ile Glu Ser Ser Lys Asn Asp
        145                 150                 155                 160

Val Asp Val Lys Arg Asn Lys Glu Ile Phe Asn Thr Ile Ser Ser Leu
                        165                 170                 175

Pro Ser Leu Glu Ile Asn Arg Asn Phe Leu Ile Leu Ala Glu Val Asp
                    180                 185                 190
```

```
Ile Ile Pro Val Val Tyr Glu Ser Ala Lys Ser Val Gly Leu Val Asp
        195                 200                 205

Pro Thr Ser Lys Trp Leu Phe Ile Gly Met Lys Thr Asp Phe Ser Asn
    210                 215                 220

His Asn Asn Ile Asn Lys Phe Ile His Ile Val Gly Asp Gly Glu Asn
225                 230                 235                 240

Val Ala Phe Ile Tyr Asn Ser Thr Asp Thr Gly Leu Cys Leu Asn
                245                 250                 255

Asn Leu Leu Cys His Ala Glu Glu Leu Val Gly Asn Leu Ala Val Ala
                260                 265                 270

Leu Asp Tyr Ser Ile Glu Glu Ile Arg Leu Ser Glu Gln Val Ser
            275                 280                 285

Asp Glu Glu Trp Glu Val Ile Lys Pro Thr Lys Gln Glu Arg Arg Glu
    290                 295                 300

Ala Ile Leu Asn Phe Met Lys Asn Lys Gln Asp Asp Ile Gly Thr Cys
305                 310                 315                 320

Asp Asn Cys Thr Leu Trp Tyr Phe Lys Ser Ser Glu Ser Trp Gly Met
                325                 330                 335

Asp Tyr Phe His Lys Gly Asn Ala Ser Leu Leu Glu Val Gly Tyr Trp
            340                 345                 350

Ala Pro Lys Pro Gly Pro Val Leu Val Asp Glu Leu Phe Pro Asn Ile
        355                 360                 365

Val His Gly Phe Arg Gly Arg Ser Ile Pro Ile Ala Thr Phe His Tyr
    370                 375                 380

Pro Pro Trp Gln Val Ile Lys Tyr Asp Asp Val Gly Lys Pro Thr Glu
385                 390                 395                 400

Tyr Lys Gly Leu Val Phe Glu Ile Ile Asn Glu Leu Ser Asn Ser Leu
                405                 410                 415

Asn Phe Thr Tyr Asp Val Ile Ile Ser Asn Arg Thr Val Leu Lys
            420                 425                 430

Ser Ile Thr Asn Ser Leu Lys Ile Asp Glu Lys Leu Gly Glu Val Ser
        435                 440                 445

Leu Asp Gly Arg Ile Glu Thr Ser Ala Trp Lys Gln Ala Leu Lys Leu
450                 455                 460

Leu Glu Asn Lys Arg Val Leu Ile Ala Ala Ala Phe Thr Val Thr
465                 470                 475                 480

Glu Asp Arg Lys Lys Glu Val Asn Phe Thr Tyr Ser Ile Ser Ile Glu
            485                 490                 495

Ala Tyr Ala Phe Leu Val Ser Arg Pro Lys Glu Leu Ser Arg Ala Leu
        500                 505                 510

Leu Phe Ile Leu Pro Phe Ser Ser Asp Thr Trp Leu Cys Ile Ile Gly
    515                 520                 525

Ala Ile Leu Leu Met Thr Pro Leu Leu Cys Phe Val His Arg Ile Ser
530                 535                 540

Pro Phe Tyr Asp His Tyr Ser His Arg Gly Lys Gly Phe Thr Lys
545                 550                 555                 560

Met Met Asn Cys Phe Trp Tyr Leu Tyr Gly Ala Leu Leu Gln Gln Gly
                565                 570                 575

Gly Gly Ile Met Pro Glu Ala Asp Ser Gly Arg Leu Val Ile Gly Thr
            580                 585                 590

Trp Trp Leu Val Val Leu Val Val Thr Thr Tyr Ser Gly Asn Leu
        595                 600                 605

Val Ala Phe Leu Thr Phe Pro Lys Met Asp Lys Ile Ile Ser Asn Val
```

```
                610                 615                 620

Asp Gln Leu Met Glu Arg Arg Glu Ser Leu Ser Trp Gly Met Pro Glu
625                 630                 635                 640

Ile Ser Thr Leu His Ser Ile Leu Lys Ser Thr Asp Asn Ser Lys Leu
                645                 650                 655

Asn Ala Leu Ser Asp Gly Ala Lys Leu His Ser Lys Leu Thr Pro Glu
                660                 665                 670

Ile Ile Ser Asp Ile Gln Asn Gly Lys His Ile Tyr Ile Asp Arg Lys
                675                 680                 685

Thr Ile Leu Ala Phe Val Met Lys Gln Glu Phe Ile Arg Thr Asn Arg
690                 695                 700

Cys Asp Phe Ser Leu Gly Glu Glu Phe Leu Glu Glu His Leu Ala
705                 710                 715                 720

Met Ala Leu Pro Val His Thr Pro Tyr Leu Lys Ile Phe Asn Ser Arg
                725                 730                 735

Ile Tyr Glu Met His Lys Val Gly Leu Ile Gln Lys Trp Leu Val Asp
                740                 745                 750

Tyr Leu Pro Lys Arg Asp Lys Cys Trp Asp Ala Lys Leu Ser Gly Glu
                755                 760                 765

Ser Asn Thr His Thr Val Asn Met Asp Asp Met Gln Gly
770                 775                 780
```

<210> SEQ ID NO 50
<211> LENGTH: 1020
<212> TYPE: PRT
<213> ORGANISM: Tetranychus urticae

<400> SEQUENCE: 50

```
Met Ile Asn His Leu Phe Phe Leu Ile Tyr Ile Leu Leu Ser Pro Val
1               5                   10                  15

Ser Cys Gln Ser Asn Lys Asp Asp Ser Glu Gln Val Ile Asn Leu Gly
                20                  25                  30

Ile Leu Ile Lys Tyr Asp Asp Glu Ile Ser Lys Ala Ile Arg Asn Glu
                35                  40                  45

Thr Leu Phe His Leu Ile Gly Glu Ile Glu Ser Phe Ser Ile Asp Asn
                50                  55                  60

Ile Thr Ile Lys Val Asp Leu Ile Asp Gly Asp Ser Asp Phe Asp Ala
65                  70                  75                  80

Leu Val Asp Gly Glu Pro Arg Asn Cys Asn Lys Tyr Ile Gly Leu Ile
                85                  90                  95

Ser Val Leu Pro Cys Ser Leu Thr Lys Ser Leu Tyr Ser Leu Ile Arg
                100                 105                 110

Asp His Cys Ser Ser Thr Leu Ile Ile Ala Ile His Asp Arg Asn Cys
                115                 120                 125

Ile Arg Pro Ser Arg Asp Gln Gly Ile Gly Phe Pro Ile Leu Ser Ser
                130                 135                 140

Val Asp His Val Val Pro Met Leu Ile Asp Met Arg His Asp Phe Leu
145                 150                 155                 160

Arg Lys Trp Asp His Ile Asn Leu Ile His Asp Asp Thr Ile Asp Val
                165                 170                 175

Met Ala Leu His Asp Leu Val Asp Gly Leu Ser Ala Val His Gly Pro
                180                 185                 190

Glu Ile Met Pro Ser Thr Val Thr Ser Tyr His Ile Gly Leu Ser Leu
                195                 200                 205
```

```
Lys Asn Lys Ile Glu Ile Thr Ser Asp Tyr Arg Asp Ile Asn Asp Ser
    210                 215                 220

Gln Val Thr Leu Phe Ser Tyr Glu Asn Val Lys Thr Asp Thr Leu Asp
225                 230                 235                 240

Leu Lys Ala Gln Val Val Asp His Ile Thr Asp Glu His Lys Tyr Phe
                245                 250                 255

Ile Val Ile Ala His Ser Lys His Ile Lys Glu Ile Ile Lys Leu Ala
                260                 265                 270

His Ser Arg Ser Leu Leu Gly Ser Pro Arg Lys Trp Ile Phe Ile Phe
            275                 280                 285

Ser Asp Asn Gln Glu Asp Pro Ala Tyr Trp Ser Gln Leu Ser Pro Ile
290                 295                 300

Leu Ala Thr Thr Gln Thr Ala Ile Val Ile Arg Glu Glu Ser Glu Tyr
305                 310                 315                 320

Gly Arg Cys Ser Glu Met Ser Glu Gly Cys Gln Phe Arg Leu Ala Val
                325                 330                 335

Glu Thr Leu Lys Ser Thr Leu Arg Lys Val Ala Leu Thr Ala Asp Tyr
            340                 345                 350

Asp Phe Thr Asp Val Asp Met Lys Arg Arg Thr Arg Asn Arg Leu Leu
        355                 360                 365

Thr Glu Met Arg Leu Gln Leu Gly Ser Asp Glu Ser Val Ser Ser Arg
370                 375                 380

Tyr Cys Gly Asn Cys Asp Arg Tyr Ser Leu Gln Met Phe Glu Lys Ala
385                 390                 395                 400

Ile Ile Gly Glu Ser Ile Lys Tyr Lys Arg Lys Pro Tyr Ser Thr Ser
                405                 410                 415

His Trp Ser Gln Thr Gln Phe Asp Asp Asp Phe Glu Ser Gly Ile Lys
            420                 425                 430

Ile Thr Arg Thr Gly Glu Trp Thr Pro Phe Lys Gly Leu Ile Gln Ser
        435                 440                 445

Ser Asp Pro Ile Pro Val Asp Ile Val Asn Gly Gly Gln Val Tyr
450                 455                 460

Lys Val Gly Val Val Asn Gln Arg Pro Leu Val Asn Val Glu Leu Ile
465                 470                 475                 480

Asp Gly Lys Cys Val Val Asn Gly Thr Thr Ile Glu Leu Leu Thr Ile
                485                 490                 495

Ile Ser Ser Arg Met Asn Phe Thr Ile Glu Tyr Val Cys Trp Ser Asp
            500                 505                 510

Ala Lys Asp Asp Lys Ile Gly Asp Ser Ile Ser Asp Glu Gly Trp Asp
        515                 520                 525

Gly Leu Leu Gly Lys Leu Ala Glu Gly Lys Val Asp Leu Ala Ala Asn
530                 535                 540

Gly Ile Trp Gln Thr Pro Ser Arg Ile Lys Ser Ser Ala Phe Glu Phe
545                 550                 555                 560

Leu Ser Ala Tyr Asp Val Asp Ile Val Ser Leu Val Val Lys Lys Gln
                565                 570                 575

Pro Glu Asp Glu Lys Phe Leu Phe Ile Phe Asn Leu Ser Phe Ser Asn
            580                 585                 590

Ile His Leu Gln Gln Thr Trp Ile Cys Val Ile Leu Thr Met Ile Val
        595                 600                 605

Ile Gly Pro Val Leu Trp Thr Val His Arg Ser Ser Ile Tyr Tyr Asp
610                 615                 620

Tyr Tyr Gly Leu Asn Asp Gly Lys Gly Phe Phe Lys Leu Ser Asn Cys
```

-continued

```
625                 630                 635                 640
Val Trp Tyr Cys Tyr Gly Ala Met Val Gln Gln Gly Asp Ile Leu
                645                 650                 655

Pro Gln Ala Ile Ser Gly Arg Val Leu Ile Ala Thr Trp Trp Leu Phe
                660                 665                 670

Val Ile Val Thr Val Thr Thr Tyr Ser Gly Asn Leu Val Ala Leu Leu
                675                 680                 685

Thr Phe Pro Lys Ile Ile Gln Pro Ile Gln Asn Ala Glu Asp Leu Ala
                690                 695                 700

Asn Thr Trp Gly Val Ser Ala Gly Ala Ala Ser Gly Ala Leu His
705                 710                 715                 720

Glu Met Ile Gln Ile Leu Glu Tyr Ser Glu Leu Ser Leu Leu Arg Asp
                725                 730                 735

Lys Met Ser Tyr Tyr Asp Phe Glu Lys Asp Lys Tyr Lys Ile Phe Asp
                740                 745                 750

Glu Ile Ser Ser Gly Ser Leu Gly Tyr Leu Met Thr Glu Tyr Glu Ala
                755                 760                 765

Arg Tyr Trp Val Ser Thr Glu Tyr Thr Arg Thr Gly Val Cys Gly Met
                770                 775                 780

His Val Ala Arg Asp Ala Val Tyr His Thr Pro Ile His Met Val Ala
785                 790                 795                 800

Arg Lys Asp Ala Phe Pro Pro Ser Leu Leu Lys Glu Leu Asn Arg Gln
                805                 810                 815

Met Thr Leu Leu Thr Arg Ala Gly Ile Ala Ile Tyr Trp Arg Leu Trp
                820                 825                 830

Tyr Gln Thr Pro Gly Asn Asp Cys Met Tyr Pro Leu Ile Ile His Ala
                835                 840                 845

Gly Asp Val Lys Lys Ile Asp Val Val His Met Ile Gly Ile Tyr Leu
                850                 855                 860

Phe Leu Ala Cys Gly Ile Gly Ile Gly Phe Leu Ile Leu Ile Ser Glu
865                 870                 875                 880

Phe Ile Thr Lys Tyr Tyr Ile Ser Ser Asp Asp Gly Leu Lys Met
                885                 890                 895

Lys Thr Ala Lys Arg Gln Phe Ser Gly Ser Gly Ile Gln Asp Val
                900                 905                 910

Leu Lys Ser Ile Tyr Thr Arg Tyr Asn Ala Asn Pro Ser Tyr Ser Lys
                915                 920                 925

Trp Ala Ser Asn Val Asp Tyr Tyr Asn Ser Ala Glu Gly Arg Ser Thr
                930                 935                 940

Gly Glu Ser Lys Leu Val Lys Leu Ser Phe Asn His Pro Thr Ile Asn
945                 950                 955                 960

Arg Asp Thr Lys Glu Ser Phe Ala Arg Ser Lys Trp Ile Gln Gly Ala
                965                 970                 975

Ser Ala Val Arg Ala Lys Ala Ser Pro Asn Leu Tyr Tyr Asp Gln Phe
                980                 985                 990

Gly Pro Met Tyr Leu Asn Gln Ile Arg Gly Ile Tyr Asn Asp Pro Asp
                995                 1000                1005

Asn Phe Gln Tyr Pro Phe Gly Gly Leu Arg Pro Lys
                1010                1015                1020
```

<210> SEQ ID NO 51
<211> LENGTH: 842
<212> TYPE: PRT
<213> ORGANISM: Phlebotomus papatasi

<400> SEQUENCE: 51

```
Leu Ile Ala Ile Ile Leu Asp Gln Glu Tyr Leu Asp Gln Lys Tyr Asp
 1               5                  10                  15

Pro Val Tyr Thr Glu Val Gln Val Ile Glu Arg Val Leu Arg Glu
                20                  25                  30

Asp Leu Lys Asn Gly Gly Leu Tyr Val Thr Tyr Tyr Ser Trp Thr Ser
            35                  40                  45

Val Asn Leu Lys Lys Asp Tyr Thr Ala Val Leu Val Val Ser Asn Cys
        50                  55                  60

Asp Asn Thr Trp Arg Val Phe Arg Glu Ala Arg Ala Asp Thr Leu Leu
65                  70                  75                  80

Leu Leu Ala Leu Thr Asp Pro Asp Cys Pro Arg Leu Pro Pro Ser Glu
                85                  90                  95

Ala Ile Met Val Ile Pro Leu Thr Ser Gly Gly Glu Glu Leu Pro Gln
               100                 105                 110

Val Leu Leu Asp Leu Lys Ser Ser Gln Ala Leu Lys Trp Lys Ser Ala
           115                 120                 125

Ile Val Leu His Asp Asp Thr Phe Ala Arg Asp Met Ile Ser Arg Val
       130                 135                 140

Ala Ile Ala Val Thr Ser Glu Ser Pro Asp Gly Tyr Val Lys Pro Met
145                 150                 155                 160

Ser Val Ser Leu Phe Lys Ile Arg Ala His Ile Gln Glu Trp Glu Arg
                165                 170                 175

Arg Lys Ser Ile Arg Arg Thr Leu Leu Ser Leu Pro Thr Asn Tyr Ile
            180                 185                 190

Gly Arg Asn Phe Leu Ala Ile Val Thr Thr Val Ile Met Glu Asn Ile
        195                 200                 205

Met Glu Val Ala Lys Asp Leu Gly Met Val Glu Pro Phe Ser Gln Trp
210                 215                 220

Met Tyr Val Ile Ser Asp Thr Asn Ser Glu Arg Asn Asn Ile Ser Ser
225                 230                 235                 240

Val Leu Pro Leu Ile Gly Glu Gly Glu Asn Val Ala Phe Ala Tyr Asn
                245                 250                 255

Val Thr Ser Lys Asp Pro Ala Cys Lys Ala Gly Ile Thr Cys His Cys
            260                 265                 270

Ala Glu Leu Leu Arg Ser Phe Val Leu Ala Leu Ser Arg Met Ile Arg
        275                 280                 285

Glu Glu Lys Ala Val Tyr Gly Gln Ile Ser Asp Glu Trp Glu Thr
    290                 295                 300

Ile Arg Pro Thr Lys Lys Glu Arg Arg Asp Met Leu Leu Glu Thr Met
305                 310                 315                 320

Arg Leu Ile Leu Lys Ser Thr Ser Val Cys Ser Asn Cys Thr Thr Trp
                325                 330                 335

Lys Val Gln Ala Gly Glu Tyr Trp Gly Thr Glu Tyr Glu Glu Trp
            340                 345                 350

Ser Ile Val Asn Thr Pro Arg Arg Ser Ser Lys Phe Leu Asp Val Gly
        355                 360                 365

Thr Trp Lys Pro Asn Asp Gly Val Gln Leu Asn Asp Val Leu Phe Pro
```

```
                370             375             380
His Val Ser Asn Gly Phe Arg Gly Lys Asn Leu His Ile Val Thr Tyr
385             390             395             400
His Asn Pro Pro Trp Gln Ile Ile Ala Tyr Asn Glu Ser Gly Val Pro
                405             410             415
Gly Val Met Arg Gly Val Val Met Asp Ile Leu Asn Glu Met Ala Lys
            420             425             430
Lys Leu Asn Phe Thr Tyr Thr Met His Val Ile Pro Val Ser Ile Pro
        435             440             445
Lys Ala Asn Glu Thr Glu Leu Ser Tyr Asn Val Ser Ser Thr Glu
    450             455             460
Glu Gly Gln Leu Pro Thr Thr Thr Ile Pro Met Glu Ile Leu Asn Leu
465             470             475             480
Val Ser Gln Asp Lys Val Phe Leu Ala Ala Val Gly Ala Thr Val Asn
                485             490             495
Glu Lys Tyr Lys Arg Phe Ile Asn Tyr Thr Ile Pro Ile Ser Ile Gln
            500             505             510
Pro Tyr Asn Phe Ile Val Ser Arg Pro Arg Glu Leu Ser Arg Leu Tyr
        515             520             525
Leu Phe Met Ala Pro Phe Thr Lys Glu Thr Trp Leu Cys Leu Ala Ala
    530             535             540
Cys Ile Val Val Met Gly Pro Leu Leu Tyr Leu Val Asn Arg Phe Ser
545             550             555             560
Pro Phe Tyr Glu Gln Lys Gly Phe Asp Ile Ala Arg Leu Gly Leu Asn
                565             570             575
Arg Ile Asn Asn Cys Phe Trp Tyr Ile Tyr Gly Ala Leu Leu Gln Gln
            580             585             590
Gly Asn Phe Trp Val Gly Gly Met Tyr Leu Pro Gln Ala Asp Ser Gly
        595             600             605
Arg Ile Ile Ile Gly Thr Trp Trp Leu Val Val Ile Val Leu Val Thr
    610             615             620
Thr Tyr Cys Gly Asn Leu Val Ala Phe Leu Thr Phe Pro Lys Ile Glu
625             630             635             640
Ile Pro Ile Thr Thr Val Gly Gln Leu Val Gly Lys Ser Gly Ala Val
                645             650             655
Ser Trp Ser Thr Lys Ser Gly Thr Phe Leu Glu Glu Phe Leu Ala Glu
            660             665             670
Thr Asp Glu Pro Lys Tyr Lys Lys Leu Leu Asp Gly Met Ala Phe Asn
        675             680             685
Thr Glu Thr Ser Ser Asp Thr Ile Glu Asn Val Arg Gln Gly Lys His
    690             695             700
Val Tyr Ile Asp Trp Lys Ser Asn Leu Gln Tyr Ile Met Lys Lys Glu
705             710             715             720
Phe Leu Val Asn Asp Arg Cys Asp Phe Ala Leu Gly Val Glu Asp Phe
                725             730             735
Leu Asp Glu Gln Ile Ala Ile Met Pro Arg Asp Ser Ala Tyr Leu
            740             745             750
Asn Leu Ile Asn Ser Glu Ile Thr Arg Leu His Gln Met Gly Phe Ile
        755             760             765
Gln Arg Trp Leu Lys Glu Tyr Leu Pro Lys Asp Arg Cys Trp Asn
    770             775             780
Val Gly Lys Ala Ile Glu Val Asn Asn His Thr Val Asn Leu Asp Asp
785             790             795             800
```

```
Met Gln Gly Ser Phe Leu Val Leu Phe Ile Gly Cys Val Leu Gly Ala
                805                 810                 815

Cys Val Ile Ile Leu Glu Cys Met Trp Phe Lys Arg Arg Glu Leu Lys
            820                 825                 830

Glu Gln Val Ile Ile Lys Pro Phe Val Lys
            835                 840
```

US 9,910,044 B2

METHODS FOR IDENTIFYING ARTHROPOD REPELLENTS BASED ON MODULATION OF SPECIFIC IONOTROPIC RECEPTORS, AND COMPOUNDS AND COMPOSITIONS IDENTIFIED BY SUCH METHODS

CROSS-REFERENCE TO RELATED APPLICATION

This application is a continuation application of International Application PCT/US14/29524, with an international filing date of Mar. 14, 2014, which claims priority to and the benefit of U.S. Provisional Application No. 61/785,572, filed Mar. 14, 2013, the disclosures of which are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 677032000801SeqList.txt, date recorded: Sep. 14, 2015, size: 323 KB).

FIELD

The present disclosure relates generally to the field of arthropod repellents, and more specifically to methods of identifying such repellents based on modulation of ionotropic receptors, including an Ir40a receptor, an Ir93a receptor and an Ir25a receptor.

BACKGROUND

Blood-feeding insects are known to transmit deadly diseases such as malaria, dengue, filariasis, West Nile fever, yellow fever, sleeping sickness and leishmaniasis, causing untold suffering and more than a million deaths every year. Insect repellents can be very effective in reducing vectorial capacity by blocking the contact between blood-seeking insects and humans; however, they are seldom used in disease-prone areas of Africa and Asia due to high costs and need for continuous application on skin.

N,N-Diethyl-m-toluamide (DEET) is an example of an insect repellent used in the developed world for more than sixty years. The use of DEET as an insect repellent, however, has several drawbacks. For example, DEET is a solvent capable of melting several forms of plastics, synthetic fabrics, painted and varnished surfaces (Krajick et al., *Science*, 313: 36, 2006). Additionally, DEET has been shown to inhibit mammalian cation channels and human acetylcholinesterase, which is also inhibited by carbamate insecticides commonly used in disease endemic areas (Corbel et al., *BMC Biol*, 7, 2009). These concerns are enhanced by the requirement of direct and continuous application of DEET to every part of exposed skin in concentrations that can be as high as 30-100%. Several instances of increased resistance to DEET have also been reported in flies, *Anopheles albimanus*, and *Aedes aegypti* (Reeder et al., *J Econ Entomol*, 94: 1584, 2001; Klun et al., *J Med Entomol*, 41: 418, 2004; Stanczyk et al., *Proc Natl Acad Sci USA*, 107: 8575, 2010). Moreover, mosquito strains with resistance to pyrethroid insecticides, the main line of defense against mosquitoes in developing countries, are spreading (Butler et al., *Nature*, 475: 19, 2011). The other major barrier in developing new repellents is the time and cost of development, which can take more than $30 million and several years to identify new compounds that not only repellent to insects, but are also safe for human use.

Thus, what is needed in the art are alternative compounds to DEET that can be used as insect repellents but are safe for human use, and methods of identifying such alternatives.

BRIEF SUMMARY

Provided are screening methods to identify compounds that modulate an Ir40a receptor, an Ir93a receptor, and an Ir25a receptor, either alone or in any combination. Such compounds may be useful as arthropod repellents.

In one aspect, provided is a method for identifying a compound that is a repellent for at least one arthropod species, by identifying a compound that modulates the activity of an Ir40a receptor, an Ir93a receptor, or an Ir25a receptor, either alone or in any combination. In some embodiments, the method involves identifying a compound that modulates the activity of an Ir40a receptor. In other embodiments, the method involves identifying a compound that modulates the activity of an Ir93a receptor. In other embodiments, the method involves identifying a compound that modulates the activity of an Ir25a receptor. In certain embodiments, the method involves identifying a compound that modulates the activity of an Ir40a receptor and an Ir93a receptor. In certain embodiments, the method involves identifying a compound that modulates the activity of an Ir93a receptor and an Ir25a receptor. In yet other embodiments, the method involves identifying a compound that modulates the activity of an Ir40a receptor, an Ir93a receptor, and an Ir25a receptor.

In some embodiments, the Ir40a receptor, the Ir93a receptor, and/or the Ir25a receptor is from an arthropod. In certain embodiments, the Ir40a receptor, the Ir93a receptor, and/or the Ir25a receptor is from an insect. In some embodiments, the compound is identified in an in vitro assay or in vivo assay.

In another aspect, provided is a method of identifying a compound that is a repellent for at least one arthropod species, by: a) contacting an Ir40a receptor or Ir40a receptor-expressing neuron with a candidate compound; b) measuring the activity of the Ir40a receptor; c) comparing the activity of the Ir40a receptor after contact with the candidate compound to the activity of the Ir40a receptor in the absence of the candidate compound; and d) identifying a compound that is a repellent for at least one arthropod species by determining whether or not the candidate compound modulates the activity of the Ir40a receptor.

In another aspect, provided is a method of identifying a compound that is a repellent for at least one arthropod species, by: a) contacting an Ir93a receptor or Ir93a receptor-expressing neuron with a candidate compound; b) measuring the activity of the Ir93a receptor; c) comparing the activity of the Ir93a receptor after contact with the candidate compound to the activity of the Ir93a receptor in the absence of the candidate compound; and d) identifying a compound that is a repellent for at least one arthropod species by determining whether or not the candidate compound modulates the activity of the Ir93a receptor.

In another aspect, provided is a method of identifying a compound that is a repellent for at least one arthropod species, by: a) contacting an Ir25a receptor or Ir25a receptor-expressing neuron with a candidate compound; b) measuring the activity of the Ir25a receptor; c) comparing the activity of the Ir25a receptor after contact with the candidate compound to the activity of the Ir25a receptor in the absence of the candidate compound; and d) identifying a compound that is a repellent for at least one arthropod species by determining whether or not the candidate compound modulates the activity of the Ir25a receptor.

In some of the foregoing embodiments, the method involves co-expressing an Ir40a receptor and an Ir93a receptor in the same neuron. In some of the foregoing embodiments, the method involves co-expressing an Ir40a receptor and an Ir25a receptor in the same neuron. In some of the foregoing embodiments, the method involves co-expressing an Ir93a receptor and an Ir25a receptor in the same neuron. In other embodiments, the method involves co-expressing an Ir40a receptor, an Ir93a receptor, and an Ir25a receptor in the same neuron. In yet other embodiments, the Ir40a receptor or Ir40a receptor-expressing neuron, the Ir93a receptor or Ir93a receptor-expressing neuron, and/or the Ir25a receptor or Ir25a receptor-expressing neuron is from an arthropod. In certain embodiments, the Ir40a receptor or Ir40a receptor-expressing neuron, the Ir93a receptor or Ir93a receptor-expressing neuron, and/or the Ir25a receptor or Ir25a receptor-expressing neuron is from an insect.

In some of the foregoing embodiments, the receptors or the receptor-expressing neurons described herein are contacted with the candidate compound in vitro or in vivo. In certain embodiments, the Ir40a receptor is expressed in a cell. In one embodiment, the Ir40a receptor is expressed in an arthropod cell. In another embodiment, the Ir40a receptor is expressed in an insect cell. In yet another embodiment, the Ir40a receptor is expressed in a cell from *Drosophila melanogaster*. In certain embodiments, the Ir40a receptor is expressed in a neuron or an oocyte. In other embodiments, the Ir40a receptor is expressed in an isolated cell. In certain embodiments, the Ir93a and/or the Ir25a receptor, either alone or in any combination with the Ir40a receptor (e.g., Ir93a alone, Ir25a alone, Ir93a and Ir25a together, Ir93a and Ir40a together, Ir25a and Ir40a together, or Ir93a, Ir25a and Ir40a together), is expressed in a cell. In one embodiment, the Ir93a and/or the Ir25a receptor, either alone or in any combination with the Ir40a receptor (e.g., Ir93a alone, Ir25a alone, Ir93a and Ir25a together, Ir93a and Ir40a together, Ir25a and Ir40a together, or Ir93a, Ir25a and Ir40a together), is expressed in an arthropod cell. In another embodiment, the Ir93a and/or the Ir25a receptor, either alone or in any combination with the Ir40a receptor (e.g., Ir93a alone, Ir25a alone, Ir93a and Ir25a together, Ir93a and Ir40a together, Ir25a and Ir40a together, or Ir93a, Ir25a and Ir40a together), is expressed in an insect cell. In yet another embodiment, the Ir93a and/or the Ir25a receptor, either alone or in any combination with the Ir40a receptor (e.g., Ir93a alone, Ir25a alone, Ir93a and Ir25a together, Ir93a and Ir40a together, Ir25a and Ir40a together, or Ir93a, Ir25a and Ir40a together), is expressed in a cell from *Drosophila melanogaster*. In certain embodiments, the Ir93a and/or the Ir25a receptor, either alone or in any combination with the Ir40a receptor (e.g., Ir93a alone, Ir25a alone, Ir93a and Ir25a together, Ir93a and Ir40a together, Ir25a and Ir40a together, or Ir93a, Ir25a and Ir40a together), is expressed in a neuron or an oocyte. In other embodiments, the Ir93a and/or the Ir25a receptor, either alone or in any combination with the Ir40a receptor (e.g., Ir93a alone, Ir25a alone, Ir93a and Ir25a together, Ir93a and Ir40a together, Ir25a and Ir40a together, or Ir93a, Ir25a and Ir40a together), is expressed in an isolated cell. In other embodiments, the Ir93a and/or the Ir25a receptor, either alone or in any combination with the Ir40a receptor (e.g., Ir93a alone, Ir25a alone, Ir93a and Ir25a together, Ir93a and Ir40a together, Ir25a and Ir40a together, or Ir93a, Ir25a and Ir40a together), is expressed in a membrane preparation.

In another aspect, provided is a method of identifying a compound that is a repellent for at least one arthropod species, by: a) providing a sample comprising a full-length or partial Ir40a receptor protein; b) contacting the sample with a candidate compound; c) measuring the activity of the Ir40a receptor in the sample; d) comparing the activity of the Ir40a receptor after contact with the candidate compound to the activity of the Ir40a receptor in the absence of the candidate compound; and e) identifying a compound that is a repellent for at least one arthropod species by determining whether or not the candidate compound modulates the activity of the Ir40a receptor.

In another aspect, provided is a method of identifying a compound that is a repellent for at least one arthropod species, by: a) providing a sample comprising a full-length or partial Ir93a receptor protein; b) contacting the sample with a candidate compound; c) measuring the activity of the Ir93a receptor in the sample; d) comparing the activity of the Ir93a receptor after contact with the candidate compound to the activity of the Ir93a receptor in the absence of the candidate compound; and e) identifying a compound that is a repellent for at least one arthropod species by determining whether or not the candidate compound modulates the activity of the Ir93a receptor.

In another aspect, provided is a method of identifying a compound that is a repellent for at least one arthropod species, by: a) providing a sample comprising a full-length or partial Ir25a receptor protein; b) contacting the sample with a candidate compound; c) measuring the activity of the Ir25a receptor in the sample; d) comparing the activity of the Ir25a receptor after contact with the candidate compound to the activity of the Ir25a receptor in the absence of the candidate compound; and e) identifying a compound that is a repellent for at least one arthropod species by determining whether or not the candidate compound modulates the activity of the Ir25a receptor.

In some of the foregoing embodiments, the Ir40a receptor and the Ir93a receptor are present in the same sample. In some of the foregoing embodiments, the Ir40a receptor and the Ir25a receptor are present in the same sample. In some of the foregoing embodiments, the Ir93a receptor and the Ir25a receptor are present in the same sample. In some embodiments, the Ir40a receptor, the Ir93a receptor, and the Ir25a receptor are present in the same sample. In some embodiments, the Ir40a receptor, the Ir93a receptor, and/or the Ir25a receptor is from an arthropod. In certain embodiments, the Ir40a receptor, the Ir93a receptor, and/or the Ir25a receptor is from an insect.

In some of the foregoing embodiments, the sample and the candidate compound are contacted in vitro or in vivo. In certain embodiments, the Ir40a receptor is expressed in a cell. In one embodiment, the Ir40a receptor is expressed in an arthropod cell. In another embodiment, the Ir40a receptor is expressed in an insect cell. In yet another embodiment, the Ir40a receptor is expressed in a cell from *Drosophila melanogaster*. In certain embodiments, the Ir40a receptor is expressed in a neuron or an oocyte. In other embodiments, the Ir40a receptor is expressed in an isolated cell. In certain embodiments, the Ir93a and/or the Ir25a receptor, either alone or in any combination with the Ir40a receptor, is expressed in a cell. In one embodiment, the Ir93a and/or the Ir25a receptor, either alone or in any combination with the Ir40a receptor, is expressed in an arthropod cell. In another embodiment, the Ir93a and/or the Ir25a receptor, either alone or in any combination with the Ir40a receptor, is expressed in an insect cell. In yet another embodiment, the Ir93a and/or the Ir25a receptor, either alone or in any combination with the Ir40a receptor, is expressed in a cell from *Drosophila melanogaster*. In certain embodiments, the Ir93a and/or the Ir25a receptor, either alone or in any combination with the Ir40a receptor, is expressed in a neuron or an oocyte. In other embodiments, the Ir93a and/or the Ir25a receptor, either alone or in any combination with the Ir40a receptor, is expressed in an isolated cell. In some embodiments, the sample further comprises a co-receptor or chaperone protein.

In yet another aspect, provided is a system that includes: a) a sample comprising an Ir40a receptor or Ir40a receptor-expressing neuron; and b) one or more compounds that each is a repellent for at least one arthropod species, wherein the one or more compound each modulates the activity of the Ir40a receptor. In some embodiments, the Ir40a receptor or Ir40a receptor-expressing neuron is from an arthropod. In certain embodiments, the Ir40a receptor or Ir40a receptor-expressing neuron is from an insect. In some embodiments, the Ir40a receptor or Ir40a receptor-expressing neuron is from an arthropod. In certain embodiments, the Ir40a receptor or Ir40a receptor-expressing neuron is from an insect.

In another aspect, provided is a system that includes: a) a sample comprising an Ir93a receptor or Ir93a receptor-expressing neuron; and b) one or more compounds that each is a repellent for at least one arthropod species, wherein the one or more compound each modulates the activity of the Ir93a receptor. In some embodiments, the Ir93a receptor or Ir93a receptor-expressing neuron is from an arthropod. In certain embodiments, the Ir93a receptor or Ir93a receptor-expressing neuron is from an insect. In some embodiments, the Ir93a receptor or Ir93a receptor-expressing neuron is from an arthropod. In certain embodiments, the Ir93a receptor or Ir93a receptor-expressing neuron is from an insect.

In another aspect, provided is a system that includes: a) a sample comprising an Ir25a receptor or Ir25a receptor-expressing neuron; and b) one or more compounds that each is a repellent for at least one arthropod species, wherein the one or more compound each modulates the activity of the Ir25a receptor. In some embodiments, the Ir25a receptor or Ir25a receptor-expressing neuron is from an arthropod. In certain embodiments, the Ir25a receptor or Ir25a receptor-expressing neuron is from an insect. In some embodiments, the Ir25a receptor or Ir25a receptor-expressing neuron is from an arthropod. In certain embodiments, the Ir25a receptor or Ir25a receptor-expressing neuron is from an insect.

The system may also include the use of one or more of Ir40a receptors, Ir93a receptors, and Ir25a receptors, either alone or in any combination (e.g., Ir93a alone, Ir25a alone, Ir93a and Ir25a together, Ir93a and Ir40a together, Ir25a and Ir40a together, or Ir93a, Ir25a and Ir40a together), with a compound that modulates the activity of one or more of an Ir40a receptor, an Ir93a receptor, and/or an Ir25a receptor. In some embodiments, an Ir40a receptor and an Ir93a receptor are present in the same system. In some embodiments, an Ir40a receptor, an Ir93a receptor, and an Ir25a receptor are present in the same system. In some embodiments, the Ir40a receptor, the Ir93a receptor, and/or the Ir25a receptor is from an arthropod. In certain embodiments, the Ir40a receptor, the Ir93a receptor, and/or the Ir25a receptor is from an insect.

In some embodiments, the Ir93a receptor and/or the Ir25a receptor, either alone or in any combination with the Ir40a receptor (e.g., Ir93a alone, Ir25a alone, Ir93a and Ir25a together, Ir93a and Ir40a together, Ir25a and Ir40a together, or Ir93a, Ir25a and Ir40a together), is expressed in a cell. In certain embodiments, the Ir93a receptor and/or the Ir25a receptor, either alone or in any combination with the Ir40a receptor, is expressed in an arthropod cell. In one embodiment, the Ir93a receptor and/or the Ir25a receptor, either alone or in any combination with the Ir40a receptor, is expressed in an insect cell. In another embodiment, the Ir93a receptor and/or the Ir25a receptor, either alone or in any combination with the Ir40a receptor, is expressed in a cell from *Drosophila melanogaster*. In certain embodiments, the Ir93a receptor and/or the Ir25a receptor, either alone or in any combination with the Ir40a receptor, is expressed in a neuron or an oocyte. In one embodiment, the Ir93a receptor and/or the Ir25a receptor, either alone or in any combination with the Ir40a receptor, is expressed in an isolated cell. In some embodiments, the sample including the Ir93a receptor and/or the Ir25a receptor, either alone or in any combination with the Ir40a receptor, further includes a co-receptor or chaperone protein. In certain embodiments, the modulation of the activity of the Ir40a, the Ir93a receptor, and/or the Ir25a receptor is an increase in receptor activity. In other embodiments, the modulation of the activity of the Ir40a, the Ir93a receptor, and/or the Ir25a receptor is a decrease in receptor activity.

In yet another aspect, provided is a system for screening a plurality of candidate compounds that includes: a) a sample comprising an Ir40a receptor or Ir40a receptor-expressing neuron; and b) a plurality of candidate compounds, wherein at least one of the candidate compounds is a repellent for at least one arthropod species, and wherein the at least one repellent compound modulates the activity of the Ir40a receptor. In some embodiments, the Ir40a receptor or Ir40a receptor-expressing neuron is from an arthropod. In certain embodiments, the Ir40a receptor or Ir40a receptor-expressing neuron is from an insect. In some embodiments, the Ir40a receptor or Ir40a receptor-expressing neuron is from an arthropod. In certain embodiments, the Ir40a receptor or Ir40a receptor-expressing neuron is from an insect.

In another aspect, provided is a system for screening a plurality of candidate compounds that includes: a) a sample comprising an Ir93a receptor or Ir93a receptor-expressing neuron; and b) a plurality of candidate compounds, wherein at least one of the candidate compounds is a repellent for at least one arthropod species, and wherein the at least one repellent compound modulates the activity of the Ir93a receptor. In some embodiments, the Ir93a receptor or Ir93a receptor-expressing neuron is from an arthropod. In certain embodiments, the Ir93a receptor or Ir93a receptor-expressing neuron is from an insect. In some embodiments, the Ir93a receptor or Ir93a receptor-expressing neuron is from an arthropod. In certain embodiments, the Ir93a receptor or Ir93a receptor-expressing neuron is from an insect.

In another aspect, provided is a system for screening a plurality of candidate compounds that includes: a) a sample comprising an Ir25a receptor or Ir25a receptor-expressing neuron; and b) a plurality of candidate compounds, wherein at least one of the candidate compounds is a repellent for at least one arthropod species, and wherein the at least one repellent compound modulates the activity of the Ir25a receptor. In some embodiments, the Ir25a receptor or Ir25a receptor-expressing neuron is from an arthropod. In certain embodiments, the Ir25a receptor or Ir25a receptor-expressing neuron is from an insect. In some embodiments, the Ir25a receptor or Ir25a receptor-expressing neuron is from an arthropod. In certain embodiments, the Ir25a receptor or Ir25a receptor-expressing neuron is from an insect.

The system may also include the use of one or more of Ir40a receptors, Ir93a receptors, and Ir25a receptors, either alone or in any combination, with a compound that modulates the activity of one or more of an Ir40a receptor, an Ir93a receptor, and/or an Ir25a receptor (e.g., Ir93a alone, Ir25a alone, Ir93a and Ir25a together, Ir93a and Ir40a together, Ir25a and Ir40a together, or Ir93a, Ir25a and Ir40a together). In some embodiments, an Ir40a receptor and an Ir93a receptor are present in the same system. In some embodiments, an Ir40a receptor, an Ir93a receptor, and an Ir25a receptor are present in the same system. In some embodiments, the Ir40a receptor, the Ir93a receptor, and/or the Ir25a receptor, or Ir40 receptor-expressing neuron, Ir93a receptor-expressing neuron, and/or Ir25a receptor-expressing neuron is from an arthropod. In certain embodiments, the Ir40a receptor, the Ir93a receptor, and/or the Ir25a receptor, or Ir40 receptor-expressing neuron, Ir93a receptor-expressing neuron, and/or Ir25a receptor-expressing neuron is from an insect.

In some embodiments, an Ir93a receptor and/or an Ir25a receptor are expressed, either alone or in any combination with an Ir40a receptor (e.g., Ir93a alone, Ir25a alone, Ir93a and Ir25a together, Ir93a and Ir40a together, Ir25a and Ir40a together, or Ir93a, Ir25a and Ir40a together), in a cell. In certain embodiments, the Ir40a receptor, the Ir93a receptor, and/or the Ir25a receptor is expressed in an arthropod cell. In one embodiment, the Ir40a receptor, the Ir93a receptor, and/or the Ir25a receptor is expressed in an insect cell. In another embodiment, the Ir40a receptor, the Ir93a receptor, and/or the Ir25a receptor is expressed in a cell from *Drosophila melanogaster*. In some embodiments, the Ir40a receptor, the Ir93a receptor, and/or the Ir25a receptor is expressed in a neuron or an oocyte. In certain embodiments, the Ir40a receptor, the Ir93a receptor, and/or the Ir25a receptor is expressed in an isolated cell. In some embodiments, the sample further includes a co-receptor or chaperone protein.

In some embodiments that may be combined with any of the preceding embodiments, the Ir40a receptor has at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoding an Ir40a receptor from *Drosophila melanogaster*. In some embodiments that may be combined with any of the preceding embodiments, the Ir40a receptor has at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoding an Ir40a receptor or an ortholog thereof from *Drosophila melanogaster*.

In some embodiments that may be combined with any of the preceding embodiments, the Ir93a receptor has at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoding an Ir93a receptor from *Drosophila melanogaster*. In some embodiments that may be combined with any of the preceding embodiments, the Ir93a receptor has at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoding an Ir93a receptor or an ortholog thereof from *Drosophila melanogaster*.

In some embodiments that may be combined with any of the preceding embodiments, the Ir25a receptor has at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoding an Ir25a receptor from *Drosophila melanogaster*. In some embodiments that may be combined with any of the preceding embodiments, the Ir25a receptor has at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a polypeptide encoding an Ir25a receptor or an ortholog thereof from *Drosophila melanogaster*.

Orthologs of an Ir40a receptor, an Ir93a receptor, and/or an Ir25a receptor may be selected from, for example, *Aedes aegypti, Anopheles gambiae, Culex quinquefasciatus, Acyrthosiphon pisum, Bombyx mori, Tribolium castenium, Pediculus humanus, Ixodes scapularis, Phlebotomus papatasi, Heliconius melpomene, Manduca sexta, Mayetiola destructor, Atta cephalotes, Acromyrmex echinatior, Solenopsis invicta, Pogonomyrmex barbatus, Camponotus floridanus, Linepithema humile, Harpegnathos saltator, Apis mellifera, Megachili rotundata, Nassonia vitripennis, Rhodnius prolixus*, and *Tetranychus urticae*.

In some embodiments that may be combined with any of the preceding embodiments, the modulation of the activity of the Ir40a receptor, the Ir93a receptor, and/or the Ir25a receptor is determined by measuring changes in one or more electrophysiological parameters, measuring changes in calcium levels, measuring electrical potential changes, measuring changes in transcription of activity-dependent gene promoters, or any combination thereof. In some embodiments that may be combined with any of the preceding embodiments, the modulation in the activity of an Ir40a receptor is an increase in the activity of an Ir40a receptor. In some embodiments that may be combined with any of the preceding embodiments, the modulation in the activity of an Ir40a receptor is a decrease in the activity of an Ir40a receptor. In some embodiments that may be combined with any of the preceding embodiments, the modulation in the activity of an Ir93a receptor is an increase in the activity of an Ir93a receptor. In some embodiments that may be combined with any of the preceding embodiments, the modulation in the activity of an Ir93a receptor is a decrease in the activity of an Ir93a receptor. In some embodiments that may be combined with any of the preceding embodiments, the modulation in the activity of an Ir25a receptor is an increase in the activity of an Ir25a receptor. In some embodiments that may be combined with any of the preceding embodiments, the modulation in the activity of an Ir25a receptor is a decrease in the activity of an Ir25a receptor.

Provided is also a composition comprising one or more compounds identified according to any one of the methods described above.

DESCRIPTION OF THE FIGURES

The present application can be best understood by references to the following description taken in conjunction with the accompanying figures.

UAS-IMPTV) and test genotypes (Ir40a-Ga14/UAS-TNTG) in the 1-choice and 2-choice traps, where N=6 trials (1-choice) and N=8-9 trials (2-choice) for each genotype and about 20 flies for each trial; error bars=S.E.M., T-test (2 tailed) *=p<0.005, **=p<0.0001.

Figure 2A:
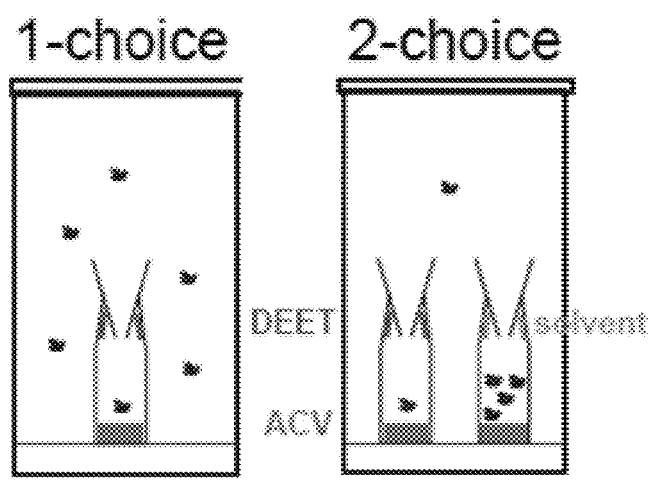
FIG. 2A is a schematic illustrating a 1-choice (left) and 2-choice (right) trap assay.
Figure 2B:
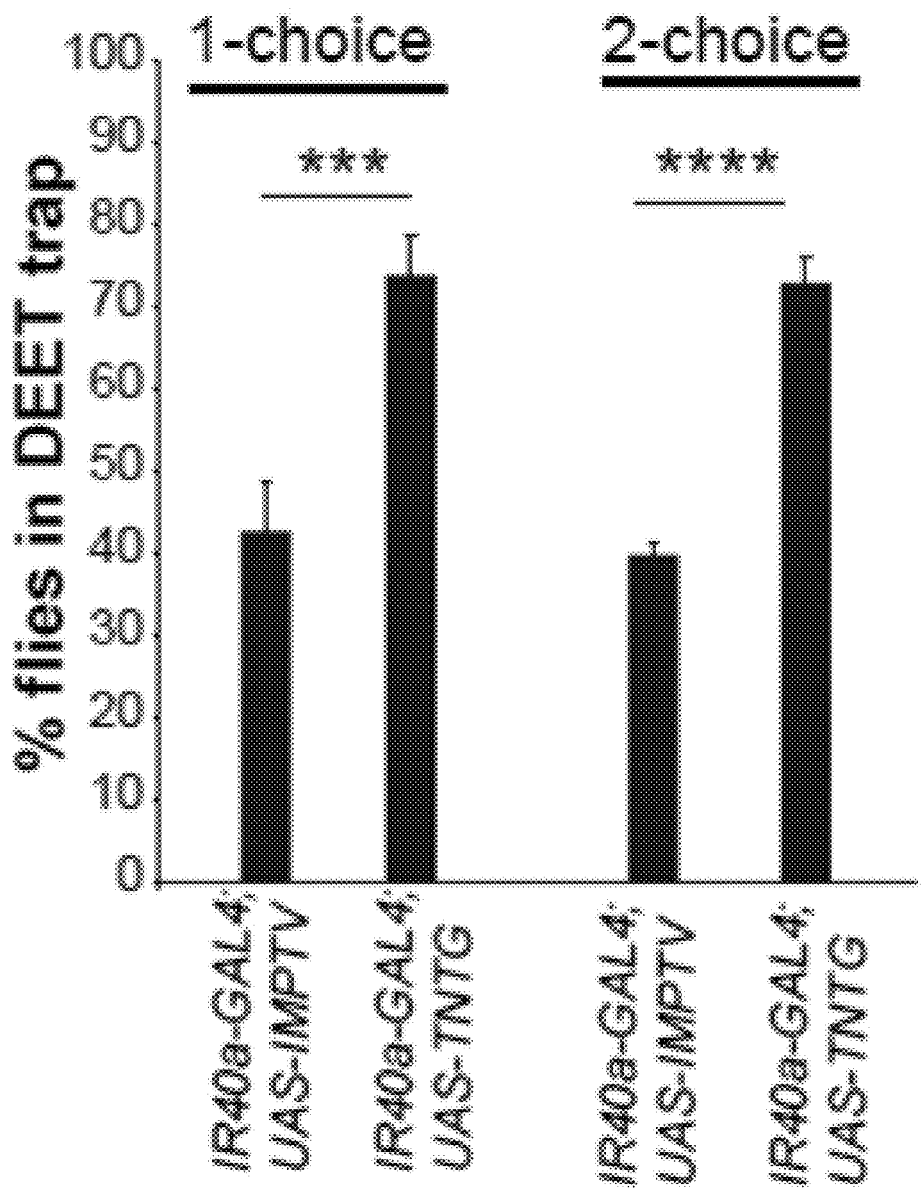
FIG. 2B is a graph showing the mean percentage of flies entering the DEET-treated trap for control (Ir40a-Gal4/
Figure 2C:
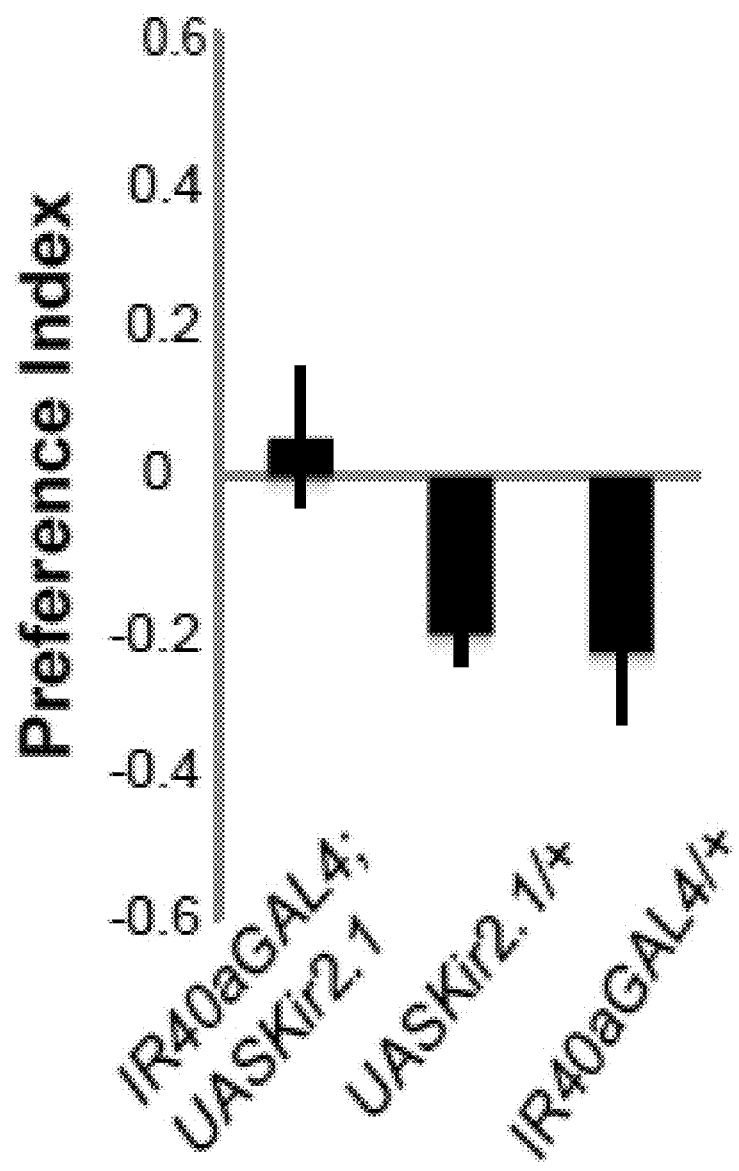

FIG. 2C is a graph showing the mean preference index for Ir40a+ neurons silenced using the Ir40a-promoter-Ga14 to express UAS-kir, and two control lines in a 2-choice trap assay lured by 10% apple cider vinegar against DEET.

Figure 2D:
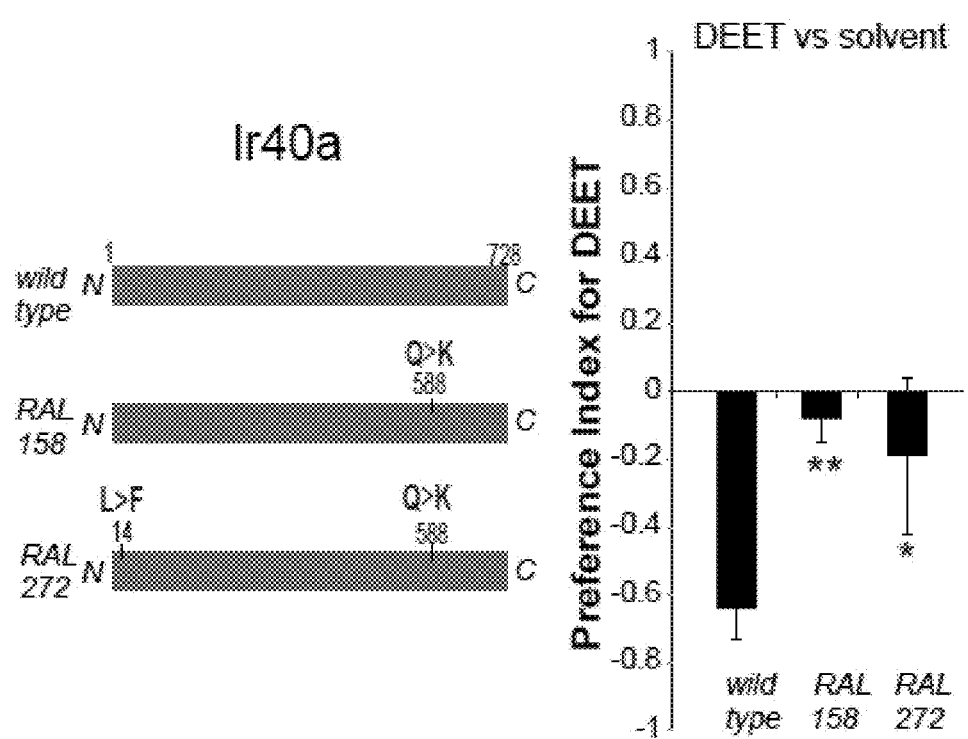

FIG. 2D depicts a schematic of variations in Ir40a (left) that were confirmed by sequencing the two DGRP lines, and a graph (right) showing mean preference index of wild-type (Canton S), RAL-158 and RAL-272 lines to DEET (50% in DMSO) with 10% apple cider vinegar (ACV) lure against solvent (DMSO) with ACV (10%), where N=6-8 trials, about 20 flies/trial; error bars=S.E.M., T-test (1 tailed) *=p<0.05, **=p<0.001.

Figure 3:
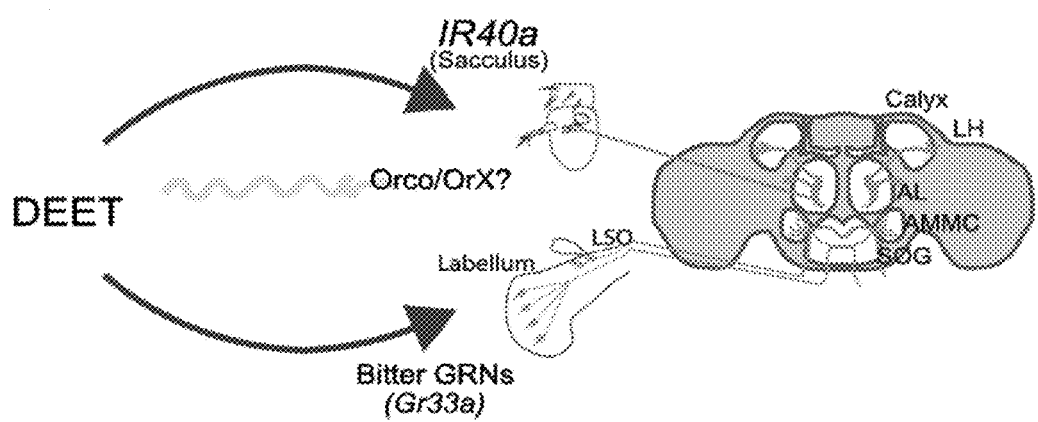

FIG. 3 is a graphical depiction of the model for DEET detection and information processing in the *Drosophila* chemosensory system.

Figure 4A:
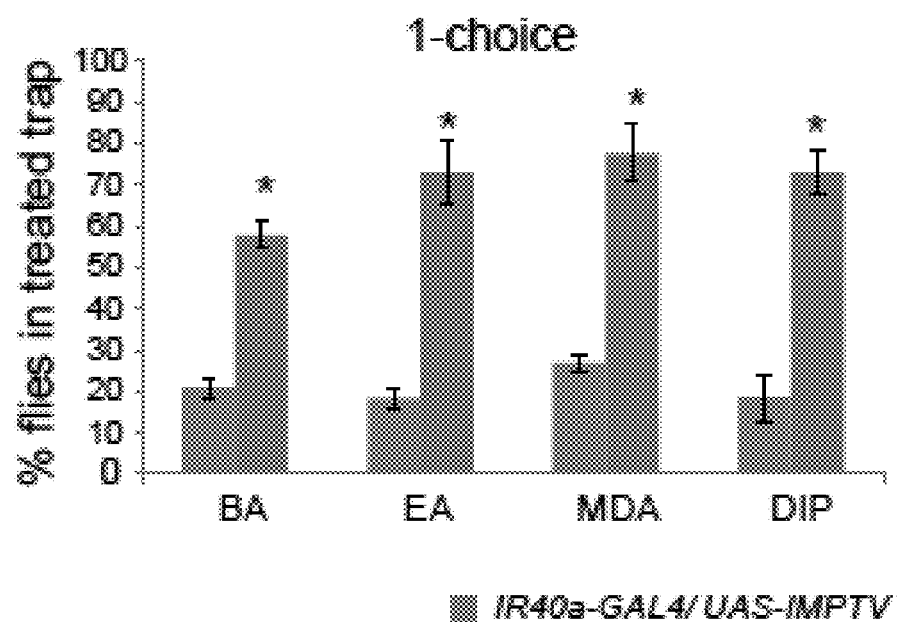
Figure 4B:
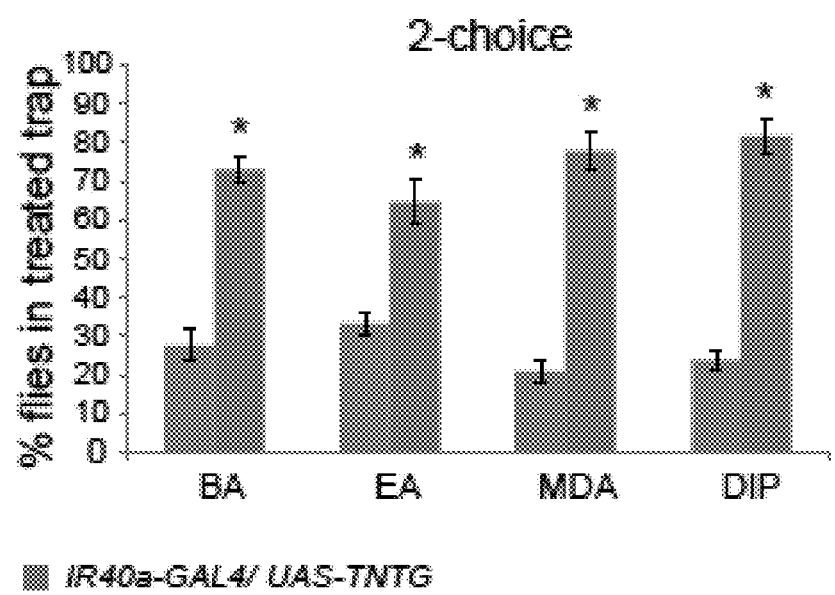

FIGS. 4A and 4B include two bar graphs illustrating the mean percentage of flies entering the treated trap for control (Ir40a-Ga14/UAS-IIVIPTV) and test genotypes (Ir40a-Ga14/UAS-TNTG) in a 1-choice assay (FIG. 4A) and a 2-choice assay (FIG. 4B), where N=6 trials (1-choice) and N=6 trials (2-choice) for each genotype and ~20 flies for each trial; error bars=S.E.M., T-test (2 tailed) *=p<0.0001; MDA=methyl N,N-dimethyl anthranilate; EA=ethyl anthranilate; BA=butyl anthranilate; DIP=2,3-dimethyl-5-isobutyl pyrazine.

Figure 5:
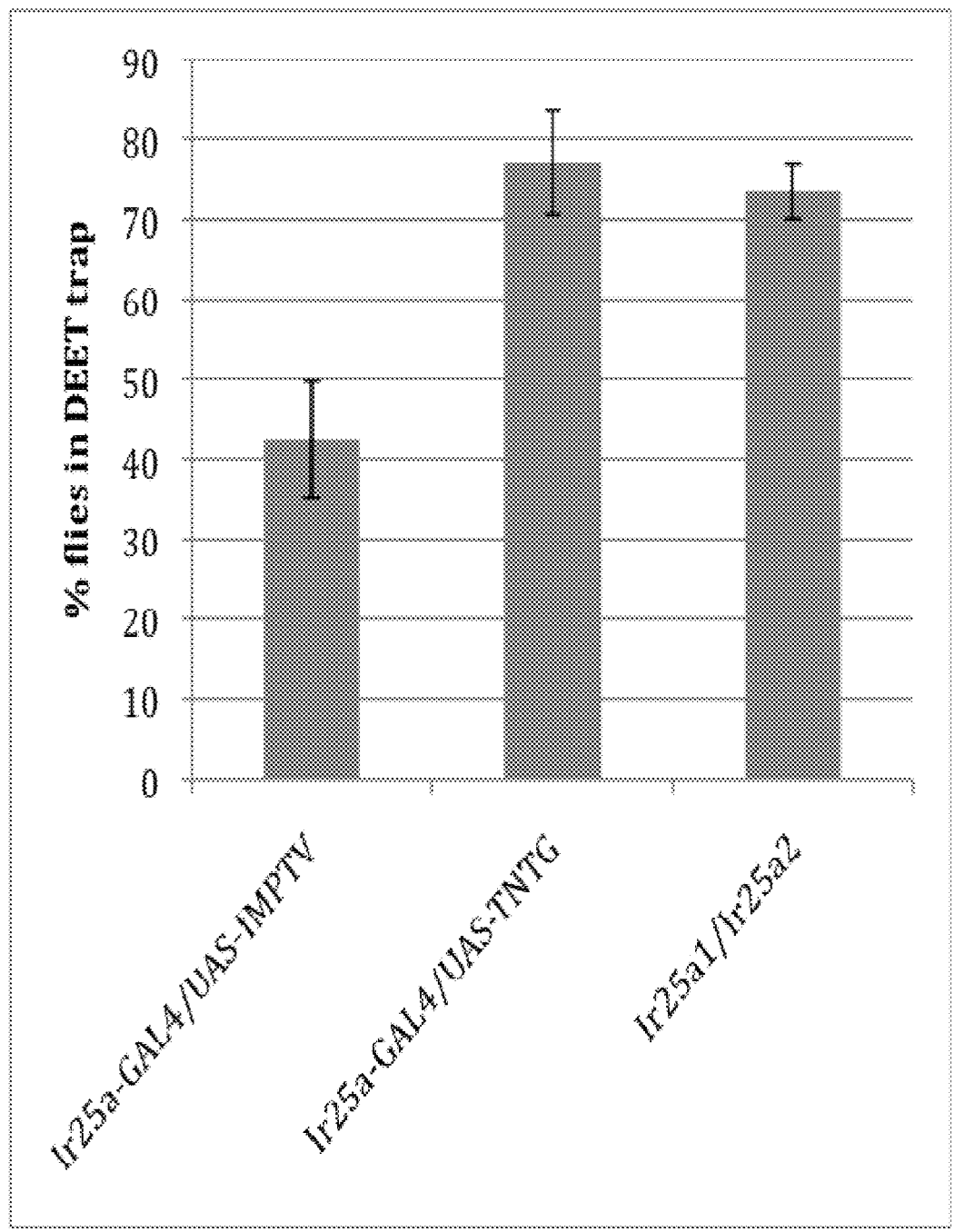

FIG. 5 is a graph showing the mean percentage of flies entering a DEET-treated trap for control (Ir25a-Ga14/UAS-IIVIPTV) and test genotypes (Ir25a-Ga14/UAS-TNTG and mutant Ir25a1/Ir25a2) in a 1-choice trap assay lured by 10% apple cider vinegar (ACV).

Figure 6A:
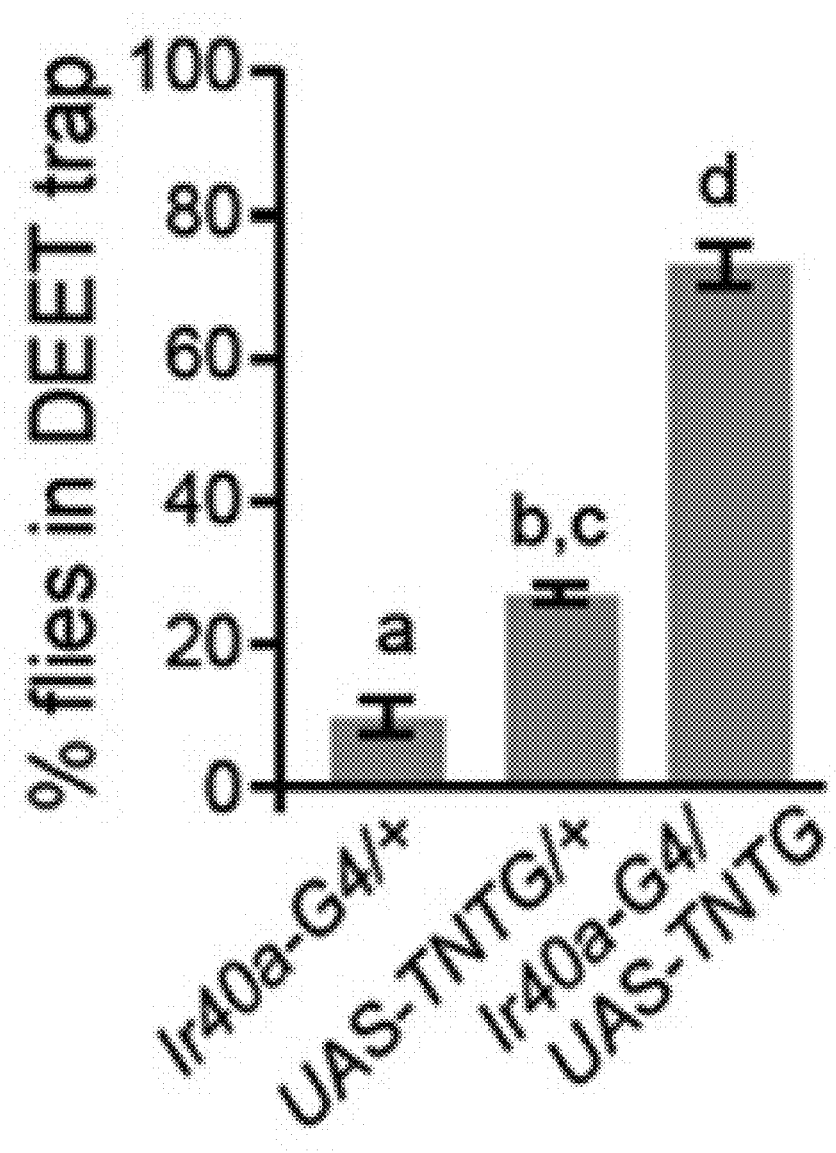

FIG. 6A is a graph showing the mean percentage of flies entering a DEET-treated trap for controls (Ir40a-G4/+ and UAS-TNTG/+) and test genotype (Ir40a-Ga4/UAS-TNTG/+) in a 1-choice trap assay lured by 10% apple cider vinegar (ACV).

Figure 6B:
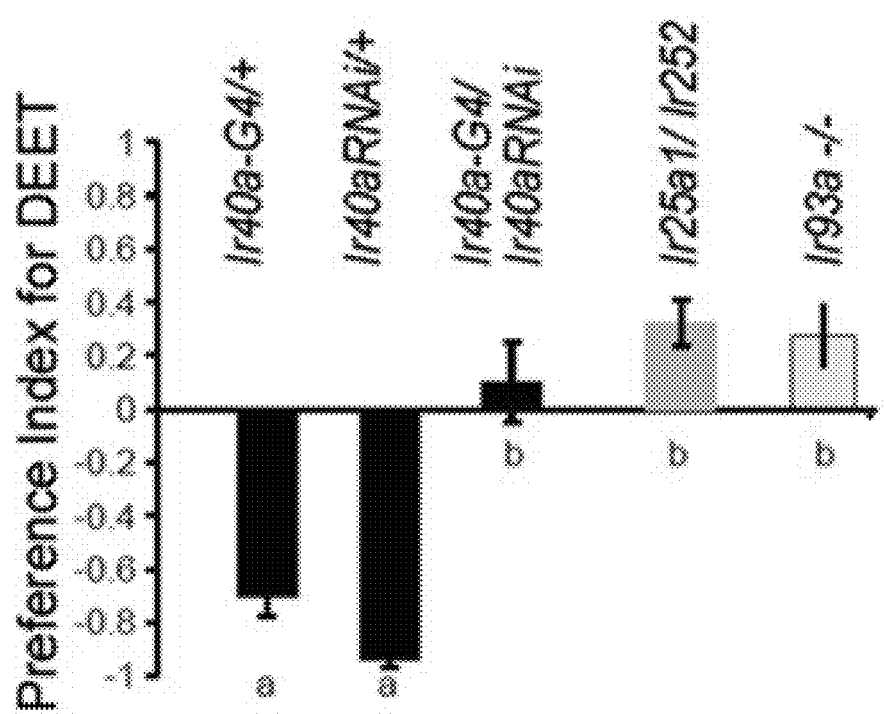

FIG. 6B is a graph showing the mean preference index for DEET trap in 2-choice olfactory avoidance assay using Ir40a RNAi and mutants for Ir25a and Ir93a. N=6-12 trials, 20 flies/trial.

DETAILED DESCRIPTION

The following description is presented to enable a person of ordinary skill in the art to make and use the various embodiments. Descriptions of specific materials, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Screening Methods

Provided herein are screening methods for identifying one or more compounds that are repellents for at least one arthropod species. Changes in the activity of one or more of an Ir40a receptor, an Ir93a receptor, and an IR25a receptor can be used to identify whether or not one or more compounds are arthropod repellents. Such methods can help with identifying new repellants to fight insect-borne diseases and plant pests.

Ionotropic receptor 40a (also known as "Ir40a"), Ionotropic receptor 93a (also known as "Ir93a"), and Ionotropic 25a (also known as Ir25a") are ionotropic receptors present in arthropods. Ionotropic receptors are a broad class of transmembrane receptors that form ion channel pores in cell membranes, such as neurons. Although ionotropic receptors exist in large gene families with multiple members, each individual member of this receptor family may have specificity for certain compounds to which each unique receptor may bind to or interact with.

Perception of a compound by an ionotropic receptor can modulate the physical status of the ion channel, and may result in a change in the flow of various ions, such as $Na^+$, $Ca^{2+}$, $K^+$, and $Cl^-$, into or out of the cell. The candidate compound screened by the methods described herein may increase or decrease the flows of various ions. The modulation of the Ir40a receptor may be direct or indirect. For example, such modulation may result from a candidate compound acting as a ligand binding to the Ir40a receptor or certain portions thereof. Such modulation may also result from a candidate compound acting as an agonist of the Ir40a receptor, for example, causing activation of the neuron downstream of the Ir40a receptor.

In some embodiments, the method includes: a) contacting an Ir40a receptor, an Ir93a receptor, and/or an Ir25a receptor, or Ir40a receptor-expressing neuron, Ir93a receptor-expressing neuron, and/or Ir25a receptor-expressing neuron with a candidate compound; b) measuring the activity of the receptor; c) comparing the activity of the receptor after contact with the candidate compound to the activity of the receptor in the absence of the candidate compound; and d) identifying a compound that is a repellent for at least one arthropod species by determining whether or not the candidate compound modulates the activity of the receptor.

In other embodiments, the method includes: a) providing a sample that includes an Ir40a receptor, an Ir93a receptor, and/or an Ir25a receptor; b) contacting the sample with a candidate compound; c) measuring the activity of the receptor in the sample; d) comparing the activity of the receptor after contact with the candidate compound to the activity of the receptor in the absence of the candidate compound; and e) identifying a compound that is a repellent for at least one arthropod species by determining whether or not the candidate compound modulates the activity of the receptor.

The method may also include the use of one or more of Ir40a receptors, Ir93a receptors, and Ir25a receptors, either alone or in any combination, in a screening method for a compound that modulates the activity of one or more of an Ir40a receptor, an Ir93a receptor, and/or an Ir25a receptor. It is to be understood that in embodiments that include all three of an Ir40a receptor, an Ir93a receptor, and an Ir25a receptor, that these receptors may form a heterotrimer. In some embodiments, the method involves identifying a compound that modulates the activity of an Ir40a receptor. In some embodiments, the method involves identifying a compound that modulates the activity of an Ir93a receptor. In some embodiments, the method involves identifying a compound that modulates the activity of an Ir25a receptor. In some embodiments, the method involves identifying a compound that modulates the activity of an Ir40a receptor and an Ir93a receptor. In other embodiments, the method involves identifying a compound that modulates the activity of an Ir93a receptor and an Ir25a receptor. In some embodiments, the method involves identifying a compound that modulates the activity of an Ir40a receptor, an Ir93a receptor, and an Ir25a receptor. The method may involve the use of an Ir93a receptor and/or an Ir25a receptor, either alone or in any combination with an Ir40a receptor.

Figure 1:
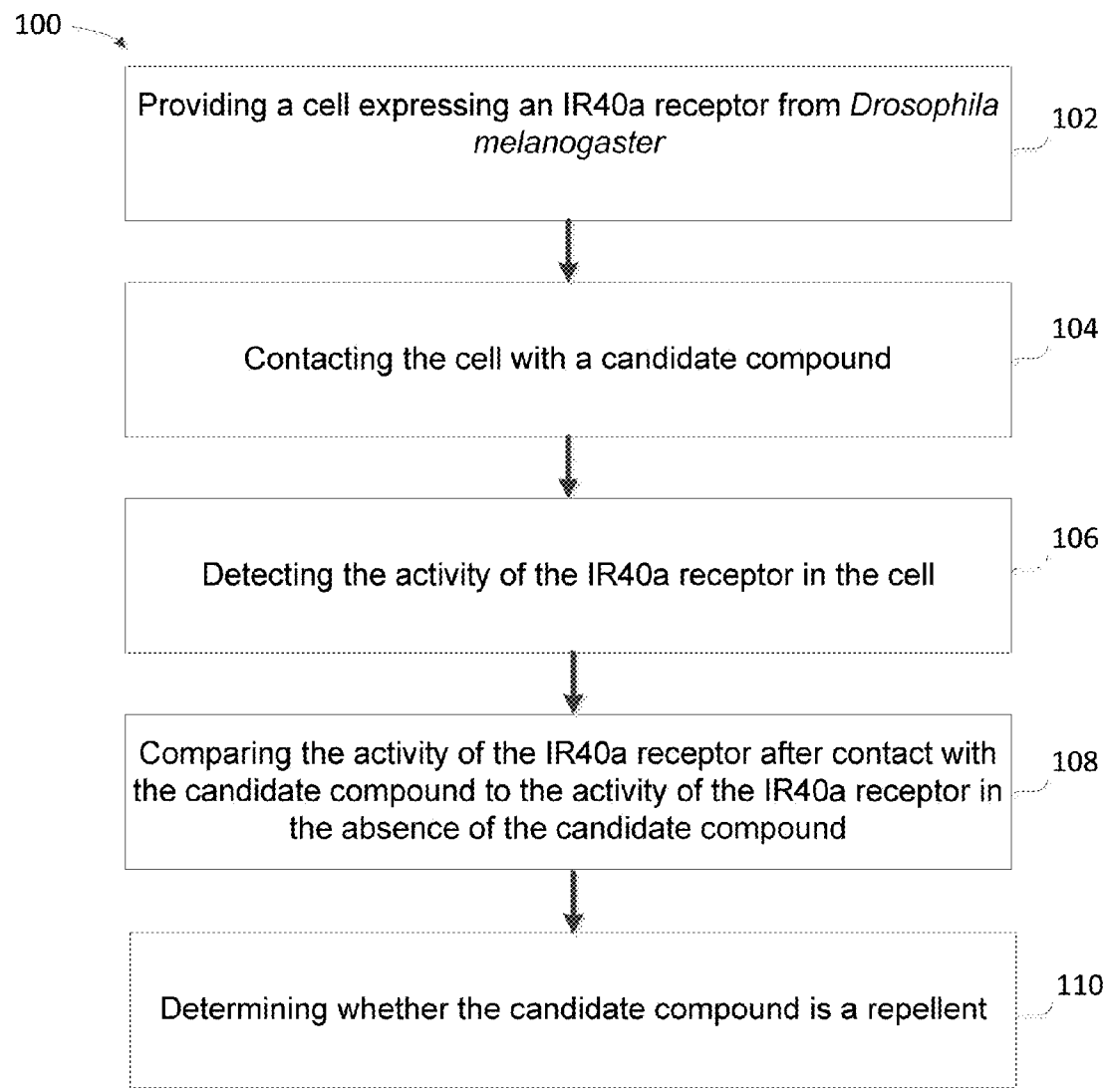
FIG. 1 depicts an exemplary method for identifying an arthropod repellent by assessing whether a candidate compound has the ability to modulate the activity of the Ir40a receptor from *Drosophila melanogaster*.

With reference to FIG. 1, method 100 is an exemplary method for determining whether a candidate compound is an arthropod repellent based on its ability to modulate the activity of an Ir40a receptor. In step 102, a cell expressing an Ir40a receptor from *Drosophila melanogaster* is provided. One of skill in the art would recognize that the Ir40a receptor from *Drosophila melanogaster* has FlyBase ID: FBgn0259683 (Ionotropic Receptor 40A, Annotation symbol CG42352). One of skill in the art would further recognize that this Ir40a receptor has NCBI Gene ID: 35449. The sequence associated with the *Drosophila melanogaster* Ir40a accession numbers is incorporated herein by reference.

The cell provided in method 100 may be, for example, a neuron or an oocyte. In a particular embodiment, the Ir40a receptor is expressed in an Ir40a+ neuron. While method 100 uses a cell that expresses the Ir40a receptor from *Drosophila melanogaster*, it should be understood that in other exemplary embodiments, the Ir40a receptor may be provided in other forms. For example, the method may use an organism that expresses an Ir40a receptor. The organism may be an arthropod, such as an insect. An example of a suitable organism is *Drosophila melanogaster*. The method may also use a sample containing a full-length or partial Ir40a receptor protein from *Drosophila melanogaster* or an ortholog thereof may be provided, or a sample containing an organism expressing an Ir40a receptor, a cell expressing an Ir40a receptor, or an isolated Ir40a receptor.

The Ir40a receptor provided in a cell, an organism, or a sample may be an endogenous receptor or a recombinant receptor. For example, a *Drosophila melanogaster* cell may express an endogenous Ir40a receptor, or an Ir40a receptor encoded by *Aedes aegypti*. In some embodiments, recombinant may refer to a polynucleotide or a polypeptide wherein the exact nucleotide sequence of the polynucleotide or amino acid sequence of the polypeptide is foreign to (not naturally found in) a given host. In other embodiments, recombinant may refer to a polynucleotide sequence naturally found in a given host, but in an unnatural context, such as if the polynucleotide includes two or more subsequences that are not found in the same relationship to each other in nature. For example, regarding the latter, a recombinant polynucleotide could have two or more sequences from unrelated polynucleotides or from homologous nucleotides arranged to make a new polynucleotide. With reference to a host genome, the polynucleotide sequence that encodes the Ir40a polypeptide is recombinant.

The Ir40a receptor provided in a cell, an organism, or a sample may also be modified. Modified Ir40a receptors may include sequence information that is endogenous to or recombinant to the organism. For example, *Drosophila melanogaster* may express an endogenous or recombinant Ir40a receptor with a GFP reporter sequence attached to the receptor polypeptide.

With reference again to FIG. 1, in step 104, the Ir40a receptor is contacted with a candidate compound. While method 100 is testing one candidate compound, the methods described herein may be used to screen a plurality of compounds. The one or more candidate compounds may be natural or synthetic compounds. For example, the one or more candidate compounds may be from bacterial, fungal, plant and animal extracts that are commercially available or readily produced. The one or more candidate compounds can also be chemically-modified compounds, such as by acylation, alkylation, esterification, or acidification of natural compounds. The one or more candidates compounds screened in the methods described herein may be pre-selected based on one or more criteria. For example, a set of compounds with structural similarities to known insect repellents, like DEET, may be screened and selected for use in the methods described herein. A computation method may be used to select such candidate compounds. Other criteria used for selecting the one or more candidate compounds include the environmental impact of the compounds, regulatory approval of the compounds for human consumption (e.g., FDA-approval), and the smell of the compounds (e.g., natural fragrances, aromas, or odors).

With reference again to FIG. 1, in step 106, the activity of the Ir40a receptor is measured. Suitable methods and techniques for measuring the activity of the Ir40a receptor may include, for example, measuring the intracellular calcium flow, measuring electrophysiological parameters, measuring electrical potential changes, and measuring changes in transcription of activity-dependent gene promoters. Specific examples of ways to measure activity of the Ir40a receptor include quantifying the intensity of a fluorescent dye using various software programs known in the art, such as Meta-Morph or Image J (National Council for Biotechnology Information), or quantifying gene expression using qRT-PCR analysis software, such as the BioRad iQ5 software package (BioRad). One of skill in the art would recognize that Ir40a receptor activity may include any biological function or consequence associated with the binding or interaction of a ligand or compound to or with the IR40 receptor.

With reference again to FIG. 1, in step 108, the activity of the Ir40a receptor after contacting the cell expressing the Ir40a receptor with the candidate compound is compared to the activity of the Ir40a receptor in the cell in the absence of the candidate compound. This allows one of skill to determine whether the candidate compound has an effect on modulating the activity of the Ir40a receptor. Receptor activity can be compared by, for example, comparing the quantitative measurements obtained from step 106 both before and after contacting the Ir40a receptor with the candidate compound.

Based on the data gathered in step 108 regarding the change in activity of the IR40 receptor, the ability of the candidate compound to act as a repellent is determined in step 110. A candidate compound may be selected as a repellent if modulation in activity of the Ir40a receptor the presence of the compound is statistically significant compared to the absence of the compound, compared to a control, or a combination thereof. Various statistical tests are known in the art for determining whether a quantitative value is significantly different from another quantitative value, such as the Student's t-test. In one embodiment, an increase in Ir40a receptor activity may indicate that the candidate compound is a repellent. In another embodiment, a decrease in the activity of the Ir40a receptor may indicate that the candidate compound is a repellent.

The components and techniques described in exemplary method 100 of FIG. 1 may be varied. For example, the Ir40a receptor may be a homolog, an ortholog, or a modified receptor. Additionally, the screening method may be performed in an in vitro or an in vivo assay. Variations of exemplary method 100 are described in further detail below.

The exemplary method outlined in FIG. 1 may also include the use of an Ir93a receptor, an Ir25a receptor, and/or an Ir40a receptor, either alone or in any combination. For example, the method may include providing a cell expressing both an Ir40a receptor and an Ir93a receptor, cell expressing both an Ir40a receptor and an Ir93a receptor, cell expressing both an Ir93a receptor and an Ir25a receptor, or cell expressing an Ir40a receptor, an Ir93a receptor, and an Ir25a receptor from *Drosophila melanogaster*, contacting the cell expressing the receptors with a candidate compound, detecting the activity of the receptors, comparing the activity of the receptors after contact with the candidate compound to the activity of the receptors in the absence of the candidate compound, and determining whether the candidate compound is a repellent. One of skill in the art would recognize variations of this exemplary method involving the use of an Ir93a receptor and/or an Ir25a receptor, either alone or in any combination with an Ir40a receptor Variations of the Ir40a Receptor Homologs and Orthologs A homolog or an ortholog or any known or putative Ir40a receptors may also be used in the methods and systems described herein. A homolog may be a protein whose nucleic acid sequence that encodes that protein has a similar sequence to the nucleic acid sequence that encodes a known or putative Ir40a receptor, or a protein whose amino acid sequence is similar to the amino acid sequence of a known or putative Ir40a receptor. Ir40a homologs may have functional, structural or genomic similarities to any known or putative Ir40a receptor. One of skill in the art would recognize the techniques that may be employed to clone homologs of a gene, using genetic probes and PCR. Homologs can also be identified by reference to various databases and identity of cloned sequences as homolog can be confirmed using functional assays and/or by genomic mapping of the genes. Additionally, one of skill in the art would understand that an ortholog is an evolutionarily-related polypeptide or polynucleotide sequence in different species that have similar sequences and functions, and that develop through a speciation event.

In some embodiments, a homolog and/or ortholog of an Ir40a receptor is a protein whose nucleic acid sequences have at least 30%, 40%, 50% 60%, 65%, 70%, 75%, 80%, 85%, 90%, 91%, 92%, 93%, 94%, 95%, 96%, 97%, 98%, or 99% identity to the nucleic acid sequence encoding any known or putative Ir40a receptor. In another embodiment, a homolog of an Ir40a receptor is a protein whose amino acid sequence has at least 30%, 40%, 50%, 60%, 65%, 70%, 75%, 80%, 85%, 90%, 91%, 92%, 93%, 94%, 95%, 96%, 97%, 98%, or 99% identity to the amino acid sequence encoding any known or putative Ir40a receptor.

The Ir40a receptor may be from one or more arthropod species. For example, in certain embodiments, the Ir40a receptor is a homolog or ortholog of the Ir40a receptor from *Drosophila melanogaster*. In some embodiments, the Ir40a receptor has at least 50, 60%, 65%, 70%, 75%, 80%, 85%, 90%, 91%, 92%, 93%, 94%, 95%, 96%, 97%, 98%, or 99% sequence identity to a polypeptide encoding an Ir40a receptor from *Drosophila melanogaster*.

While *Drosophila melanogaster* is one reference point for homology, it should be understood that other known or putative receptors may serve as reference points for homology to the Ir40a receptor. For example, known or putative Ir40a receptors may include [GI:281365361, Accession NP_610140, ionotropic receptor 40a, *Drosophila melanogaster*], [GI:193904091, Accession EDW02958, ligand-gated ion channel, *Drosophila grimshawi*], [GI:333469626, Accession EAA13593, ligand-gated ion channel, *Anopheles gambiae*], [GI:167870272, Accession EDS33655, ionotropic glutamate receptor-invertebrate, *Culex quinquefasciatus*], [GI:40909715, Accession CK525472, predicted protein BGIBMGA010939-TA, *Bombyx mori*], [GI:270013267, Accession EFA09715, hypothetical protein TcasGA2_TC011848, *Tribolium castaneum*], [GI:328712650, Accession XP_001949860, predicted glutamate/NMDA receptor subunit 1-like, *Acyrthosiphon pisum*], [GI:212510105, Accession EEB13339, glutamate receptor U1 precursor, putative, *Pediculus humanus*], and [GI:321470562, Accession EFX81538, hypothetical protein DAPPUDRAFT_102366, *Daphnia pulex*]. Each sequence associated with the foregoing accession numbers is incorporated herein by reference.

In other embodiments, the Ir40a receptor has at least 50%, 60%, 65%, 70%, 75%, 80%, 85%, 90%, 91%, 92%, 93%, 94%, 95%, 96%, 97%, 98%, or 99% sequence identity to a polypeptide encoding an Ir40a receptor from an ortholog of *Drosophila melanogaster*. Such orthologs may include, for example, *Aedes aegypti* Aaeg (AAEL014270), *Anopheles gambiae* Agam (AGAP004021), *Culex quinquefasciatus* Cqui (CPIJ009722), *Acyrthosiphon pisum* (Pea aphid) Apim (ACYPI20767), *Bombyx mori* (Silkmoth) Bmor (BGIB-MGA010939), *Pediculus humanus* (Human body louse) Phum (PHUM235670).

The amino acid sequences of the Ir40a receptor from *Drosophila melanogaster* and some orthologs thereof are provided in Table 1 below.

TABLE 1

Amino acid sequences of the Ir40a receptor from *Drosophila melanogaster* and orthologs thereof

| Arthropod Species | Amino Acid Sequence |
| --- | --- |
| DmelIr40a (*Drosophila melanogaster*) | MHKFLALGLLPYLLGLLNSTRLTFIGN DESDTAIALTQIVRGLQQSSLAILALP SLALSDGVCQKERNVYLDDFLQRLHRS NYKSVVFSQTELFFQHIEENLQGANEC ISLILDEPNQLLNSLHDRHLGHRLSLF IFYWGARWPPSSRVIRFREPLRVVVVT RPRKKAFRIYYNQARPCSDSQLQLVNW YDGDNLGLQRIPLLPTALSVYANFKGR TFRVPVFHSPPWFWVTYCNNSFEEDEE FNSLDSIEKRKVRVTGGRDHRLLMLLS KHMNFRFKYIEAPGRTQGSMRSEDGKD SNDSFTGGIGLLQSGQQADFFLGDVGL SWERRKAIEFSFFTLADSGAFATHAPR RLNEALAIMRPFKQDIWPHLILTIIFS GPIFYGIIALPYIWRRRWANSDVEHLG ELYIHMTYLKEITPRLLKLKPRTVLSA HQMPHQLFQKCIWFTLRLFLKQSCNEL HNGYRAKFLTIVYWIAATYVLADVYSA QLTSQFARPAREPPINTLQRLQAAMIH DGYRLYVEKESSSLEMLENGTELFRQL YALMRQQVINDPQGFFIDSVEAGIKLI AEGGEDKAVLGGRETLFFNVQQYGSNN FQLSQKLYTRYSAVAVQIGCPFLGSLN NVLMQLFESGILDKMTAAEYAKQYQEV EATRIYKGSVQAKNSEAYSRTESYDST VISPLNLRMLQGAFIALGVGSLAAAAL NNTINVRSLNSRDKFICGGPVKIWYYL VLLLWYYFNRGLVGIYQLWHKTSIRNT GKGMPFLGE (SEQ ID NO: 1) |
| AaegIr40a (*Aedes aegypti*) | MNKVLATPASKADKLESLISIGLVVQN LCSQLQSMRMEAHLSNPSLLQELVDKL PANIKLHWALHQRQVPVVDFRAFTYHA HLAPLPDLSNHSGMVLGLSEMINLLAP KTLAILVLKETKIDKIDRLTVMIHHHN IPTCIFNNQDEYFQYIGNNLKKSLETT SLLFCHPEEMLGELIDRRLAHRLSLYI FYWGARKAPTNLDRSLMREPLRVAVIT NPRKNIFRIFYNQAKPNNRGELLSANW FDGNDMTFQKVPLLPTPTTVYKNFEGR VFTIPVIHKPPWHFVTYRKVNESSLNE TDVDQLELSANGTDNEQLEVFEVTGGR |

TABLE 1-continued

Amino acid sequences of the Ir40a receptor from *Drosophila melanogaster* and orthologs thereof

| Arthropod Species | Amino Acid Sequence |
|---|---|
| | DHNLIQLIAHRMNFSFKYVDQEDRIQG TAVGPPENAIFTGALGMLQRREVDLFL GDVAVTWERMQAVEFSFFTLADSAAFV THAPRKLSEALALVRPFQVAVWPLVLL TIMMSGPILYMIIAMPYRLEDWARGTM ARRRRFKVQRGPAFYHMQYIQEMNYGT LPGGTEIAGTPRHPSLDRCIWYTINVY LRQSATIPYNGHVSRFFSILLWLCATY VLGDVYSAQLTSQLARPAREGPIDTLG KLEVFMERDGYQLLVERQSAFQAALVN STGILQRLYRITQRQSHNESYLVSSVE EGIRILVDNSKRAVFGGRETLYFNTKR YGAHRFQLSEKLYTRYSAVAVQFGSPF LDSLNEVIMRLFEAGIIEKITIAEYER MFGSQLGQFGDESAKTTKPESSETEGG KSKKSTESNEKLQPMNLRMLQGAFLAL ACGHLLGVLTLVLENKTKCIQISFGWI KAWLHRIGLIFCKLGKAVWRSWRRLHN DD (SEQ ID NO: 2) |
| AgamIr40a (*Anopheles gambiae*) | MGVGSNSKYILALVLLRVALVWGAFPT QRNLIALYERSNQSGMIRGISEMVNLL APKSLVILVQNETKIDRLDKLTVMIHH HNIPTCVYYDLEAYFSLIEENLKKSLE ITSLIFCHPEDMLQDITDRRLAHRLSL FIFYWGAAQLPPTLNPNLLMEPFRVAI ITNPRRNIFRIFYNQAKPNNRGDMLSV NWFDGNDMTFKRVPLLPSPTEVYKNFE GRIFTIPVIHKPPWHFIVYGNGSASVG DNQNSSSSDAAGGFELELDENVTVESD DTYFTVKGGRDHNLMQLIAERMNFTFQ YVEPPEKIQGIALGSEDNASFSGALGM LQRREVELYLGDVAVTWERMKAVEFSF FTLADSAAFVTHAPRKLNEALALVRPF QITVWPPVIITILISGPILYIIISTPY RWRSAQTVHARNARWRPTRSRLRKPAF YNLRYIEEMSYTRFRAERTSLINNHHH SRGQDYPSLDRCIWYTINVYLRQSANI PFDGHLARFFSILLWLCATYVLGDVYS AQLTSQLARPARESPINTLGRLENRMN REGYQLLVERQSAFHAALVNSTGVLQR LYRLTRQRSVNDSFLVKSVEEGIRVLQ ADPKYAVFGGRETLYFNTKRYGANRFQ LSEKLYTRYSAVAVQIGCPFLDSLNEV IIVIRLFEAGIVEKITIAEYEQMFGRQ KGGVSHAEETVRTVKSTNSECDTDGTG SGKRKTDSNDKLQPMNLRMLQGAFLVL ACGHLLGGICLFIERHMGMINPCGDTL RQGWRHLNRVVRKLGRGGSFKTQSN (SEQ ID NO: 3) |
| CquiIr40a (*Culex quinquefasciatus*) | MKVGIVWCLFVLLGRSFVQAYHSQLVP IADPSNHSGMVTGLSEMINLLSPKTLV LLVLNETKIHKIDRLTVAIHSYNIPTC IFYDLEQYFEYIANNLKNSLDTTSLLL CHPADMLVDLVDRRLAHRLSLYIFYWG ARRLPAGFDRALLREPLRVAVITNPKK KIFRIFYNQAKPNNLGELLSANWFDGS DMTFKRVPLLPTPTEVYKNFEGRVFTI PVIHKPPWHFLTYTNLNESCNDTDTEF DMANVTSFQVTGGRDHNLMQLIAARMN FTPRYIEPEEKIQGTAMGSGDNVSISG ALGMLQRREVDLFLGDVAVTWERMQAV EFSFFTLADSAAFVTHAPRKLSEALAL VRPFQVTVWPLVIFTIILSGPVLYLII AMPFRLEDWMKGTLDKARRLQVRRGPP FYDMQYIREMGYGLVPRADIAGTPQHP SLNRCVWYTINVYLRQSATIPYNGHVA RFFSILLWLCATYVLGDVYSAQLTSQL ARPAREGPINTLGKLEELMESPGGGYQ LLVERQSAFQVALANSTGILQRLYRIT QRHPDNESYLVGSVEEGIQILLVNSKR AVFGGRETLYFNTKRYGAHRFQLSDNL YTRYSAVAVQFGSPFLDSLNEVIMRLF EAGIIGKITVAEYERMFGSKSGGQFAD |

TABLE 1-continued

Amino acid sequences of the Ir40a receptor from *Drosophila melanogaster* and orthologs thereof

| Arthropod Species | Amino Acid Sequence |
|---|---|
| | ETVESTKSDDGVDATGKAKKSAESSEK LQPMNLRMLQGAFLALGFGHSVGAIIL LVENQLKGIKSVYQRVLGVLTRTGRVV RKIWTAIRRSL (SEQ ID NO: 4) |
| ApisIr40a (*Acyrthosiphon pisum*) | IYIFFLIRSTIYYVSFSGRDIFKNTVA SAICNEYSIVVLTNXNANIIMLILINI IFISLYLSSSIILIDYNTYLIIQNLLV NVTIYINIYRLLGLHRDGDFLFFTQIR RSNLMSRNVVYVFLWLRSSVSRTFKAD ILEAMRVCVITSPRPGFYQIYYSQASA RPGYGSSLKMVNWWSAMDGLVRFPLLP PPKQVYKNFEGRYFNVPVLHKPPWTFV EYLNDSFRVEGGRDDKLINLLADKLHF QFKYIDPPDRTQGSGLDRGSSMQGVLG LIWQREADWFVGDLSITYERNLVVDFS FLTLVDNEAFLTHAPGRLNEAFSLIRP FHWSVWPLLLITVIFAGPILYILVDTT DGHPQGKSMLYWKCVWWSVTVFLQQAA IIPSENNKIRFVAGLLMLSVTYVIGDM YSASLTSILARPPKEPPINTLKELSEA MRDSGLQLLVEVQSASQAMLENGTGVY EELSQLVTRQREYLIGSTEKGMQLVRD NKNYAVIGGRETFYYDIKRFGAQHFHL SEKELNTRYSAIAFQRACPYRDNFDDVL MRLFEGGILSKITEEEYQKLNDKLMGS EEFDSTSVVIEPVLEGSEPRQEDDDKQ LTIAMSMKTLQGAFYVLAIGSILAGLL LLIEMRSHDKLEKDKVIKLVEAPFVYK RKVPNKFQNRLYDLK (SEQ ID NO: 5) |
| BmorIr40a (*Bombyx mori*) | MTKLPKDFNVAIKDIAESLPSKEMTVV RGNSTNIRSQDVFELLRLLCQHNIQVV NLDIAAMENKEMYYGYLKKALDVSDER TNLILCEPYECENLLLELRENNLIHRT ILYIFFWPYGSVSDRFLNTMVEAMRVA VITNPRESVFRIYYNQATPNRLNHLSL VNWWAFRLYKSPLLPSADKVYKNFRGR VFDVPVLHAPPWHFVKYNNDSSINVTG GRDDKLLKLIANKLNFRYRYYDPPDRS QGSGIIGNGTFKGTLGLIWKRQADFFL GDVTMTWERLQAVEFSFLTLADSGAFL THAPAKLSETLAIIRPFRWEVWPLVCA TLFITGPALWIVIAAPSLWQRKKRDQM GLLNNCCWFTVTLFLRQSSTKEPSSTH KARLVTVLISLGATYVIGDMYSANLTS LLARPAKEPPIGTLPALEEAMREHGYE LVVESHSSSLSILENGTGVYGRLAKLM KRQRVQRVHNVEAGVRLVLNRRRVAVL GGRETLYYDTERFGSHNFHLSEKLYTR YSAIAFQIGSPYLETINNVVMTLFEAG ILGKMTTDEYKNLPEQSRRSEPVTESE NLSTEKTGETAAVTQIQNETSKGLEPV SLTMLRGAFCLLGIGHLLAGVTLLIEI QLYRRARKRALPPQTRNPTNTFKAKAK KCILRGWRRIKAAAILAIDRALAPDRG ID (SEQ ID NO: 6) |
| TcasIr40a (*Tribolium castenium*) | MRRDHGGDLVSASFDIVAGFLFEEICI CFDKNTNINFLQHLLVRFVSNNIAIKL FNITTVEVQDKYFAFLNYQVTNHLGAN TIFFSSHKFYEHVLLEINERDFIRRNL IYIFNWGRRPPFSRYFVRNIINVMKVPV ITNPRNDTFRIFYNQAVPYKKHHLEMV NWWQHGVGLFNHPTLPAKYNNVFKDPK ENVFKIPVIHKPPWHFVQYGNDSIKVT GGRDDRILSLLSKKLNFRYDFPPPER IQGSSASENGTFKGVLGLIWKRQAEFF IGDVALSHERANYVEFSFITLADSGAF ITHAPSKLNEALALLRPFQWQVWPAIG VTFVVVGPVLYAIIALPNAWRPRFRVR SHARLFFDCTWFTTTVLLKQTGKEPSS SHKARFFIIILSISSTYVINDMYSANL TSLLAKPGREKAINNLNQLEKAMATRG |

TABLE 1-continued

Amino acid sequences of the Ir40a receptor from *Drosophila melanogaster* and orthologs thereof

| Arthropod Species | Amino Acid Sequence |
|---|---|
| | YDLYVERHSSSYSLFENGTGIYSRLWQ MMNRRQTHFLLESVEEGVQLVRDSTNK AVIAGRETLFFDIQRFGASNFHLSEKL NTAYSAIALQLGCPYIEEINKILMAIF EAGIITKMTENEYEQLGKKKQTTSETE KELIPGVKKENRRVAKVSEDNEKLQPI SIKMLQGTFYLLCIGNIFSGFILLAEI LVYKHRKTYKHKKRRHRFVYLRKIRHS VASKFGAVVDAVRRVYRRAMHDAFVAT LEYLE (SEQ ID NO: 7) |
| PhumIr40a (*Pediculus humanus*) | TPTFCFSYMKIFFFLFNFGGIIIRGHH LTENDFDDDEDMMMSLSLAVKDIIIGL PSSHVTLLFENITDSTFPMILSKTLQK SLITTSIYTIEKGENQKEVEQEDLMHR KILYILYRDHNLRDNDFFSGQFEAMRI SLLTKTQNGMFVRYKFFLKIFFFFFFL ENLIYNRSTRFFSDDKLLTIIAQKLNF RYKYVDPPERLQGTGIFTNGTFSGVLG QVWQREFDFFMGDVTITYDRAKTVEFT FFTLVDSEAFVTHRPSKLNEAFALIRP FQWQVWPPILCTFTIYGPILFFIIESQ NYLMKIKRDSKERKKLFFHCVWFSIST FLKQGGIYPSKSHKVRLLLIIVTLAAT YVIGDMYSANLTSLLARPGREKPITVL EQLDTAMETRGYQLLVEKHSSSLTTLQ NGTGIYEKIWEKMKNQKNYLIESVESG MKMVRKNKNIVILGGRETLYFDSRRFG SYNFQMSEKLNTRYAGIAMQLGCPYIE NFNKILMQLFEGGILTKMTVEEYERLG EEQRAEFENVKKKKNVSQIKNEDIQVS TTHALQPLNTKMLQGAFYILFIGYLLS GFTLFLEIQFENICRFLKLIKCHPFIK SIKFNKFFNKIYRKKF (SEQ ID NO: 8) |
| PpapIr40a (*Phlebotomus papatasi*) | MCYLSENSDQENELMIGLVEIVKSLDI KNLVIFLPTENSTYDIDKFIMRVHERQ LQSVIFFNPDDYYNHIAQCKSDSVETT SLIFSEPREIVREIQERILDHRLNLFM FYWGSHGLPKRGQLCLKEPMKVVILTT PRQNIYYNQATPDGNGTLTLVNWYDGN SLGLFKVPVLPSPSQVYQNFRERVFYI PVIHSPPWHFVIYRNESSDNETFPMEE YDDMDISFKVIGGRDDSLLQLLAKKMN FKYEYIDPPERTQGSAFGSNDNLSFSG GLGLLQRREANLLLGDIAITSERSKAV EFSFFTLVDSGAFVTHAPRRLSEALAL VRPFRLNVWPALIITSLSGPVLYLVII MPQWWRKSSQKEKENRDSFHHIDYIEE MNYGVPRRRIQAMKFTKRKELPQNLLG RQFLVDRCVWFTINLFLKQSACLPYGG NRARFVSSILWLSATYILGDFYSAQLT SQLARPAREAPINDLYRLEAAMKWKGY ELYVERQSASLAILENGTEIFHRLHLM MMAQNRKSNESYLISSIEEGVHMVMMG DRKVVLGGRETLFFNIKRYGMKKFQLS EKLYTRYSAVAVPNGCPFLDSLNKVYV TPFFHKIMHLFEGGILDRMTNEEYEKM FNSIKFKTPKEEVDKTTKKSNKEVPQE EHLLKPVSLKLLQGAFYTLLIGYILSG IVLLLESGKSPEGIAQRQLPGAISVCI YMKIIIAKCFSFIAEEIYDCFKDDEDD E (SEQ ID NO: 9) |

One of skill in the art would recognize the methods and techniques that may be employed to determine the percent identity between two amino acid sequences, or between two nucleic acid sequences. One of skill in the art would also recognize that the sequences can be aligned for optimal comparison purposes. For example, gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions can then be compared. Methods of comparing nucleic acid or amino acid sequences are well-known in the art.

Variations of the Ir93a Receptor

Homologs and Orthologs

A homolog or an ortholog or any known or putative Ir93a receptor may also be used in the methods and systems described herein. A homolog may be a protein whose nucleic acid sequence that encodes that protein has a similar sequence to the nucleic acid sequence that encodes a known or putative Ir93a receptor, or a protein whose amino acid sequence is similar to the amino acid sequence of a known or putative Ir93a receptor. Ir93a homologs may have functional, structural or genomic similarities to any known or putative Ir93a receptor.

In some embodiments, a homolog and/or ortholog of an Ir93a receptor is a protein whose nucleic acid sequences have at least 30%, 40%, 50%, 60%, 65%, 70%, 75%, 80%, 85%, 90%, 91%, 92%, 93%, 94%, 95%, 96%, 97%, 98%, or 99% identity to the nucleic acid sequence encoding any known or putative Ir93a receptor. In another embodiment, a homolog of an Ir93a receptor is a protein whose amino acid sequence has at least 30%, 40%, 50%, 60%, 65%, 70%, 75%, 80%, 85%, 90%, 91%, 92%, 93%, 94%, 95%, 96%, 97%, 98%, or 99% identity to the amino acid sequence encoding any known or putative Ir93a receptor.

The Ir93a receptor may be from one or more arthropod species. For example, in certain embodiments, the Ir93a receptor is a homolog or ortholog of the Ir93a receptor from *Drosophila melanogaster*. In some embodiments, the Ir93a receptor has at least 50%, 60%, 65%, 70%, 75%, 80%, 85%, 90%, 91%, 92%, 93%, 94%, 95%, 96%, 97%, 98%, or 99% sequence identity to a polypeptide encoding an Ir93a receptor from *Drosophila melanogaster*.

While *Drosophila melanogaster* is one reference point for homology, it should be understood that other known or putative receptors may serve as reference points for homology to the Ir93a receptor. For example, known or putative Ir93a receptors may include *Mayetiola destructor*\Mdes015305, *Aedes aegypti* Aaeg\AAEL005012, *Anopheles gambiae* Agam\AGAP000256, *Culex quinquefasciatus* Cqui\ CPIJ009222, *Heliconius melpomene*\HMEL002270, *Manduca sexta*\Msex000431, *Bombyx mori* (Silkmoth) Bmor\BGIBMGA010960, *Tribolium castaneum*\TC000374, *Atta cephalotes*\ACEP27701, *Acromyrmex echinatior*\AECH20041, *Solenopsis invicta*\SINV12854, *Pogonomyrmex barbatus*\PB25907, *Camponotus floridanus*\CFLO19836, *Linepithema humile*\LH25937, *Harpegnathos saltator*\HSAL21373, *Apis mellifera*\GB42136, *Apis mellifera*\GB50521, *Megachili rotundata*\MROT 00005973, *Nassonia vitripennis*\Nasvi2EG001464, *Acyrthosiphon pisum* (Pea aphid) Apim\ACYPI20767,ACYPI43510, *Rhodnius prolixus*\RPTMP07829, *Pediculus humanus* (Human body louse) Phum\PHUM513120, *Tetranychus urticae*\tetur02g05540, and *Ixodes scapularis*\ISCW007957. Each sequence associated with the foregoing accession numbers is incorporated herein by reference.

Further, the amino acid sequences of the IR93a receptor from *Drosophila melanogaster* and some orthologs thereof are provided in Table 2 below.

TABLE 2

Amino acid sequences of the IR93a receptor from
*Drosophila melanogaster* and orthologs thereof

| Arthropod Species | Amino Acid Sequence |
|---|---|
| DmelIR93a (*Drosophila melanogaster*) | MNPGEMRPSACLLLLAGLQLSILVPTEANDFSSFLSANASLA VVVDHEYMTVHGENILAHFEKILSDVIRENLRNGGINV KYFSWNAVRLKKDFLAAITVTDCENTWNFYKNTQETSILLIA ITDSDCPRLPLNRALMVPIVENVEENALLVKSIVHESI TNHITPISLILYEINDSLRGQQKRVALRQALSQFAPKKHEEMR QQFLVISAFHEDIIEIAETLNMFHVGNQWMIFVLDMV ARDFDAGTVTINLDEGANIAFALNETDPNCQDSLNCTISEISL ALVNAISKITVEEESIYGEISDEEWEAIRFTKQEKQA EILEYMKEFLKTNAKCSSCARWRVETAITWGKSQENRKFRST PQRDAKNRNFEFINIGYWTPVLGFVCQELAFPHIEHHF RNITMDILTVHNPPWQILTKNSNGVIVEHKGIVMEIVKELSRA LNFSYYLHEASAWKEEDSLSTSAGGNESDELVGSMTF RIPYRVVEMVQGNQFFIAAVAATVEDPDQKPFNYTQPISVQK YSFITRKPDEVSRIYLFTAPFTVETWFCLMGIILLTAP TLYAINRLAPLKEMRIVGLSTVKSCFWYIFGALLQQGGMYLP TADSGRLVVGFWWIVVIVLVTTYCGNLVAFLTFPKFQP GVDYLNQLEDHKDIVQYGLRNGTFFERYVQSTTREDFKHYL ERAKIYGSAQEEDIEAVKRGERINIDWRINLQLIVQRHF EREKECHFALGRESFVDEQIAMIVPAQSAYLHLVNRHIKSMF RMGFIERWHQMNLPSAGKCNGKSAQRQVTNHKVNMDDM QGCFLVLLLGFTLALLIVCGEFWYRRFRASRKRRQFTN (SEQ ID NO: 10) |
| AaegIR93a (*Aedes aegypti*) | MLPRLKWLVLVLVVCKLDHSRGDDFPSLISANASIAVILDRE YLDAQYDDILEGTKRLFERILRDNFRNGGLIVKYFSWT SINLRRDFTAVLSISNCENTWDVYKNAAKENLVIMSITDSDCL RLPLNNAIMVNLKSIVALSKESEDVRPLSLSLFRIES HTHMWEKRKAIRKVLVNLPTRYIGRNFIAIITTQTMELVMEIA KELRMVTPLAQWLYVVSDTSADRNNISAVHPIISEGD NIAFVYNLRRNAQSCESHMLCYVENLITSLVHGLSKLIREEK AVYGQIADEEWEVIRMTKAERKDEILKIMRSDLIGKDS CNECSMWKVEAGETWGYTYQSAADELLTGVMSTHRKQISL LDVGYWTPQDGFVMRDNMFPHVADGFRGVHLNFYSYHNPP WQFVTYNESGHLSLSRGVVMDILTELSRKLNFTFNILISQTNL EYIGNMTDDANNTINRDAHSITTDIPNEILRSLMDNK ILLAAVGATVSPKQKKYVNFTTPISIQTYSFIVSRPKELSRVFL FLSPFTIDTWLCLSATVLLMGPFLYVVNRLSPFYEH HGRSNTIGLGKLYNCFWYIYGALLQQGGLYLPYADSGRIIIGT WWLVVLVIVTTYCGNLVAFLTFPKIAIPITTVNQLIR NEQGVSWSIRRGTFLEQFLQETDDPKYIKLHNHAGYVSEESE QMVERIRTGRHVHIDWRTNLKYLMKKEFLKNDRCDFAL SVDEFLDEQIALAMPKNSPYLELINAELTKMHQFGFIQRWLG SYMPSEDKCSNARKSTEVENHTVNNDDMAGSYYVLMIG FSMGLFMFVLEYGWRWYKRSKEETLQPFTE (SEQ ID NO: 11) |
| AgamIR93a (*Anopheles gambiae*) | MVLRLVGLWSILLLLLLLVLRPDPAVGDDFPSLLSTNASMG KLNITPLLSIILDREYLGADYERTLDETKNVVEKLIRE HLKNGGLIVKYYSWTSINLKRDFSAVLSVSSCKNTWDIYQEA VRERLVMLSITDPDCPRLPTNNAIMIPRSDGSGSNAFD EVSQIILDMKSSRAINWHTATLLYDQVYDAEISRCILSLLEDR EGIKPLTLTEFKINAPTHSWEKRKEIRRTLLGIPTAY TGRNFIAIVNIATLTLLMEISKDLKLVNPFAQWLYLIPNTEKA NSNFTTRSTLINEGDNVAFVYNSGSKAQNCTVSVLCY IESYLLHFIRSLSKLIREEQVVFGQISDEEWEIIRPSKQERKTKF LQMIKAAITSKDECNKCSQWKIQSAETWGYVYRTD FLTDGADLQERRKYTMLDIGYWSPQDGFMLTDALFPHTQYG FRGVQLIFYSYHNPPWQFVAYNDSGSPVISSGVVYDILN ELSRKLNFTYTMVISQPAEINGSLVEGNTSSVYDLKTISSDIPQ EIFSTLVNNKILLAAVGATVNEKQKKFVSFTDPISI QTYSFVISRPRPYYEVHNKPTDTGLGKVNNCFWYIYGALLQQ GLYLPYADSGRIIIGTWWLVVLVIVTTYCGNLVAFLTF PKIDIPVNRVMQLLRNDRGMTWSIRRGTFLEEMLMVQVISSPI IYDSTEPKYMQLYKGSQIIGELTDELVERIEAGQHVH IDWRNNLRYLMKRQFLRTDRCDFALSTDEFLDEQIALVMPK DSPYLELVNEEIKRMHQFGFIQRWVAQYLPAKDKCSGTG RVMDVQNHTVNSSDMAGSYWILLLGFVSGLFVFVCEFAVA WYRKHRAARAATVAYRD(SEQ ID NO: 12) |
| CquiIR93a (*Culex quinquefasciatus*) | MAAVILDREYLDNQYEALLENTKRTFEQILRDNFKNGGLIVK YFSWTSINLRRDFTAVLSVSNCENTWDVYRNAAKENLV IMAITDTDCPRLPSHNAIMIPKSIPASGIFEELPQVIMDMKTMK AFSWKSAILLYDDSFDRDIVARSVLALSKESEDVLP LSLSLFRIESHTHMWEKRKAVRKVLLGLPTRYIGTNFIAIVTA TTMELVMDIAKELKMVNPLAQWLYVISDTTAEQNNIS SVHSIISEGDNIAFVYNMRKTAASCESQTLCYIENLVNALVKG |

TABLE 2-continued

Amino acid sequences of the IR93a receptor from
*Drosophila melanogaster* and orthologs thereof

| Arthropod Species | Amino Acid Sequence |
|---|---|
| | LSKLIREEKAVYGQIADEEWEVIRMTKVERKNDILQI<br>IKEERVGKDTCNECSMWKVQSGETWGYTYQLPADDVLSGT<br>AVGRRKQVEMLDVGYWTPQDGFVMADFLFPHISHGFRGIH<br>LNFYTYHNPPWQFVSFNESGHPTLSGGVVMDILEELSRKLNF<br>TYTVIVAQTNIEYVGNLTEDGNNTSIREIHTVTTDIPS<br>EIMKSLIDNKILLAAVGATVSEKQKKFINFTVPISIQTYSFIVSR<br>PKELSRVFLFLSPFTVDTWMCLGLTILMMAPLLYV<br>VNRVSPFYEHHGKSNKLGLGKLNNCFWYLYGALLQQGGLY<br>LPYADSGRIIIGTWWLVVLVIVTTYCGNLVAFLTFPKIAV<br>PITTISQLVRNNEGITWSIRKGTFLEQFLRETDDAKYLKLSHG<br>ATFISDESDSMVQSIRNGHHVHIDWRTNLKYLLKREF<br>LKNDRCDFALSLDEFLDEQIALALPKASPYLDVINAEITKMH<br>QFGFIHKWLSNYMPSEDKCSKARKNTDVENHTVNNDDM<br>AGSYYVLLIGFSSGMFLFLIEFGWRFYKKSKEQSLQPFTD<br>(SEQ ID NO: 13) |
| ApisIR93a<br>(*Acyrthosiphon pisum*) | MTGYNTDCPRLPTDEAITIPLTVHHSELSQMILDLRMSNAFS<br>WKSAVLMHDNSIGDSVLQHIVTSLTKYYPSNIMSPSIT<br>IFEIYTQGSEWKRRKLFMEDLQHFLKMSEINSNYICIVSILYVP<br>LILDVAKSLNLMTAENSWLIIIPDIDSSRNNTSSFT<br>NLLSEGENISFIYNSTKTGSKCIGGILCLVDELMSVFIMAFSALI<br>QQEIELSQRVSEEEWDEIRPSKIDRRQSMVSFIKF<br>RLNESGVCETCPLWQIDSGVTWGQEHFGQGCYILPVGNWNT<br>KTGLKLTEPLFLHLANGFRGIALPIATFNFPPWQIVNFN<br>RSGHLIGYSGLVFDIINQLAKTLNFTYNVIVISNTEQMNTTRT<br>LFMQNNVLGEHDAVVSKPLWDKMIDLVRSEKVFIAAA<br>AFAVKEANQILVNYTTHISLEPHQILVARPKELSRALLFTAPF<br>TLLTWLCIAIVVGLMGPLLNVFHVLSPYYEYHNIPRK<br>GGLNSPLNCFWYVYGALLQQGGAHLPDADSGRLVVGTWW<br>LFVLVIVTTYSGNLVAYLTFPQMDSMVSNVADLMARKPQGY<br>SWGIPKTSNLHSLLTVNDTMVKELIKNAEHHEELSRSIIERVR<br>SGKHAFIHRRTNLMYIMKNDFLKTNRCDFAIGNEDFA<br>EEKLAMMLSKESPYLSRINREIEKMHKVGLINKWLVDTLPKK<br>DQCWTNTQLEVTNHKVNLDDMQGSFIVLLLGVLSSLVS<br>FVFEYILHKYINRRQIVITPFIN (SEQ ID NO: 14) |
| BmorIR93a<br>(*Bombyx mori*) | MKIWVLGVLCLAISVQGEDFPSLITANASIAVILDRQYLGDKY<br>QTVLDELKDYIKELARVELKHGGVLVHYYSWTNISLN<br>KGFLAVFSIASCEDTWELFSRTEEEDLLLFALTEVDCPRLPQR<br>SAITVTYSEPGEELPQLLLDLRSSNAISWKSAVILHD<br>DTLGRDMVSRVVQSLTSQIDEESARPVSVTVFKMKHEMNEY<br>LRRKEMHRVLSKLPVKYIGENFIAIVTSDVMTTMAEIAR<br>ELLMSHTMAQWLYISDTNAHASNLSGFINTLNEGENVAFIY<br>NITENGPDCKNGLMCYSQEMMSAFISALDAAIQAEFDV<br>AAQVSDEEWEAIRPSKVQRRDILLKHMQQYILAKSVCGNCT<br>LWRALAADTWGVTYRQNDVPEQINEHANGSTGVIEHLEL<br>MNVGIWRPIDAMTFADLLFPHVHHGFRGKELPIITYHNPPWT<br>FLQANESGAIVKYSGLMFDIVNQLAKNKNFTPRELSRA<br>LLFLLPFTTDTWLCLGFAVILMGPMLYIVHRLSPYYEAMEITR<br>EGGLATIHNCLWYIYGALLQQGGMYLPRADSGRLVIG<br>TWWLVVLVIVTTYSGNLVAFLTFPKLEAPVTTISELLKNSDA<br>YTWSVTKGSYLEMELKNSEEPKYKRLIKEAELLKETGG<br>IEGTIHAARGTLDRVRGQRHLIFDWRLRLTYLMSADHIATET<br>CDFALAVEDFMEEQVAMIVPAGSPYLPVINKEINRMHK<br>AGLISKWLSAYLPKPNRCLKISTVTQEVSNHTVNLSDMQGSF<br>FVLFLGNDKIYVYMYIAELI (SEQ ID NO: 15) |
| TcasIR93a<br>(*Tribolium castenium*) | MLLELVLSSAFVCVIRAVIIDREFLSNEYEVIKHAIESYLVFAK<br>REILKHGGVNVQYYSWTTINIKKDVTAIFSIASCPD<br>TWRLFRQARDANLLHMAISESDCPRLPPDEAITVPLITRGEEL<br>PQLLLDLRTRQTYNWNSAFILYDDTLSRDQVTRVVKS<br>ITAQYSNLRVNAAAISFVKLETRLPMDEIRRQVKEILSSVSIKT<br>VGGNFLAIIGYELVELLMEYAKMFGLVNTRTQWLYI<br>ISNTHFPRHKDINRFRQLLSEGDNIAFLYNNTVNNDTCTGGIQC<br>HCEEILSGFTRALDEAILFEWETSSQVSDEEWEAIRP<br>SKLDRRNSLLQGIKTFLLQRGQCDNCTSWLMKTGDTWGREY<br>QQNGTDSGGLISVGNWRPSDGPSMSDELFPHIVHGFRKR<br>NLPIVTFHNPPWQIIRSNESGAVSEYAGVIFELIKELSKNLNFT<br>YTVELAKIGQEFSANLTKNEAQVVTNFIPDSILDMI<br>RNKSVAFGACAFTVTEESKRLINFTSPISTQTYTFLVSRPRELS<br>RALLFMSPFTGDTWLCLSASIVSMGPILYYIHKYSP<br>VYEYKGLSKRGLSSVQNCIWYMYGALLQQGGMHLPQADSA<br>RIIVGAWWLVVLATTYCGNLVAFLTFPKIDIPITTIDE<br>LLAHSGTVTWSMPKGSYLERTLKYTTEPRFRYLFDKKVEVG<br>NFKNMIEDIENGKHVHIDWKIKLQYIMKQQYLDSDRCDL |

TABLE 2-continued

Amino acid sequences of the IR93a receptor from *Drosophila melanogaster* and orthologs thereof

| Arthropod Species | Amino Acid Sequence |
|---|---|
| | ALGLDEFLNEQLAMVVSQDTPYLEIINDEIKKLHQVGLIQKW<br>LTDYLPKKDRCWKNNRHIVEVNNHTVNMDDMQGSFFVL<br>FLGFLLSFFITIGEKLWHKYVTKKKMKIIQPFTT (SEQ ID NO: 16) |
| PhumIR93a<br>(*Pediculus humanus*) | MLLFIFRIVFFLIIFCKKTGGNYFSDSHNVTLAVIVEQKFASKD<br>DLSFVIKNLISDARKKFVKNGDLTVQYHTNTNTIPK<br>KNLIAVLSIASCENTWKIFRNAEDDSILHLAITEADCPRLPFEE<br>AITVPLIREGGEISQIILDIRTIHGIDWKSAVIFYD<br>TSAIDGEEIQGITSALSMSVPIHSVDPASVSIFKLERKKNEWSR<br>RKQIRNILTNFPPSKILGSNFLVIAKRDLVGVIMEVA<br>KSTGLVHPLSQWLYIIPDTNVIRDNITALSTLLMEGDNVSFIY<br>NGTSDNPDCIVRLICHVDELIKSFTVSLNELIREEIE<br>LSSQVSDEEWETIKPTKLDRRISLLSHIKTKLSESGGCDKCVT<br>WLLKAGETWGKEFEIRKKGESRYDDFLQDVGLWHPRS<br>GHVMKDILFPHIVHGFRGRSLPLISFNHPPWQIINHNESGQFV<br>EFKGLVFEIVNELAKSLNFSYSVIYPQQKDKQNFFND<br>SAKYEGLNGTQDFSTIAANWEIIIEAIKNKKVFLGAVAFIVSPE<br>HKRFINFTTPIGIEPYTFLVARPQELSRALLFLSPF<br>GGDTWLCIALAVAIVGPLLNWFHRSTPYYDYFNTRTSGGLQ<br>TVTNCLWYMYGALLQQGGIHLPMADSGRIIVGAWWLFVL<br>VIVTTYSGNLVAFLTFPKMDVPINTIQELLLRKNSLNWGFVR<br>GSPVDLRLKNNVDPKYKELYDNAQLYRKLESETIEKIR<br>KGEHVYMDWKTNMLFLTKKQYVETGTCDFTFGTEEFLEEQL<br>AMVIAQGNPYLPRIDQEIRRIHRVGLIYKWLQDYLPKKD<br>KCWSTNRLTEVTSHTVNMRDMQGSFFVLFLGIILSTILILTEY<br>FYKKKTDREKNVIKPFTT (SEQ ID NO: 17) |
| IscaIR93a<br>(*Ixodes scapularis*) | MNNKNMMTFHREFVSVVTQPIDDDFQKLVVGFPDGANVLA<br>AYPEIADNDCPVEPGCQLPLAMETVAKTIGDKLEKGTYRT<br>TEFFTTKFIFSNTSKSLLLASGKCGQCARFIIRSVAKVQGIQEF<br>LKIGEWTPAVGLKMTHKQFFPGIMGNLGGIRLTIGV<br>INDPPMSVVEMSPDRKTVKNVTGTMADMVEALAKGLNFTY<br>TWKVPKEEIPGSKENGNWNGLIGMLATGEADLGAYGFSVT<br>KERSEVVNFTSAYDESPYKILVPKPRANYKYLFLDPFTWDTW<br>VAVLVSLVLIGPILWGIHCASPFYDYHGLRDNKGLFLL<br>QNCEWYCFGAIIQQGGIHLPEAISGRILVGFWWLFVIVTLTTY<br>SGNLVADLTFPKIRNPVDSVENLVAHRGYMRWGAFKG<br>QAVFELLKSQEQGPLKVLSDRMNVFEPNHEMWVLDQVRLG<br>YMALIGSEVNMFHYLGRELNRTGECDFAVARGEVIRDVKS<br>LAVAPNFAFLERLNNEPDHDGRPPPRRLKRLVESGLVMRWK<br>KKYWPQDNECTVESKPQAGDIRKITLRHMTGSFWVLGVG<br>FFSSFAALFVEFVRRKRELTAPPTHKPPTVIHTKSPFFTRTEYS<br>GKDTLTTDRFATDYGGRGPRDNAGFAFSPPNSPFRY<br>NGYPNNRSDLIPYNYPARR (SEQ ID NO: 18) |
| HmelIr93a<br>(*Heliconius melpomene*) | MKLWMVACVIWSSLQYGQAEDFPSLITANASIAVVLDRQFL<br>GDEYQTTLDEIKDYIKELARVELKHGGVNVHYFSWTAIS<br>LKKGYLAVFSVASCEGTWSLFQKTEEEQLLLFALTEVDCPRL<br>PTDSAITVTYAAVGQELPQLFLDLRTQKGMNWKSAIIL<br>HDDTLNLCYIFLLLRRLIHKKQENLESLSFYLLNHDDDVPSIS<br>VTVFKMKHEVNEYLRRKEVNRVLSKLPVKYIGEKFIA<br>IVTTAVMATIAEAARELLMSHTQAQWLYVISDTSGRGNFSNL<br>INDLYEGENVAYIYNVTENDEGCKNGLICYAKEMMSAF<br>ISELDSAVQEEFDVAAQQYIMVKSECGNCSWWRALAADTW<br>GATYREKTYETKRNVTSIVIEHVELLNTWLCLGFAVILMG<br>PTLYIIHRLSPYYDAMEITREGGLSTIHNCLWYIYGALLQQGG<br>MYLPRADSGRLVVGTWWIVVLVVVTTYSGNLVAFLTF<br>PKLEIPVTTISELLESKTYTWSISKGSFLEMQLKSSDEPKYKAL<br>VKGAEVTGGINVVEGSLVSGSEILNRVRNQRHALID<br>WRLRLSYLMRAETVKTDTCDFALSAEEFMDEQIAMIVPAGSP<br>LNRMHKAGLITKWLSAYLPKRDRCWKTSTVEEVNNHTV<br>NLSDMQGSFFVLFLEK (SEQ ID NO: 19) |
| MsexIr93a<br>(*Manduca sexta*) | MRLKLVGFLCLVCRVSGEEFPSLITANASIAVVLDRQYLGDK<br>YQAVLDELKDYIKELARVDLTHGGVVVHYYSWTSISLN<br>KGFLAVFSVASCLDTWDLFSRTEEEELLLFALTEVDCPRLPLR<br>SAITVTYAEAGEELPQLLLDLRTSNAFKWKSAVILHD<br>DTLNRDMVSRVVQSLTSQIDDESASPVSVSVFKMKHEINEYL<br>RKKEMHRVLSKLPVKTVGENFIAIVTSDVMTTMADTAR<br>ELLMSHTMAQWLYVISDTNIHNSNLSGLIRALYEGENVAFIY<br>NQTDNSPDCKNGIMCYCQEIMNAFISALDAAIQDEFDV<br>AAQVSDEEWEAIRPNKIQRRDMLLKHMQQHISTKSRCGNCT<br>TWRALAADTWGATYRHFTEDDILKENDNGTEATGVIEKV<br>TLLDVGFWRPIDAMTFFDVLFPHVQHGFRGKELPVITYHNPP |

TABLE 2-continued

Amino acid sequences of the IR93a receptor from
*Drosophila melanogaster* and orthologs thereof

| Arthropod Species | Amino Acid Sequence |
|---|---|
| | WTILHTNESGAIVKYGGLMFDIVNQLAKNKNFTIKILL<br>PGNVKNEISNETDALHSRRAMLALAAIAKGQAALAAASFTIL<br>PNPTPGINYTIPVSTQPYAFLVARPRALSRAMLFFLPF<br>TADTWLCLGLAVITMGPVLYIIHRMSPYYEAMKITRQGGLAT<br>IHNCLWYIYGALLQQGGMYLPRADSGRLVVGTWWLVVL<br>VVVTTYSGNLVAFLTFPKLEIPVTSIAELIENRALYTWSINKGS<br>YLEMELKNSEEPKYKALLKGAELTKPTHSSETNAHA<br>GVEDFMDERVAMIVPAGSPYLALLNKEINRMHKAGLITKWL<br>SAYLPKRDRCYSMSSMAAEVNNHTVNLNDMQGSFFVLLL<br>GDFFFIVLNDETSLPFV (SEQ ID NO: 20) |
| MdesIr93a<br>(*Mayetiola destructor*) | MMLRAHSCLTLCAVLVVSINQSEANDFPSLLVANATMGVIID<br>HGYLGDRYESTLDTMKQIIERVIREDLRGAGLFVKYFS<br>WSRINFNKDLTVIFSIASCKSTWETFFHARRERLLLLAITDPDC<br>PRLPSHEALTIPRIKVGMELPQIILDIRTSKSVNWK<br>TVAILYDDIFDRDTISRVATALTVESSSMAMSISLLKLNSSTDS<br>FERRENIKRSLLSFPNRFIGKNYLVVATIPTTILEI<br>ATEMNMIDSKSQWLFLVSNPKKTNISTLLPFIKEGGNVAIATN<br>NTANDDNNCAKTDECLYHELIKYVALSLSKLLREEEA<br>IYGQISDEEWEAIRLTKRERRDSMLEYIQDKLKNSPICTPCVK<br>WKFEAAETWGLRFNNIQGFA (SEQ ID NO: 21) |
| AcepIr93a<br>(*Atta cephalotes*) | MWSLHDAARKEELVHLAITDEDCPRLPDSEGVSIPLILPGKEL<br>SQIFFDMRSIDALLWNNVNILHDDTFDRDTIGRVTKA<br>LSTSLPNKKFNLVSRTLFTFKHANSERNRRYDIKNMLESFHV<br>EQLGKCFLVIVTIDTAADVMEVAKSLNMALPDSQWLYI<br>ITDSVVRNSTNITSFADLLTEGSNVAFIYNVTDSDTYCNELVS<br>ALANALKMSLMTEIELYSHMTDEEFELIRLNKQERRQ<br>EILKSIKIQLIEDTFSTNGVCGKCLFWRFASAITWGNFFIHGKN<br>VAHLIESGTWIPVLGANFTDVLFPHVMHGFRGINVP<br>IATYHNPPWQTISLTNSGEKEYGGLLFDVVRYLGKKLNFTYN<br>VLSPAINRTKFTRNATVANVVLTSTTREMPSQIIDMIL<br>EKKVLFAACAYTVNDHGRKQINFTLPIFMQTYSFLTAKPGQL<br>SRALLFTAPFTKETWACLAASIIIMGPVLYLIHKYSPS<br>STKTSGLNSCWQCVWYIYGALLQQGGMYLPHSDSARLLVG<br>VWWLVVMVLVATYSGSLVAFLTFPNTDTAILTVDDLIAHK<br>NKLTWGFPNGSFLEEYLKNVEEEKYHILLERAIIHNATQEAD<br>MVEQIKMGKHVLIDWRSTLRLHRMHESGLMNKWIAEQI<br>PVKDKCSDSFANQVVEERKVNVTDMQGIFFVLFMGNVFFAIP<br>SFGECNNISWE (SEQ ID NO: 22) |
| AechIr93a<br>(*Acromynnex echinatior*) | MNMISFFFLAWILNSGDAFSDFPSLMSTNASMAVVIDKSFFD<br>NKAEYRDTVKNIYNFITAITRKEIHMADIDVHIFEGTK<br>VHNLRDFTVLLSVTSCYQMWSLHDAARKEDLVHLAITDQDC<br>PRLPDSEGVSIPLILPGKELSQIFFDMRSIDALLWNNVN<br>ILHDDTFDRDTIGRVTKALSISLPNKKFNLVSRALFAFKHANS<br>ERNRRYYIKNMLESFHVEQLGKCFLVIVTIDTAADVM<br>EVAKSLNMALPDSQWLYIITDSVVRNSTNITSFIDLLTEGSNV<br>AFIYNMTDSDTYCNVSLKCYIQELVSTLANALKMSLM<br>TEIELYSHMTEEEFELIRLNKQERRQEILKSIKIQLIEDTFSTSG<br>VCGKCLFWRFASAITWGNFFVRGKNVAHLIDSGTW<br>IPVLGANFTDVLFPHVVHGFRGIRIPIATYHNPPWQTISLTNSG<br>EKEYGGLLFDVVKYLGKKLNFTYNVLSPAINQTKFT<br>RNATVANVVLTSTTREMPSQIIDMILEKKVLLAACAYTVNDY<br>GKKQINFTLPIFIQTYSFLTSKPGQLSRALLFTAPFTK<br>ETWACVAASIIIMGPILYLIHKYSPSSTKTSGLNSCWQCVWYI<br>YGALLQQGGMYLPHSDSARLLVGVWWLVVMVLVATYS<br>GSLVAFLTFPNTDIAILTVNDLIAHKNKLTWGFPNGSFLEEYL<br>KNAEEEKYHILLERAIIHNATQEADMIEQIKMGKHVL<br>IDWRSTLR (SEQ ID NO: 23) |
| SinvIr93a<br>(*Solenopsis invicta*) | CLNLAAVIIDKNFFDDKVEYRDVMKNIHGLIASITREEIHTIDI<br>DIQIIRGTKINFRDYTVLLSVTTCHQMWSLHDAARK<br>EELIHLAITDEDCPRLPDTEGVSIPIILPGQELAQIFFDIRSTDAL<br>LWNNVNIIHDDTFDRDTIGRVTKALSTALPNKKF<br>NMVSRALFTFKYSDSATTRRYYIKDSLENFHVDQLGRCFLVI<br>VTIDTASDVMEVTKTLNMALPDSQWLYIITDSVVRNST<br>NITILTDLLSEGSNMAFIYNATDNDTYCNVSLKCHIQELVAAF<br>VNALKISLMTEIELFSHLSDEEFELVRLNKAERRREI<br>LKNIRIKLIDENFATGGVCGKCLFWRFASAITWGNFFLHSKN<br>VAHLIESGTWIPGLGLNLTDEIFPHVVHGFRGISLPIA<br>TYNVCKYVPFSLSTIKFVRFDFFFQNPPWQTISLNNAGEKEYG<br>GLVFDVIKYLGKKLNFTYTVLTPASNRAVKFIRNETA<br>DVVLASTTREMPPQIIDMVLEKKVLLAACAYTVNNFGRKV<br>NFTLPIFMQTYSFMTAKPGQLSRALLFTAPFAKETWACL |

TABLE 2-continued

Amino acid sequences of the IR93a receptor from
*Drosophila melanogaster* and orthologs thereof

| Arthropod Species | Amino Acid Sequence |
|---|---|
| | ASSIIIMGPILYLIRKYSPDNTETSGLNSCWQCMWYVYGALLQ QVPMILGGMYLPHSDSARLLIAVWWLIVMVVVATYSG SLVAFLTFPNMDAAILTVDDLIAHKNRITWGFPNGSFLEEYLK NSEEEKYHILLERSIIHNETTASKVIEKVKAGKHALIDWRSTL (SEQ ID NO: 24) |
| PbarIr93a (*Pogonomyrmex barbatus*) | MLQYDLSLDMISIFFLAWILNSGDAFGDFPSLVSANTSMAVVI DKSFFDNKAEYRDIVRNIYNYIATVTKEETNTIDIDV HIFRGTRVNNLRDYTVLLSVATCHQMWSLHDAARKEELVHL AITDHDCPRLPDSEGVSIPLVSPGEELSQIIFDIREIDA FAWTNVNILHDDTFDRDTINRVTKAISRSLPNKKFNLISRALF AFKNADSERSRRYYIKHVLENYRVDQLGRCFLVIVTI DAAADVMEVAKSLNMALPDSQWLYIITDSVMRNSTNITSFV NLLTEGSNVAFIYNTTDSDTYCNVSLKCHIQELVGALIN ALKLSFMIEIELYSHMSDEEFELIKLIEDTFATGGVCGKCLFW RLASAITWGNFFVHGKNTAHLIDSGTWMPNLGANLTG PIFPHVVHGFRGISVPIATYHNPPWQTISLSDSGEKEYGGLVF DVVKYLGRKLNFTYSVISPASNRIVKFTRNATTDMIL TSTTREMPSQIIDMILEKKILLAACAYTVNGKGKGHINFTLPIF MQTYSFLTAKPSQLSRALLFTAPFAKETWACLAASI IIMGPILYLIHKYSPSNTRKSGLNSSWQCIWYVYGALLQQGG MYLPHSDSARLMVAVWWLVVMVLVATYSGSLVAFLTFP NMDITILTVEDLITHKDRLTWGFPNGSFLEEYLKNAEEEKYH TLLEKAIIHNATQEAEVIKKVKAGKHALIDWRSTLRIT ITMHCPSRFLMRNDMLTTDECAFALSTDEFMDEPIAMIISENS PYLNIINAELHRMHESGLMNKWTSEQIPLKDKCSESL TNQAVVERKVNVADMQGIFFVLFMAVSSAFAYRYDPWYRA DTQRPVDVITDVINELGVRILQQYSTRGNVAFSPTGVAFV LAALYEGSAGRGSQQIAQALGLPANRDVTRIGFRDIHRRLRS YLNADGFLGGLTLSRENTRLRPEYEDILRFYGFDLSSI EQEANVTVSTGDSSGTTKLPTSTVGVTTLPTETTNTGSVPDM TTTTTMMSTDVGTTLPPSGAETMIPSTVTDASTQQPLT MVPTGATDVPSTLAPVTGDGAAVQNASPTQSANSTTAVTSG ESVQSTTSAGAESVAGSPNTITPAVNADSQTTPTTVAGA GDQSPQTSPTVAADGVGTGEIVTSTIVPDATAADVTAAAATD AAGGMVSTSTQAQVSSTVATSTEAPMTTNTPSSAAMII ANTDSLAAAIDVNVTPANVTSPSEAILNTVTTNSLTTVAIANV ANVTIPSPVTETTADSVVSQPSTLADTPATTDIPGST ATNNLAMTTMTNIDGAAATTASLVDENTISMNRKKKDLTDV RINDNTVKQESTNESLNVRKRKARSPRGYFSSYPDEGIW MQDLEIWKSYNTVNPGDSSAGDSSAEISFLVNGCDVSSVSAS RYIAVLPFAYFPSLQAVALEFPLDDPRYNIILFMPTDK TDTHRLARDLSGKSLRLLRKRLQPTWVRATIPSFMLRGFVTL TSFLQREKETEIEEG (SEQ ID NO: 25) |
| CfloIr93a (*Camponotus floridanus*) | MDMISVFFLVWILNSVDAFNDFPSLVSNNASMAIIIEKSFFDN KAEYRSVVSNIYNFISNITSDIEVHVFHDTKIDSFQD YTVLLSVTTCDQTWNLYNAVRKDEIIHLAITEQDCPRLPEGV SIPLILPGKELSQIFFDIRMADALLWNNVNILHDDTFD RDTINRVTKAISIALPNKKFNLVSRSLFVFKHADSERNKRYYI KEMLESFHVDQLGKCFLVIVTIDTVADVMEAAKMLNM VQPDSQWLYVITDIVKNNSTNITSLIDLLSEGSNVAFIYNATD NNTYCNNNLICHIQELTMALNNALKISLMTEIELYNH VSNEEFEIVRLNKRERRREILKFIRTKLAQDNFATGGICGKCL FWRFASAITWGNFFIRDKSTAHLIDSGSWIPTLGMNL TDVIFPHVVHGFRGINLPIATYHNPPWQIISMTNSGEKEYGGL LFDVVKYLGNKLNFTYSVLSPVSNRTIKFTQNETQAD MTYSFLTAKPGQLSRALLFTAPFAKETWACLASSIIIMGPSLY LIHKYGPTSTKTSGLNSSWQCIWYVYGALLQQGGMYL PYSDSARLLIGIWWLIVMVVVATYSGSLVAFLTFPNMDSSILT IDALLANKNRLTWGFPNGSYLEEYLKNAEEEKYHIML KRAKIYNATQEAEVIEKVKAGKYALIDWRSTLRFLMRTDML TTGRCSFSLSTDEFMDEPIAMIINQDNPYIKIINAELHR MHESGLMNKWVTEQIPMKDKCSDILANQAVNERKVNVAD MQGIFFVLFMGVAGSIFLLCCEFYWHKRQVAKRRKLIQPFLS (SEQ ID NO: 26) |
| LhumIr93a (*Linepithema humile*) | MNTRCLNAIVIDKSFFDNKIEYRDTVRNIVDFITNVTNEEAHM SDINMHIFRDTNVNNLRDYTVLLSVATCYQTWSLHDV ARKEELVHLAITNQDCPRFSDSEGVIIPLIPMGDELSQIFFDIRT ADALFWNSVNILHDDTFDKNTISRVTKAISTALPN KKFNLVSRSLFVFKHANSDRSRRYYIKDMLETFHVEQLGKCF LIIVTIDAAADVMEVAKTLDMVQPDSQWLYIITDSVIR NSTNITTFIDLLTEGSNVAFIYNATDSDAYCNVTLMCHVQELI AALSNALKLSLMTEMELYNRMSEEEFELIRLNKNERR |

TABLE 2-continued

Amino acid sequences of the IR93a receptor from *Drosophila melanogaster* and orthologs thereof

| Arthropod Species | Amino Acid Sequence |
|---|---|
| | QEILKNIKIKLVEDTFATGGTCGKCLFWRFASAITWGNFFIHG
KTSAHLINSGTWIPTLGVNLTDAIFPHIVHGFRGINL
PIATYHNPPWQTISLTNTGEKEYGGLVFDVIRYLGKKLNFTY
TVHSPRSNRTVKFIRNESDIEVVLTSTTRKIPPEIVDM
VAEKKVLLAACAYTVNDRGRGKINFTLPIFMQTYSFLTAKPG
QLSRALLFTAPFTKETWACLAASIIIMGPILYLIHKYS
PSSTRTSGLNSPWQCIWYVYGALLQQEKCDEKMFLGGMYLP
HSDSARLLVGVWWLVVMVLVATYSGSLVAFLTFPNMDTA
ILTVDDLIAHKSQLTWGFPNGSFLEEYLKNAEEEKYHILLERS
IIHNTTQEAEVIKKVKAGKHVLIDWRSTLIRLISTSD
KNDDNDILLEQVCDEKRSVIN (SEQ ID NO: 27) |
| HsalIr93a (*Harpegnathos saltator*) | MISVLFLAWILNFGNAFNEFPSLMSANASMAVVIDKSFFDKK
HEYIDVTKRIHEYITNIAREEMHMGDINVRVFRNAKIN
NLREQDCPRFPDTDGVSIPLVVAGQELSQIFYDLRSYDVLNW
NNINILHDDTFDRDTISRVTKAVSTPLPNKKFNMVSRS
LFAFKHANSERSKKYYIKEILEKFHVDQLGKCFLVIVTTDVAF
DVMEVPDSQWLYVIADSMVRNATNITSFTEYLSEGAN
VAFAYNSTDNDTYCDAKLLCRVQELIGSLANALKLSLMIEIE
LYNRVSEEEFEFIRLNKRERRREILKNIQIKLTDDTFA
SGGGCGKCLFWRFASAITWGNFFLRGKNIAHLIDSGMWIPSL
GANLTDVIFPPHISHGFRGISLPVATYHNPPWQSISLTN
SGEKEYGGLIFDVIKYLGKKLNFTYTVLSPTSNRTVKFTQNET
QADVTYSFLTAKPNQLSRALLFTAPFAKETWACLAAS
IIIMGPILYLIHKYSPGTKTSGLNSSWQCVWYVYGALLQQGG
MYLPRCDSARLLVGVWWLVVMVLVATYSGSLVAFLTFP
NMDVAILTVDDLIAHKGRVTWGFPNGSFLEEYLKNAEEEKY
HIMWERSEIYNSTQEVEVIEKVKTGKHVLIDWRSTLRFL
MRNDLLSTGGCSFSLSTDEFMDEPIAMIISQDSPYTKIINAELH
RMHESGLMTKWITEQIPMKDKCSDSSGKQGVDERKV
NVLDMQGIFFVLFMGVVGSIFLLCCEFYWHRRQITRRSKLIQP
FLS (SEQ ID NO: 28) |
| AdarIr93a | MSPEEGKNGQKINQTCQPVEESTYAPDSNEMNSSNDAEKDH
EMQSNIQYVMDILPHLDPYYVRRIIEHFDSVEKALAILL
EGNEDAQSKDSRKDINGEIVPEDPLDSFYLQTGIDRLNIFDGD
EFDVMSKSHVKGTIKKGKGMPGNPKSFKALLDDKSHV
NEMRHVYRQYSTLADMDDDEYDDTFEAMAESESRHIKFAK
GTRISGIEESDDDDESDTEDSDPEAEPHKMAGFEFCENPE
ITRKRYEERLISKGVKPQAPKETADVRGNPKASNDANNDKVI
KTRDLYRSGHLPDETCVKKLCPSNGTDVTLLILVTSAP
THREQRLAIRQSWGYYGSRRDISIGFIVGQTDESRIEDQLAAE
SYMYSDLIRGNFIDSYKNLTLKTISLLEWTKLHCSNA
SFLLKTDDDMFINVPKLLQFMEVHNNQRRTIFGRLAKKWKPI
RNKKSKYYVRPAYLLTADIISELFEKSLSQTYLKLEDV
YTTGIVAQLLNIRRTNVKEFLNRRIAFNQCSIKKAISIHMVKN
NEQLDLWKKLIDVNILCYIESFLVHFIRSLSKLIREE
QVVFGQISDEEWEIIRPSKVERKKKMLQMIQNPPWQFVSYNE
SGSPVITGGVIYDVLSELSRKLNFTYTLVITQGASEQN
GSLIDDNSTVSDGNSMVISRLRFFMKCFCLLQTLYETNGLTSD
IPQEIYSTLVNNKILLAAIGTTVTEKRKKYISFTDPI
SIQTYSFIDIPVNRIMQLLRNERGMTWSIRKGTFLEEVLMVRQ
HYRQQLQLHLANRMSFPSPVWTQESDENKYIELYRGS
QVITELTDDLVRRIEAGQHVHIDWRNNLKYLIKKQFLATDRC
DFALSTDEFLDEQIALVMPKDSPYLELVNDEIRRMHQF
GFIQRWISQYLPSKDRCSGTSNKAMDVQNHTVNSSDMAGSY
WILLLGFSSGLIIFIGEFAIHWYRQRRLAKAVVTSYSS (SEQ ID NO: 29) |
| AfloIr93a | MISVLLLVWCINYGSSYNDFPSLITSNATMDPDCPRIPDTDGIT
VPSIVPGEELSQIFLDLRMTDILSWNVINILHDDTF
GDKATSSNDNVTILLSNANTSIFSLRHGNTGGGRKSSVKKTL
NDFHVDQLGHCFLVIATVDMADVMTVANSLNMVHPGS
QWLYVITNSVSGNLINTTFINLLAEGGNVAFMYNATNLDGFY
KIKLKCYIKNLIEALAKALEYSLTNEIELFKRMNEDEF
EMIRLTKSKRRTELLKNVRNPPWQIISMSKTGKKLYEGLIFDA
INYLSMKLNFTYTVIMPETSQISRSWNTSQFAKLGEK
IKEMTMSTTKKVPLEIIDLVRQKKVLLAACALTVNECGNTTF
NYTVPIFVQTYSFLTAKPSQLSRVLLFASPFTKETWAC
LAVSIIIMGPILYLIHKYSPYSTKASGLNSSWQCVWYVYGALL
QQGGMYLPHNDSARILIGIWWLVVMVLVATYSGSLVA
FLTFPRMDTSILSVEDLIAHKDRISWGFPNGSFLEMYLQNAEE
PKYHVLLSRAERHNDTEEERLVGRVKEGKHALIDWRS
SLRFLMRKDFLLTGSCHFSLSMDEFLDEPIAMIIPYGSPYLPVI
NAELHRMLESGLMNKWITERMPMKDKCWEAPGSNQA |

TABLE 2-continued

Amino acid sequences of the IR93a receptor from
*Drosophila melanogaster* and orthologs thereof

| Arthropod Species | Amino Acid Sequence |
|---|---|
| | VNKRKVNVADMQGIFFVLFIVSSVFVHGYDNVGFDGWYQP<br>QYTAHGNVAFSPTGVGFVLAALYEGSAGRGRQQIVDALGL<br>PRDRDITRIGFRDIHRRLRTYLNADGFLGGLTLNHENTRLRPE<br>YEDILRFYGFDLSIPEEEMNETTFAPETTSSVAIEQS<br>TTETKTVIPDEITTQSITTQGIQSFETITNSGTPISTTSSVELTGIV<br>TSSTIEQDKLTQTTPAASVLTNNPNAAMTTVSS<br>SIVVTSSSTETTTTSSIPTIINPNLITTSSSEIVTTTPSVTSTPPS<br>TIPSTTPIIIITTVASTISEEPQTTIANLTQPIT<br>TVTLSNQSPSIEESTSTLSTSTSTSTTPFTTTTTSTTTSTTSIPSS<br>TSETPLPPTTLIIVETPESTTISTGQTTKESVV<br>MTESIPESTIMPPTMSAPINAGATVTEVSTTLPVNITEISTNSTI<br>PTTIQTNEMSINETSRFTNKPDDENTISVDSLNNQ<br>SSISNEMESTELPVTIVAGEIGSTIGQKTITTTVSSNTMMNRRK<br>RSDRSPRGFFSSYPDEGIWMQDLGIWKPYSTSLNEA<br>SVRDSTEISFLVNGCDVSSVTASRYFAVLPFAYFPSLHAVALE<br>FPLDDPRYNIILMMATDRRDTYRLARDLGGKSLRLLR<br>KQLQATWVRATIPSFMLRGFVTLTSFLQRLGILDVFEPRTADL<br>SPMTPDLGVYARDVQQSIGVNIRNYMKPDRTHSRNGL<br>FERAGPVPFTVVHPFLYFIVDAETSVVLIAGRVNDPLNSRIL<br>(SEQ ID NO: 30) |
| BimpIr93a | MISVLLLLWCVNYGDSYNNFPSLITTNATMAVIIDKSFFDNN<br>GEHRNVMGVVHDLIINTVKKEMHIGGIVVRIFRDADVN<br>LWQGYTILLSVASCCITWRLHEVARKEELIHLAITDPDCPRIPE<br>TDGMSMPVVVPGEELSQIFLDLRMMNILPWNVINIL<br>HDDTFGRDTISRVMTAISDKLPNKQVNLISRSIFTLKHETTRSE<br>RKSSVKKTLNDFHVEQLGHCFLVIATVDMIADVMGV<br>ARSLKMVHPGSQWLYVITDSATKNMTNMTAFVDLLAEGGN<br>VAFMYNATNLSNYCEIKLICYVEKLIQALAKALEYSLTNE<br>IDLFKSMEEEKFEMIRLTKRERRAELLKNIRIHLSQNAFASEGF<br>CGRCLLWRFSSSITWGNFFSRGRNMAHLLDIGTWSP<br>GFGVNLTDVIFPHIAHGFRGTNLPIATYHNPPWQIISVSKTGQ<br>KLYEGLVFDAINYLGSKLNFSYTAITPEVTRNSNFTV<br>NENKKDAINFTVPIFVQTYSFLTSRPKQLSRALLFASPFTKET<br>WACLAVSIIVMGPILYLVHKYSPYSIKTSGLKSSFQC<br>VWYVYGALLQQGGMYLPHCDSARILIGVWWLIVMVVVATY<br>SGSLVAFLTFPPRMDASILTVDDLLARKDGITWSFPNGSFL<br>EMYLQETDEPKYHTLLSRAESHNDTEEEKLVERVKDGKHAL<br>IDWRSSLRFLMRKDLLLTGVCHFSLSMDEFLDEPIAMII<br>PHDSPYLPVINAELHRMLESGMMNKWITERMPIKDKCWEVP<br>GSNQAVNKRKVNVTDMQGIFFVLFMGIILAFFFLFCECY<br>CHRRKISKERKLIHPFVS (SEQ ID NO: 31) |
| BterIr93a | MISVLLLLWCVNYGDSYNNFPSLITTNATMAVIIDKSFFDNN<br>GDHRNVMGVVHDLIINTVKKEMHIGGIVVRIFRDADVN<br>LWQGYTILLSVASCCITWRLHEVARKEELIHLAITDPDCPRIPE<br>TDGMSMPVVVPGEELSQIFLDLRMMNILPWNVINIL<br>HDDTFDRDTISRVMTAISDKLPNKQVNLISRSIFTLKHETTRSE<br>RKSSVKKTLNDFHVEQLGHCFLVIATVDMIADVMGV<br>ARSLKMVHPGSQWLYVITDSASKNMTNMTAFVDLLAEGGN<br>VAFMYNATNLSNYCEIKLICYVEELIQALAKALEYSLTSE<br>IDLFKSMEEEKFEMIRLTKRERRAELLKNIRIHLSQNAFASEGF<br>CGRCLLWRFSSSITWGNFFSRGRNMAHLLDIGTWSP<br>GFGVNLTDVIFPHIAHGFRGTNLPIATYHNPPWQIISVSKTGQ<br>KLYEGLVFDAINYLGSKLNFSYTAITPEVTRNSNFTV<br>NENKKDAINFTVPIFVQTYSFLTSRPKQLSRALLFASPFTKET<br>WACLAVSIIVMGPILYLVHKYSPYSIKTSGLKSSFQC<br>VWYVYGALLQQGGMYLPHCDSARILIGVWWLIVMVVVATY<br>SGSLVAFLTFPPRMDASILTVDDLLARKDGITWSFPNGSFL<br>EMYMQETDEPKYHTLLSRAESHNDTEEEKLVERVKDGKHAL<br>IDWRSSLRFLMRKDLLLTGVCHFSLSMDEFLDEPIAMII<br>PHDSPYLPVINAELHRMLESGMMNKWITERMPIKDKCWEVP<br>GSNQAVNKRKVNVTDMQGIFFVLFMGIILAFFFLFCECY<br>CHRRKISKERKLIHPFVS (SEQ ID NO: 32) |
| DanaIr93a | MKDYLKANSKCASCARWQIETAITWGKSQENRKFRAAPTRD<br>AKNQNFEFINIGYWSPLLGFVCQELTFPHIDHHFRNITM<br>DVVTVHNPPWQILTKDSHGVILEHKGIVMELLKELSRALNFS<br>YYLHEASNWKDDYSITTSSSNESDELAGSMTFRIPYR<br>LVEMVQGNQFFMAAVAATVEDPDHKPFNYTLPISVQKYSFIT<br>RQPDEVSRIYLFTAPPFTTETWACLVGIILLTAPMLYAI<br>NRLAPLQEMQIIGLSTVKSCFWYIFGALLQQGGMYLPRADSG<br>RLVVGFWWIVVIVLVTTYCGNLVAFLTFPKFQPGVDYL<br>SQLPRHKEISQYGLRNGTFFFERYVQTTTRDDFKHYMARAQIY<br>GNSQEENIEAVKQGHRINIDWRINLQLIVQQHFERDKE |

TABLE 2-continued

Amino acid sequences of the IR93a receptor from *Drosophila melanogaster* and orthologs thereof

| Arthropod Species | Amino Acid Sequence |
|---|---|
| | CRFALGKESFVDEQIAMIVPSHSVPYLHLINSHIDRLFRMGFM<br>ERWHQMNLPSADKCTGKSSLRQVTNHKVNMDDMQGCF<br>LVLLLGFMVAFAIGCGEFWYHHLYVHKTSRQPPSSVFTT<br>(SEQ ID NO: 33) |
| DereIr93a | MRQQFLVISAFHEDIIEIAETLNMFHVGNQWMIFVLDMVGRD<br>FDAGTATINLDEGANIAFALNETDPNCQDSLNCTISEI<br>SLALVTSISKITVEEESIYGEISDEEWEAIRFTKQEKQAEILEY<br>MKESLKTNAKCSSCARWRVETAITWGKSQENRKFRS<br>IPSRDAKNRNFEFINIGYWTPLLGFVCQELAFPHIEHHFRNITM<br>DILTVHNPPWQILTKNSHGVIVEHKGIVMEIVKELS<br>RALNFSYYLHEASSWKEEYSVSTSAGSNESDELVGSMTFRIP<br>YRVVEMVQGNQFFIAAVAATVEDFDQKPFNYTVPISVQ<br>KYSFITRKPDEVSRIYLFTAPFTMETWFCLMGIILLTAPTLYAI<br>NRLAPLKEMRIVGLSTVKSCFWYIFGALLQQGGMYL<br>PTADSGRLVVGFWWIVVIVLVTTYCGNLVAFLTFPKFQPGVD<br>YLNQLEHHKDIVQYGLRNGTFFERYVQSSTREDFKRYL<br>ERARIYGSAQEEDIEAVKRGERINIDWRINLQLIVQRHFERDK<br>ECRFALGKESFVDEQIAMIVPAQSAYLHLVNRHINSM<br>FRMGFIERWHQMNLPSAGKCNGKSAQRQVTNHKVNMDDM<br>QGCFLVLLLGFTVALLIVCGEFWYRRFRASRKQRQFTN (SEQ<br>ID NO: 34) |
| DgriIr93a | MRGQQKRISLRKALIQFAPTKHELRRQQFLVLSRFHEDIIEIAE<br>TLSMFHVNNQWMFFVLEDPHNEFDANTVTINLDEGA<br>NIAFALNETNFNCVDTLNCTITEVSMALVTSLSRMILEEQSIY<br>GEISDEEWESIRFTKQEKQDEMLEYMKDYLKTNSKCA<br>SCARWRFETAITWGKSQENRKFRAAPTRDAKNRNFDFINIGY<br>WSPLLGFVCHELIFPHIEHHFRNITMDIVTEHNPPWQI<br>LTKDSRGVIVEHNGIVMEILKELSRALNFSYYLHDATAQDYD<br>NQLGPSTNESDELMGSMTFRIPYRVVEMVQGNEFFMAA<br>VAATIDEQHKKRFNYTQPISVQKYTFILRQPDEVSRIYLFTAPF<br>TIETWACLAGILMVTAPMLYIVNRLVPLQELQIRGL<br>STVKNCFWYIYGALLQQGGMYLPRADSGRLVVGFWWIVVI<br>VLVTTYCGNLVAFLTFPKFQPGIDYLNQLFGHTEIKQYGL<br>RNGTFFEKYVETTTRPEFKRFIERATIYSSVQSENIAAVKHGD<br>RINIDWRINLQLIVQQHFDKDKECRFALGKEDFVDEQ<br>IGLIVPTSSAYLHLINQHLDKLFRMGFIERWHKTNLPSMDKC<br>NGRNVQRQIANHKVNMDDMQGCFMVLLFGIILALFISC<br>IEFWYYRFFVVGRDRKSIAFAN (SEQ ID NO: 35) |
| DmojIr93a | MKEYLKANSKCASCARWRIETAITWGKSQENRKFRTTPTRD<br>AKNRNFEFINIGYWTPLLGFMCHELTFPHIDHHFRNITM<br>DIVTVHNPPWQILTKDSRGVIVEHSGIVMEILKELSRALNFSY<br>YLHEGHSSDTDDTIRQNMNDSDELMGSMTYRIPYRVV<br>ELMQSNAYFMGAVAATIDEPSKKHFNYTQPISIQKYTFILRQP<br>DEVSRIYLFTAPFTLETWGCLAGILLFTAPILYFVNR<br>LMPLPELRIHGLSTVKNCFWYIYGALLQQGGMYLPRADSGR<br>LVVGFWWLVVIVLVTTYCGNLVAFLTFPKFQPGVDYLHQ<br>LFAHKEIKQYGLRNGTFFEKYVEATTREDFKRFIARSSIYNSV<br>QSENIDAVKHGDRINIDWRINLQLIVQQHFELDKECR<br>FALGKEDFVDEQIGLMVPTGSAYLHLINHHIDRLFRMGFIDR<br>WHKTNLPSMDKCNGKNMQRQIANHKVNMDDMQGCFMVL<br>LFGVILATIVSCFEFWYHRFFVVSRERKRVPFSN (SEQ ID NO:<br>36) |
| DperIr93a | MNMFHVGNQWMFFVFETMRQDFDASTVTINLAEGANIAFA<br>LNETNTDCMDTLNCTISEISMALVTAISKMTVDEQSIYGE<br>ISDEEWESIRFTKQEKQYEILMYMKEYLKTNSKCASCAKWRF<br>ETAITWGKSQQNRQFRTAPTRDARNQNFEFVDIGYWSP<br>LLGFVCQELTFPHIAQHFRNITMDIVTMHNPPWQILTKNSHG<br>VIVEHKGITLEILKELSRALNFSYYLHEAKTYDDEFPL<br>NQSTNESDELLGSMTYGIPYRVVEMVQGNQFFMAAVAATVE<br>DPDKKAFNYTQPVSVQKYSFITRQPDEVSRIYLFTAPFT<br>TETWGCLVGIIFLTAPMLYAINRLAPLQELQIHGLSSVKSCFW<br>YIFGALLQQGGMYLPRADSGRLVVGFWWIVVIVLVTT<br>YCGNLVAFLTFPKFQPGVDYLNQLHRHTEISQYGLRNGTFFE<br>KYVQRTTRDDFKQYVAKAIIYNNGQGEDIEAVKDGQRI<br>NIDWRINLQLVVQQHFERDKECRFALGKESFVDEQIALIVPSQ<br>SAYLHLINQHIDRMFRMGFIERWHRTNLPSADKCNGK<br>SILRQITNHKVNMDDMQGCFLVLLLGFILAVFVGCIEYWFYR<br>LYVQSDSRKPTVFTN (SEQ ID NO: 37) |

TABLE 2-continued

Amino acid sequences of the IR93a receptor from *Drosophila melanogaster* and orthologs thereof

| Arthropod Species | Amino Acid Sequence |
|---|---|
| DpleIr93a | METVVLDHQFLGDEYQMMLEDLEDYIKELVRVELKHGGINV<br>HYYSWTSINLKKGFLAIFSIASCEDTWSLFLRAEEEDLL<br>HIAVTEVDCPRLPSDSAITVTFADPGQELPQLVLDLRTRKAFN<br>WKSAIILHDETLNRDMVSRVVESLTSQIDDISSISVS<br>VYKMRHENNEYLRRKEVYRVLKKLPVKYIGENFIAIVTTDV<br>MATIAEIARELRMSHTQAQWLYLVPDTDSHTGNVTNLIN<br>DLYEGENIAYIFNFTDDRGCKNGLKCYAHEVLDSFISALEAA<br>VLDELEAALQVSDEEWEAVRPTKLQRRNSLLWHMQQYL<br>STRSVCGNCSSWRALSADTWGATYDRADENTSSLIEQVHLV<br>QVGFWRPIDGVTFEDVLFPHIQHGFRGKQLPIMTYHSPP<br>WTIVTYNASGAVTSYGGLLFDIVNQLAKNKNFTYAIYILLLA<br>ENLRLNYTNETTTDTLYNTNRQLILSAIAKGHAALVAA<br>PFTVSPDTHPGVNFTVPVSTQSYSFIIARPRELNRALLFLLPFT<br>TDTWLCIAFAVVLMGPTLYVVHRVSPYYEAMEITRE<br>GGLSTIYNCLWYIYGALLQQGGMYLPRADSGRLVVGTWWL<br>VVLVVVTTYSGNLVVFLTFPKLEIPVTTVSELLDSGTYSW<br>SIRSGSFLESQLKNSNEPKYEALLKRAELTSPSDGAENDAIVE<br>RVRFSHHALFDWKLRLRYLMRADTEQTDSCDFALSTE<br>EFMDEQVAMILPAGSPYLPVINKEINRMKKAGLITKWLSAYL<br>PKRDRCWKTSAITQEVNNHTVNLSDMQGSFLVLFLAIV<br>ERVRFSHHALFDWKLRLRYLMRADTEQTDSCDFALSTEEFM<br>DEQVAMILPAGSPYLPVINKEINRMKKAGLITKWLSAYL<br>PKRDRCWKTSAITQEVNNHTVNLSDMQGSFLVLFLDSQKTC<br>APEKAVVELTPGTVWSTRY (SEQ ID NO: 38) |
| DpseIr93a | MRSSGCLLLLFGFQLYFLSWPMAVEGNDFSSFLSANASLAVV<br>VDHEYMTRHGQNIMAHFEKILSDIIRENLKNGGINVRY<br>FRWNAVRLKKDFLAAITVTDCANTWNFYRSTQETSVLLIAIT<br>DSDCPRLPLNKALMAPMVEHGDELPQIILDAKVQQILN<br>WKTAVVLVDQNILDNNSELVKAIVHESTTNHIAPISLILYKID<br>DSLRGQKKRAALRHALSHFSPINHEQKNQQFLVLSKF<br>HDDIIEIGETMNMFHVGNQWMFFVFETMRQDFDASTVTINL<br>AEGANIAFALNETNTDCMDTLNCTISEISMALVTAISKM<br>TVEEQSIYGEISDEEWESIRFTKQEKQYEILKYMKEYLKTNSK<br>CASCAKWRFETAITWGKSQQNRQFRTAPTRDARNQNF<br>EFVDIGYWSPLLGFVCQELTFPHIAQHFRNITMDIVTMHNPP<br>WQILTKNSDGVIVEHKGITLEILKELSRALNFSYYLHE<br>AKTYDDEFPLNQSTNESDELLGSMTYGIPYRVVEMVQGNRF<br>FMAAVAATVEDPDKKAFNYTQPVSVQKYSFITRQPDEVS<br>RIYLFTAPFTTETWGCLVGIIFLTAPMLYAINRLAPLQELQIHG<br>LSSVKSCFWYIFGALLQQGGMYLPRADSGRLVVGFW<br>WIVVIVLVTTYCGNLVAFLTFPKFQPGVDYLNQLHRHTEISQ<br>YGLRNGTFFEKYVQRTTRDDFKQYVAKAIIYNNGQED<br>IEAVKDGQRINIDWRINLQLVVQQHFERDKECRFALGKESFV<br>DEQIALIVPSESAYLHLINQHIDRMFRMGFIERWHRTN<br>LPSADKCNGKSILRQITNHKVNMDDMQGCFLVLLLGFILAVF<br>VGCIEYWFYRLYVQSDSRKPTVFTN (SEQ ID NO: 39) |
| Dpul-1Ir93a | MMQHLGANWSQWANIFNQVPAFSNLWEPIGHKWDNIFNQV<br>PLSNHWELIGHKWDNIFNQVPFSNHWELIGHKTTFTRINP<br>DTKFLDDEDVEGVHLVHDFDLVREMQVRLGKFAKGQAVFF<br>PVMWSVSLSMKNVQSLASKPYVVGPKPSGPRFLLYIDSSG<br>DIFLENMTQHIFRVDEDHAIKIETFEGKPITDTVLDGVITREKS<br>DDDASCNGNIKEDGTTGKLKFVILDAIRCSGNDLTG<br>LNILERIAFVREEIIIPMTPTEAELHVGGPKTKFEIKYDMIRLTD<br>EMKMLDGCIIDCRYFDHQWIFIKQRHDRNHPNGSE<br>AVKETTANANSSSERVNDLSCYTSNLLQVYVKALHQVIREEE<br>THYFQTTEDDWNRSKPSAGDRRNNIFRTLQNMWKDATK<br>WSSWLNWALKAVEIKETRKPTLLDVGVWDAAHGLVVYDDF<br>FPHFTGGLRQRVISVTTMEFPPWQIFERNSQGKVVRHTGL<br>VLELTKELGNLSMLWNHVEPADGKWGSRLSFSRWTGMVEQ<br>VRTGSVAFAAAGCTVTADRMSAVNFSMSLDAQPYTFMFAR<br>PKQLSRAYLFIQPYTPNAWITIFAMTIGAGSLIWSFNNITPFYD<br>FYPDRPGSPIFSIWPYFYAKEKCLSL (SEQ ID NO: 40) |
| Dpul-2Ir93a | MLLRVLLVLASAFIHVQSAHYELYSELRPDERWFLDDTKLIP<br>VSCENGDCSALFNKHNKHKIAKRAAVQVETMKDYIKFL<br>LRGNKTKDDDTNTDPYRTANITLGVVMDKNLIGNLQTFTNIF<br>DVANMPSNPEIDYLRLQKFNVTYLNPQDKLPSNINAVL<br>SILPCDVLTRFDKNLASLPILHIAITSDNCPRITRWAVLMVPVV<br>KTGAELPQIFTDLRLSDTLNWKEAVVIAEEHANKEL<br>FDGLVDSLSRPVHKKDPLALTVVKLHGPVALRKKNFESQLL<br>NLQVRPKGRNFILVSKQDTALWAFDAASHVGLVNPYSQW<br>LFLITDSTDPAIFLPNVEDGQNISFLYNISDIETTANANSSSERV |

TABLE 2-continued

Amino acid sequences of the IR93a receptor from *Drosophila melanogaster* and orthologs thereof

| Arthropod Species | Amino Acid Sequence |
|---|---|
| | NDLPCYTSNLLQVYVKALHQLIREEETHYFQTTED DWIRSKPSAGDRRNNIFRTLQNMWKDATKCSSWLNWAMKA VEIKETRKPTLLDVGVWDAAHGLVVYDDFFPHFTGGLRQR VINVTTMEFPPWQIFERNSHGKVVRHTGLVLELTKELGNRLN FSVNVVEPADGKWGSRLSFSRWTGMVEQVRTGSVAFAA AGFTVTADRMSAVNFSMSLDAQPYTFMFARPKQLSRAYLFI QPYTPNAWITIFAMTIGAGPLIWAFNKITPFYDFYPDRP GSPIFSIWYNIWYCIGALLFQGQREMPIALSGRMVVGFFWLF VIVVLTAYSGNLVAFLTFPTYTNPINTLQDLIDNKGSL TWGILRGTALEDYLKTSDEKMYRELYEGAILHDTADDVLLD MIRNQQHVYIEWKTNLQWLMKQDFMKTNSCDFSLGTENF FLQQVALAFPRDSPILERVNLEIIYMQRGGLIEHWRQEFWPSA DRCSETATGGSDGDTIQAISVADMQGSFYVLFFGKTK NLGTLYNLFINGKFMYE (SEQ ID NO: 41) |
| DsecIr93a | MRQQFLVISAFHEDIIEIAETLNMFHVGNQWMIFVLDMVARD FDAGTVTINLDEGANIAFALNETEPNCQDSLNCTISEI SLALVDAISKITVEEESIYGEISDEEWEAIRFTKQEKQSEILGY MKEFLKTNAKCSSCARWRVETAITWGKSQENRKFRS TPQRDAKNRNFEFINIGYWTPVLGFVCQELAFPHIEHHFRNIT MDILTVHNPPWQILTKNSNGDIVEHKGIVMEIVKELS RALNFSYYLHEASSWKEEDSLSTSAGGNESDELVGSMTFRIP YRVVEMVQGNQFFIAAVAATLEDPDQKPFNYTQPISVQ KYSFITRKPDEVSRIYLFTAPFTVETWFCLMGIILLTAPTLYAI NRLAPLKEMRIVGLSTVKSCFWYIFGALLQQGGMYL PTADSGRLVVGFWWIVVIVLVTTYCGNLVAFLTFPKFQPGVD YLNQLEDHKDIVQYGLRNGTFFERYVQSTTREDFKHYL ERAKIYGSAQEEDIEAVKRGERINIDWRINLQLIVQRHFERDK ECRFALGRESFVDEQIAMIVPAQSAYLHLVNRHIKSM FRMGFIERWHQMNLPSAGKCNGKSAQRQVTNHKVNMDDM LGCFLVLLLGFTFALLIVCGEFWYRRFPASRKRRQFTN (SEQ ID NO: 42) |
| DsimIr93a | MRQQFLVISAFHEDIIEIAETLNMFHVGNQWMIFVLDMVARD FDAGTVTINLDEGANIAFALNETEPNCQDSLNCTISEI SLALVDAISKITVEEESIYGEISDEEWEAIRFTKQEKQSEILGY MKEFLKTNAKCSSCARWRVETAITWGKSQENRKFRS TPQRDAKNRNFEFINIGYWTPVLGFVCQELAFPHIEHHFRNIT MDILTVHNPPWQILTKNSNGDIVEHKGIVMEIVKELS RALNFSYYLHEASSWKEEDSLSTSAGGNESDELVGSMTFRIP YRVVEMVQGNQFFIAAVAATLDDPDQKPFNYTQPISVQ KYSFITRKPDEVSRIYLFTAPFTVETWFCLMGIILLTAPTLYAI NRLAPLKEMRIVGLSTVKSCFWYIFGALLQQGGMYL PTADSGRLVVGFWWIVVIVLVTTYCGNLVAFLTFPKFQPGVD YLNQLEDHKDIVQYGLRNGTFFERYVQSTTREDFKHYL ERAKIYGSAQEEDIEAVKRGERINIDWRINLQLIVQRHFERDK ECRFALGRESFVDEQIAMIVPAQSAYLHLVNRHIKSM FRMGFIERWHQMNLPSAGKCNGKSAQRQVTNHKVNMDDM QGCFLVLLLGFTFALLIVCGEFWYRRFRASRKRRQFTN (SEQ ID NO: 43) |
| DvirIr93a | MKEYLKANSKCASCAKWRFETAITWGKSQENRKFRMAPTR DTKNRNFEFINIGYWSPLLGFVCHELAFPHIDQHFRNITM DIVTVHNPPWQILTKDSRGAIVEHTGIVMEILKELSRALNFSY YLHEARSPDYEYSLAQSTNESDELMGSMTYRIPYRVV ELVQGSGYFMAAVAATIDEPHKKRFNYTQPISIQKYTFILRQP DEVSRIYLFTAPFTLETWGCLAGILLVTAPMLYIVNR LVPLQELQIRGLSTVKNCFWYIYGALLQQGGMYLPRADSGR LVVGFWWLVVIVLVTTYCGNLVAFLTFPKFQPGIDYLNQ LFDHKEIKQYGLRNGTFFEKYVHSTTRHDFKRFMERALVYN SSQSENIAAVKQGERINIDWRINLQLIVQQHFEQDKECR FALGKEDFVSEQIGLIVPSSSAYLHLINQHIDRLFRMGFIDRW HDTNLPSMDKCNGKHMQRQIANHKVNMDDMQGCFMVL LFGIIAALLVSCIEFWYYRFLVLNKGQSIAFAN (SEQ ID NO: 44) |
| DwilIr93a | MPKHEQKHQQFLVISKFHEDIIEIAETLNMFHVSNQWMFFVL EELRRDFDASTVTINLDEGANIAFALNETYPDCQDTLN CTISEVSMALVTSISKMISEEQSIYGEISDEEWESIRFTKQEKQ DELLEYMKDYLKLNSKCASCARWRIDTAITWGKTQE SRQFRTAPTRDAKNRNFDFINIGYWSPLLGFVVQELTFPHIEH HFRNITMDILTVHNPPWQILTKNSLGHIVESKGIVME IVRELSRALNFTYQLHEAKSWEDEYAISQSKNESEMELLGSM TYRIPSRVTELAQGNQYFLAAVAATIYDPEKRFFNFTQ PISVQKYTFITRQPDEVSRIYLFTAPFTQETWGCLVGIIILTAPL |

TABLE 2-continued

Amino acid sequences of the IR93a receptor from *Drosophila melanogaster* and orthologs thereof

| Arthropod Species | Amino Acid Sequence |
|---|---|
| | LYGINRLAPLEELRIRGLSTIKSCFWYVLGALLQQ<br>GGMYLPKADSGRLIVGFWWIVVIVLVTTYCGNLVAFLTFPK<br>YQPGIDYLTQLAHHKHISQYGLRNGTFFEKYTKTTTRKD<br>FKRFMEKAIIYNNAESERIDAVKSGQRINIDWRINLQLIVQQH<br>FEQDKECHFALGKEDFVDEQIGLVVPLNSAYLHLINL<br>HIDRMFRMGFIERWHQMNLPNSDKCNGKSVLRQITNHKVN<br>MNDMQGCFLVLIFGFIVAVLVASIEFWYYRYHLHHQKRKQ<br>SVFVN (SEQ ID NO: 45) |
| DyakIr93a | MRQQFLVISAFHEDIIEIAETLNMFHVGNQWMIFVLGMVGRD<br>FDVGAATINLDEGANIAFALNETDPNCQDSLNCTISEL<br>SLALVTSISKITVEEESIYGEISDEEWEAIRFTKQEKQAEILEY<br>MKDYLKNNAKCSSCARWRVETATTWGKSQENRKFRS<br>TPLRDAKNRNFEFINIGYWSPVLGFVCQELAFPHIEHHFRNIT<br>MDILTVHNPPWQILTKNSHGVIVEHKGIVMEIVKELS<br>RALNFSYYLHEASSWKEEYSLSTSAGSNESDELVGSMTFRIP<br>YRVVEMVQGNQFFIAAVAATVEDSEQKPFNYTLPISVQ<br>KYSFITRKPDEVSRIYLFTAPFTVETWFCLMGIILLTAPTLYAI<br>NRLAPLKEMRIVGLSTVKSCFWYIFGALLQQGGMYL<br>PTADSARLVVGFWWIVVIVLVTTYCGNLVAFLTFPKFQPGVD<br>YLNQLANHKDIVQYGLRNGTFFERYVQSSTREDFKHYL<br>ERARIYGSAQEEDIEAVKRGERINIDWRINLQLIVQRHFERDK<br>ECRFALGKESFVDEQIAMIVPAKSAYLHLVNRHINSM<br>FRMGFIERWHQMNLPSAGKCNGKSAQRQVTNHKVNMDDM<br>QGCFLVLLLGFTVALLIVCGEFWCRRFRASRERRQFIN (SEQ ID NO: 46) |
| MrotIr93a (*Megachili rotundata*) | MLSVLLLLWNVNYGNSFNDFPSLISTNVTMGTSLFSFLNDSY<br>YRSDRTITLINCLYYISDQAVVVDRSLFDSKEEYHNIA<br>GVIYDLITDTVKKEMQVGGIVVQVFRDGNVNLRQDYTILLSF<br>ASCYLTWRLHEAAANKELMHLAITDPDCPRIPETDGLS<br>VPLIMPGKELSQIFLDLRMTNILSWNVINILHDDTFDRDTISRV<br>MKAISDKLPNRQLSLVSRSIFTLKHEDTEMARKKAV<br>KKILDDFHVEQLGHCFLVIATVDMARSLRMVHPGSQWLYVV<br>TNTAPNRTNITSFVELLAEGGNVAFIYNATDFNDFCEVK<br>VTYYAKKLVQALAKALEYSLTNEIDMLKRVGGEDFEMIRLT<br>KRERRKEILTNFKMYLERDVLNSETVHGRCVLWKFTSSI<br>TWGNFFSHGKNVAHLLDIGTWTLAAGVITVNEKGERSYEGL<br>VFDVINHLSKKLNFTYTVILPEVNSTKPWSSSRFSKLGD<br>KINEMTMSNTRRVPKEVIKLVREKKVLLAACAYTVQEYEDTI<br>NFTVPTWFCLAVTVIIMGPILYLIHKYSPYSTKTSGLN<br>SSWQCVWYVYGALLQQGGMYLPQSDSARMLIGVWWLIVM<br>VVVATYSGSLVAFLTFPKMDASILTVEDLIARKDKITWGFP<br>NDSFLELYLRNTDEQKYQILLAYSERHNDTEEETFLMRKDLL<br>LTGGCHFSLSADEFLDEPIAMIIPQDSPYLAESGLMNK<br>WISEKMPMKDKCWEVPGSNQAVNKRKVNVADMQGIFFVLF<br>MVWSVVVHGYDNVGFDGWYQPVPHRPVDIITDVINDLGVR<br>ILQQYTSHGNVAFSPTGVAFVLAALYEGSAGRGRQQIADALG<br>LPRDRDITRIGFRDIHRRLRTYLNANGFLGGLTLNQEN<br>TNLRPEYEDILRFYGFDLSIPEDMNDTTIVPETEPTEKNIETET<br>VTGTVPSTSTTPVETLGTMTADVQNRFTQTTLPSAM<br>ESTVTVESTGAGETDVPEVSTMSSTTMASVTSPTTVPPVTLST<br>TIAPATSPTTITPVTPITTISPVTSPTTISPVTSPTT<br>ISPMTSPTTMSASTEPFMTTEDVLSTLTADDQPVTTQSSTSTS<br>ASTSATTSALPMESTIPTDSTITTESGVTELPESTTT<br>STITVPTTVNVMETSTSSTIPTQTGLPDVDANTVSTGSSNNQS<br>VSDEIGSTDSPITTIIDTGETGSNEQTTVESTTSGTI<br>NRRKRNIRAPRGFFSSYPDEGIWMQDLGIWKPYSSSLNEASV<br>RDSTEISFLVNGCDVSSVTASRYIAVLPFAYFPSLHAV<br>ALEFPPLDVRIIFTVHNSGSWNVSNLSFQDPRYNILLMMSTDRR<br>DTYRLARDLGGKSLRLLRKQLQATWVRATIPSFMLRG<br>FLGILDVFEPRAADLSPMTPDLGVYARDVQQSIGVNIRNYMK<br>PDRTHSRNGLFERAGPVPFTVVQPYLYFIIDAETSVTL IAGR (SEQ ID NO: 47) |
| NvitIr93a (*Nassonia vitripennis*) | MLLALLVLLAGWIEIGTGYNDFPSLMTANATMAVIVEKGFF<br>KSADNYRHTLDEISDVANAVIRKNMEISGIALHVFGDAD<br>VNLARDYTVLLSVASCQTTWHLFKRAQKEKLVYLAVTDPD<br>CPRLPEDAGISLPLTNPGEELPQIFLDLRTTGSLSWPKVN<br>LIHDDTFARDTISRVVKALSLELPDKRVSLSAQALFSTRFEKN<br>ENAMRQRVHRILSNYHVDQLGSCFMVVVTVDMVSIVM<br>EVAKSLRLVHPGSQWLYVISDAAGREAKVTSFAELLAEGEN<br>VAFVHNATKHVANCNMGLMCHVKELVRALAISLENSLLN<br>ELELYDRVTEEEFEVVRLSKAERKQEIVKSVNRELSYARAHT<br>SSCGKCVNWRFSSAITWGTSFASSEEKQRRESGEKRRR |

TABLE 2-continued

Amino acid sequences of the IR93a receptor from
*Drosophila melanogaster* and orthologs thereof

| Arthropod Species | Amino Acid Sequence |
|---|---|
| | ENSKRHSEDDLGEKSLGLGELLDAGTWSPGPGVNMSEPLFPH
VEHGFRGRSLPVSTFHNPPWQIIKYSNTGAQEYGGLIF
DVLNYLSLKLNFTYTVRLASSPAAEAPTRLPSAGDSSKSMDL
AAMSVAQKVPQEVVELVRSKQVFIAASAFTVGKNSGGL
NFTAAIVMQNYALLSAKPKPLSRALLFTAPYTNETWACLTSV
LIVIGPILYLTVKLSPRPRDIDNSLSLSTTWQCSWYVY
GALLQQGGMSLPKADSARLVIGTWWLVVMIVVATYSGNLIA
FLTFPRIDAPIDNVDDLLARSDAFHWSFPNGSALESYLI
AAVNDDPKYKQLLDGAERQDPSKPKQILDRVKAGNQVLID
WRISLAFLMREDLIDTGGCHFHVSAEDFMHENMAMIISGD
SPYLPLINDAIERMHESGLMKKWITEKMPMKDKCWEIAKTN
QEATNHKVDMGDMQGIFFVLAIGFVIAAIAIGVEFAWHK
RKEAFERSLIRPFVS (SEQ ID NO: 48) |
| RproIr93a
(*Rhodnius prolixus*) | MYPKFRYFENKLKEIVNSRIHKFLDDGSLSVIYNGRDLKSKE
DLTAIFSITSCEEMWNLYSNFTGNGIIFITITEPDCPR
LPQHVGTTLPVYERGSEISQLILDLRSKEKLDWQSVTIVHDNS
ISDKLVEKITLAVTKSLPITNSTCAISLYKIESSKND
VDVKRNKEIFNTISSLPSLEINRNFLILAEVDIIPVVYESAKSVG
LVDPTSKWLFIGMKTDFSNHNNINKFIHIVGDGEN
VAFIYNSTDDTGLCLNNLLCHAEELVGNLAVALDYSIEEEIRL
SEQVSDEEWEVIKPTKQERREAILNFMKNKQDDIGTC
DNCTLWYFKSSESWGMDYFHKGNASLLEVGYWAPKPGPVL
VDELFPNIVHGFRGRSIPIATFHYPPWQVIKYDDVGKPTE
YKGLVFEIINELSNSLNFTYDVIIISNRTVLKSITNSLKIDEKLG
EVSLDGRIETSAWKQALKLLENKRVLIAAAAFTVT
EDRKKEVNFTYSISIEAYAFLVSRPKELSRALLFILPFSSDTWL
CIIGAILLMTPLLCFVHRISPFYDHYSHRGKGGFTK
MMNCFWYLYGALLQQGGGIMPEADSGRLVIGTWWLVVLV
VVTTYSGNLVAFLTFPKMDKIISNVDQLMERRESLSWGMPE
ISTLHSILKSTDNSKLNALSDGAKLHSKLTPEIISDIQNGKHIYI
DRKTILAFVMKQEFIRTNRCDFSLGEEEFLEEHLA
MALPVHTPYLKIFNSRIYEMHKVGLIQKWLVDYLPKRDKCW
DAKLSGESNTHTVNMDDMQG (SEQ ID NO: 49) |
| TurtIr93a
(*Tetranychus urticae*) | MINHLFFLIYILLSPVSCQSNKDDSEQVINLGILIKYDDEISKAI
RNETLFHLIGEIESFSIDNITIKVDLIDGDSDFDA
LVDGEPRNCNKYIGLISVLPCSLTKSLYSLIRDHCSSTLIIAIHD
RNCIRPSRDQGIGFPILSSVDHVVPMLIDMRHDFL
RKWDHINLIHDDTIDVMALHDLVDGLSAVHGPEIMPSTVTSY
HIGLSLKNKIEITSDYRDINDSQVTLFSYENVKTDTLD
LKAQVVDHITDEHKYFIVIAHSKHIKEIIKLAHSRSLLGSPRK
WIFIFSDNQEDPAYWSQLSPILATTQTAIVIREESEY
GRCSEMSEGCQFRLAVETLKSTLRKVALTADYDFTDVDMKR
RTRNRLLTEMRLQLGSDESVSSRYCGNCDRYSLQMFEKA
IIGESIKYKRKPYSTSHWSQTQFDDDFESGIKITRTGEWTPFKG
LIQSSDPIPVDIVNGGGQVYKVGVVNQRPLVNVELI
DGKCVVNGTTIELLTIISSRMNFTIEYVCWSDAKDDKIGDSIS
DEGWDGLLGKLAEGKVDLAANGIWQTPSRIKSSAFEF
LSAYDVDIVSLVVKKQPEDEKFLFIFNLSFSNIHLQQTWICVIL
TMIVIGPVLWTVHRSSIYYDYYGLNDGKGFFKLSNC
VWYCYGAMVQQGGDILPQAISGRVLIATWWLFVIVTVTTYS
GNLVALLTFPKIIQPIQNAEDLANTWGVSAGAAASGALH
EMIQILEYSELSLLRDKMSYYDFEKDKYKIFDEISSGSLGYLM
TEYEARYWVSTEYTRTGVCGMHVARDAVYHTPIHMVA
RKDAFPPSLLKELNRQMTLLTRAGIAIYWRLWYQTPGNDCM
YPLIIHAGDVKKIDVVHMIGIYLFLACGIGIGFLILISE
FITKYYISSDDDGLKMKTAKRQFSGSSGIQDVLKSIYTRYNAN
PSYSKWASNVDYYNSAEGRSTGESKLVKLSFNHPTIN
RDTKESFARSKWIQGASAVRAKASPNLYYDQFGPMYLNQIR
GIYNDPDNFQYPFGGLRPK (SEQ ID NO: 50) |
| *Phlebotomus papatasi* | LIAIILDQEYLDQKYDPVYTEVQVIIERVLREDLKNGGLYVTY
YSWTSVNLKKDYTAVLVVSNCDNTWRVFREARADTLLLLA
LTDPDCPRLPPSEAIMVIPLTSGGEELPQVLLDLKSSQALKWK
SAIVLHDDTFARDMISRVAIAVTSESPDGYVKPMSVSLFKIRA
HIQEWERRKSIRRTLLSLPTNYIGRNFLAIVTTVIMENIMEVA
KDLGMVEPFSQWMYVISDTNSERNNISSVLPLIGEGENVAFA
YNVTSKDPACKAGITCHCAELLRSFVLALSRMIREEKAVYGQ
ISDEEWETIRPTKKERRDMLLETMRLILKSTSVCSNCTTWKV
QAGEYWGTEYEEEWSIVNTPRRSSKFLDVGTWKPNDGVQLN
DVLFPHVSNGFRGKNLHIVTYHNPPWQIIAYNESGVPGVMRG
VVMDILNEMAKKLNFTYTMHVIPVSIPKANETEELSYNVSST
EEGQLPTTTIPMEILNLVSQDKVFLAAVGATVNEKYKRFINY
TIPISIQPYNFIVSRPRELSRLYLFMAPFTKETWLCLAACIVVM |

TABLE 2-continued

Amino acid sequences of the IR93a receptor from
Drosophila melanogaster and orthologs thereof

| Arthropod Species | Amino Acid Sequence |
|---|---|
| | GPLLYLVNRFSPFYEQKGFDIARLGLNRINNCFWYIYGALLQ<br>QGNFWVGGMYLPQADSGRIIIGTWWLVVIVLVTTYCGNLVA<br>FLTFPKIEIPITTVGQLVGKSGAVSWSTKSGTFLEEFLAETDEP<br>KYKKLLDGMAFNTETSSDTIENVRQGKHVYIDWKSNLQYIM<br>KKEFLVNDRCDFALGVEDFLDEQIAIIMPRDSAYLNLINSEITR<br>LHQMGFIQRWLKEYLPKKDRCWNVGKAIEVNNHTVNLDDM<br>QGSFLVLFIGCVLGACVIILECMWFKRRELKEQVIIKPFVK<br>(SEQ ID NO: 51) |

Variations of the Ir25a Receptor

Homologs and Orthologs

A homolog or an ortholog or any known or putative Ir25a receptor may also be used in the methods and systems described herein. A homolog may be a protein whose nucleic acid sequence that encodes that protein has a similar sequence to the nucleic acid sequence that encodes a known or putative Ir25a receptor, or a protein whose amino acid sequence is similar to the amino acid sequence of a known or putative Ir25a receptor. Ir25a homologs may have functional, structural or genomic similarities to any known or putative Ir25a receptor.

In some embodiments, a homolog and/or ortholog of an Ir25a receptor is a protein whose nucleic acid sequences have at least 30%, 40%, 50%, 60%, 65%, 70%, 75%, 80%, 85%, 90%, 91%, 92%, 93%, 94%, 95%, 96%, 97%, 98%, or 99% identity to the nucleic acid sequence encoding any known or putative Ir25a receptor. In another embodiment, a homolog of an Ir25a receptor is a protein whose amino acid sequence has at least 30%, 40%, 50%, 60%, 65%, 70%, 75%, 80%, 85%, 90%, 91%, 92%, 93%, 94%, 95%, 96%, 97%, 98%, or 99% identity to the amino acid sequence encoding any known or putative Ir25a receptor.

The Ir25a receptor may be from one or more arthropod species. For example, in certain embodiments, the Ir25a receptor is a homolog or ortholog of the Ir25a receptor from Drosophila melanogaster. In some embodiments, the Ir40a receptor has at least 50%, 60%, 65%, 70%, 75%, 80%, 85%, 90%, 91%, 92%, 93%, 94%, 95%, 96%, 97%, 98%, or 99% sequence identity to a polypeptide encoding an Ir25a receptor from Drosophila melanogaster. One of skill in the art will be able to readily identify Ir25a receptors, homologs thereof, and orthologs thereof that may be used in the methods and compositions of the present disclosure.

While Drosophila melanogaster is one reference point for homology, it should be understood that other known or putative receptors may serve as reference points for homology to the Ir25a receptor. For example, known or putative Ir25a receptors may include Mayetiola destructor\Mdes015305, Aedes aegypti Aaeg\AAEL005012, Anopheles gambiae Agam\AGAP000256, Culex quinquefasciatus Cqui\ CPIJ009222, Heliconius melpomene\HMEL002270, Manduca sexta\Msex000431, Bombyx mori (Silkmoth) Bmor\BGIBMGA010960, Tribolium castaneium\TC000374, Atta cephalotes\ACEP27701, Acromyrmex echinatior\AECH20041, Solenopsis invicta\SINV12854, Pogonomyrmex barbatus\PB25907, Camponotus floridanus\CFLO19836, Linepithema humile\LH25937, Harpegnathos saltator\HSAL21373, Apis mellifera\GB42136, Apis mellifera\GB50521, Megachili rotundata\MROT 00005973, Nassonia vitripennis\Nasvi2EG001464, Acyrthosiphon pisum (Pea aphid) Apim\ACYPI20767,ACYPI43510, Rhodnius prolixus\RPTMP07829, Pediculus humanus (Human body louse) Phum\PHUM513120, Tetranychus urticae\tetur02g05540, and Ixodes scapularis\ISCW007957. Each sequence associated with the foregoing accession numbers is incorporated herein by reference.

Modified Receptors

In other embodiments, modified Ir40a receptors, modified Ir93a receptors, and/or modified Ir25a receptors may also be used in the methods and systems described herein. Modified polypeptides refer to polypeptides that have been altered relative to the endogenous sequence of the polypeptide in the organism from which they originated. Modifications may include, for example, deletion or addition of sequence information, attached of probes or molecular dyes to the polypeptide, or any other polypeptide modifications known in the art.

A modified receptor, such as a modified Ir40a receptor, a modified Ir93a receptor, and/or a modified Ir25a receptor functions in a substantially similar fashion as an unmodified receptor, such as an unmodified Ir40a receptor, an unmodified Ir93a receptor, and/or an unmodified Ir25a. For example, a modification to an Ir40a, an Ir93a receptor, and/or an Ir25a receptor may include addition of sequence information to the full length polypeptide sequence, or removal of sequence information from the full length polypeptide sequence. In some embodiments, modified Ir40a receptors, modified Ir93a receptors, and/or modified Ir25a receptors may contain additional sequence information in the polypeptide. For example, a modified Ir40a receptor, a modified Ir93a receptor, and/or a modified Ir25a receptor may include reporter polypeptides such as GFP. In some embodiments, a modification to a receptor, such as modified Ir40a receptors, modified Ir93a receptors, and/or modified Ir25a receptors, may include a truncation of the receptor. Truncated receptors may include, for example, a polypeptide composed of a ligand-binding domain. In some embodiments, a modified receptor, such as modified Ir40a receptors, modified Ir93a receptors, and/or modified Ir25a receptors, may have both additional sequence information and deleted sequence information relative to the full-length polypeptide. For example, a modified Ir40a receptor may include a truncated Ir40a polypeptide composed of a ligand-binding domain fused to a reporter polypeptide, such as GFP.

In some embodiments, modified Ir40a receptors, modified Ir93a receptors, and/or modified Ir25a receptors may also be used in the methods and systems described herein. Modified Ir93a receptors and/or modified Ir25a receptors may be used either alone or in any combination with a modified Ir25a receptor in the methods and compositions described herein.

Arthropod Species

Ir40a receptors, Ir93a receptors, and Ir25a receptors may be found in certain arthropods. One of skill in the art would recognize that arthropods are invertebrate animals characterized as having an exoskeleton, a segmented body, and jointed appendages. Arthropods belong to the Phylum Arthropoda under Kingdom Animalia. The Phylum of Arthropoda, or an "arthropod," includes any invertebrate animal from the Classes of Insecta, Arachnida, Diplopoda, Chilopoda, Crustacea, and Xiphosura. In some embodiments, arthropod may refer to insects and arachnids that are exoparasitic sanguinivorous feeding pests, including any insect from the Order Diptera, such as mosquitoes, and any arachnid from the Order Ixodida, such as ticks. Examples of mosquitoes include *Anopheles*, Mimomyia, *Culiseta*, Orthopodomyia, *Mansonia, Culex*, Heizmannia, *Aedes*, Armigeres, Uranotaenia, Tripteroides, Topomyia, Malaya, and Toxorhynchite. As a specific type of such mosquito, an example of the *Anopheles* includes *anopheles* sinesis wiedemann. Examples of the *Culex* include *Culex quinquefasciatus, Culex pipiens pallens, Culex pipiens* molestus, and *Culex tritaeniorhynchus*. Examples of the *Aedes* include *Aedes albopictus* and *Aedes aegypti*. An example of the Armigeres includes Armigeres subalbatus.

It should be understood that only certain arthropods have Ir40a receptors, Ir93a receptors, and/or Ir25a receptors. Ir40a receptors, Ir93a receptors, and Ir25a receptors are conserved in species such as *Drosophila*, mosquitoes, head lice; however, it is not present in the honey bee. Specific examples of arthropods which have an Ir40a, an Ir93a receptor, and/or an Ir25a receptor include *Drosophila melanogaster, Drosophila grimshawi, Daphnia pulex, Anopheles gambiae, Zootermopsis nevadensis, Pediculus humanus, Acyrthosiphon pisum, Bombus terrestris, Harpegnathos saltator, Linepithema humile, Camponotus floridanus, Pogonomyrmex barbatus, Solenopsis invicta, Acromyrmex echinatior, Atta cephalotes, Tribolium castaneum, Bombyx mori, Aedes aegypti, Culex quinquefasciatus, Ixodes scapularis*, and *Mayetiola destructor.*

Additional Polypeptides

Additional polypeptides may also be co-expressed with the Ir40a receptor, the Ir93a receptor, and/or the Ir25a receptor in a host cell or organism. These additional polypeptides may include, for example, a co-receptor, a chaperone protein, or any combinations thereof.

Expression of a co-receptor to any one of the Ir40a receptors, Ir93a receptors, and/or Ir25a receptors described herein at the cell surface may enhance the respective receptor's sensitivity to volatile compounds, thus enhancing the sensitivity of the screening methods described herein. Expression of these additional polypeptides in addition to the ionotropic receptor may be beneficial with regards to enhancing receptor sensitivity without disrupting receptor specificity to a given compound/ligand. For example, an Ir25a receptor may be co-expressed with an Ir40a receptor in a host cell or organism. The Ir25a polypeptide may be recombinant to the host cell or organism. The Ir25a polypeptide may be a modified Ir25a receptor. In some embodiments, an Orco receptor may be co-expressed with an Ir40a receptor in a host cell or organism. The Orco polypeptide may be recombinant to the host cell or organism. The Orco polypeptide may be a modified Orco receptor.

Expression of a chaperone in the Ir40a-expressing cell, an Ir93a-expressing cell, and/or an Ir25a-expressing cell may enhance the sensitivity of the screening methods described herein. Expression of these additional polypeptides in addition to the respective ionotropic receptor may be beneficial with regards to enhancing receptor sensitivity without disrupting receptor specificity to a given compound/ligand. In some embodiments, an RTP1 chaperone protein may be co-expressed with an Ir40a receptor in a host cell or organism. The RTP1 polypeptide may be recombinant to the host cell or organism. The RTP1 polypeptide may be a modified RTP1 polypeptide.

Screening Assays

In Vitro

The methods described herein may be performed as part of an in vitro assay. For example, an isolated Ir40a receptor may be isolated and incubated with a candidate compound for use in an in vitro assay. In other embodiments, an isolated Ir93a receptor may be isolated and incubated with a candidate compound for use in an in vitro assay. In other embodiments, an isolated Ir25a receptor may be isolated and incubated with a candidate compound for use in an in vitro assay. In other embodiments, an Ir40a receptor and an Ir93a receptor may be isolated and incubated with a candidate compound for use in an in vitro assay. In other embodiments, an Ir40a receptor and an Ir25a receptor may be isolated and incubated with a candidate compound for use in an in vitro assay. In other embodiments, an Ir93a receptor and an Ir25a receptor may be isolated and incubated with a candidate compound for use in an in vitro assay. In other embodiments, an Ir40a receptor, an Ir93a receptor, and an Ir25a receptor may be isolated and incubated with a candidate compound for use in an in vitro assay. In some embodiments, an Ir93a receptor and/or an Ir25a receptor may be isolated and incubated, either alone or in any combination with an Ir40a receptor, with a candidate compound for use in an in vitro assay. Incubation can be accomplished using any suitable methods known in the art.

Any suitable in vitro assay format may be used. For example, an isolated Ir40a receptor, an isolated Ir93a receptor, and/or an isolated Ir25a receptor or a candidate compound may be non-diffusibly bound to an insoluble support having isolated sample-receiving areas such as a microtiter plate or an array. Suitable insoluble supports may include, for example, microtiter plates, arrays, membranes and beads. These supports may be made of glass, plastic (e.g., polystyrene), polysaccharides, nylon, or nitrocellulose, and similar materials. Additional methods for assembling in vitro activity assays will be apparent to those skilled in the art.

Measuring in vitro activity of an isolated receptor, such as an isolated Ir40a receptor or modification thereof, an isolated Ir93a receptor or modification thereof, and/or an isolated Ir25a receptor or modification thereof, may involve incubating the one or more receptors with a radiolabeled compound. Methods of generating radiolabeled compounds are well known in the art, such as incorporation of radioactive carbon into the compound molecule. Measuring an interaction between the receptor and the radioactive compound, such as physical binding of the compound to the receptor, can be assayed using techniques such as gel shift mobility assays or measuring radiolabeled compound binding to the purified receptor in a plate or well.

The Ir40a receptor, the Ir93a receptor, and/or the Ir25a receptor for use in in vitro assays may be isolated from a cell or an organism. One of skill in the art would recognize the methods and techniques for isolating and purifying polypeptides. The one or more isolated receptor polypeptides may be obtained, for example, by extraction from a natural source (e.g., an arthropod tissue or cell sample) by purification techniques such as centrifugation, column chromatography, polyacrylamide gel electrophoresis, and HPLC analysis; by expression of a recombinant nucleic acid encoding the receptor polypeptide; or by chemically synthesizing the protein. Purity can be measured by any appropriate method, e.g., column chromatography, polyacrylamide gel electrophoresis, or HPLC analysis.

An isolated receptor generally refers to an isolated receptor substantially free of naturally-associated components (such as other proteins, lipids, or other cell membrane components) when it is separated from those naturally-associated components. For example, a polypeptide which is isolated and from a cell from which it naturally originates or is chemically synthesized or produced in a cellular system different from the cell from which it naturally originates (heterologous expression) will be substantially free from its naturally associated components.

In Vivo

The methods described herein may be performed as part of an in vivo assay. Organisms and cells expressing an Ir40a receptor or modification thereof, an Ir93a receptor or modification thereof, and/or an Ir25a receptor or modification thereof have been discussed above. Organisms and cells expressing an Ir93a receptor and/or an Ir25a receptor, expressed either alone or in any combination with an Ir40a receptor, may also be used herein. Methods of monitoring activity of a biological receptor in an in vivo system are well-known in the art.

Measuring in vivo activity of an Ir40a receptor or modification thereof in an organism or in a cell may involve measuring electrophysiological parameters of the Ir40a receptor. Electrophysiological parameters may be measured both before and after contacting an Ir40a-expressing cell with a compound. Electrophysiological parameters may include measuring extracellular voltage or intracellular voltage, measuring potential changes, or similar parameters known in the art. Various methods of measuring electrophysiological parameters and/or measuring electrical potential changes are known in the art. Such methods may include, for example, the use of a patch clamp or the use of reporter nanoparticles or nanocrystals. Note that these methods of measuring electrophysiological parameters may also apply to measuring activity of an Ir93a receptor and/or an Ir25a receptor, either alone or in any combination with an Ir40a receptor.

Measuring in vivo activity of an ionotropic receptor or modification thereof, such as a modified Ir40a receptor, Ir93a receptor, and/or Ir25a receptor, in an organism or in a cell may involve measuring changes in intracellular or extracellular ion levels. Ion levels may be measured both before and after contacting an Ir40a-expressing cell with a compound. Ions whose concentrations may be measured may include, for example, calcium, sodium, potassium, chloride, or any other ion which may serve as a proxy of Ir40a receptor activity. Methods of measuring the concentration of an ion in a cellular context are well known in the art and described herein. Measuring changes in intra- or extracellular ion concentration may involve using fluorescent voltage sensor dyes or other ion-specific molecular probes. Note that these methods of measuring in vivo activity of an ionotropic receptor may also apply to measuring activity of an Ir93a receptor and/or an Ir25a receptor, either alone or in any combination with an Ir40a receptor.

Measuring in vivo activity of an Ir40a receptor or modification thereof in an organism or in a cell may involve measuring changes in transcription of activity-dependent gene promoters or directly assaying changes in transcription of genes. It is well known that the activity of ion channels, such as Ir40a receptors, in a cell can impact cellular gene expression. A modulated activity of an Ir40a receptor, such as in response to incubation with a compound, may impact the expression of one or more genes in the cell and this change in gene expression may be assayed using conventional techniques. Methods of monitoring gene expression in a cell may include quantitative reverse transcription polymerase chain reaction (qRT-PCR) and in situ hybridization. Additionally, changes in the expression of all genes may be assayed by generating whole-genome transcriptional profiles using next generation sequencing technologies, such as the Illumina sequencing platform. Note that these methods of measuring changes in transcription of activity-dependent gene promoters may also apply to measuring activity of an Ir93a receptor and/or an Ir25a receptor, either alone or in any combination with an Ir40a receptor.

Screening Systems

Provided herein are also systems used for identifying one or more compounds that are repellents for at least one arthropod species, based on modulation of the activity of an Ir40a receptor. Also provided herein are also systems used for identifying one or more compounds that are repellents for at least one arthropod species, based on modulation of the activity of an Ir93a receptor. Also herein are also systems used for identifying one or more compounds that are repellents for at least one arthropod species, based on modulation of the activity of an Ir25a receptor. Further provided herein are systems used for identifying one or more compounds that are repellents for at least one arthropod species, based on modulation of the activity of an Ir40a receptor, an Ir93a receptor, and/or an Ir25a receptor.

In one embodiment, the system includes: a) a sample that includes an Ir40a receptor, an Ir93a receptor, and/or an Ir25a receptor; and one or more compounds that each is a repellent for at least one arthropod species, wherein the one or more compound each modulates the activity of the receptor. In certain embodiments, the receptor is an Ir40a receptor, and the system may further include an Ir93a receptor and/or an Ir25a receptor, either alone or in any combination with the Ir40a receptor. In certain embodiments, the receptor is an Ir93a receptor, and the system may further include an Ir25a receptor and/or an Ir40a receptor, either alone or in any combination with the Ir93a receptor. In certain embodiments, the receptor is an Ir25a receptor, and the system may further include an Ir93a receptor and/or an Ir40a receptor, either alone or in any combination with the Ir25a receptor.

In another embodiment, the system includes: a) a sample that includes an Ir40a receptor, an Ir93a receptor, and/or an Ir25a receptor; and b) a plurality of candidate compounds, wherein at least one of the candidate compounds is a repellent for at least one arthropod species, and wherein the at least one repellent compound modulates the activity of the receptor. In certain embodiments, the receptor is an Ir40a receptor, and the system may further include an Ir93a receptor and/or an Ir25a receptor, either alone or in any combination with the Ir40a receptor. In certain embodiments, the receptor is an Ir93a receptor, and the system may further include an Ir25a receptor and/or an Ir40a receptor, either alone or in any combination with the Ir93a receptor. In certain embodiments, the receptor is an Ir25a receptor, and the system may further include an Ir93a receptor and/or an Ir40a receptor, either alone or in any combination with the Ir25a receptor.

The sample may include a cell in which Ir40a, Ir93a, and/or Ir25a are expressed, as described above. The Ir40a receptor, Ir93a receptor, and/or Ir25a receptor may be provided with other polypeptides, such as co-receptor(s) and chaperone protein(s), in the sample. The system may include a cell in which an Ir93a receptor and/or an Ir25a receptor, either alone or in any combination with an Ir40a receptor, is expressed.

Repellent Compounds and Compositions Thereof

Provided herein are also the one or more compounds identified according to any of the methods or systems described herein.

Compounds identified by the methods or systems described herein may be perceived by the olfactory system, or both the olfactory and gustatory systems. For example, with reference to FIG. 3, perception by the olfactory system may be transduced from Ir40a receptors through Ir40a+ sacculus neurons, whereas perception by the gustatory pathway may be transduced through Bitter GRN receptors.

The compounds identified by the methods or systems described herein modulate the activity of the Ir40a receptor, the Ir93a receptor, and/or the Ir25a receptor, either directly or indirectly. For example, some compounds may be ligands, binding to certain parts of the Ir40a receptor. Some compounds may be agonists of the Ir40a receptor, in which the agonist causes activation of the neuron downstream of the Ir40a. Additionally, some compounds may be ligands for or agonists of the Ir93a receptor and/or the Ir25a receptor.

Compounds that activate Ir40a receptor, the Ir93a receptor, and/or the Ir25a receptor, alone or in combination, may be repellants for arthropods, such as flies (including *Drosophila melanogaster*) or mosquitoes. The arthropod repellents identified according to the methods or systems described herein may be formulated into a repellent for topical application, such as in the form of a lotion, cream, spray or dust. In some embodiments, the repellent may be included in, for example, a vaporizer, a treated mat, treated outerwear, an oil, a candle, or a wicked apparatus.

ENUMERATED EMBODIMENTS

The following enumerated embodiments are representative of some aspects of the invention.

1. A method for identifying a compound that is a repellent for at least one arthropod species, comprising identifying a compound that modulates the activity of at least one receptor selected from the group consisting of an Ir40a receptor, an Ir93a receptor, and an Ir25a receptor.
2. The method of embodiment 1, wherein the at least one receptor is from an arthropod.
3. The method of embodiment 1 or 2, wherein the at least one receptor is from an insect.
4. The method of any one of embodiments 1 to 3, wherein the at least one receptor has at least 50% sequence identity to a polypeptide encoding a receptor from *Drosophila melanogaster* or an ortholog thereof.
5. The method of embodiment 4, wherein the ortholog of *Drosophila melanogaster* is selected from the group consisting of *Aedes aegypti, Anopheles gambiae, Culex quinquefasciatus, Acyrthosiphon pisum, Bombyx mori, Tribolium castenium, Pediculus humanus, Ixodes scapularis,* and *Phlebotomus papatasi*.
6. The method of any one of embodiments 1 to 5, wherein the compound is identified in an in vitro assay or in vivo assay.
7. The method of any one of embodiments 1 to 6, wherein the modulation of the activity of the at least one receptor is determined by measuring changes in one or more electrophysiological parameters, measuring changes in calcium levels, measuring electrical potential changes, measuring changes in transcription of activity-dependent gene promoters, or any combination thereof.
8. The method of any one of embodiments 1 to 7, wherein the modulation in the activity of the at least one receptor is an increase in the activity of the at least one receptor.
9. The method of any one of embodiments 1 to 7, wherein the at least one receptor is an Ir40a receptor.
10. The method of embodiment 9, wherein modulation in the activity of the at least one receptor is an increase in the activity of the Ir40a receptor.
11. The method of embodiment 9 or 10, wherein the compound further modulates the activity of an Ir93a receptor.
12. The method of any one of embodiments 9 to 11, wherein the compound further modulates the activity of an Ir25a receptor.
13. The method of embodiment 9 or 10, wherein the compound further modulates the activity of an Ir93a receptor and an Ir25a receptor.
14. The method of any one of embodiments 1 to 7, wherein the receptor is an Ir93a receptor.
15. The method of embodiment 14, wherein modulation in the activity of the receptor is an increase in the activity of the Ir93a receptor.
16. The method of embodiment 14 or 15, wherein the compound further modulates the activity of an Ir25a receptor.
17. A method of identifying a compound that is a repellent for at least one arthropod species, comprising:
    a) contacting at least one receptor or a receptor-expressing neuron comprising at least one receptor with a candidate compound, wherein the at least one receptor is selected from the group consisting of an Ir40a receptor, an Ir93a receptor, and an Ir25a receptor;
    b) measuring the activity of the at least one receptor;
    c) comparing the activity of the at least one receptor after contact with the candidate compound to the activity of the at least one receptor in the absence of the candidate compound; and
    d) identifying a compound that is a repellent for at least one arthropod species by determining whether or not the candidate compound modulates the activity of the at least one receptor.
18. The method of embodiment 17 wherein the at least one receptor or receptor-expressing neuron is from an arthropod.
19. The method of embodiment 17 or 18, wherein the at least one receptor or receptor-expressing neuron is from an insect.
20. The method of any one of embodiments 17 to 19, wherein the at least one receptor has at least 50% sequence identity to a polypeptide encoding a receptor from *Drosophila melanogaster* or an ortholog thereof.
21. The method of embodiment 20, wherein the ortholog of *Drosophila melanogaster* is selected from the group consisting of *Aedes aegypti, Anopheles gambiae, Culex quinquefasciatus, Acyrthosiphon pisum, Bombyx mori, Tribolium castenium, Pediculus humanus, Ixodes scapularis,* and *Phlebotomus papatasi*.
22. The method of any one of embodiments 17 to 21, wherein the at least one receptor or receptor-expressing neuron and the candidate compound are contacted in vitro or in vivo.
23. The method of any one of embodiments 17 to 22, wherein the at least one receptor is expressed in a cell.

24. The method of any one of embodiments 17 to 23, wherein the at least one receptor is expressed in an arthropod cell.
25. The method of any one of embodiments 17 to 24, wherein the at least one receptor is expressed in an insect cell.
26. The method of any one of embodiments 17 to 25, wherein the at least one receptor is expressed in a cell from *Drosophila melanogaster* or an ortholog thereof.
27. The method of any one of embodiments 17 to 26, wherein the at least one receptor is expressed in a neuron or an oocyte.
28. The method of any one of embodiments 17 to 27, wherein the at least one receptor is expressed in an isolated cell.
29. The method of any one of embodiments 17 to 28, wherein the at least one receptor is provided with a co-receptor or chaperone protein, or wherein the receptor-expressing neuron further expresses a co-receptor or chaperone protein.
30. The method of any one of embodiments 17 to 29, wherein the activity of the at least one receptor is measured by one or more electrophysiological parameters, calcium levels, electrical potential, transcription of activity-dependent gene promoters, or any combination thereof.
31. The method of any one of embodiments 17 to 30, wherein the modulation of the activity of the at least one receptor is an increase in the activity of the at least one receptor.
32. The method of any one of embodiments 17 to 31, wherein the at least one receptor is an Ir40a receptor.
33. The method of embodiment 32, wherein modulation of the activity of the at least one receptor is an increase in the activity of the Ir40a receptor.
34. The method of embodiment 32 or 33, wherein, in step (a), the candidate compound further contacts an Ir93a receptor.
35. The method of any one of embodiments 32 to 34, wherein, in step (a), the candidate compound further contacts an Ir25a receptor.
36. The method of embodiment 32 or 33, wherein in step (a), the candidate compound further contacts an Ir93a receptor and a an Ir25a receptor.
37. The method of any one of embodiments 17 to 30, wherein the receptor is an Ir93a receptor.
38. The method of embodiment 37, wherein modulation in the activity of the receptor is an increase in the activity of the Ir93a receptor.
39. The method of embodiment 37 or 38, wherein, in step (a), the candidate compound further contacts an Ir25a receptor.
40. A method of identifying a compound that is a repellent for at least one arthropod species, comprising:
    a) providing a sample comprising at least one full-length or partial receptor protein from *Drosophila melanogaster* or an ortholog thereof, wherein the at least one receptor protein is selected from the group consisting of an Ir40a receptor, an Ir93a receptor, and an Ir25a receptor;
    b) contacting the sample with a candidate compound;
    c) measuring the activity of the at least one receptor protein in the sample;
    d) comparing the activity of the at least one receptor protein after contact with the candidate compound to the activity of the at least one receptor protein in the absence of the candidate compound; and
    e) identifying a compound that is a repellent for at least one arthropod species by determining whether or not the candidate compound modulates the activity of the at least one receptor protein.
41. The method of embodiment 40, wherein the at least one receptor protein has at least 50% sequence identity to a polypeptide encoding the receptor from *Drosophila melanogaster* or an ortholog thereof.
42. The method of embodiment 41, wherein the ortholog of *Drosophila melanogaster* is selected from the group consisting of *Aedes aegypti, Anopheles gambiae, Culex quinquefasciatus, Acyrthosiphon pisum, Bombyx mori, Tribolium castenium, Pediculus humanus, Ixodes scapularis,* and *Phlebotomus papatasi.*
43. The method of any one of embodiments 40 to 42, wherein the sample and the candidate compound are contacted in vitro or in vivo.
44. The method of any one of embodiments 40 to 43, wherein the sample further comprises a co-receptor or chaperone protein.
45. The method of any one of embodiments 40 to 44, wherein the activity of the at least one receptor protein is measured based on one or more electrophysiological parameters, calcium levels, electrical potential, transcription of activity-dependent gene promoters, or any combination thereof.
46. The method of any one of embodiments 40 to 45, wherein the modulation of the activity of the at least one receptor protein is an increase in the activity of the at least one receptor protein.
47. The method of any one of embodiments 40 to 45, wherein the at least one receptor protein is an Ir40a receptor.
48. The method of embodiment 47, wherein the modulation of the activity of the at least one receptor protein is an increase in the activity of the Ir40a receptor.
49. The method of embodiment 47 or 48, wherein the sample further comprises a full-length or partial Ir93a receptor protein from *Drosophila melanogaster* or an ortholog thereof.
50. The method of any one of embodiments 47 to 49, wherein the sample further comprises a full-length or partial Ir25a receptor protein from *Drosophila melanogaster* or an ortholog thereof.
51. The method of embodiment 47 or 48, wherein the sample further comprises a full-length or partial Ir93a receptor protein from *Drosophila melanogaster* or an ortholog thereof, and a full-length or partial Ir25a receptor protein from *Drosophila melanogaster* or an ortholog thereof.
52. The method of any one of embodiments 40 to 45, wherein the at least one receptor protein is an Ir93a receptor.
53. The method of embodiment 52, wherein modulation in the activity of the at least one receptor protein is an increase in the activity of the Ir93a receptor.
54. The method of embodiment 52 or 53, wherein the sample further comprises a full-length or partial Ir25a receptor protein from *Drosophila melanogaster* or an ortholog thereof.
55. A system, comprising:
    a) a sample comprising at least one receptor or a receptor-expressing neuron comprising at least one receptor, wherein the at least one receptor is selected from the group consisting of an Ir40a receptor, an Ir93a receptor, and an Ir25a receptor; and b) one or more compounds that each is a repellent for at least one arthropod species, wherein the one or more compounds each modulates the activity of the at least one receptor.

56. The system of embodiment 55, wherein the at least one receptor or receptor-expressing neuron is from an arthropod.

57. The system of embodiment 55 or 56, wherein the at least one receptor or receptor-expressing neuron is from an insect.

58. The system of any one of embodiments 55 to 57, wherein the at least one receptor has at least 50% sequence identity to a polypeptide encoding a receptor from *Drosophila melanogaster* or an ortholog thereof.

59. The system of embodiment 58, wherein the ortholog of *Drosophila melanogaster* is selected from the group consisting of *Aedes aegypti, Anopheles gambiae, Culex quinquefasciatus, Acyrthosiphon pisum, Bombyx mori, Tribolium castenium, Pediculus humanus, Ixodes scapularis*, and *Phlebotomus papatasi*.

60. The system of any one of embodiments 55 to 59, wherein the at least one receptor is expressed in a cell.

61. The system of any one of embodiments 55 to 60, wherein the at least one receptor is expressed in an arthropod cell.

62. The system of any one of embodiments 55 to 61, wherein the at least one receptor is expressed in an insect cell.

63. The system of any one of embodiments 55 to 62, wherein the at least one receptor is expressed in a cell from *Drosophila melanogaster* or an ortholog thereof.

64. The system of any one of embodiments 55 to 63, wherein the at least one receptor is expressed in a neuron or an oocyte.

65. The system of any one of embodiments 55 to 64, wherein the at least one receptor is expressed in an isolated cell.

66. The system of any one of embodiments 55 to 65, the sample further comprises a co-receptor or chaperone protein.

67. The system of any one of embodiments 55 to 66, wherein the modulation of the activity of the at least one receptor or receptor-expressing neuron is an increase in the activity of the at least one receptor or receptor-expressing neuron.

68. The system of any one of embodiments 55 to 66, wherein the at least one receptor is an Ir40a receptor.

69. The system of embodiment 68, wherein modulation of the activity of the at least one receptor or receptor-expressing neuron is an increase in the activity of an Ir40a receptor or Ir40a receptor-expressing neuron.

70. The system of embodiment 68 or 69, wherein the sample further comprises an Ir93a receptor or the neuron co-expresses an Ir40a receptor and an Ir93a receptor.

71. The system of any one of embodiments 68 to 70, wherein the sample further comprises an Ir25a receptor or the neuron co-expresses an Ir40a receptor and an Ir25a receptor.

72. The system of embodiment 68 or 69, wherein the sample further comprises an Ir93a receptor, or the neuron co-expresses an Ir40a receptor, an Ir93a receptor, and an Ir25a receptor.

73. The system of any one of embodiments 55 to 66, wherein the at least one receptor is an Ir93a receptor.

74. The system of embodiment 73, wherein modulation of the activity of the receptor or receptor-expressing neuron is an increase in the activity of an Ir93a receptor or Ir93a receptor-expressing neuron.

75. The system of embodiment 73 or 74, wherein the sample further comprises an Ir25a receptor or the neuron co-expresses an Ir93a receptor and an Ir25a receptor.

76. A system for screening a plurality of candidate compounds, comprising:
a) a sample comprising at least one receptor or a receptor-expressing neuron comprising at least one receptor, wherein the at least one receptor is selected from the group consisting of an Ir40a receptor, an Ir93a receptor, and an Ir25a receptor; and; and
b) a plurality of candidate compounds, wherein at least one of the candidate compounds is a repellent for at least one arthropod species, and wherein the at least one repellent compound modulates the activity of the at least one receptor.

77. The system of embodiment 76, wherein the at least one receptor or receptor-expressing neuron is from an arthropod.

78. The system of embodiment 76 or 77, wherein the at least one receptor or receptor-expressing neuron is from an insect.

79. The system of any one of embodiments 76 to 78, wherein the at least one receptor has at least 50% sequence identity to a polypeptide encoding a receptor from *Drosophila melanogaster* or an ortholog thereof.

80. The system of embodiment 79, wherein the ortholog of *Drosophila melanogaster* is selected from the group consisting of *Aedes aegypti, Anopheles gambiae, Culex quinquefasciatus, Acyrthosiphon pisum, Bombyx mori, Tribolium castenium, Pediculus humanus, Ixodes scapularis*, and *Phlebotomus papatasi*.

81. The system of any one of embodiments 76 to 80, wherein the at least one receptor is expressed in a cell.

82. The system of any one of embodiments 76 to 81, wherein the at least one receptor is expressed in an arthropod cell.

83. The system of any one of embodiments 76 to 82, wherein the at least one receptor is expressed in an insect cell.

84. The system of any one of embodiments 76 to 83, wherein the at least one receptor is expressed in a cell from *Drosophila melanogaster*.

85. The system of any one of embodiments 76 to 84, wherein the at least one receptor is expressed in a neuron or an oocyte.

86. The system of any one of embodiments 76 to 85, wherein the at least one receptor is expressed in an isolated cell.

87. The system of any one of embodiments 76 to 86, wherein the sample further comprises a co-receptor or chaperone protein.

88. The system of any one of embodiments 76 to 87, wherein the modulation of the activity of the at least one receptor or receptor-expressing neuron is an increase in the activity of the at least one receptor or receptor-expressing neuron.

89. The system of any one of embodiments 76 to 87, wherein the at least one receptor is an Ir40a receptor.

90. The system of embodiment 89, wherein the modulation of the activity of the at least one receptor is an increase in the activity of the Ir40a receptor.

91. The system of embodiment 89 or 90, wherein the sample further comprises an Ir93a receptor or the neuron co-expresses an Ir40a receptor and an Ir93a receptor.

92. The system of any one of embodiments 89 to 91, wherein the sample further comprises an Ir25a receptor or the neuron co-expresses an Ir40a receptor and an Ir25a receptor.

93. The system of embodiment 89 or 90, wherein the sample further comprises an Ir93a receptor and an Ir25a receptor, or the neuron co-expresses an Ir40a receptor, an Ir93a receptor, and an Ir25a receptor.

94. The system of any one of embodiments 76 to 87, wherein the receptor is an Ir93a receptor.

95. The system of embodiment 94, wherein modulation of the activity of the at least one receptor or receptor-expressing neuron is an increase in the activity of an Ir93a receptor or Ir93a receptor-expressing neuron.
96. The system of embodiment 94 or 95, wherein the sample further comprises an Ir25a receptor or the neuron co-expresses an Ir93a receptor and an Ir25a receptor.
97. A composition comprising a compound identified according to the method of any one of embodiments 1 to 54.

EXAMPLES

The following examples are merely illustrative and are not meant to limit any embodiments of the present disclosure in any way.

Example 1

Involvement of Ir40a Neurons in DEET Avoidance

This Example demonstrates the involvement of the Ir40a+ Olfactory Sensory Neurons (OSNs) in DEET repellency.
Materials and Methods
*Drosophila* Olfactory Avoidance Assay for DEET:
For each trial, three- to six-day old flies (10 males and 10 females) were starved for 18 hours. Flies were transferred to a cylindrical 38.1 mm D×84.1 mm H chamber containing two traps each fashioned from an upturned 1.5 ml microcentrifuge tube with 2 mm removed from the tapered end. A pipette tip (1000 µl), was cut 2.5 cm from narrow end and 0.5 cm from top and inserted into the bottom of the inverted microcentrifuge tube. A 15 mm×16 mm #1 Whatmann filter paper was inserted in between the pipette tip and tip of microcentrifuge tube in a manner that entering flies cannot make physical contact with it. With reference to FIG. 2A, for the 1-choice test, a 50 µl sample of test odorant (50% DEET in DMSO) was applied to filter paper and 125 µl of 10% apple cider vinegar (ACV) is applied to the upturned lid of the microcentrifuge tube as attractant. With reference again to FIG. 2A, for the 2-choice test, two 10% ACV lured traps were placed in the cylinder, one with DMSO as the solvent (right) and another with DEET (left).
Results
Synaptic transmission was blocked from Ir40a+ neurons using the Ir40a-promoter-Gal4 to express active form of tetanus toxin. A majority of control flies expressing a non-functional version of tetanus toxin (IMPTV) was observed to avoid DEET in the 1-choice trap assay lured by 10% apple cider vinegar (ACV) (FIG. 2A). However, avoidance was observed to be substantially decreased in Ir40a neuron-TNTG flies (FIG. 2B). Similar results were obtained from a 2-choice assay, confirming the involvement of Ir40a+ neurons in DEET avoidance (FIG. 2B). The test and control lines were observed to exhibit strong attraction to the 10% ACV lure in control 2-choice trap experiments, suggesting that they are able to detect and respond to the attractive cue to the same extent.

The involvement of the Ir40a+ OSNs in DEET repellency was further investigated by silencing the Ir40a+ neurons using the Ir40a-promoter-Gal4 to express UAS-kir, an inward rectifying potassium channel. The two control lines showed a robust and reproducible avoidance response to volatile DEET in a 2-choice trap assay lured by 10% apple cider vinegar (ACV) (FIG. 2C). However, avoidance was observed to be lost in Ir40a neuron-silenced flies.

Example 2

Involvement of Ir40a in DEET Avoidance

This Example also demonstrates the involvement of the Ir40a receptor for DEET avoidance. Behavior assays (according to the protocol in Example 1) using mutant flies were performed. While no reported mutants or transposon insertion lines were available for Ir40a, two lines from the *Drosophila* Genome Reference Panel (DGRP) were identified that contain missense point mutations in Ir40a, which were confirmed by sequencing the appropriate portion of Ir40a in both lines (FIG. 2D). A common wild-type strain (Canton-S) of *D. melanogaster* showed a robust and reproducible avoidance response to volatile DEET in a 2-choice trap assay lured by 10% apple cider vinegar (ACV). This strong olfactory avoidance to DEET was observed to be nearly abolished in the two DGRP lines that contain mutations in Ir40a (FIG. 2D). The two DGRP lines were observed to exhibit strong attraction to the 10% ACV lure in control 2-choice trap experiments, suggesting that they are able to detect and respond to the attractive cue to the same extent as Canton-S flies. Thus, the highly-conserved Ir40a receptor was observed to be involved in OSN-mediated detection and avoidance of volatile DEET.

Example 3

Behavior Experiments in Synaptic Activity Silenced Flies

In order to investigate the involvement of the Ir40a+ neurons in mediating avoidance to newly discovered repellents, behavior experiments in synaptic activity silenced flies were performed as before (FIG. 2B). A majority of control flies expressing a non-functional version of tetanus toxin (IMPTV) avoided volatile repellents in both a 1-choice and 2-choice trap assay lured by 10% apple cider vinegar (ACV). As seen in FIGS. 4A and 4B, avoidance was observed to be substantially decreased in Ir40a neuron-TNTG flies, demonstrating that these neurons were involved in repellency to the newly identified repellents. These results demonstrate that Ir40a+ neurons can be used in identifying new natural DEET substitutes.

Example 4

Involvement of Ir25a Receptor in DEET Avoidance

This Example demonstrates the involvement of the Ir25a receptor in DEET avoidance. Behavior assays (according to the protocol in Example 1) were performed. Synaptic transmission was blocked from Ir25a+ neurons using the Ir25a-promoter-Gal4 to express an active form of tetanus toxin. A majority of control flies expressing a non-functional version of tetanus toxin (IMPTV) were observed to avoid DEET in the 1-choice trap assay lured by 10% apple cider vinegar (ACV) (FIG. 5). However, avoidance was observed to be substantially decreased in Ir25a neuron-TNTG flies (FIG. 5). A trans-heterozygote of two previously available Ir25a mutant fly lines (Ir25a1 and Ir25a2) was tested and the strong olfactory avoidance to DEET was nearly abolished (FIG. 5). Thus, the highly-conserved Ir25a receptor was also observed to be involved in OSN-mediated detection and avoidance of volatile DEET in addition to the involvement of the Ir40a receptor.

Example 5

Involvement of Ir25a and Ir93a Receptors in DEET Avoidance

This Example demonstrates that the Ir93a and Ir25a receptors are involved in DEET avoidance. This Example also indicated that that the receptors Ir40a, Ir93a, and Ir25a may be involved in DEET avoidance. Behavior assays (according to the protocol in Example 1) were performed.

Synaptic transmission was blocked from e Ir40a+ neurons using the Ir40a-promoter-Ga14 (Ir40a-G4) to express an active form of tetanus toxin (TNTG). A majority of control flies expressing either the Ir40a-promoter-Ga14 alone or the tetanus toxin alone (UAS-TNTG) was observed to avoid DEET in the 1-choice trap assay lured by 10% apple cider vinegar (ACV) (FIG. 6A). However, avoidance was observed to be substantially decreased in Ir40a neuron-TNTG flies (Ir40a-G4/UAS-TNTG), demonstrating the involvement of Ir40a+ neurons in DEET avoidance (FIG. 6A).

To test directly whether Ir40a is required for olfactory avoidance to DEET, the behaviour of flies in which Ir40a expression was decreased in Ir40a+ neurons was examined using the Ir40a-promoter-Ga14 (Ir40a-G4) with UAS-Ir40a-RNAi. In a 2-choice trap assay lured by 10% apple cider vinegar (ACV), a loss of DEET avoidance was observed in the Ir40a-RNAi flies as compared to control flies expressing either the Ir40a-promoter-Ga14 alone or the UAS-Ir40a-RNAi alone (FIG. 6B).

The Ir40a+ neuron in the sacculus has previously been shown to express two other highly conserved Ir genes, Ir93a and a broadly expressed Ir25a (Benton, R., et al., *Cell,* 2009. 136(1): p. 149-62). Previously described receptor mutants of Ir93a and Ir25a receptors were each tested for their involvement in olfactory avoidance to DEET (FIG. 6B). The Ir25a1 and Ir25a2 mutant alleles were generated as previously described (Benton, R., et al., *Cell,* 2009. 136(1): p. 149-62). The Ir93a−/− mutant *Drosophila melanogaster* was trans-heterozygous for two Minos-element insertion alleles obtained from the Bloomington *Drosophila* Stock Center: y[1] w[*]; Mi{y[+mDint2]=MIC}Ir93a[MI05555], and w[1118]; Mi{ET1}Ir93a[MB04433]. As shown in FIG. 6B, both Ir93a and Ir25a were each found to be involved in olfactory DEET avoidance. It has been shown previously that the Ir40a, Ir25a1, and Ir25a2 receptors are co-expressed in the same neuron of the sacculus in *Drosophila melanogaster* (Benton, R., et al., *Cell,* 2009. 136(1): p. 149-62). As such, these results indicate that co-expression of all three Irs receptors (i.e., Ir40a, Ir25a1, and Ir25a2) may function together in a heteromeric complex, or in combinations, as other members of this gene family have been shown to do, to detect DEET.

---

What is claimed is:

1. A method for identifying a compound that is a repellent for at least one arthropod species, comprising identifying a compound that modulates the activity of an Ir40a receptor.

2. The method of claim 1, wherein the Ir40a receptor has at least 50% sequence identity to a polypeptide encoding an Ir40a receptor from *Drosophila melanogaster* or an ortholog thereof.

3. The method of claim 2, wherein the ortholog of *Drosophila melanogaster* is selected from the group consisting of *Aedes aegypti, Anopheles gambiae, Culex quinquefasciatus, Acyrthosiphon pisum, Bombyx mori, Tribolium castenium, Pediculus humanus, Ixodes scapularis*, and *Phlebotomus papatasi*.

4. The method of claim 1, wherein the modulation of the activity of the Ir40a receptor is determined by measuring changes in one or more electrophysiological parameters, measuring changes in calcium levels, measuring electrical potential changes, measuring changes in transcription of activity-dependent gene promoters, or any combination thereof.

5. The method of claim 1, wherein the modulation in the activity of the Ir40a receptor is an increase in the activity of the Ir40a receptor.

6. The method of claim 1, wherein the compound further modulates the activity of an Ir93a receptor, an Ir25a receptor, or a combination thereof.

7. A method of identifying a compound that is a repellent for at least one arthropod species, comprising:
   a) contacting an Ir40a receptor or Ir40a receptor-expressing neuron with a candidate compound;
   b) measuring the activity of the Ir40a receptor;
   c) comparing the activity of the Ir40a receptor after contact with the candidate compound to the activity of the Ir40a receptor in the absence of the candidate compound; and
   d) identifying a compound that is a repellent for at least one arthropod species by determining whether or not the candidate compound modulates the activity of the Ir40a receptor.

8. The method of claim 7, wherein the Ir40a receptor has at least 50% sequence identity to a polypeptide encoding an Ir40a receptor from *Drosophila melanogaster* or an ortholog thereof.

9. The method of claim 8, wherein the ortholog of *Drosophila melanogaster* is selected from the group consisting of *Aedes aegypti, Anopheles gambiae, Culex quinquefasciatus, Acyrthosiphon pisum, Bombyx mori, Tribolium castenium, Pediculus humanus, Ixodes scapularis*, and *Phlebotomus papatasi*.

10. The method of claim 7, wherein the Ir40a receptor is provided with a co-receptor or chaperone protein, or wherein the Ir40a receptor-expressing neuron further expresses a co-receptor or chaperone protein.

11. The method of claim 7, wherein the activity of the Ir40a receptor is measured by one or more electrophysiological parameters, calcium levels, electrical potential, transcription of activity-dependent gene promoters, or any combination thereof.

12. The method of claim 7, wherein the modulation of the activity of the Ir40a receptor is an increase in the activity of the Ir40a receptor.

13. The method of claim 7, wherein, in step (a), the candidate compound further contacts an Ir93a receptor, or an Ir25a receptor, or a combination thereof.

14. A method of identifying a compound that is a repellent for at least one arthropod species, comprising:
   a) providing a sample comprising a full-length or partial Ir40a receptor protein from *Drosophila melanogaster* or an ortholog thereof;
   b) contacting the sample with a candidate compound;
   c) measuring the activity of an Ir40a receptor in the sample;
   d) comparing the activity of the Ir40a receptor after contact with the candidate compound to the activity of the Ir40a receptor in the absence of the candidate compound; and
   e) identifying a compound that is a repellent for at least one arthropod species by determining whether or not the candidate compound modulates the activity of the Ir40a receptor.

15. The method of claim 14, wherein the Ir40a receptor has at least 50% sequence identity to a polypeptide encoding an Ir40a receptor from *Drosophila melanogaster* or an ortholog thereof.

16. The method of claim 15, wherein the ortholog of *Drosophila melanogaster* is selected from the group consisting of *Aedes aegypti, Anopheles gambiae, Culex quinquefasciatus, Acyrthosiphon pisum, Bombyx mori, Tribolium castenium, Pediculus humanus, Ixodes scapularis*, and *Phlebotomus papatasi*.

17. The method of claim 14, wherein the sample further comprises a co-receptor or chaperone protein.

18. The method of claim 14, wherein the activity of the Ir40a receptor is measured based on one or more electrophysiological parameters, calcium levels, electrical potential, transcription of activity-dependent gene promoters, or any combination thereof.

19. The method of claim 14, wherein the modulation of the activity of the Ir40a receptor is an increase in the activity of the Ir40a receptor.

20. The method of claim 14, wherein the sample further comprises (i) a full-length or partial Ir93a receptor protein from *Drosophila melanogaster* or an ortholog thereof; or (ii) a full-length or partial Ir25a receptor protein from *Drosophila melanogaster* or an ortholog thereof, or a combination of (i) and (ii).

21. A system, comprising:
a) a sample comprising an Ir40a receptor or Ir40a receptor-expressing neuron; and
b) one or more compounds that each is a repellent for at least one arthropod species, wherein the one or more compounds each modulates the activity of the Ir40a receptor.

22. The system of claim 21, wherein the Ir40a receptor has at least 50% sequence identity to a polypeptide encoding an Ir40a receptor from *Drosophila melanogaster* or an ortholog thereof.

23. The system of claim 21, wherein the sample further comprises a co-receptor or chaperone protein.

24. The system of claim 21, wherein the sample further comprises (i) an Ir93a receptor or the neuron co-expresses Ir40a receptor and Ir93a receptor; or (ii) an Ir25a receptor or the neuron co-expresses Ir40a receptor and Ir25a receptor, or a combination thereof.

25. A system for screening a plurality of candidate compounds, comprising:
a) a sample comprising an Ir40a receptor or Ir40a receptor-expressing neuron; and
b) a plurality of candidate compounds, wherein at least one of the candidate compounds is a repellent for at least one arthropod species, and wherein the at least one repellent compound modulates the activity of an Ir40a receptor.

26. The system of claim 25, wherein the Ir40a receptor has at least 50% sequence identity to a polypeptide encoding an Ir40a receptor from *Drosophila melanogaster* or an ortholog thereof.

27. The system of claim 25, wherein the sample further comprises a co-receptor or chaperone protein.

28. The system of claim 25, wherein the sample further comprises (i) an Ir93a receptor or the neuron co-expresses an Ir40a receptor and an Ir93a receptor; or (ii) an Ir25a receptor or the neuron co-expresses an Ir40a receptor and an Ir25a receptor, or a combination of (i) and (ii).

* * * * *